(12) United States Patent
Prissette et al.

(10) Patent No.: US 12,110,502 B2
(45) Date of Patent: Oct. 8, 2024

(54) MODELS OF TAUOPATHY

(71) Applicant: Regeneron Pharmaceuticals, Inc., Tarrytown, NY (US)

(72) Inventors: Marine Prissette, Brooklyn, NY (US); Matthew Koss, Pleasantville, NY (US); Mathieu Desclaux, Brooklyn, NY (US); John McWhirter, Hastings-on-Hudson, NY (US); Arijit Bhowmick, Astoria, NY (US); David Frendewey, New York, NY (US); Brian Zambrowicz, Sleepy Hollow, NY (US); Claudia Racioppi, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/502,516

(22) Filed: Nov. 6, 2023

(65) Prior Publication Data

US 2024/0076613 A1 Mar. 7, 2024

Related U.S. Application Data

(62) Division of application No. 16/900,432, filed on Jun. 12, 2020, now Pat. No. 11,845,957.

(60) Provisional application No. 62/861,553, filed on Jun. 14, 2019.

(51) Int. Cl.
| | |
|---|---|
| *C12N 15/113* | (2010.01) |
| *A61K 9/00* | (2006.01) |
| *A61K 48/00* | (2006.01) |
| *C12N 5/0793* | (2010.01) |
| *C12Q 1/68* | (2018.01) |
| *C07H 21/02* | (2006.01) |

(52) U.S. Cl.
CPC .......... *C12N 5/0619* (2013.01); *A61K 9/0019* (2013.01); *A61K 48/0058* (2013.01); *C12N 15/113* (2013.01); *A01K 2267/0312* (2013.01); *A01K 2267/0318* (2013.01); *C12N 2310/11* (2013.01)

(58) Field of Classification Search
None
See application file for complete search history.

(56) References Cited

U.S. PATENT DOCUMENTS

| | | | |
|---|---|---|---|
| 9,910,048 B2 | 3/2018 | Diamond et al. | |
| 11,001,829 B2 | 5/2021 | Zhang et al. | |
| 11,781,131 B2 | 10/2023 | Prissette et al. | |
| 11,845,930 B2 | 12/2023 | Fury et al. | |
| 11,845,931 B2 | 12/2023 | Prissette et al. | |
| 11,845,957 B2 | 12/2023 | Prissette et al. | |
| 2014/0031291 A1 | 1/2014 | Mohler et al. | |
| 2014/0162306 A1 | 6/2014 | Robitzki et al. | |
| 2014/0286954 A1 | 9/2014 | Moe et al. | |
| 2016/0272965 A1 | 9/2016 | Zhang et al. | |
| 2018/0291370 A1 | 10/2018 | Gersbach et al. | |
| 2018/0305704 A1 | 10/2018 | Zhang | |
| 2019/0032155 A1 | 1/2019 | Gong et al. | |
| 2019/0284572 A1 | 9/2019 | Hunt et al. | |
| 2019/0365924 A1 | 12/2019 | Conway et al. | |
| 2019/0390195 A1 | 12/2019 | Tondera et al. | |
| 2020/0165601 A1 | 5/2020 | Zhang et al. | |
| 2020/0299681 A1 | 9/2020 | Prissette et al. | |
| 2020/0299682 A1 | 9/2020 | Prissette et al. | |
| 2021/0009949 A1 | 1/2021 | Prissette et al. | |
| 2023/0416728 A1 | 12/2023 | Prissette et al. | |

FOREIGN PATENT DOCUMENTS

| | | |
|---|---|---|
| EP | 3011033 | 2/2020 |
| WO | WO 2014/089104 A1 | 6/2014 |
| WO | WO 2016/205711 A1 | 12/2016 |
| WO | WO 2017/015637 A1 | 1/2017 |
| WO | WO 2017/100343 A1 | 6/2017 |
| WO | WO 2018/157769 A1 | 9/2018 |
| WO | WO 2018/224531 A1 | 12/2018 |
| WO | WO 2019/010384 A1 | 1/2019 |
| WO | WO 2019/028032 A1 | 2/2019 |
| WO | WO 2019/183123 A1 | 9/2019 |
| WO | WO 2019/237069 A1 | 12/2019 |
| WO | WO 2019/246203 A1 | 12/2019 |
| WO | WO 2020/190927 A1 | 9/2020 |
| WO | WO 2020/190932 A1 | 9/2020 |
| WO | WO 2020/252340 A1 | 12/2020 |

OTHER PUBLICATIONS

"The 96th Annual Meeting of the Physiological Society of Japan," Journal of Physiological Sciences, Springer Japan KK, 69(Suppl 1), (2019).
Adli, "The CRISPR tool kit for genome editing and beyond," Nat. Commun., 9(1):1911, 13 pages, (2018).
Anders et al., "Differential expression analysis for sequence count data," Genome Biol., 11:R106, pp. 1-12, (2010).
Anonymous, "Identification of genetic regulators for intracellular aggregation by genome-wide CRISPR screening," 2016 Fiscal Year Annual Research Report, the University of Tokyo, KAKEN, 2 pages, (2018).
Anonymous, Abstracts: Oral Presentations, Cell Biology, ASCB Annual Meeting, 84 pages, (2016).

(Continued)

*Primary Examiner* — Sean McGarry
(74) *Attorney, Agent, or Firm* — Yongjin Choi; Alston & Bird LLP

(57) ABSTRACT

BANF1, PPP2CA, and ANKLE2 were identified as genes that promote tau aggregation when disrupted. Improved tauopathy models such as cells, tissues, or animals having mutations in or inhibition of expression of BANF1 and/or PPP2CA and/or ANKLE2 are provided. Methods of using such improved tauopathy models for assessing therapeutic candidates for the treatment of a tauopathy, methods of making the improved tauopathy models, and methods of accelerating or exacerbating tau aggregation in a tauopathy model are also provided.

42 Claims, 47 Drawing Sheets
Specification includes a Sequence Listing.

(56) References Cited

OTHER PUBLICATIONS

Asencio et al., "Coordination of Kinase and Phosphatase Activities by Lem4 Enables Nuclear Envelope Reassembly during Mitosis," Cell, 150(1):122-135, (2012).
Bajar et al., "A Guide to Fluorescent Protein FRET Pairs," Sensors (Basel), 16:E1488, pp. 1-24, (2016).
Bennett et al., "Enhanced Tau Aggregation in the Presence of Amyloid β," Am. J. Pathol., 187(7):1601-1612, (2017).
Boettcher, et al., "Choosing the Right Tool for th eJob: RNAi, Talen, or CRISPR," Mol. Cell 58(4):575-585, (May 2014).
Brandt et al., "Tau alteration and neuronal degeneration in tauopathies: mechanisms and models," Biochim. Biophys. Acta, 1739(2-3):331-354, (2005).
Chen et al., "Compromised function of the ESCRT pathway promotes endolysomal escape of tau seeds and propagation of tau aggregation," J. Biol. Chem., 294(50):18952-18966, (2019).
Chen et al., "Genome-wide CRISPR Screen in a Mouse Model of Tumor Growth and Metastasis," Cell, 160(6):1246-1260 plus supplementary materials, (2015).
Chiu et al., "Identification of Calcium and Integrin-Binding Protein 1 as a Novel Regulator of Production of Amyloid β Peptide Using CRISPR/Cas9-based Screening System," FASEB J., 34(6):7661-7674, (2020).
Cox, et al., "Banf1 is required to maintain the self-renewal of both mouse and human embryonic stem cells," J. Cell Sci., 124(15):2654-2665, (2011).
Croft et al., "rAAV-based brain slice culture models of Alzheimer's and Parkinson's disease inclusion pathologies," J. Exp. Med., 216(3):539-555, (2019).
Eftekharzadeh et al., "Tau Protein Disrupts Nucleocytoplasmic Transport in Alzheimer's Disease," Neuron, 99(5): 925-940, (2018).
Frost et al., "Lamin Dysfunction Mediates Neurodegeneration in Tauopathies," Curr. Biol., 26(1):129-136, (2016).
Furman et al., "Sensitive Detection of Proteopathic Seeding Activity with FRET Flow Cytometry," J. Vis. Exp., 106:e53205, pp. 1-12, (2015).
Goodwin et al., "Large-scale discovery of mouse transgenic integration sites reveals frequent structural variation and insertional mutagenesis," Genome Res., 29(3):494-505, (2019).
Gorjanacz et al., "Caenorhabditis elegans BAF-1 and its kinase VRK-1 participate directly in post-mitotic nuclear envelope assembly," EMBO J., 26(1):132-143, (2007).
Gorjanacz, "LEM-4 promotes rapid dephosphorylation of BAF during mitotic exit," Nucleus, 4(1):14-17, (2013).
Gratuze et al., "Insulin deprivation induces PP2A inhibition and tau hyperphosphorylation in hTau mice, a model of Alzheimer's disease-like tau pathology," Sci. Rep., 7:46359, 13 pages, (2017).
Hall et al., "Modeling tauopathy: a range of complementary approaches," Biochim. Biophys. Acta, 1739(2-3):224-239, (2005).
Hannan et al., "Cellular and molecular modifier pathways in tauopathies: the big picture from screening invertebrate models," J. Neurochem., 137(1):12-25, (2016).
Hart et al., "High-Resolution CRISPR Screens Reveal Fitness Genes and Genotype-Specific Cancer Liabilities," Cell, 163(6):1515-1526, (2015).
Holmes et al., "Prion-like Properties of Tau Protein: The Importance of Extracellular Tau as a Therapeutic Target," J. Biol. Chem., 289(29):19855-19861, (2014).
Holmes et al., "Proteopathic tau seeding predicts tauopathy in vivo," Proc. Natl. Acad. Sci. U.S.A., 111(41):E4376-E4385, (2014).
Jamin et al., "Barrier to Autointegration Factor (BANF1): interwoven roles in nuclear structure, genome integrity, innate immunity, stress responses and progeria," Curr. Opin. Cell Biol., 34:61-68, (2015).
Jamin et al., "Barrier to Autointegration Factor (BANF1): interwoven roles in nuclear structure, genome integrity, innate immunity, stress responses and progeria," Curr. Opin. Cell Biol., 34:61-68, Author Manuscript, (2015).
Joung et al., "Genome-scale CRISPR-Cas9 knockout and transcriptional activation screening," Nat. Protoc., 12(4):828-863, (2017).
Jucker et al., "Self-propagation of pathogenic protein aggregates in neurodegenerative diseases," Nature, 501(7465):45-51, (2013).
Kampmann, "A CRISPR Approach to Neurodegenerative Diseases," Trends Mol. Med., 23(6):483-485, (2017).
Kampmann, "CRISPRi and CRISPRa Screens in Mammalian Cells for Precision Biology and Medicine," ACS Chem. Biol., 13(2):406-416, (2017).
Kaufman et al., "Tau Prion Strains Dictate Patterns of Cell Pathology, Progression Rate, and Regional Vulnerability In Vivo," Neuron, 92(4):796-812, (2016).
Kfoury et al., "Trans-cellular Propagation of Tau Aggregation by Fibrillar Species," The Journal of Biological Chemistry, 287(23):19440-19451, (2012).
Konermann et al., "Genome-scale transcriptional activation by an engineered CRISPR-Cas9 complex," Nature, 517(7536):583-588 plus supplementary materials, (2015).
Kurreck et al., "Design of antisense oligonucleotides stabilized by locked nucleic acids," Nucleic Acids Res., 30(9):1911-1918, (2002).
Lee et al., "Transgenic animal models of tauopathies," Biochim. Biophys. Acta, 1739(2-3):251-259, (2005).
Molitor et al., "Depletion of the protein kinase VRK1 disrupts nuclear envelope morphology and leads to BAF retention on mitotic chromosomes," Mol. Biol. Cell, 25(6):891-903, (2014).
Nagai et al., "Astrocytes expressing ALS-linked mutated SOD1 release factors selectively toxic to motor neurons," Nat. Neurosci., 10(5):615-622, (2007).
Nathaniel et al., "Elucidating Cellular Trafficking Pathways Controlling Prion-like Spread of Tau Aggregation Using CRISPR Interference Screens [abstract]," Abstracts; Poster Presentations, Cell Biology 2016, ASCB Annual Meeting, P887, (2016).
Nicholls et al., "Characterization of TauC3 antibody and demonstration of its potential to block tau propagation," PLOS ONE, 12(5):e0177914, 11 pages, (2017).
Nobuhara et al., "Tau Antibody Targeting Pathological Species Blocks Neuronal Uptake and Interneuron Propagation of Tau in Vitro," Am. J. Pathol., 187(6):1399-1412, (2017).
Park et al., "A genome-wide CRISPR screen identifies a restricted set of HIV host dependency factors," Nat. Genet., 49(2):193-203 plus online methods, (2017).
Prisette, et al., "Disruption of nuclear envelope integrity as a possible initiating event in tauopathies," Cell Reports 40, 111249, (Aug. 23, 2022).
Puente et al., "Exome Sequencing and Functional Analysis Identifies BANF1 Mutation as the Cause of a Hereditary Progeroid Syndrome," Am. J. Hum. Genet., 88(5):650-656, (2011).
Reczek et al., "A CRISPR screen identifies a pathway required for paraquat-induced cell death," Nat. Chem. Biol., 13(12):1274-1279 plus online methods, (2017).
Samson et al., "Structural analysis of the ternary complex between lamin A/C, BAF and emerin identifies an interface disrupted in autosomal recessive progeroid diseases," Nucleic Acids Res., 46(19):10460-10473, (2018).
Sanjana et al., "Improved vectors and genome-wide libraries for CRISPR screening," Nat. Methods, 11(8):783-784, (2014).
Shalem et al., "Genome-Scale CRISPR-Cas9 Knockout Screening in Human Cells," Science, 343:84-87 and Supplementary Material, (2014).
Simic et al., "Tau Protein Hyperphosphorylation and Aggregation in Alzheimer's Disease and Other Tauopathies, and Possible Neuroprotective Strategies," Biomolecules, 6(1):6, 28 pages, (2016).
Snyers, et al., "LEM4/ANKLE-2 deficiency impairs post-mitotic re-localization of BAF, LAP2α and LaminA to the nucleus, causes nuclear envelope instability in telophase and leads to hyperploidy in HeLa cells," Eur. J. Cell. Biol., 97(1):63-74, (2018).
Tzelepis et al., "A CRISPR Dropout Screen Identifies Genetic Vulnerabilities and Therapeutic Targets in Acute Myeloid Leukemia," Cell Reports, 17:1193-1205, (2016).
Wang et al., "Gene Essentiality Profiling Reveals Gene Networks and Synthetic Lethal Interactions with Oncogenic Ras," Cell, 168(5):890-903 plus supplemental materials, (2017).
Wang et al., "Identification and characterization of essential genes in the human genome," Science, 350(6264):1096-1101, (2015).

(56) References Cited

OTHER PUBLICATIONS

Wolfe et al., "Tau Mutations in Neurodegenerative Diseases," J. Biol. Chem., 284(10):6021-6025, (2009).
Yoshiyama et al., "Synapse Loss and Microglial Activation Precede Tangles in a P301S Tauopathy Mouse Model," Neuron, 53(3):337-351, (2007).
Zhu et al., "Protein Phosphatase 2A Facilitates Axonogenesis by Dephosphorylating CRMP2," The Journal of Neuroscience, 30(10):3839-3848, (2010).
U.S. Appl. No. 16/900,432, Non-Final Office Action mailed Jan. 12, 2023.
U.S. Appl. No. 16/900,432, Notice of Allowance mailed Aug. 7, 2023.
U.S. Appl. No. 16/900,432, Requirement for Restriction/Election mailed Jul. 12, 2022.
WIPO Application No. PCT/US2020/037533, PCT International Search Report and Written Opinion of the International Searching Authority mailed Sep. 28, 2020.
U.S. Appl. No. 62/861,553, filed Jun. 14, 2019, Expired.
U.S. Appl. No. 16/900,432, filed Jun. 12, 2019, U.S. Pat. No. 11,845,957, Issued.
PCT/US2020/037533, Jun. 12, 2020, WO 2020/252340, Expired.
Skotte et al., "Integrative Characterization of the R6/2 Mouse Model of Huntington's Disease Reveals Dysfunctional Astrocyte Metabolism," Cell Rep., 23(7):2211-2224, (2018).

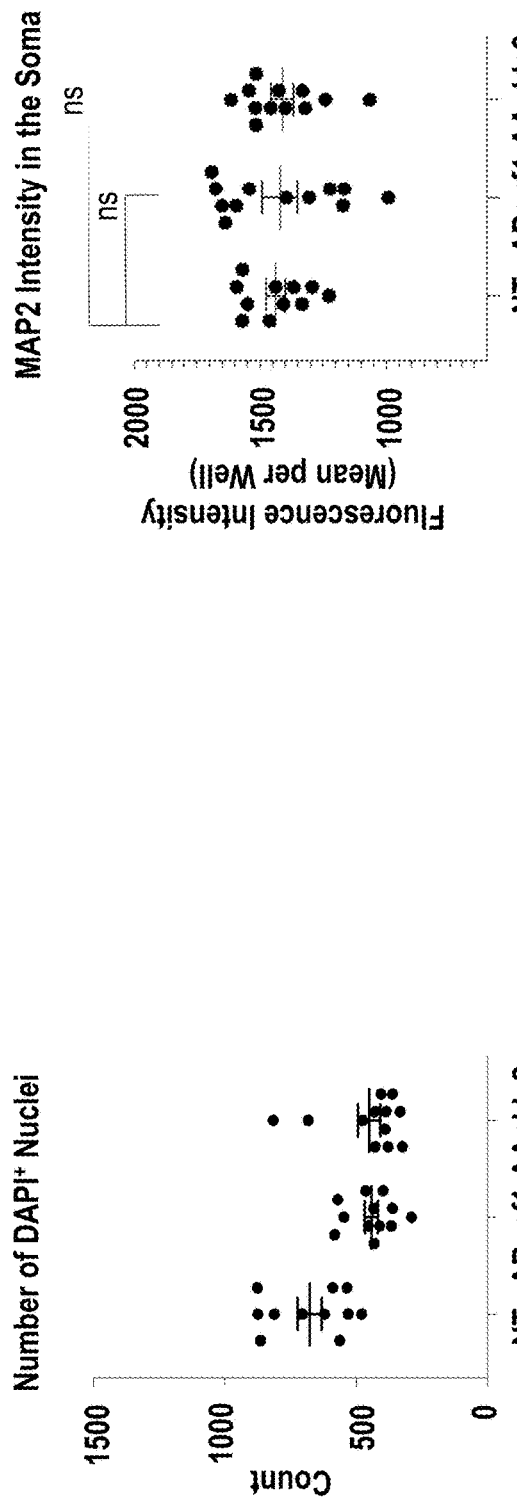
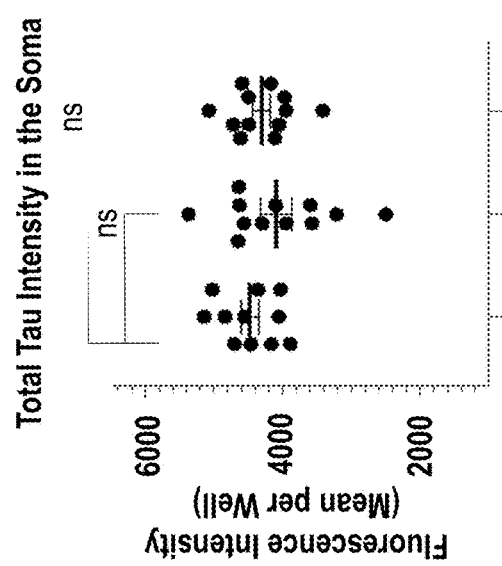
FIG. 32A
FIG. 32B
FIG. 32C

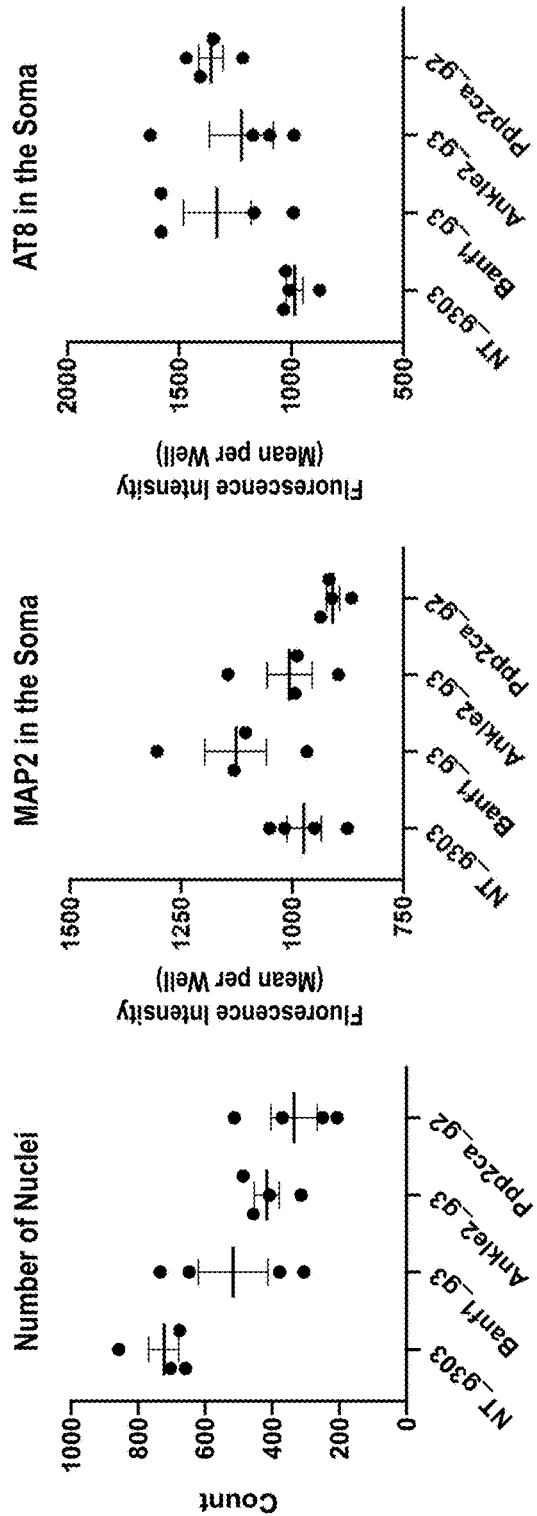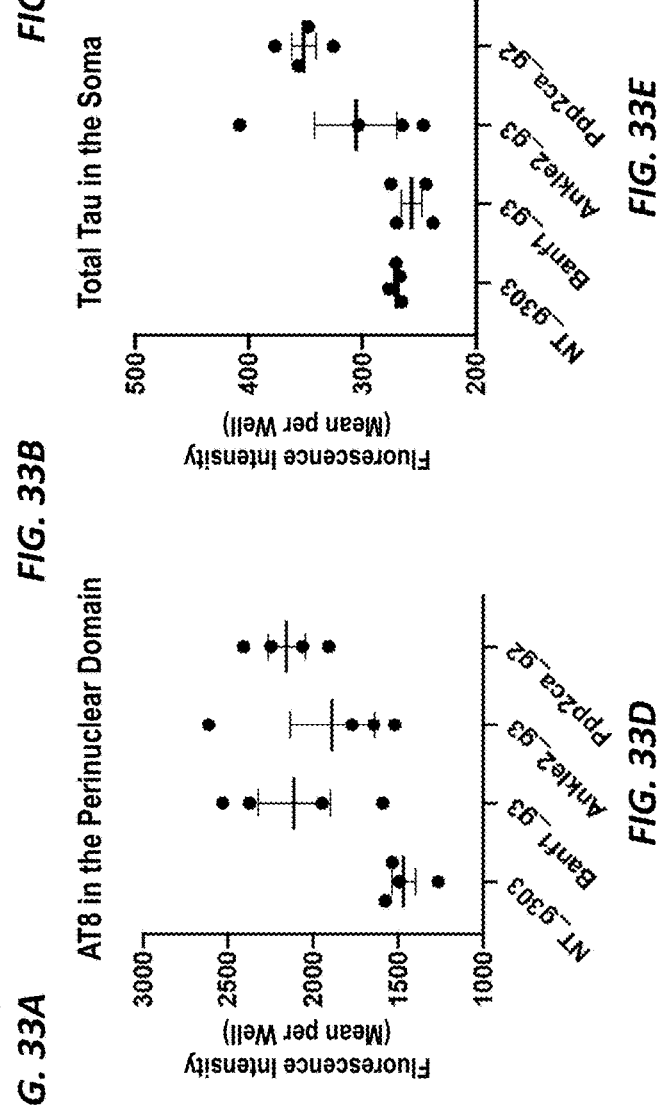
FIG. 33A, FIG. 33B, FIG. 33C, FIG. 33D, FIG. 33E

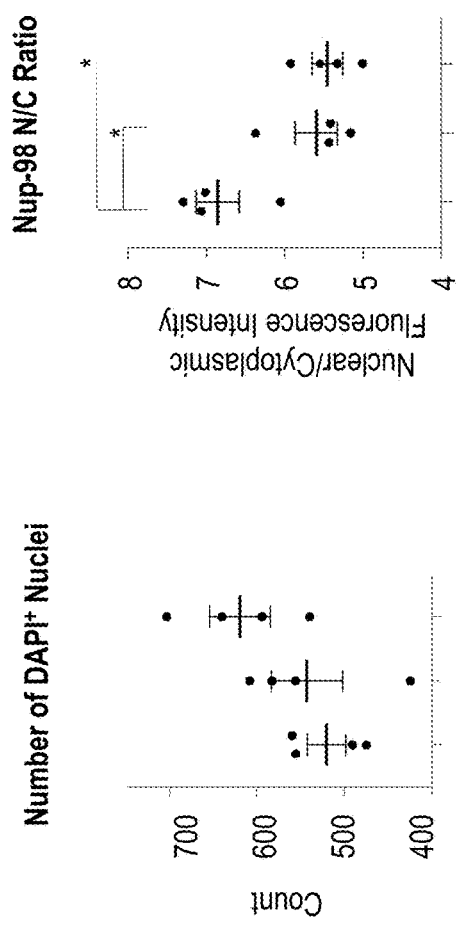
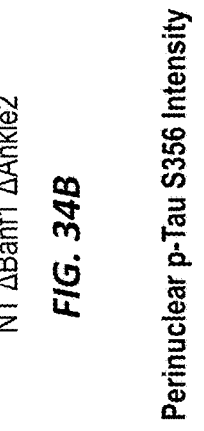
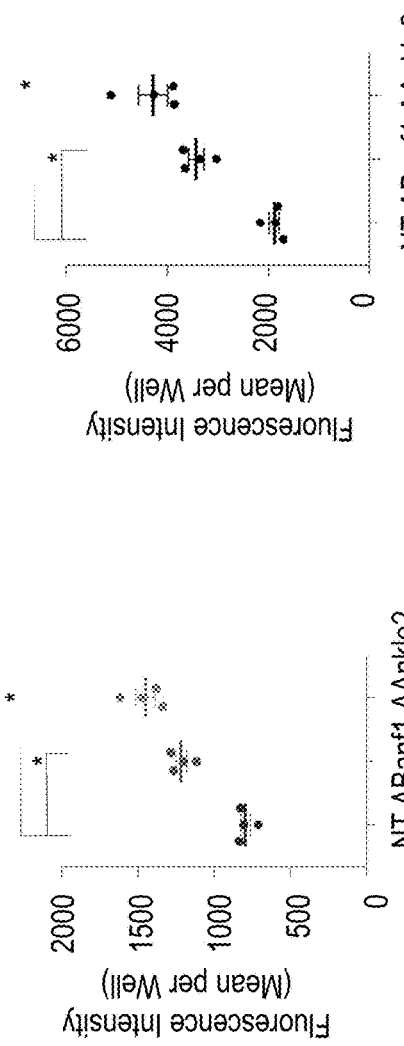
FIG. 34A
FIG. 34B
FIG. 34C
FIG. 34D

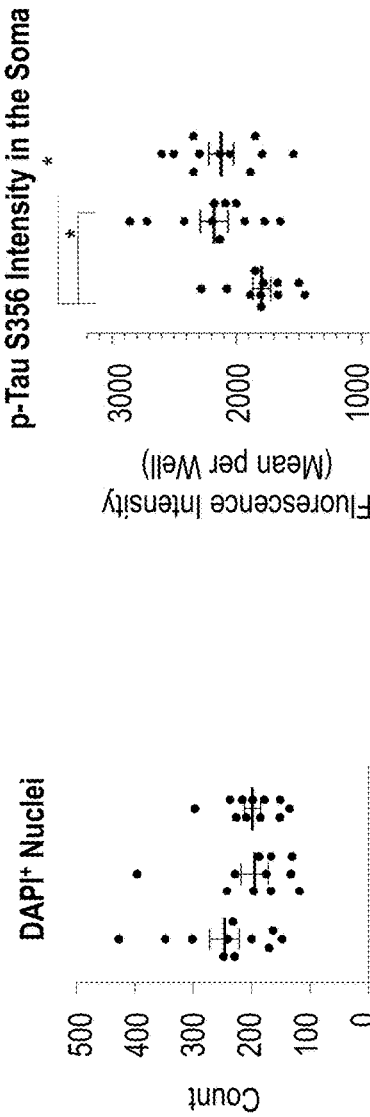
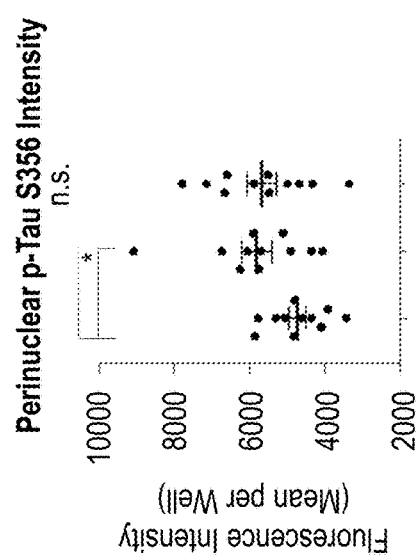
FIG. 36A  FIG. 36B  FIG. 36C  FIG. 36D

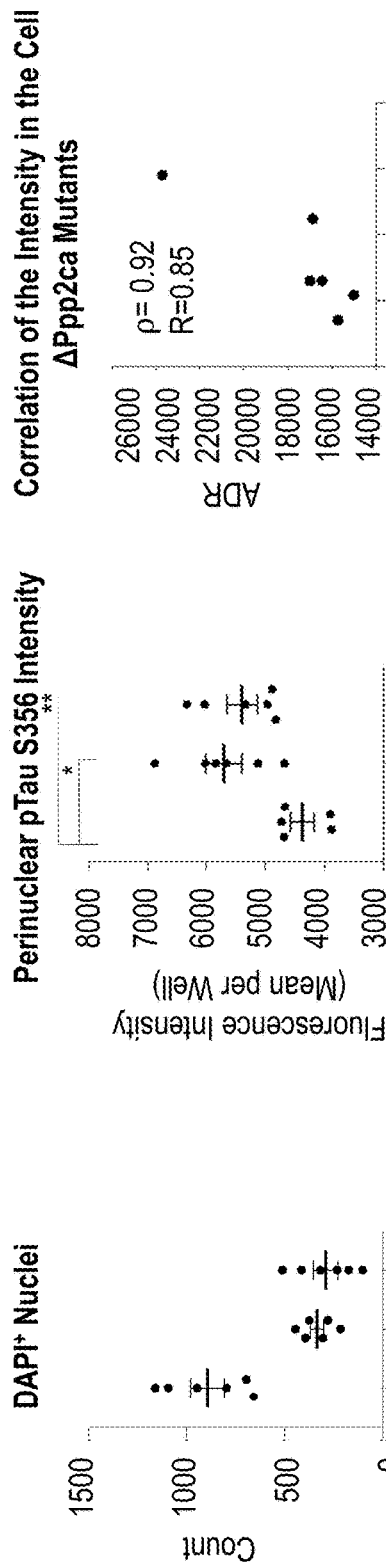
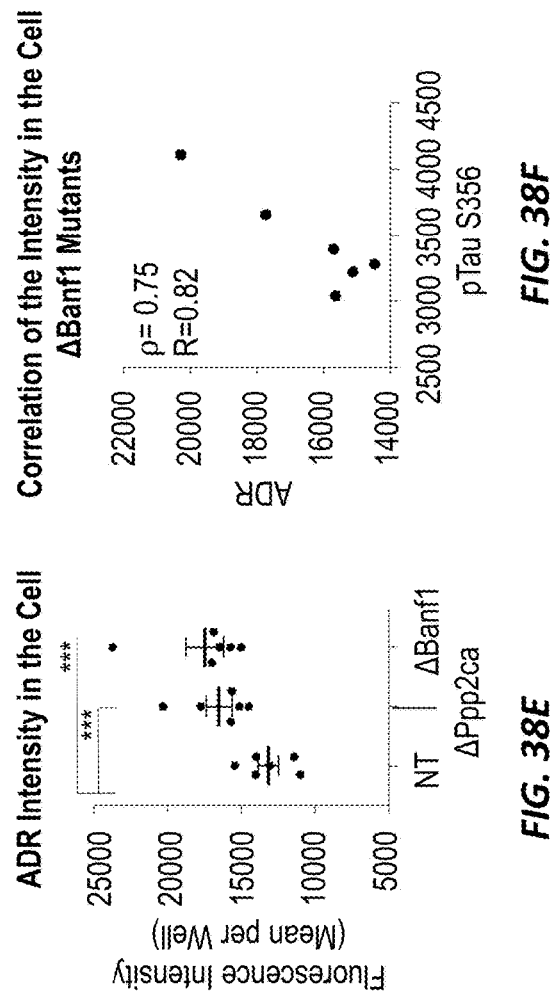
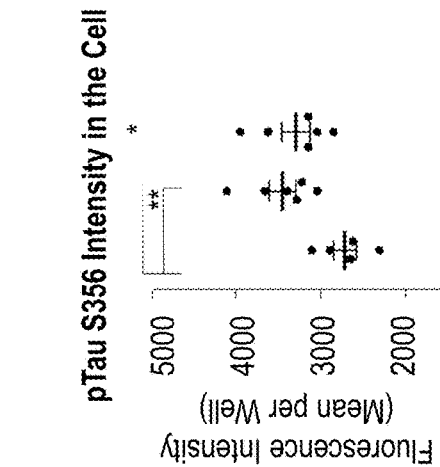
FIG. 38A  FIG. 38B  FIG. 38C
FIG. 38D  FIG. 38E  FIG. 38F

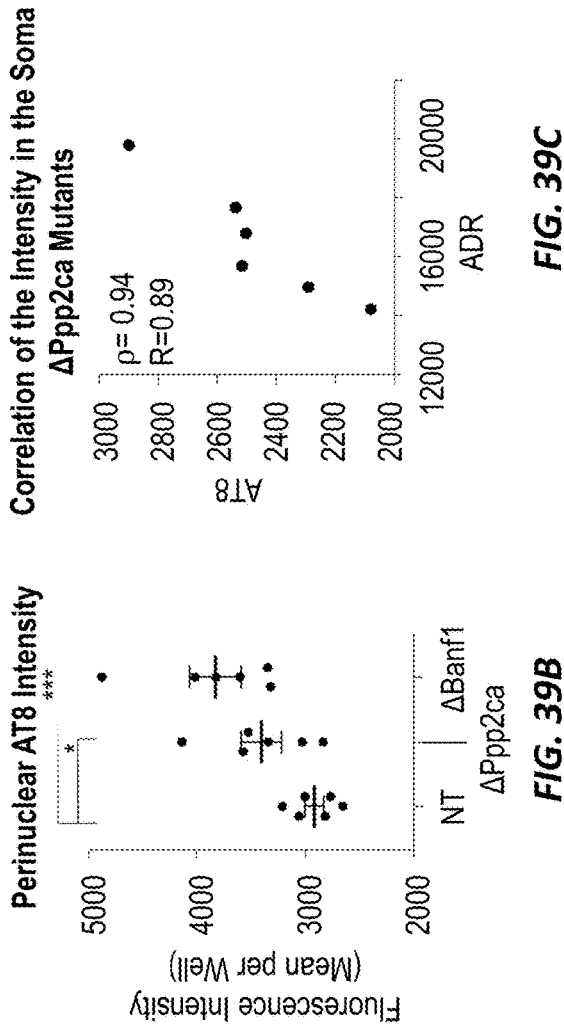
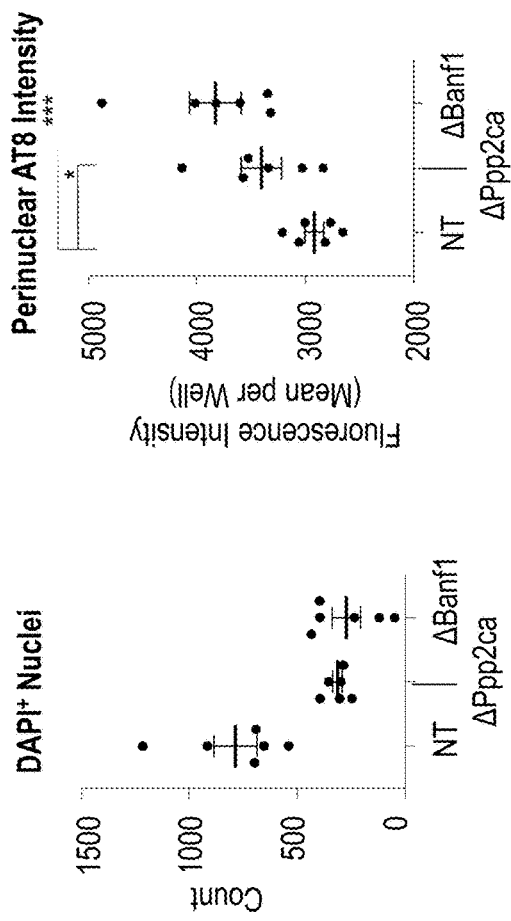
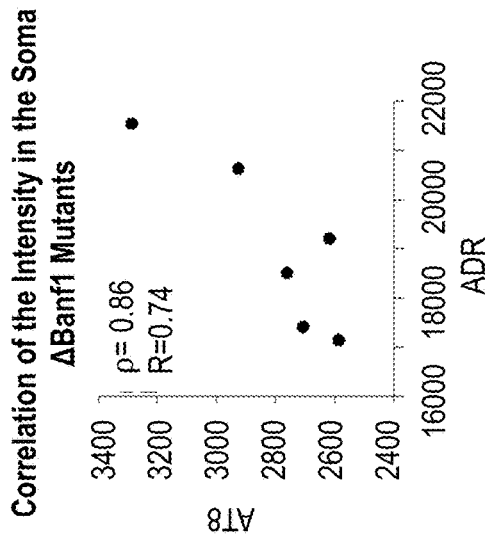
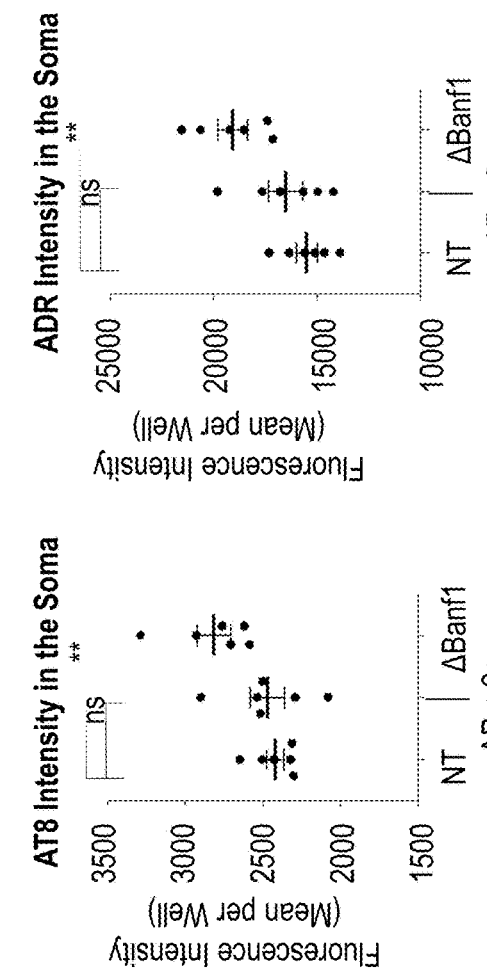
FIG. 39A  FIG. 39B  FIG. 39C
FIG. 39D  FIG. 39E  FIG. 39F

MODELS OF TAUOPATHY

CROSS-REFERENCE TO RELATED APPLICATIONS

This application is a divisional of U.S. application Ser. No. 16/900,432, filed Jun. 12, 2020, which claims the benefit of U.S. Application No. 62/861,553, filed Jun. 14, 2019, each of which is herein incorporated by reference in its entirety for all purposes.

REFERENCE TO A SEQUENCE LISTING SUBMITTED AS AN XML FILE

The Sequence Listing written in file 603010SEQLIST.txt is 533,017 bytes, was created on Nov. 6, 2023, and is hereby incorporated by reference.

BACKGROUND

Abnormal aggregation or fibrillization of proteins such as tau is a defining feature of many diseases, notably including a number of neurodegenerative diseases such as Alzheimer's disease (AD), frontotemporal dementia (FTD), and others. In many of these diseases, the fibrillization of certain proteins into insoluble aggregates is not only a hallmark of disease, but has also been implicated as a causative factor of neurotoxicity. Furthermore, these diseases are characterized by propagation of aggregate pathology through the central nervous system following stereotypical patterns, a process which correlates with disease progression. The identification of genes and genetic pathways that modify the processes of abnormal protein aggregation, or cell-to-cell propagation of aggregates, are therefore of great value in better understanding neurodegenerative disease etiology as well as in devising strategies for therapeutic intervention.

SUMMARY

Provided herein are non-human animals, animal tissues, and populations of animal cells that are improved tauopathy models and methods of making and using such models. Such improved tauopathy models can have a genetic modification in one or more or all of BANF1, PPP2CA, and ANKLE2 that reduces expression of the one or more or all of BANF1, PPP2CA, and ANKLE2, respectively, and/or can comprise one or more agents that reduce expression of one or more or all of BANF1, PPP2CA, and ANKLE2 in the one or more cells. Some such improved tauopathy models can also comprise a microtubule-associated protein tau coding sequence (e.g., endogenous or exogenous). Some such improved tauopathy models can also comprise an exogenous microtubule-associated protein tau coding sequence (e.g., an exogenous human microtubule-associated protein tau coding sequence). Alternatively, some such improved tauopathy models can comprise a tau coding sequence (endogenous or exogenous) that encodes a tau protein comprising a tauopathy-associated mutation or tau pathogenic mutation.

In one aspect, provided are a non-human animal, an animal tissue, or a population of animal cells comprising: (a) a microtubule-associated protein tau coding sequence in one or more cells; and (b)(i) a genetic modification in one or more or all of BANF1, PPP2CA, and ANKLE2 that reduces expression of the one or more or all of BANF1, PPP2CA, and ANKLE2, respectively, in the one or more cells and/or (ii) one or more agents that reduce expression of one or more or all of BANF1, PPP2CA, and ANKLE2 in the one or more cells. Optionally, the microtubule-associated protein tau coding sequence is a human microtubule-associated protein tau coding sequence. Optionally, the microtubule-associated protein tau coding sequence is an exogenous human microtubule-associated protein tau coding sequence. In one aspect, provided are a non-human animal, an animal tissue, or a population of animal cells comprising: (a) an exogenous human microtubule-associated protein tau coding sequence in one or more cells; and (b)(i) a genetic modification in one or more or all of BANF1, PPP2CA, and ANKLE2 that reduces expression of the one or more or all of BANF1, PPP2CA, and ANKLE2, respectively, in the one or more cells and/or (ii) one or more agents that reduce expression of one or more or all of BANF1, PPP2CA, and ANKLE2 in the one or more cells. Optionally, the one or more cells are neuronal cells.

In some such non-human animals, animal tissues, or populations of animal cells, the exogenous human microtubule-associated protein tau coding sequence is genomically integrated. In some such non-human animals, animal tissues, or populations of animal cells, the exogenous human microtubule-associated protein tau coding sequence comprises a complementary DNA (cDNA) sequence. In some such non-human animals, animal tissues, or populations of animal cells, the exogenous human microtubule-associated protein tau coding sequence is codon-optimized for expression in the non-human animal, the animal tissue, or the population of animal cells.

In some such non-human animals, animal tissues, or populations of animal cells, the exogenous human microtubule-associated protein tau coding sequence is operably linked to a heterologous promoter. Optionally, the heterologous promoter is a mouse prion protein promoter. Optionally, the heterologous promoter is a neuron-specific promoter. Optionally, the neuron-specific promoter is a synapsin-1 promoter.

In some such non-human animals, animal tissues, or populations of animal cells, the microtubule-associated protein tau comprises a tauopathy-associated mutation. In some such non-human animals, animal tissues, or populations of animal cells, the tauopathy-associated mutation comprises a P301S mutation. Optionally, the microtubule-associated protein tau comprises the sequence set forth in SEQ ID NO: 98. In some such non-human animals, animal tissues, or populations of animal cells, the tauopathy-associated mutation comprises an A152T/P301L/S320F triple mutation. Optionally, the microtubule-associated protein tau coding sequence comprises the sequence set forth in SEQ ID NO: 83 or the microtubule-associated protein tau comprises the sequence set forth in SEQ ID NO: 84.

In some such non-human animals, animal tissues, or populations of animal cells, the exogenous human microtubule-associated protein tau comprises a tauopathy-associated mutation. In some such non-human animals, animal tissues, or populations of animal cells, the tauopathy-associated mutation comprises a P301S mutation. Optionally, the exogenous human microtubule-associated protein tau comprises the sequence set forth in SEQ ID NO: 98. In some such non-human animals, animal tissues, or populations of animal cells, the tauopathy-associated mutation comprises an A152T/P301L/S320F triple mutation. Optionally, the exogenous human microtubule-associated protein tau coding sequence comprises the sequence set forth in SEQ ID NO: 83 or the exogenous human microtubule-associated protein tau comprises the sequence set forth in SEQ ID NO: 84.

In some such non-human animals, animal tissues, or populations of animal cells, the non-human animal, the animal tissue, or the population of animal cells comprises the genetic modification in the one or more or all of BANF1, PPP2CA, and ANKLE2 that reduces expression of the one or more or all of BANF1, PPP2CA, and ANKLE2, respectively, in the one or more cells. In some such non-human animals, animal tissues, or populations of animal cells, the non-human animal, the animal tissue, or the population of animal cells comprises the one or more agents that reduce expression of the one or more or all of BANF1, Ppp2ca, and ANKLE2 in the one or more cells.

In some such non-human animals, animal tissues, or populations of animal cells, the one or more agents comprise a nuclease agent targeting BANF1, PPP2CA, or ANKLE2 or a nucleic acid encoding the nuclease agent. In some such non-human animals, animal tissues, or populations of animal cells, the nuclease agent is a Zinc Finger Nuclease (ZFN), a Transcription Activator-Like Effector Nuclease (TALEN), or a Clustered Regularly Interspaced Short Palindromic Repeats (CRISPR)-associated (Cas) protein and a guide RNA. Optionally, the nuclease agent is the Cas protein and the guide RNA. Optionally, the Cas protein is a Cas9 protein. Optionally, the Cas protein is a catalytically active Cas protein. Optionally, the Cas protein is a catalytically inactive Cas protein fused to a transcriptional repressor domain, optionally wherein the transcriptional repressor domain is a Krüppel associated box (KRAB) domain. In some such non-human animals, animal tissues, or populations of animal cells, the guide RNA targets mouse Banf1 and comprises any one of the sequences set forth in SEQ ID NOS: 44-46 or the guide RNA targets human BANF1 and comprises any one of the sequences set forth in SEQ ID NOS: 27-30. In some such non-human animals, animal tissues, or populations of animal cells, the guide RNA targets mouse Ppp2ca and comprises any one of the sequences set forth in SEQ ID NOS: 47-49 or the guide RNA targets human PPP2CA and comprises any one of the sequences set forth in SEQ ID NOS: 31-32. In some such non-human animals, animal tissues, or populations of animal cells, the guide RNA targets mouse Ankle2 and comprises any one of the sequences set forth in SEQ ID NOS: 50-52 or the guide RNA targets human ANKLE2 and comprises the sequence set forth in SEQ ID NO: 38.

In some such non-human animals, animal tissues, or populations of animal cells, the one or more agents comprise a transcriptional repressor targeting BANF1, PPP2CA, or ANKLE2 or a nucleic acid encoding the transcriptional repressor. Optionally, the transcriptional repressor comprises a catalytically inactive Cas protein (e.g., Cas9 protein) fused to a transcriptional repressor domain, optionally wherein the transcriptional repressor domain is a Krüppel associated box (KRAB) domain. In some such non-human animals, animal tissues, or populations of animal cells, the guide RNA targets mouse Banf1 and comprises any one of the sequences set forth in SEQ ID NOS: 44-46 or the guide RNA targets human BANF1 and comprises any one of the sequences set forth in SEQ ID NOS: 27-30. In some such non-human animals, animal tissues, or populations of animal cells, the guide RNA targets mouse Ppp2ca and comprises any one of the sequences set forth in SEQ ID NOS: 47-49 or the guide RNA targets human PPP2CA and comprises any one of the sequences set forth in SEQ ID NOS: 31-32. In some such non-human animals, animal tissues, or populations of animal cells, the guide RNA targets mouse Ankle2 and comprises any one of the sequences set forth in SEQ ID NOS: 50-52 or the guide RNA targets human ANKLE2 and comprises the sequence set forth in SEQ ID NO: 38.

In some such non-human animals, animal tissues, or populations of animal cells, the one or more agents comprise an antisense oligonucleotide, an antisense RNA, a small interfering RNA (siRNA), or a short hairpin RNA (shRNA) targeting BANF1, PPP2CA, or ANKLE2. In some such non-human animals, animal tissues, or populations of animal cells, the one or more agents comprise an antisense oligonucleotide or an RNAi agent targeting BANF1, PPP2CA, or ANKLE2 or a nucleic acid encoding the antisense oligonucleotide or the RNAi agent. Optionally, the antisense oligonucleotide or RNAi agent comprises the sequence set forth in any one of SEQ ID NOS: 105-324 or a modified version thereof. Optionally, the antisense oligonucleotide or RNAi agent comprises the sequence set forth in any one of SEQ ID NOS: 105, 106, 110-113, 115, 120-122, 124, 125, 130, 133, 136, 137, 150, 152, 153, 155, 158-160, 162, 165, 166, 169, 171-173, 175, 177, 181-184, 187, 194, 197, 211, 213, 215, 216, 220-223, 225, 230-232, 234, 235, 240, 243, 246, 247, 260, 262, 263, 265, 268-270, 272, 275, 276, 279, 281-283, 285, 287, 291-294, 297, 304, 307, 321, and 323 or a modified version thereof. Optionally, the antisense oligonucleotide or RNAi agent comprises one or more phosphorothioate linkages and/or one or more 2'-methoxyethyl modified bases. Optionally, the antisense oligonucleotide is a 5-10-5 gapmer comprising a phosphorothioate backbone, a 5' wing of 2'-methoxyethyl modified bases, a central 10-nucleotide core of DNA, and a 3' wing of 2'-methoxyethyl modified bases.

In some such non-human animals, animal tissues, or populations of animal cells, at least one sign or symptom of tauopathy is increased in the non-human animal, the animal tissue, or the population of animal cells relative to a non-human animal, an animal tissue, or a population of animal cells that does not comprise the genetic modification in the one or more or all of BANF1, PPP2CA, and ANKLE2 or does not comprise the one or more agents that reduce expression of one or more or all of BANF1, PPP2CA, and ANKLE2. Optionally, the at least one sign or symptom comprises tau hyperphosphorylation or tau aggregation. Optionally, the at least one sign or symptom comprises tau hyperphosphorylation and tau aggregation. Optionally, the at least one sign of symptom comprises increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, decreased Ran GTPase-activating protein 1 (RanGAP1) nuclear-to-cytoplasmic ratio in neurons, or any combination thereof.

In some such populations of animal cells, the cells are in vivo. In some such populations of animal cells, the cells are in vitro. In some such populations of animal cells, the cells are human cells. In some such populations of animal cells, the cells are rodent cells, optionally wherein the rodent cells are mouse cells or rat cells. Optionally, the cells are mouse cells. In some such populations of animal cells, the cells comprise neuronal cells. Optionally, the neuronal cells comprise neurons derived from human induced pluripotent stem cells. Optionally, the neuronal cells comprise neurons derived from mouse embryonic stem cells. Optionally, the neuronal cells comprise primary mouse neurons.

In some such animal tissues, the tissue is in vivo. In some such animal tissues, the tissue is ex vivo. In some such animal tissues, the animal is a rodent, optionally wherein the rodent is a mouse or a rat. Optionally, the animal is the mouse. In some such animal tissues, the tissue is a nervous system tissue. Optionally, the tissue comprises a brain slice (e.g., an organotypic brain slice culture).

In some such non-human animals, the non-human animal is a rodent, optionally wherein the rodent is a mouse or a rat. Optionally, the non-human animal is the mouse. Optionally, the mouse is a PS19 transgenic mouse further comprising the genetic modification in the one or more or all of BANF1, PPP2CA, and ANKLE2 that reduces expression of the one or more or all of BANF1, PPP2CA, and ANKLE2, respectively, in the one or more cells and/or further comprising the one or more agents that reduce expression of one or more or all of BANF1, PPP2CA, and ANKLE2 in the one or more cells.

In another aspect, provided are methods for assessing a therapeutic candidate for the treatment of a tauopathy using any of the above non-human animals, animal tissues, and populations of animal cells. Some such methods comprise: (a) administering a candidate agent to any of the above non-human animals, animal tissues, and populations of animal cells; (b) performing one or more assays to determine if the candidate agent has an effect on one or more signs or symptoms associated with the tauopathy; and (c) identifying the candidate agent that has an effect on the one or more signs or symptoms associated with the tauopathy as a therapeutic candidate. In some such methods, the one or more signs or symptoms comprise tau hyperphosphorylation or tau aggregation. Optionally, the one or more signs or symptoms comprise tau hyperphosphorylation and tau aggregation. In some such methods, the one or more signs or symptoms comprise increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, decreased Ran GTPase-activating protein 1 (RanGAP1) nuclear-to-cytoplasmic ratio in neurons, or any combination thereof.

In some such methods, the candidate agent is administered to the non-human animal. In some such methods, the candidate agent is administered to the animal tissue ex vivo. In some such methods, the candidate agent is administered to the population of animal cells in vitro.

In another aspect, provided are methods of making any of the above non-human animals, animal tissues, and populations of animal cells. Some such methods comprise: (a) introducing the one or more agents that reduce expression of one or more or all of BANF1, PPP2CA, and ANKLE2 into a non-human animal, an animal tissue, or a population of animal cells that comprises the microtubule-associated protein tau coding sequence; and (b) screening the non-human animal, the animal tissue, or the population of animal cells to confirm the presence of the one or more agents. Some such methods comprise: (a) introducing the one or more agents that reduce expression of one or more or all of BANF1, PPP2CA, and ANKLE2 into a non-human animal, an animal tissue, or a population of animal cells that comprises the exogenous human microtubule-associated protein tau coding sequence; and (b) screening the non-human animal, the animal tissue, or the population of animal cells to confirm the presence of the one or more agents.

Some such methods comprise: (a) introducing into a non-human animal, an animal tissue, or a population of animal cells: (i) an exogenous human microtubule-associated protein tau coding sequence; and (ii) the one or more agents that reduce expression of one or more or all of BANF1, PPP2CA, and ANKLE2; and (b) screening the non-human animal, the animal tissue, or the population of animal cells to confirm the presence of the one or more agents and the exogenous human microtubule-associated protein tau coding sequence. Optionally, the exogenous human microtubule-associated protein tau coding sequence is delivered via adeno-associated virus, lentivirus, or lipid nanoparticle.

In some such methods, the one or more agents are delivered via adeno-associated virus, lentivirus, or lipid nanoparticle. In some such methods, the method is for making the non-human animal, and the one or more agents are administered to the non-human animal by intrathecal injection, intracranial injection, or intracerebroventricular injection. Optionally, the method is for making the non-human animal, and the one or more agents are administered to the non-human animal by stereotactic injection into the brain or a region of the brain (e.g., hippocampus). Optionally, the method is for making the non-human animal, and the one or more agents are administered to the non-human animal by stereotactic injection into the hippocampus.

In another aspect, provided are methods for accelerating or exacerbating tau aggregation in a tauopathy model non-human animal, a tauopathy model animal tissue, or a tauopathy model population of animal cells. Some such methods comprise introducing into the tauopathy model non-human animal, the tauopathy model animal tissue, or the tauopathy model population of animal cells one or more agents that reduce expression of one or more or all of BANF1, PPP2CA, and ANKLE2.

In some such methods, the tauopathy model non-human animal, the tauopathy model animal tissue, or the tauopathy model population of animal cells comprises an exogenous human microtubule-associated protein tau coding sequence. In some such methods, the exogenous human microtubule-associated protein tau coding sequence is genomically integrated. In some such methods, the exogenous human microtubule-associated protein tau coding sequence comprises a complementary DNA (cDNA) sequence. In some such methods, the exogenous human microtubule-associated protein tau coding sequence is codon-optimized for expression in the non-human animal, the animal tissue, or the population of animal cells.

In some such methods, the exogenous human microtubule-associated protein tau coding sequence is operably linked to a heterologous promoter. Optionally, the heterologous promoter is a mouse prion protein promoter. Optionally, the heterologous promoter is a neuron-specific promoter. Optionally, the neuron-specific promoter is a synapsin-1 promoter.

In some such methods, the exogenous human microtubule-associated protein tau comprises a tauopathy-associated mutation. In some such methods, the tauopathy-associated mutation comprises a P301S mutation. Optionally, the exogenous human microtubule-associated protein tau comprises the sequence set forth in SEQ ID NO: 98. In some such methods, the tauopathy-associated mutation comprises an A152T/P301L/S320F triple mutation. Optionally, the exogenous human microtubule-associated protein tau coding sequence comprises the sequence set forth in SEQ ID NO: 83 or the exogenous human microtubule-associated protein tau comprises the sequence set forth in SEQ ID NO: 84.

In some such methods, the one or more agents comprise a nuclease agent targeting BANF1, PPP2CA, or ANKLE2 or a nucleic acid encoding the nuclease agent. In some such methods, the nuclease agent is a Zinc Finger Nuclease (ZFN), a Transcription Activator-Like Effector Nuclease (TALEN), or a Clustered Regularly Interspaced Short Palindromic Repeats (CRISPR)-associated (Cas) protein and a guide RNA. Optionally, the nuclease agent is the Cas protein and the guide RNA. Optionally, the Cas protein is a Cas9 protein. Optionally, the Cas protein is a catalytically active Cas protein. Optionally, the Cas protein is a catalytically inactive Cas protein fused to a transcriptional repressor domain, optionally wherein the transcriptional repressor domain is a Krüppel associated box (KRAB) domain. In some such methods, the guide RNA targets mouse Banf1 and comprises any one of the sequences set forth in SEQ ID NOS: 44-46 or the guide RNA targets human BANF1 and comprises any one of the sequences set forth in SEQ ID NOS: 27-30. In some such methods, the guide RNA targets mouse Ppp2ca and comprises any one of the sequences set forth in SEQ ID NOS: 47-49 or the guide RNA targets human PPP2CA and comprises any one of the sequences set forth in SEQ ID NOS: 31-32. In some such methods, the guide RNA targets mouse Ankle2 and comprises any one of the sequences set forth in SEQ ID NOS: 50-52 or the guide RNA targets human ANKLE2 and comprises the sequence set forth in SEQ ID NO: 38.

In some such methods, the one or more agents comprise a transcriptional repressor targeting BANF1, PPP2CA, or ANKLE2 or a nucleic acid encoding the transcriptional repressor. Optionally, the transcriptional repressor comprises a catalytically inactive Cas protein (e.g., Cas9 protein) fused to a transcriptional repressor domain, optionally wherein the transcriptional repressor domain is a Krüppel associated box (KRAB) domain. In some such non-human animals, animal tissues, or populations of animal cells, the guide RNA targets mouse Banf1 and comprises any one of the sequences set forth in SEQ ID NOS: 44-46 or the guide RNA targets human BANF1 and comprises any one of the sequences set forth in SEQ ID NOS: 27-30. In some such non-human animals, animal tissues, or populations of animal cells, the guide RNA targets mouse Ppp2ca and comprises any one of the sequences set forth in SEQ ID NOS: 47-49 or the guide RNA targets human PPP2CA and comprises any one of the sequences set forth in SEQ ID NOS: 31-32. In some such non-human animals, animal tissues, or populations of animal cells, the guide RNA targets mouse Ankle2 and comprises any one of the sequences set forth in SEQ ID NOS: 50-52 or the guide RNA targets human ANKLE2 and comprises the sequence set forth in SEQ ID NO: 38.

In some such methods, the one or more agents comprise an antisense oligonucleotide, an antisense RNA, a small interfering RNA (siRNA), or a short hairpin RNA (shRNA) targeting BANF1, PPP2CA, or ANKLE2. In some such methods, the one or more agents comprise an antisense oligonucleotide or an RNAi agent targeting BANF1, PPP2CA, or ANKLE2 or a nucleic acid encoding the antisense oligonucleotide or the RNAi agent. Optionally, the antisense oligonucleotide or RNAi agent comprises the sequence set forth in any one of SEQ ID NOS: 105-324 or a modified version thereof. Optionally, the antisense oligonucleotide or RNAi agent comprises the sequence set forth in any one of SEQ ID NOS: 105, 106, 110-113, 115, 120-122, 124, 125, 130, 133, 136, 137, 150, 152, 153, 155, 158-160, 162, 165, 166, 169, 171-173, 175, 177, 181-184, 187, 194, 197, 211, 213, 215, 216, 220-223, 225, 230-232, 234, 235, 240, 243, 246, 247, 260, 262, 263, 265, 268-270, 272, 275, 276, 279, 281-283, 285, 287, 291-294, 297, 304, 307, 321, and 323 or a modified version thereof. Optionally, the antisense oligonucleotide or RNAi agent comprises one or more phosphorothioate linkages and/or one or more 2'-methoxyethyl modified bases. Optionally, the antisense oligonucleotide is a 5-10-5 gapmer comprising a phosphorothioate backbone, a 5' wing of 2'-methoxyethyl modified bases, a central 10-nucleotide core of DNA, and a 3' wing of 2'-methoxyethyl modified bases.

In some such methods, the one or more agents are delivered via adeno-associated virus, lentivirus, or lipid nanoparticle. In some such methods, the one or more agents are administered to the non-human animal by intrathecal injection, intracranial injection, or intracerebroventricular injection, optionally wherein the one or more agents are administered to the non-human animal by stereotactic injection into the brain or a region of the brain (e.g., hippocampus), and optionally wherein the one or more agents are administered to the non-human animal by stereotactic injection into the hippocampus.

In some such methods, at least one sign or symptom of tauopathy is increased in the non-human animal, the animal tissue, or the population of animal cells relative to a non-human animal, an animal tissue, or a population of animal cells that does not comprise the one or more agents that reduce expression of one or more or all of BANF1, PPP2CA, and ANKLE2. Optionally, the at least one sign or symptom comprises tau hyperphosphorylation or tau aggregation. Optionally, the at least one sign or symptom comprises tau hyperphosphorylation and tau aggregation. Optionally, the at least one sign or symptom comprises increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, decreased Ran GTPase-activating protein 1 (RanGAP1) nuclear-to-cytoplasmic ratio in neurons, or any combination thereof.

In some such methods, the cells are in vivo. In some such methods, the cells are in vitro. In some such methods, the cells are human cells. In some such methods, the cells are rodent cells, optionally wherein the rodent cells are mouse cells or rat cells. Optionally, the cells are mouse cells. In some such methods, the cells comprise neuronal cells. Optionally, the neuronal cells comprise neurons derived from human induced pluripotent stem cells. Optionally, the neuronal cells comprise neurons derived from mouse embryonic stem cells. Optionally, the neuronal cells comprise primary mouse neurons.

In some such methods, the tissue is in vivo. In some such methods, the tissue is ex vivo. In some such methods, the animal tissue is a rodent tissue, optionally wherein the rodent is a mouse or a rat. Optionally, the animal tissue is a mouse tissue. In some such methods, the tissue is a nervous system tissue. Optionally, the tissue comprises a brain slice (e.g., an organotypic brain slice culture).

In some such methods, the non-human animal is a rodent, optionally wherein the rodent is a mouse or a rat. Optionally, the non-human animal is the mouse. Optionally, the mouse is a PS19 transgenic mouse further comprising the one or more agents that reduce expression of one or more or all of BANF1, PPP2CA, and ANKLE2.

In another aspect, provided is a non-human animal genome comprising an exogenous human microtubule-associated protein tau coding sequence and a genetic modification in one or more or all of Banf1, Ppp2ca, and Ankle2 that reduces expression of the one or more or all of Banf1, Ppp2ca, and Ankle2, respectively.

In another aspect, provided is an agent that reduces or inhibits expression of BANF1, PPP2CA, or Ankle2 in a cell or a nucleic acid encoding the agent, optionally wherein the agent is a nuclease agent or an antisense oligonucleotide, an antisense RNA, a small interfering RNA (siRNA), or a short hairpin RNA (shRNA) targeting BANF1, PPP2CA, or ANKLE2. Optionally, the agent is a nuclease agent or an antisense oligonucleotide or an RNAi agent targeting BANF1, PPP2CA, or ANKLE2. Optionally, the antisense oligonucleotide or RNAi agent comprises the sequence set forth in any one of SEQ ID NOS: 105-324 or a modified version thereof. Optionally, the antisense oligonucleotide or RNAi agent comprises the sequence set forth in any one of SEQ ID NOS: 105, 106, 110-113, 115, 120-122, 124, 125, 130, 133, 136, 137, 150, 152, 153, 155, 158-160, 162, 165, 166, 169, 171-173, 175, 177, 181-184, 187, 194, 197, 211, 213, 215, 216, 220-223, 225, 230-232, 234, 235, 240, 243, 246, 247, 260, 262, 263, 265, 268-270, 272, 275, 276, 279, 281-283, 285, 287, 291-294, 297, 304, 307, 321, and 323 or a modified version thereof. Optionally, the antisense oligonucleotide or RNAi agent comprises one or more phosphorothioate linkages and/or one or more 2'-methoxyethyl modified bases. Optionally, the antisense oligonucleotide is a 5-10-5 gapmer comprising a phosphorothioate backbone, a 5' wing of 2'-methoxyethyl modified bases, a central 10-nucleotide core of DNA, and a 3' wing of 2'-methoxyethyl modified bases.

BRIEF DESCRIPTION OF THE FIGURES

FIG. 32A shows the count of DAPI+ nuclei in non-targeted mouse primary cortical neurons and in ΔBANF1 and ΔANKLE2 mutant cortical neurons. FIG. 32B shows MAP2 intensity in the soma as measured by fluorescence intensity in non-targeted mouse primary cortical neurons and in ΔBANF1 and ΔANKLE2 mutant cortical neurons. FIG. 32C shows total tau intensity in the soma as measured by fluorescence intensity in non-targeted mouse primary cortical neurons and in ΔBANF1 and ΔANKLE2 mutant cortical neurons. Two-tailed unpaired Student's t test was used (ns=not significant; error bar represents s.e.m.).

FIG. 33A shows the count of nuclei in non-targeted mouse primary cortical neurons and in ΔBANF1 and ΔANKLE2 and ΔPPP2CA mutant cortical neurons. FIG. 33B shows MAP2 intensity in the soma as measured by fluorescence intensity in non-targeted mouse primary cortical neurons and in ΔBANF1 and ΔANKLE2 and ΔPPP2CA mutant cortical neurons. FIG. 33C shows phospho-tau AT8 (S202, T205) intensity in the soma as measured by fluorescence intensity in non-targeted mouse primary cortical neurons and in ΔBANF1 and ΔANKLE2 and ΔPPP2CA mutant cortical neurons. FIG. 33D shows phospho-tau AT8 (S202, T205) intensity in the perinuclear domain as measured by fluorescence intensity in non-targeted mouse primary cortical neurons and in ΔBANF1 and ΔANKLE2 and ΔPPP2CA mutant cortical neurons. FIG. 33E shows total tau intensity in the soma as measured by fluorescence intensity in non-targeted mouse primary cortical neurons and in ΔBANF1 and ΔANKLE2 and ΔPPP2CA mutant cortical neurons.

FIG. 34A shows the count of DAPI+ nuclei in non-targeted mouse primary cortical neurons and in ΔBANF1 and ΔANKLE2 mutant cortical neurons. FIG. 34B shows the Nup98 nuclear/cytoplasmic ratio in non-targeted mouse primary cortical neurons and in ΔBANF1 and ΔANKLE2 mutant cortical neurons. FIG. 34C shows phospho-Tau S356 intensity in the soma (as measured by fluorescence intensity) in non-targeted mouse primary cortical neurons and in ΔBANF1 and ΔANKLE2 mutant cortical neurons. FIG. 34D shows perinuclear phospho-Tau S356 intensity (as measured by fluorescence intensity) in non-targeted mouse primary cortical neurons and in ΔBANF1 and ΔANKLE2 mutant cortical neurons. Two-tailed unpaired Student's t test was used (*=p<0.05; error bar represents s.e.m.).

FIG. 36A shows the count of DAPI+ nuclei in non-targeted mouse primary cortical neurons and in ΔBANF1 and ΔANKLE2 mutant cortical neurons when tau-cDNA 3MUT was added. FIG. 36B shows phospho-Tau S356 intensity in the soma (as measured by fluorescence intensity) in non-targeted mouse primary cortical neurons and in ΔBANF1 and ΔANKLE2 mutant cortical neurons when tau-cDNA 3MUT was added. FIG. 36C shows perinuclear phospho-Tau S356 intensity (as measured by fluorescence intensity) in non-targeted mouse primary cortical neurons and in ΔBANF1 and ΔANKLE2 mutant cortical neurons when tau-cDNA 3MUT was added. FIG. 36D shows MAP2 intensity in the soma (as measured by fluorescence intensity) in non-targeted mouse primary cortical neurons and in ΔBANF1 and ΔANKLE2 mutant cortical neurons when tau-cDNA 3MUT was added. Two-tailed unpaired Student's t test was used (*=p<0.05, **=p<0.002—ns, not significant; error bar represents s.e.m.).

FIG. 38A shows the count of DAPI+ nuclei in non-targeted mouse primary cortical neurons and in ΔBANF1 and ΔPPP2CA mutant cortical neurons. FIG. 38B shows phospho-tau (S356) intensity in the perinuclear domain as measured by fluorescence intensity in non-targeted mouse primary cortical neurons and in ΔBANF1 and ΔPPP2CA mutant cortical neurons. FIG. 38C shows correlation of phospho-tau (S356) intensity with an increased detection of misfolded tau in the soma in ΔPPP2CA mutant cortical neurons. FIG. 38D shows phospho-tau (S356) intensity in the cell as measured by fluorescence intensity in non-targeted mouse primary cortical neurons and in ΔBANF1 and ΔPPP2CA mutant cortical neurons. FIG. 38E Aggresome Detection Reagent (ADR) intensity in the cell in non-targeted mouse primary cortical neurons and in ΔBANF1 and ΔPPP2CA mutant cortical neurons. FIG. 38F shows correlation of phospho-tau (S356) intensity with an increased detection of misfolded tau in the soma in ΔBANF1 mutant cortical neurons. Two-tailed unpaired Student's t test was used (*=p<0.05; =p<0.02; *=p<0.004; error bar represents s.e.m.; Pearson correlation (ρ)—R squared—Two-tailed P value<0.05).

FIG. 39A shows the count of DAPI+ nuclei in non-targeted mouse primary cortical neurons and in ΔBANF1 and ΔPPP2CA mutant cortical neurons. FIG. 39B shows phospho-tau AT8 (S202, T205) intensity in the perinuclear domain as measured by fluorescence intensity in non-targeted mouse primary cortical neurons and in ΔBANF1 and ΔPPP2CA mutant cortical neurons. FIG. 39C shows correlation of phospho-tau AT8 (S202, T205) intensity with an increased detection of misfolded tau in the soma in ΔPPP2CA mutant cortical neurons. FIG. 39D shows phospho-tau AT8 (S202, T205) intensity in the soma as measured by fluorescence intensity in non-targeted mouse primary cortical neurons and in ΔBANF1 and ΔPPP2CA mutant cortical neurons. FIG. 39E Aggresome Detection Reagent (ADR) intensity in the soma in non-targeted mouse primary cortical neurons and in ΔBANF1 and ΔPPP2CA mutant cortical neurons. FIG. 39F shows correlation of phospho-tau AT8 (S202, T205) intensity with an increased detection of misfolded tau in the soma in ΔBANF1 mutant cortical neurons. Two-tailed unpaired Student's t test was used (*=p<0.05; =p<0.02; *=p<0.004; ns=not significant; error bar represents s.e.m.; Pearson correlation (ρ)—R squared—Two-tailed P value<0.05).

FIG. 41A shows results from a primary screen carried out at 100 nM ASO concentration (two replicates; upper dashed line indicates 75% knockdown);

FIG. 41B shows results from a secondary screen carried out at 50 nM ASO concentration (two replicates; lowest dashed line indicates 75% knockdown), and FIG. 41C shows results from a secondary screen carried out at 5 nM ASO concentration (two replicates; middle dashed line indicates 25% knockdown).

FIG. 42A shows results from a primary screen carried out at 100 nM ASO concentration (dotted line indicates 75% knockdown), FIG. 42B shows results from a secondary screen carried out at 50 nM ASO concentration (three replicates; lower dotted line indicates 75% knockdown), and FIG. 42C shows results from a secondary screen carried out at 5 nM ASO concentration (three replicates; lower dotted line indicates 40% knockdown).

DEFINITIONS

Figure 1:
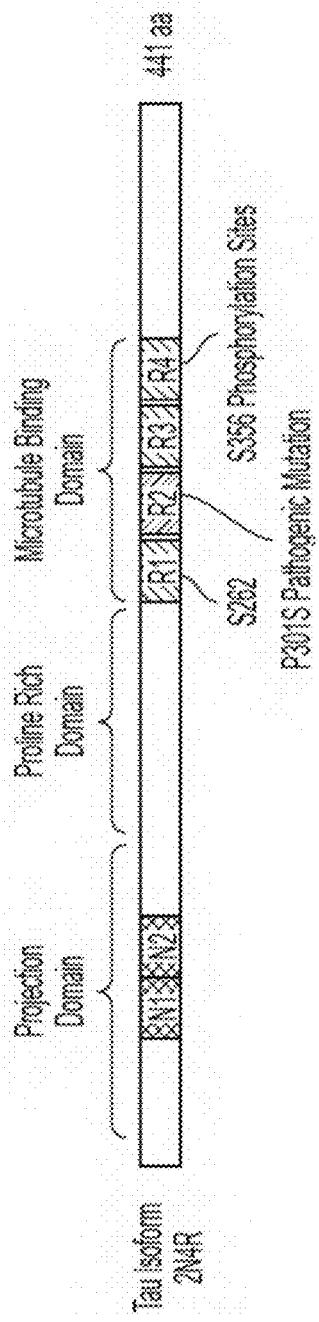
FIG. 1 (not to scale) shows a schematic of tau isoform 2N4R. The tau biosensor lines include only tau4RD-YFP and tau4RD-CFP as transgenes, not the full 2N4R.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells in vitro, ex vivo, or in vivo. Numerous forms of viral vectors are known.

The term "isolated" with respect to cells, tissues (e.g., brain slices), proteins, and nucleic acids includes cells, tissues (e.g., brain slices), proteins, and nucleic acids that are relatively purified with respect to other bacterial, viral, cellular, or other components that may normally be present in situ, up to and including a substantially pure preparation of the cells, tissues (e.g., brain slices), proteins, and nucleic acids. The term "isolated" also includes cells, tissues (e.g., brain slices), proteins, and nucleic acids that have no naturally occurring counterpart, have been chemically synthesized and are thus substantially uncontaminated by other cells, tissues (e.g., brain slices), proteins, and nucleic acids, or has been separated or purified from most other components (e.g., cellular components) with which they are naturally accompanied (e.g., other cellular proteins, polynucleotides, or cellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or organism. For example, an endogenous MAPT sequence of a cell or organism refers to a native MAPT sequence that naturally occurs at the MAPT locus in the cell or organism.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome or in a different location in a chromosome or in a different chromosome, such as a human tau transgene randomly inserted into a genomic locus other than the endogenous MAPT locus). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a tau protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Res.* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "MAPT locus" may refer to the specific location of a MAPT gene, MAPT DNA sequence, microtubule-associated-protein-tau-encoding sequence, or MAPT position on a chromosome of the genome of an organism that has been identified as to where such a sequence resides. A "MAPT locus" may comprise a regulatory element of a MAPT gene, including, for example, an enhancer, a promoter, 5' and/or 3' untranslated region (UTR), or a combination thereof.

The term "gene" refers to DNA sequences in a chromosome that may contain, if naturally present, at least one coding and at least one non-coding region. The DNA sequence in a chromosome that codes for a product (e.g., but not limited to, an RNA product and/or a polypeptide product) can include the coding region interrupted with non-coding introns and sequence located adjacent to the coding region on both the 5' and 3' ends such that the gene corresponds to the full-length mRNA (including the 5' and 3' untranslated sequences). Additionally, other non-coding sequences including regulatory sequences (e.g., but not limited to, promoters, enhancers, and transcription factor binding sites), polyadenylation signals, internal ribosome entry sites, silencers, insulating sequence, and matrix attachment regions may be present in a gene. These sequences may be close to the coding region of the gene (e.g., but not limited to, within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a human cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter, such as a neuron-specific promoter like the synapsin-1 promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

The term "variant" refers to a nucleotide sequence differing from the sequence most prevalent in a population (e.g., by one nucleotide) or a protein sequence different from the sequence most prevalent in a population (e.g., by one amino acid).

The term "fragment," when referring to a protein, means a protein that is shorter or has fewer amino acids than the full-length protein. The term "fragment," when referring to a nucleic acid, means a nucleic acid that is shorter or has fewer nucleotides than the full-length nucleic acid. A fragment can be, for example, when referring to a protein fragment, an N-terminal fragment (i.e., removal of a portion of the C-terminal end of the protein), a C-terminal fragment (i.e., removal of a portion of the N-terminal end of the protein), or an internal fragment (i.e., removal of a portion of each of the N-terminal and C-terminal ends of the protein). A fragment can be, for example, when referring to a nucleic acid fragment, a 5' fragment (i.e., removal of a portion of the 3' end of the nucleic acid), a 3' fragment (i.e., removal of a portion of the 5' end of the nucleic acid), or an internal fragment (i.e., removal of a portion each of the 5' and 3' ends of the nucleic acid).

"Sequence identity" or "identity" in the context of two polynucleotides or polypeptide sequences refers to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLO- SUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

TABLE 1

Amino Acid Categorizations.

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube or an isolated cell or cell line). The term "in vivo" includes natural environments (e.g., a cell or organism or body) and to processes or reactions that occur within a natural environment. The term "ex vivo" includes cells or tissues (e.g., brain slice cultures such as organotypic brain slice cultures) that have been removed from the body of an individual and processes or reactions that occur within such cells.

The term "reporter gene" refers to a nucleic acid having a sequence encoding a gene product (typically an enzyme) that is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include, but are not limited, to genes encoding beta-galactosidase (lacZ), the bacterial chloramphenicol acetyl-transferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreenl), yellow fluorescent proteins (e.g., YFP, eYFP, Citrine, Venus, YPet, PhiYFP, and ZsYellowl), blue fluorescent proteins (e.g., BFP, eBFP, eBFP2, Azurite, mKalamal, GFPuv, Sapphire, and T-sapphire), cyan fluorescent proteins (e.g., CFP, eCFP, Cerulean, CyPet, AmCyanl, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which the event or circumstance does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means p≤0.05.

DETAILED DESCRIPTION

I. Overview

Tauopathies are a group of heterogeneous neurodegenerative conditions characterized by the deposition of abnormal tau protein in the brain. In the brains of individuals with Alzheimer's disease, for example, tau is abnormally hyperphosphorylated and appears fibrillized into paired helical filaments (PHFs), which manifest as neurofibrillary tangles (NFTs). The intracellular aggregation of hyperphosphorylated tau in NFTs is therefore a neuropathological hallmark of tauopathy.

We conducted a genome-wide screen to identify modifier genes that promote tau aggregation when disrupted. High-confidence hits emerged for two genes, BANF1 and PPP2CA, that contribute to the processes that maintain nuclear envelope integrity. From an examination of other proteins that participate in this biological process, we identified one additional gene, ANKLE2, that also enhanced tau aggregation when disrupted.

Barrier-to-autointegration factor (BANF1/BAF) connects chromatin to the nuclear envelope, and serine/threonine-protein phosphatase 2A catalytic subunit alpha isoform (PPP2CA) regulates BANF1 function. BANF1 is a small (10 kDa), abundant, highly conserved DNA binding protein. BANF1 is involved in multiple pathways including mitosis, nuclear assembly, viral infection, chromatin and gene regulation, and the DNA damage response. BANF1 connects chromatin to the nuclear envelope and binds to DNA in a sequence-independent manner. BANF1 also binds to one LEM (LAP2/Emerin/MAN1) domain of the inner nuclear membrane (INM) proteins. The localization of BANF1 changes during the cell cycle.

During mitosis, the breakdown and re-assembly of the nuclear envelope are controlled by protein phosphorylation. Phosphorylation of BANF1 by VRK1 upon entry into mitosis breaks the link between chromatin, BANF1, and LEM proteins. BANF1 is distributed uniformly throughout the cell. Upon nuclear envelope reformation, ankyrin repeat and LEM domain-containing protein 2 (ANKLE2) inhibits VRK1 enzymatic activity. ANKLE2 also binds to PPP2CA and promotes its activity to dephosphorylate BANF1 so it can re-associate with LEM proteins, chromatin and the nuclear envelope. PPP2CA is the main tau phosphatase. PPP2CA can bind tau-4RD and has been linked to Alzheimer's disease.

Here we reveal new models of tau aggregation for ex vivo and in vivo studies of tauopathy. These new models, for example, can combine mutations in or decreased/inhibition of expression of BANF1 and/or PPP2CA and/or ANKLE2 with existing models of tauopathy. Disclosed herein are improved tauopathy models (e.g., non-human animals, animal tissues, or animal cells), methods of using such improved tauopathy models for assessing therapeutic candidates for the treatment of a tauopathy, methods of making the improved tauopathy models, and methods of accelerating or exacerbating tau aggregation in a tauopathy model.

II. Improved Tauopathy Models

Disclosed herein are tauopathy models comprising gene alterations or decreased/inhibited expression of BANF1, PPP2CA, or ANKLE2 in order to accelerate the formation of tau aggregates in cells and animals. Such tauopathy models can comprise, for example, genomes, cells, tissues, or animals comprising a microtubule-associated protein tau coding sequence and gene alterations or decreased/inhibited expression of BANF1, PPP2CA, or ANKLE2 to accelerate the formation of tau aggregates in cells and animals, allowing the development of better in vitro, ex vivo, and in vivo models of tauopathy. As a specific example, the animal (e.g., non-human animal), animal tissue (e.g., non-human animal tissue), or animal cell or population of animal cells (e.g., non-human animal cell or cells) can comprise (a) a microtubule-associated protein tau coding sequence in one or more cells, and (b)(i) a genetic modification in one or more or all of BANF1, PPP2CA, and ANKLE2 that reduces expression of the one or more or all of BANF1, PPP2CA, and ANKLE2, respectively, in the one or more cells and/or (ii) one or more agents that reduce expression of one or more or all of BANF1, PPP2CA, and ANKLE2 in the one or more cells. The one or more cells can be any type of cell. In one example, they are neuronal cells.

The animal, tissue, or population of cells can have at least one sign or symptom of tauopathy that is increased relative to an animal, tissue, or population of cells that does not comprise the genetic modification in the one or more or all of BANF1, PPP2CA, and ANKLE2 or does not comprise the one or more agents that reduce expression of one or more or all of BANF1, PPP2CA, and ANKLE2. Such signs and symptoms are discussed in more detail elsewhere herein and can include, for example, tau hyperphosphorylation and tau aggregation. Other signs and symptoms can include, for example, increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, or decreased Ran GTPase-activating protein 1 (RanGAP1) nuclear-to-cytoplasmic ratio in neurons. The phospho-tau can be, for example, phospho-tau (S356) or phospho-tau AT8 (S202, T205).

The microtubule-associated protein tau coding sequence is one that is expressed in the one or more cells. The tau coding sequence can be endogenous or exogenous, and it can encode a wild type tau protein or a tau protein comprising a mutation (e.g., comprising a tauopathy-associated mutation or tau pathogenic mutation). The tau coding sequence can encode a human microtubule-associated protein tau, such as an exogenous human microtubule-associated protein tau. The coding sequence can comprise both coding and non-coding sequences (e.g., exons and introns), or it can comprise a complementary DNA (cDNA) sequence. The coding sequence can optionally be codon-optimized for expression in the animal, tissue, or cell(s) (e.g., codon-optimized for expression in human or mouse cells).

The tau coding sequence can be genomically integrated or can be extrachromosomal. If genomically integrated, the coding sequence can be randomly integrated in the genome (transgenic) or it can be integrated in a targeted manner into a targeted genomic locus. The coding sequence can be present or genomically integrated in all of the cells in the animal, tissue, or population of cells, or it can be present or genomically integrated in a portion of the cells (e.g., neurons). An animal comprising the genomically integrated sequence can comprise the genomically integrated sequence in its germline.

The tau coding sequence can be operably linked to a promoter, such as a heterologous promoter. The promoter can be endogenous in the cell, tissue, or animal, or it can be exogenous. As one specific example, the promoter can be a prion protein promoter such as a mouse prion protein promoter. As another example, the promoter can be a neuron-specific promoter. Examples of neuron-specific promoters are well-known and include, for example, a synapsin-1 promoter (e.g., a human synapsin-1 promoter or a mouse synapsin-1 promoter).

The microtubule-associated protein tau can be any tau isoform. In one specific example, the tau coding sequence encodes the 1N4R isoform. The microtubule-associated protein tau can be a wild type tau protein or it can comprise one or mutations such as a tauopathy-associated mutation or tau pathogenic mutation. Examples of such mutations are well-known and are discussed in more detail elsewhere herein. In one specific example, the tau comprises a P301S mutation (optionally wherein the tau coding sequence is operably linked to a mouse prion protein promoter). In another specific example, the tau comprises an A152T/P301L/S320F triple mutation (optionally wherein the tau coding sequence is operably linked to a synapsin-1 promoter). DNA and protein sequences for the 3MUT Tau 1N4R (A152T, P301L, S320F) are set forth in SEQ ID NOS: 83 and 84, respectively.

Examples of agents that can reduce expression of BANF1, PPP2CA, or ANKLE2 include nuclease agents (e.g., ZFNs, TALENs, or CRISPR/Cas), DNA-binding proteins fused to transcriptional repressor (e.g., transcriptional repressors such as a catalytically inactive Cas fused to KRAB (dCas-KRAB)), or antisense oligonucleotides, siRNAs, shRNAs, or antisense RNAs. Examples of these are discussed in more detail elsewhere herein.

BANF1 (also called BAF, BCRG1, BCRP1, and L2BP1) encodes barrier-to-autointegration factor (also called breakpoint cluster region protein 1 and LAP2-binding protein 1). It plays fundamental roles in nuclear assembly, chromatin organization, gene expression, and gonad development, and it may potently compress chromatin structure and be involved in membrane recruitment and chromatin decondensation during nuclear assembly. Exemplary human barrier-to-autointegration factor proteins are assigned Accession Numbers NP_001137457.1 and NP_003851.1 (NCBI) and O75531 (UniProt). Exemplary human BANF1 mRNAs are designated by NCBI Accession Numbers NM_001143985.1 and NM_003860.3. An exemplary human BANF1 coding sequence is designated by CCDS ID CCDS8125.1. An exemplary human BANF1 gene is designated by NCBI RefSeq GeneID 8815. Exemplary mouse barrier-to-autointegration factor proteins are assigned Accession Numbers NP_001033320.1, NP_001273537.1, and NP_035923.1 (NCBI) and O54962 (UniProt). Exemplary mouse Banf1 mRNAs are designated by NCBI Accession Numbers NM_001038231.2, NM_001286608.1, and NM_011793.3. An exemplary mouse Banf1 coding sequence is designated by CCDS ID CCDS29458.1. An exemplary mouse Banf1 gene is designated by NCBI RefSeq GeneID 23825. Exemplary rat barrier-to-autointegration factor proteins are assigned Accession Numbers NP_446083.1 (NCBI) and Q9R1T1 (UniProt). An exemplary rat Banf1 mRNA is designated by NCBI Accession Number NM_053631.3. An exemplary rat Banf1 gene is designated by NCBI RefSeq GeneID 114087.

PPP2CA encodes serine/threonine-protein phosphatase 2A catalytic subunit alpha isoform (also called PP2A-alpha, replication protein C, RP-C, protein phosphatase 2, protein phosphatase 2A, or PP2A). PP2A is the major phosphatase for microtubule-associated proteins (MAPs). PP2A can modulate the activity of phosphorylase B kinase casein kinase 2, mitogen-stimulated S6 kinase, and MAP-2 kinase. Exemplary human serine/threonine-protein phosphatase 2A catalytic subunit alpha isoform proteins are assigned Accession Numbers NP_002706.1 (NCBI) and P67775 (UniProt). An exemplary human PPP2CA mRNA is designated by NCBI Accession Number NM_002715.2. An exemplary human PPP2CA coding sequence is designated by CCDS ID CCDS4173.1. An exemplary human PPP2CA gene is designated by NCBI RefSeq GeneID 5515. Exemplary mouse serine/threonine-protein phosphatase 2A catalytic subunit alpha isoform proteins are assigned Accession Numbers NP_062284.1 (NCBI) and P63330 (UniProt). An exemplary mouse Ppp2ca mRNA is designated by NCBI Accession Number NM_019411.4. An exemplary mouse Ppp2ca coding sequence is designated by CCDS ID CCDS24666.1. An exemplary mouse Ppp2ca gene is designated by NCBI RefSeq GeneID 19052. Exemplary rat serine/threonine-protein phosphatase 2A catalytic subunit alpha isoformproteins are assigned Accession Numbers NP_058735.1 (NCBI) and P63331 (UniProt). An exemplary rat Ppp2ca mRNA is designated by NCBI Accession Number NM_017039.2. Exemplary rat Ppp2ca genes are designated by NCBI RefSeq GeneIDs 24672 and 103694903.

ANKLE2 (also called KIAA0692, LEM4, and D5Ertd585e) encodes ankyrin repeat and LEM domain-containing protein 2 (also called LEM domain-containing protein 4 and liver regeneration-related protein LRRG057). It is involved in mitotic nuclear envelope reassembly by promoting dephosphorylation of BAF/BANF1 during mitotic exit. It coordinates the control of BAF/BANF1 dephosphorylation by inhibiting VRK1 kinase and promoting dephosphorylation of BAF/BANF1 by protein phosphatase 2A (PP2A), thereby facilitating nuclear envelope assembly. Exemplary human ankyrin repeat and LEM domain-containing protein 2 proteins are assigned Accession Numbers NP_055929.1 (NCBI) and Q86XL3 (UniProt). An exemplary human ANKLE2 mRNA is designated by NCBI Accession Number NM_015114.2. An exemplary human ANKLE2 coding sequence is designated by CCDS ID CCDS41869.1. An exemplary human ANKLE2 gene is designated by NCBI RefSeq GeneID 23141. Exemplary mouse ankyrin repeat and LEM domain-containing protein 2 proteins are assigned Accession Numbers NP_001240743.1 and NP_082198.1 (NCBI) and Q6P1H6 (UniProt). Exemplary mouse Ankle2 mRNAs are designated by NCBI Accession Numbers NM_001253814.1 and NM_027922.2. Exemplary mouse Ankle2 coding sequences are designated by CCDS IDs CCDS57372.1 and CCDS80360.1. An exemplary mouse Ankle2 gene is designated by NCBI RefSeq GeneID 71782. Exemplary rat ankyrin repeat and LEM domain-containing protein 2 proteins are assigned Accession Numbers NP_001041366.1 (NCBI) and Q7TP65 (UniProt). An exemplary rat Ankle2 mRNA is designated by NCBI Accession Number NM_001047901.1. An exemplary rat Ankle2 gene is designated by NCBI RefSeq GeneID 360829.

Various models of tauopathy have been developed. Any of these models can be adapted as disclosed herein by mutating or inhibiting/reducing expression of BANF1 and/or PPP2CA and/or ANKLE2. These include cellular/cell culture models (non-neuronal cell lines, neuronal cell lines such as PC12, SY5Y, and CN1.4 cells, or primary neuronal cells), tissue models (e.g., brain slice cultures such as organotypic brain slice cultures), and whole animal transgenic models (e.g., *C. elegans, Drosophila*, zebrafish, or mouse). See, e.g., Hall et al. (2005) *Biochim. Biophys. Acta* 1739:224-239, Brandt et al. (2005) *Biochim. Biophys. Acta* 1739:331-354, and Lee et al. (2005) *Biochim. Biophys. Acta* 1739:251-259, each of which is herein incorporated by reference in its entirety for all purposes. Typically such models are transgenic models in which wild type or mutant human tau isoforms are overexpressed under the control of a variety of promoters to produce neurofibrillary pathology. The cell-based models have the advantage of greater accessibility to manipulation and flexibility, whereas the whole animal models (e.g., transgenic mouse models) are more complete and more directly relevant to human disease.

The animal, tissue, or population of cells can be male or female. The population of cells can be in vitro, ex vivo, or in vivo. Likewise, the tissue can be ex vivo or in vivo. In one specific example, the tissue can be a brain slice (e.g., a brain slice culture such as an organotypic brain slice culture).

The population of cells can be any type of cells. The cells can be a monoclonal cell line or population of cells. The cells can be from any source. Such cells can be from a model organism such as *C. elegans, Drosophila*, or zebrafish. Such cells can be fish cells or bird cells, or such cells can be mammalian cells, such as human cells, non-human mammalian cells, rodent cells, mouse cells, or rat cells. Mammals include, for example, humans, non-human primates, monkeys, apes, cats, dogs, horses, bulls, deer, bison, sheep, rodents (e.g., mice, rats, hamsters, guinea pigs), livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. In a specific example, the cells are human cells (e.g., HEK293T cells or neuronal cells) or are mouse cells (e.g., neuronal cells).

A cell can be, for example, a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

A cell can also be a primary somatic cell, or a cell that is not a primary somatic cell. Somatic cells can include any cell that is not a gamete, germ cell, gametocyte, or undifferentiated stem cell. The cell can also be a primary cell. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, neurons. For example, primary cells can be derived from nervous system tissues (e.g., primary neurons such as primary mouse neurons).

Such cells also include would normally not proliferate indefinitely but, due to mutation or alteration, have evaded normal cellular senescence and instead can keep undergoing division. Such mutations or alterations can occur naturally or be intentionally induced. Examples of immortalized cells include Chinese hamster ovary (CHO) cells, human embryonic kidney cells (e.g., HEK293T cells), and mouse embryonic fibroblast cells (e.g., 3T3 cells). Numerous types of immortalized cells are well known. Immortalized or primary cells include cells that are typically used for culturing or for expressing recombinant genes or proteins. Examples of neuronal cell lines include rat PC12 pheochromocytoma cells, human SH-SY5Y neuroblastoma cells, human N-Tera 2 (NTERA-2 or NT2) teratocarcinoma cells, H4 human neuroglioma cells, human neuronal BE(2)-M17D cells, C1.4 mouse cortical neurons, or HCN2A human cortical neurons.

The cell can also be a differentiated cell, such as a neuronal cell (e.g., a human neuronal cell). Such neuronal cells can be primary neuronal cells (e.g., mouse primary neuronal cells), neurons derived from induced pluripotent stem (iPS) cells such as human iPS cells, or neurons derived from embryonic stem (ES) cells (e.g., mouse ES cells). For example, the cells can be iCELL GABA neurons, which are a highly pure population of human neurons derived from iPS cells. They are a mixture of post-mitotic neural subtypes, comprised primarily of GABAergic neurons, with typical physiological characteristics and responses.

Non-human animals as described herein can be made by the methods described elsewhere herein. The term "animal" includes any member of the animal kingdom, including, for example, mammals, fishes, reptiles, amphibians, birds, and worms. The animal can be, for example, *Drosophila, C. elegans*, or zebrafish. In a specific example, the non-human animal is a non-human mammal. Non-human mammals include, for example, non-human primates, monkeys, apes, orangutans, cats, dogs, horses, bulls, deer, bison, sheep, rabbits, rodents (e.g., mice, rats, hamsters, and guinea pigs), and livestock (e.g., bovine species such as cows and steer; ovine species such as sheep and goats; and porcine species such as pigs and boars). Birds include, for example, chickens, turkeys, ostrich, geese, and ducks. Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, and 129T2.

See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

In one specific example, the mouse strain is a PS19 (Tau P301S (Line PS19); PS19Tg; B6; C3-Tg(Prnp-MAPT*P301S)PS19Vle/J) line. The genetic background of this strain is C57BL/6×C3H. PS19 transgenic mice express mutant human microtubule-associated protein tau, MAPT, driven by the mouse prion protein (Prnp) promoter. The transgene encodes the disease-associated P301S mutation and includes four microtubule-binding domains and one N-terminal insert (4R/1N). The transgene inserted at Chr3: 140354280-140603283 (Build GRCm38/mm10), causing a 249 Kb deletion that does not affect any known genes. See Goodwin et al. (2019) *Genome Res.* 29(3):494-505, herein incorporated by reference in its entirety for all purposes. Expression of the mutant human tau is fivefold higher than that of the endogenous mouse protein. See Yoshiyama et al. (2007) *Neuron* 53(3):337-351, herein incorporated by reference in its entirety for all purposes. PS19 mice develop neuronal loss and brain atrophy by eight months of age. They also develop widespread tau aggregates, known as neurofibrillary tangle-like inclusions, in the neocortex, amygdala, hippocampus, brain stem, and spinal cord. See Yoshiyama et al. (2007). Prior to the appearance of overt tau pathology by histological methods, the brains of these mice were shown to display tau seeding activity. That is, tau aggregates present in brain homogenate can elicit further tau aggregation, presumably via a prion-like mechanism. See Holmes (2014) *Proc. Natl. Acad. Sci. U.S.A.* 111(41):E4376-E4385, herein incorporated by reference in its entirety for all purposes.

A. Tau and Tauopathies

Microtubule-associated protein tau (also called neurofibrillary tangle protein, paired helical filament-tau (PHF-tau), or tau) is a protein that promotes microtubule assembly and stability and is predominantly expressed in neurons, where it is preferentially localized to the axonal compartment. Tau is encoded by the MAPT gene (also called MAPTL, MTBT1, TAU, or MTAPT). Tau has a role in stabilizing neuronal microtubules and thus in promoting axonal outgrowth. In humans, it appears as a set of six isoforms which are differentially spliced from transcripts of a single gene located on chromosome 17. Each tau isoform contains a series of ¾ tandem repeat units (depending on the isoform) that bind to microtubules and serve to stabilize them. The microtubule-binding repeat region of tau is flanked by serine/threonine-rich regions which can be phosphorylated by a variety of kinases and that are associated with tau hyperphosphorylation in Alzheimer's diseases (AD) and a family of related neurodegenerative diseases called tauopathies.

The tau protein in the models and methods disclosed herein can be a tau protein from any animal or mammal, such as human, mouse, or rat. In one specific example, the tau is a human tau protein. An exemplary human tau protein is assigned UniProt accession number P10636 and GeneID 4137. An exemplary mouse tau protein is assigned UniProt accession number P10637 and GeneID 17762. An exemplary rat tau protein is assigned UniProt accession number P19332.

The tau proteins are the products of alternate splicing from a single gene that in humans is designated MAPT (microtubule-associated protein tau). The tau repeat domain carries the sequence motifs responsible for aggregation (i.e., it is the aggregation-prone domain from tau). Depending on splicing, the repeat domain of the tau protein has either three or four repeat regions that constitute the aggregation-prone core of the protein, which is often termed the repeat domain (RD). Specifically, the repeat domain of tau represents the core of the microtubule-binding region and harbors the hexapeptide motifs in R2 and R3 that are responsible for Tau aggregation. In the human brain, there are six tau isoforms ranging from 352 to 441 amino acids in length. These isoforms vary at the carboxyl terminal according to the presence of either three repeat or four repeat domains (R1-R4), in addition to the presence or absence of one or two insert domains at the amino-terminus. The repeat domains, located at the carboxyl-terminal half of tau, are believed to be important for microtubule binding as well as for the pathological aggregation of tau into paired helical filaments (PHFs), which are the core constituents of the neurofibrillary tangles found in tauopathies. Exemplary sequences for the four repeat domains (R1-R4) are provided in SEQ ID NOS: 88-91, respectively. Exemplary coding sequences for the four repeat domains (R1-R4) are provided in SEQ ID NOS: 92-95. An exemplary sequence for the Tau four-repeat domain is provided in SEQ ID NO: 96. An exemplary coding sequence for the Tau four-repeat domain is provided in SEQ ID NO: 97. An exemplary sequence for the Tau four-repeat domain with the P301S mutation is provided in SEQ ID NO: 98. An exemplary coding sequence for the Tau four-repeat domain with the P301S mutation is provided in SEQ ID NO: 99.

Tauopathies are a group of heterogeneous neurodegenerative conditions characterized by deposition of abnormal tau in the brain. These include, for example, Alzheimer's disease, Down's syndrome, Pick's disease, progressive supranuclear palsy (PSP), corticobasal degeneration (CBD), and frontotemporal dementia with parkinsonism linked to chromosome 17 (FTDP-17). In AD and other tauopathies, tau protein is abnormally hyperphosphorylated and aggregated into bundles of filaments (paired helical filaments), which manifest as neurofibrillary tangles.

There are several tau pathogenic mutations, such as pro-aggregation mutations, that are associated with (e.g., segregate with) or cause a tauopathy. Pathogenic tau mutations, which can be either exonic or intronic, generally alter the relative production of tau isoforms and can lead to changes in microtubule assembly and/or the propensity of tau to aggregate. As one example, such a mutation can be an aggregation-sensitizing mutation that sensitizes tau to seeding but does not result in tau readily aggregating on its own. For example, the mutation can be the disease-associated P301S mutation. By P301S mutation is meant the human tau P301S mutation or a corresponding mutation in another tau protein when optimally aligned with the human tau protein. Other pathogenic tau mutations include, for example, A152T, G272V, K280del, P301L, S320F, V337M, R406W, P301L/V337M, K280del/1227P/1308P, G272V/P301L/R406W, and A152T/P301L/S320F. See alzforum.org/mutations/mapt, Brandt et al. (2005) *Biochim. Biophys. Acta* 1739:331-354, and Wolfe (2009) *J. Biol. Chem.* 284(10): 6021-6025, each of which is herein incorporated by reference in its entirety for all purposes. DNA and protein sequences for the wild type Tau 1N4R are set forth in SEQ ID NOS: 81 and 82, respectively. DNA and protein sequences for the 3MUT Tau 1N4R (A152T, P301L, S320F) are set forth in SEQ ID NOS: 83 and 84, respectively.

Some examples of signs and symptoms of tauopathy at the cellular level include tau hyperphosphorylation (e.g., in the somatodendritic compartment of a neuron because although generally considered an axonal protein, tau is found in the dendritic compartment of degenerating neurons, and this redistribution is thought to be a trigger of neurodegeneration in Alzheimer's disease), tau aggregation, abnormal shape of nuclear lamina, and impaired nucleocytoplasmic transport. Other signs and symptoms at an organism level can include neurofibrillary tangles (e.g., in the neocortex, amygdala, hippocampus, brain stem, or spinal cord), neuron loss (e.g., in the hippocampus, amygdala, or neocortex), microgliosis, synaptic loss, cognitive impairment, or motor deficits. Other signs and symptoms can include, for example, increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, or decreased Ran GTPase-activating protein 1 (RanGAP1) nuclear-to-cytoplasmic ratio in neurons. The phospho-tau can be, for example, phospho-tau (S356) or phospho-tau AT8 (S202, T205).

B. Agents for Reducing Expression of BANF1, PPP2CA, or ANKLE2

Any suitable agent can be used to reduce or inhibit expression of BANF1, PPP2CA, or ANKLE2. Examples of agents that can reduce expression of BANF1, PPP2CA, or ANKLE2 include nuclease agents (e.g., ZFNs, TALENs, or CRISPR/Cas), DNA-binding proteins fused to a transcriptional repressor (e.g., transcriptional repressors such as a catalytically inactive/dead Cas (dCas) fused to a KRAB domain (dCas-KRAB)), or antisense oligonucleotides, siRNAs, shRNAs, or antisense RNAs. Other examples of agents that can reduce expression of BANF1, PPP2CA, or ANKLE2 include nucleic acids encoding nuclease agents (e.g., ZFNs, TALENs, or CRISPR/Cas), DNA-binding proteins fused to a transcriptional repressor (e.g., transcriptional repressors such as a catalytically inactive/dead Cas (dCas) fused to a KRAB domain (dCas-KRAB)), or antisense oligonucleotides, siRNAs, shRNAs, or antisense RNAs. Examples of these are discussed in more detail below.

1. Nuclease Agents and Transcriptional Repressors

Nuclease agents can be used to decrease expression of BANF1, PPP2CA, or ANKLE2. For example, such nuclease agents can be designed to target and cleave a region of a BANF1, PPP2CA, or ANKLE2 gene that will disrupt expression of the BANF1, PPP2CA, or ANKLE2 gene. As a specific example, a nuclease agent can be designed to cleave a region of a BANF1, PPP2CA, or ANKLE2 near the start codon. For example, the target sequence can be within about 10, 20, 30, 40, 50, 100, 200, 300, 400, 500, or 1,000 nucleotides of the start codon, and cleavage by the nuclease agent can disrupt the start codon. Alternatively, nuclease agents designed to cleave regions near the start and stop codons can be used in order to delete the coding sequence between the two nuclease target sequences. DNA-binding proteins fused to transcriptional repressor domains can also be used to decrease expression of BANF1, PPP2CA, or ANKLE2. For example, a DNA-binding protein fused to a transcriptional repressor domain (e.g., catalytically inactive Cas fused to a KRAB transcriptional repressor domain) can be designed to target a region of BANF1, PPP2CA, or ANKLE2 near the start codon e.g., within about 10, 20, 30, 40, 50, 100, 200, 300, 400, 500, or 1,000 nucleotides of the start codon).

Cleavage by a nuclease agent can result in a double-strand break that can be repaired by non-homologous end joining (NHEJ). NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. These insertions and deletions (indels) can disrupt expression of the target gene through, for example, frameshift mutations or disruption of the start codon.

Any nuclease agent that induces a nick or double-strand break into a desired recognition site can be used in the methods and compositions disclosed herein. A naturally occurring or native nuclease agent can be employed so long as the nuclease agent induces a nick or double-strand break in a desired recognition site. Alternatively, a modified or engineered nuclease agent can be employed. An "engineered nuclease agent" includes a nuclease that is engineered (modified or derived) from its native form to specifically recognize and induce a nick or double-strand break in the desired recognition site. Thus, an engineered nuclease agent can be derived from a native, naturally occurring nuclease agent or it can be artificially created or synthesized. The engineered nuclease can induce a nick or double-strand break in a recognition site, for example, wherein the recognition site is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a recognition site or other DNA can be referred to herein as "cutting" or "cleaving" the recognition site or other DNA.

Active variants and fragments of the exemplified recognition sites are also provided. Such active variants can comprise at least 65%, 70%, 75%, 80%, 85%, 90%, 91%, 92%, 93%, 94%, 95%, 96%, 97%, 98%, 99% or more sequence identity to the given recognition site, wherein the active variants retain biological activity and hence are capable of being recognized and cleaved by a nuclease agent in a sequence-specific manner. Assays to measure the double-strand break of a recognition site by a nuclease agent are known in the art (e.g., TaqMan® qPCR assay, Frendewey et al. (2010) *Methods in Enzymology* 476:295-307, herein incorporated by reference in its entirety for all purposes).

The recognition site of the nuclease agent can be positioned anywhere in or near the target locus. The recognition site can be located within a coding region of a gene, or within regulatory regions that influence the expression of the gene (e.g., near the start codon). A recognition site of the nuclease agent can be located in an intron, an exon, a promoter, an enhancer, a regulatory region, or any non-protein coding region. Alternatively, the recognition site can be positioned within the polynucleotide encoding the selection marker. Such a position can be located within the coding region of the selection marker or within the regulatory regions, which influence the expression of the selection marker. Thus, a recognition site of the nuclease agent can be located in an intron of the selection marker, a promoter, an enhancer, a regulatory region, or any non-protein-coding region of the polynucleotide encoding the selection marker. A nick or double-strand break at the recognition site can disrupt the activity of the selection marker, and methods to assay for the presence or absence of a functional selection marker are known.

One type of nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *Proc. Natl. Acad. Sci. U.S.A.* 107(50):21617-21622; Scholze & Boch (2010) *Virulence* 1:428-432; Christian et al. *Genetics* (2010) 186:757-761; Li et al. (2010) *Nucleic Acids Res.* (2011) 39(1):359-372; and Miller et al. (2011) *Nature Biotechnology* 29:143-148, each of which is herein incorporated by reference in its entirety for all purposes.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety for all purposes. In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2; US20130123484; US20100291048; WO/2011/017293A2; and Gaj et al. (2013) *Trends in Biotechnology,* 31(7):397-405, each of which is herein incorporated by reference in its entirety for all purposes.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition site and hence retain nick or double-strand-break-inducing activity. For example, any of the nuclease agents described herein can be modified from a native endonuclease sequence and designed to recognize and induce a nick or double-strand break at a recognition site that was not recognized by the native nuclease agent. Thus, some engineered nucleases have a specificity to induce a nick or double-strand break at a recognition site that is different from the corresponding native nuclease agent recognition site. Assays for nick or double-strand-break-inducing activity are known and generally measure the overall activity and specificity of the endonuclease on DNA substrates containing the recognition site.

The nuclease agent may be introduced into the cell by any known means. The polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally, or constitutively expressed within the cell. Thus, the polynucleotide encoding the nuclease agent can be contained in an expression cassette and be operably linked to a conditional promoter, an inducible promoter, a constitutive promoter, or a tissue-specific promoter. Such promoters of interest are discussed in further detail elsewhere herein. Alternatively, the nuclease agent is introduced into the cell as an mRNA encoding a nuclease agent.

A polynucleotide encoding a nuclease agent can be stably integrated in the genome of the cell and operably linked to a promoter active in the cell. Alternatively, a polynucleotide encoding a nuclease agent can be in a targeting vector (e.g., a targeting vector comprising an insert polynucleotide, or in a vector or a plasmid that is separate from the targeting vector comprising the insert polynucleotide).

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

CRISPR/Cas Systems. The methods and compositions disclosed herein can utilize Clustered Regularly Interspersed Short Palindromic Repeats (CRISPR)/CRISPR-associated (Cas) systems or components of such systems to modify a genome or alter expression of a gene within a cell. CRISPR/Cas systems include transcripts and other elements involved in the expression of, or directing the activity of, Cas genes. A CRISPR/Cas system can be, for example, a type I, a type II, a type III system, or a type V system (e.g., subtype V-A or subtype V-B). The methods and compositions disclosed herein can employ CRISPR/Cas systems by utilizing CRISPR complexes (comprising a guide RNA (gRNA) complexed with a Cas protein) for site-directed binding or cleavage of nucleic acids.

CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR/Cas systems employ non-naturally occurring CRISPR complexes comprising a gRNA and a Cas protein that do not naturally occur together, employ a Cas protein that does not occur naturally, or employ a gRNA that does not occur naturally.

Cas Proteins. Cas proteins generally comprise at least one RNA recognition or binding domain that can interact with guide RNAs. Cas proteins can also comprise nuclease domains (e.g., DNase domains or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from a Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) Nat. Commun. 8:14500, herein incorporated by reference in its entirety for all purposes. SaCas9 is smaller than SpCas9, and CjCas9 is smaller than both SaCas9 and SpCas9. Exemplary DNA and protein sequences for the SpCas9 are set forth in SEQ ID NOS: 86 and 87, respectively. Cas9 from *Neisseria meningitidis* (Nme2Cas9) is another exemplary Cas9 protein. See, e.g., Edraki et al. (2019) *Mol. Cell* 73(4):714-726, herein incorporated by reference in its entirety for all purposes. Cas9 proteins from *Streptococcus thermophilus* (e.g., *Streptococcus thermophilus* LMD-9 Cas9 encoded by the CRISPR1 locus (St1Cas9) or *Streptococcus thermophilus* Cas9 from the CRISPR3 locus (St3Cas9)) are other exemplary Cas9 proteins. Cas9 from *Francisella novicida* (FnCas9) or the RHA *Francisella novicida* Cas9 variant that recognizes an alternative PAM (E1369R/E1449H/R1556A substitutions) are other exemplary Cas9 proteins. These and other exemplary Cas9 proteins are reviewed, e.g., in Cebrian-Serrano and Davies (2017) *Mamm. Genome* 28(7):247-261, herein incorporated by reference in its entirety for all purposes.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida*, *Prevotella albensis*, Lachnospiraceae bacterium MC20171, *Butyrivibrio proteoclasticus*, Peregrinibacteria bacterium GW2011_GWA2_33_10, Parcubacteria bacterium GW2011_GWC2_44_17, *Smithella* sp. SCADC, *Acidaminococcus* sp. BV3L6, Lachnospiraceae bacterium MA2020, *Candidatus* Methanoplasma *termitum*, *Eubacterium eligens*, *Moraxella bovoculi* 237, *Leptospira inadai*, Lachnospiraceae bacterium ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A. These and other modified Cas proteins are reviewed, e.g., in Cebrian-Serrano and Davies (2017) *Mamm. Genome* 28(7):247-261, herein incorporated by reference in its entirety for all purposes. Another example of a modified Cas9 protein is xCas9, which is a SpCas9 variant that can recognize an expanded range of PAM sequences. See, e.g., Hu et al. (2018) *Nature* 556:57-63, herein incorporated by reference in its entirety for all purposes.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of or a property of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break within a double-stranded target DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of xCas9 are the same as those described above for SpCas9. Examples of inactivating mutations in the catalytic domains of *Staphylococcus aureus* Cas9 proteins are also known. For example, the *Staphylococcus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes. Examples of inactivating mutations in the catalytic domains of Nme2Cas9 are also known (e.g., combination of D16A and H588A). Examples of inactivating mutations in the catalytic domains of St1Cas9 are also known (e.g., combination of D9A, D598A, H599A, and N622A). Examples of inactivating mutations in the catalytic domains of St3Cas9 are also known (e.g., combination of D10A and N870A). Examples of inactivating mutations in the catalytic domains of CjCas9 are also known (e.g., combination of D8A and H559A). Examples of inactivating mutations in the catalytic domains of FnCas9 and RHA FnCas9 are also known (e.g., N995A).

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), Lachnospiraceae bacterium ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins can also be operably linked to heterologous polypeptides as fusion proteins. For example, a Cas protein can be fused to a cleavage domain, an epigenetic modification domain, or a transcriptional repressor domain. See WO 2014/089290, herein incorporated by reference in its entirety for all purposes. Examples of transcriptional repressor domains include inducible cAMP early repressor (ICER) domains, Kruppel-associated box A (KRAB-A) (or Kruppel-associated box (KRAB)) repressor domains, YY1 glycine rich repressor domains, Sp1-like repressors, E(sp1) repressors, IκB repressor, and MeCP2. Other examples include transcriptional repressor domains from A/B, KOX, TGF-beta-inducible early gene (TIEG), v-erbA, SID, SID4X, MBD2, MBD3, DNMT1, DNMG3A, DNMT3B, Rb, ROM2, See, e.g., EP3045537 and WO 2011/146121, each of which is incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreenl), yellow fluorescent proteins (e.g., YFP, eYFP, Citrine, Venus, YPet, PhiYFP, ZsYellowl), blue fluorescent proteins (e.g., eBFP, eBFP2, Azurite, mKalamal, GFPuv, Sapphire, T-sapphire), cyan fluorescent proteins (e.g., eCFP, Cerulean, CyPet, AmCyanl, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRedl, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10):1328-1332; Goodman et al. (2009) *Chembiochem.* 10(9):1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The labeled nucleic acid can be tethered to the C-terminus, the N-terminus, or to an internal region within the Cas protein. In one example, the labeled nucleic acid is tethered to the C-terminus or the N-terminus of the Cas protein. Likewise, the Cas protein can be tethered to the 5' end, the 3' end, or to an internal region within the labeled nucleic acid. That is, the labeled nucleic acid can be tethered in any orientation and polarity. For example, the Cas protein can be tethered to the 5' end or the 3' end of the labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of a cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding a gRNA. Alternatively, it can be in a vector or plasmid that is separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

Guide RNAs. A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 65). Any of the DNA-targeting segments (guide sequences) disclosed herein can be joined to the 5' end of SEQ ID NO: 65 to form a crRNA. Such DNA-targeting segments include, for example, SEQ ID NOS: 44-46 (mouse Banf1), SEQ ID NOS: 27-30 (human BANF1), SEQ ID NOS: 47-49 (mouse Ppp2ca), SEQ ID NOS: 31-32 (human PPP2CA), SEQ ID NOS: 50-52 (mouse Ankle2), and SEQ ID NO: 38 (human ANKLE2).

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of

```
                                              (SEQ ID NO: 66)
AGCAUAGCAAGUUAAAAUAAGGCUAGUCCGUUAUCAACUUGAAAAGUG
GCACCGAGUCGGUGCUUU, (SEQ ID NO: 100)
AAACAGCAUAGCAAGUUAAAAUAAGGCUAGUCCGUUAUCAACUUGAAAA
AGUGGCACCGAGUCGGUGCUUUU,
or (SEQ ID NO: 101)
GUUGGAACCAUUCAAAACAGCAUAGCAAGUUAAAAUAAGGCUAGUCCGU
UAUCAACUUGAAAAAGUGGCACCGAGUCGGUGC.
```

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that hybridizes to the complementary strand of a target DNA. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence on the complementary strand of the target DNA, as described in more detail below. The DNA-targeting segment of a gRNA interacts with the target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have, for example, a length of at least about 12, 15, 17, 18, 19, 20, 25, 30, 35, or 40 nucleotides. Such DNA-targeting segments can have, for example, a length from about 12 to about 100, from about 12 to about 80, from about 12 to about 50, from about 12 to about 40, from about 12 to about 30, from about 12 to about 25, or from about 12 to about 20 nucleotides. For example, the DNA targeting segment can be from about 15 to about 25 nucleotides (e.g., from about 17 to about 20 nucleotides, or about 17, 18, 19, or 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment of the guide RNA and the complementary strand of the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the target DNA can be at least 60% over about 20 contiguous nucleotides. As an example, the percent complementarity between the DNA-targeting segment and the complementary strand of the target DNA can be 100% over the 14 contiguous nucleotides at the 5' end of the complementary strand of the target DNA and as low as 0% over the remainder. In such a case, the DNA-targeting segment can be considered to be 14 nucleotides in length. As another example, the percent complementarity between the DNA-targeting segment and the complementary strand of the target DNA can be 100% over the seven contiguous nucleotides at the 5' end of the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the complementary strand of the target DNA. For example, the DNA-targeting segment can be 20 nucleotides in length and can comprise 1, 2, or 3 mismatches with the complementary strand of the target DNA. In one example, the mismatches are not adjacent to the region of the complementary strand corresponding to the protospacer adjacent motif (PAM) sequence (i.e., the reverse complement of the PAM sequence) (e.g., the mismatches are in the 5' end of the DNA-targeting segment of the guide RNA, or the mismatches are at least 2, 3, 4, 5, 6, 7, 8, 9, 10, 11, 12, 13, 14, 15, 16, 17, 18, or 19 base pairs away from the region of the complementary strand corresponding to the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs can comprise a DNA-targeting segment and a scaffold sequence (i.e., the protein-binding or Cas-binding sequence of the guide RNA). For example, such guide RNAs can have a 5' DNA-targeting segment joined to a 3' scaffold sequence. Exemplary scaffold sequences comprise, consist essentially of, or consist of: GUUUUAGAGC-UAGAAAUAGCAAGUUAAAAUAAGGCUAGU-CCGUUAUCAACUUGA AAAAGUGGCACCGAGUC-GGUGCU (version 1; SEQ ID NO: 67); GUUGGAAC-CAUUCAAAACAGCAUAGCAAGUUAAAAUAAGGC-UAGUCCGUUAUCA ACUUGAAAAAGUGGCACCGA-GUCGGUGC (version 2; SEQ ID NO: 68); GUUUUAGAGCUAGAAAUAGCAAGUUAAAAUAA-GGCUAGUCCGUUAUCAACUUGA AAAAGUGG-CACCGAGUCGGUGC (version 3; SEQ ID NO: 69); GUUUAAGAGCUAUGCUGGAAACAGCAUAGCAA-GUUUAAAUAAGGCUAGUCCGUU AUCAAC-UUGAAAAAGUGGCACCGAGUCGGUGC (version 4; SEQ ID NO: 70); GUUUUAGAGCUAGAAAUAGCA-AGUUAAAAUAAGGCUAGUCCGUUAUCAACUUGA AAAAGUGGCACCGAGUCGGUGCUUUUUUU (version 5; SEQ ID NO: 102); GUUUUAGAGCUA-GAAAUAGCAAGUUAAAAUAAGGCUAGUCCGUU-AUCAACUUGA AAAAGUGGCACCGAGUCGGUGC-UUUU (version 6; SEQ ID NO: 103); or GUUUAAGAGC-UAUGCUGGAAACAGCAUAGCAAGUUUAAAUAA-GGCUAGUCCGUU AUCAACUUGAAAAAGUGGC-ACCGAGUCGGUGCUUUUUU (version 7; SEQ ID NO: 104). Guide RNAs targeting any of the guide RNA target sequences disclosed herein can include, for example, a DNA-targeting segment on the 5' end of the guide RNA fused to any of the exemplary guide RNA scaffold sequences on the 3' end of the guide RNA. That is, any of the DNA-targeting segments (guide sequences) disclosed herein can be joined to the 5' end of any one of the above scaffold sequences to form a single guide RNA (chimeric guide RNA). Such DNA-targeting segments include, for example, SEQ ID NOS: 44-46 (mouse Banf1), SEQ ID NOS: 27-30 (human BANF1), SEQ ID NOS: 47-49 (mouse Ppp2ca), SEQ ID NOS: 31-32 (human PPP2CA), SEQ ID NOS: 50-52 (mouse Ankle2), and SEQ ID NO: 38 (human ANKLE2).

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs. For example, Cas mRNAs can be modified by depletion of uridine using synonymous codons.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Rep.* 22(9):2227-2235, each of which is herein incorporated by reference in its entirety for all purposes. Other possible modifications are described in more detail elsewhere herein. In a specific example, a guide RNA includes 2'-O-methyl analogs and 3' phosphorothioate internucleotide linkages at the first three 5' and 3' terminal RNA residues. Such chemical modifications can, for example, provide greater stability and protection from exonucleases to guide RNAs, allowing them to persist within cells for longer than unmodified guide RNAs. Such chemical modifications can also, for example, protect against innate intracellular immune responses that can actively degrade RNA or trigger immune cascades that lead to cell death.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis. For example, a guide RNA can be chemically synthesized to include 2'-O-methyl analogs and 3' phosphorothioate internucleotide linkages at the first three 5' and 3' terminal RNA residues.

Guide RNAs (or nucleic acids encoding guide RNAs) can be in compositions comprising one or more guide RNAs (e.g., 1, 2, 3, 4, or more guide RNAs) and a carrier increasing the stability of the guide RNA (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly (lactic acid) (PLA) microspheres, poly(D,L-lactic-cogly-colic-acid) (PLGA) microspheres, liposomes, micelles, inverse micelles, lipid cochleates, and lipid microtubules. Such compositions can further comprise a Cas protein, such as a Cas9 protein, or a nucleic acid encoding a Cas protein.

Guide RNA Target Sequences. Target DNAs for guide RNAs include nucleic acid sequences present in a DNA to which a DNA-targeting segment of a gRNA will bind, provided sufficient conditions for binding exist. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the gRNA can be called the "complementary strand," and the strand of the target DNA that is complementary to the "complementary strand" (and is therefore not complementary to the Cas protein or gRNA) can be called "noncomplementary strand" or "template strand."

The target DNA includes both the sequence on the complementary strand to which the guide RNA hybridizes and the corresponding sequence on the non-complementary strand (e.g., adjacent to the protospacer adjacent motif (PAM)). The term "guide RNA target sequence" as used herein refers specifically to the sequence on the non-complementary strand corresponding to (i.e., the reverse complement of) the sequence to which the guide RNA hybridizes on the complementary strand. That is, the guide RNA target sequence refers to the sequence on the non-complementary strand adjacent to the PAM (e.g., upstream or 5' of the PAM in the case of Cas9). A guide RNA target sequence is equivalent to the DNA-targeting segment of a guide RNA, but with thymines instead of uracils. As one example, a guide RNA target sequence for an SpCas9 enzyme can refer to the sequence upstream of the 5'-NGG-3' PAM on the non-complementary strand. A guide RNA is designed to have complementarity to the complementary strand of a target DNA, where hybridization between the DNA-targeting segment of the guide RNA and the complementary strand of the target DNA promotes the formation of a CRISPR complex. Full complementarity is not necessarily required, provided that there is sufficient complementarity to cause hybridization and promote formation of a CRISPR complex. If a guide RNA is referred to herein as targeting a guide RNA target sequence, what is meant is that the guide RNA hybridizes to the complementary strand sequence of the target DNA that is the reverse complement of the guide RNA target sequence on the non-complementary strand.

A target DNA or guide RNA target sequence can comprise any polynucleotide, and can be located, for example, in the nucleus or cytoplasm of a cell or within an organelle of a cell, such as a mitochondrion or chloroplast. A target DNA or guide RNA target sequence can be any nucleic acid sequence endogenous or exogenous to a cell. The guide RNA target sequence can be a sequence coding a gene product (e.g., a protein) or a non-coding sequence (e.g., a regulatory sequence) or can include both.

Site-specific binding and cleavage of a target DNA by a Cas protein can occur at locations determined by both (i) base-pairing complementarity between the guide RNA and the complementary strand of the target DNA and (ii) a short motif, called the protospacer adjacent motif (PAM), in the non-complementary strand of the target DNA. The PAM can flank the guide RNA target sequence. Optionally, the guide RNA target sequence can be flanked on the 3' end by the PAM (e.g., for Cas9). Alternatively, the guide RNA target sequence can be flanked on the 5' end by the PAM (e.g., for Cpf1). For example, the cleavage site of Cas proteins can be about 1 to about 10 or about 2 to about 5 base pairs (e.g., 3 base pairs) upstream or downstream of the PAM sequence (e.g., within the guide RNA target sequence). In the case of SpCas9, the PAM sequence (i.e., on the non-complementary strand) can be 5'-$N_1$GG-3', where $N_1$ is any DNA nucleotide, and where the PAM is immediately 3' of the guide RNA target sequence on the non-complementary strand of the target DNA. As such, the sequence corresponding to the PAM on the complementary strand (i.e., the reverse complement) would be 5'-CC$N_2$-3', where N2 is any DNA nucleotide and is immediately 5' of the sequence to which the DNA-targeting segment of the guide RNA hybridizes on the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

An example of a guide RNA target sequence is a 20-nucleotide DNA sequence immediately preceding an NGG motif recognized by an SpCas9 protein. For example, two examples of guide RNA target sequences plus PAMs are $GN_{19}NGG$ (SEQ ID NO: 71) or $N_{20}NGG$ (SEQ ID NO: 72). See, e.g., WO 2014/165825, herein incorporated by reference in its entirety for all purposes. The guanine at the 5' end can facilitate transcription by RNA polymerase in cells. Other examples of guide RNA target sequences plus PAMs can include two guanine nucleotides at the 5' end (e.g., $GGN_{20}NGG$; SEQ ID NO: 73) to facilitate efficient transcription by T7 polymerase in vitro. See, e.g., WO 2014/065596, herein incorporated by reference in its entirety for all purposes. Other guide RNA target sequences plus PAMs can have between 4-22 nucleotides in length of SEQ ID NOS: 71-73, including the 5' G or GG and the 3' GG or NGG. Yet other guide RNA target sequences plus PAMs can have between 14 and 20 nucleotides in length of SEQ ID NOS: 71-73. Examples of guide RNA target sequence for BANF1, PPP2CA, and ANKLE2 include SEQ ID NOS: 1-4 (human BANF1), SEQ ID NOS: 5-6 (human PPP2CA), SEQ ID NO: 12 (human ANKLE2), SEQ ID NOS: 18-20 (mouse Banf1), SEQ ID NOS: 21-23 (mouse Ppp2ca), and SEQ ID NOS: 24-26 (mouse Ankle2).

Formation of a CRISPR complex hybridized to a target DNA can result in cleavage of one or both strands of the target DNA within or near the region corresponding to the guide RNA target sequence (i.e., the guide RNA target sequence on the non-complementary strand of the target DNA and the reverse complement on the complementary strand to which the guide RNA hybridizes). For example, the cleavage site can be within the guide RNA target sequence (e.g., at a defined location relative to the PAM sequence). The "cleavage site" includes the position of a target DNA at which a Cas protein produces a single-strand break or a double-strand break. The cleavage site can be on only one strand (e.g., when a nickase is used) or on both strands of a double-stranded DNA. Cleavage sites can be at the same position on both strands (producing blunt ends; e.g. Cas9)) or can be at different sites on each strand (producing staggered ends (i.e., overhangs); e.g., Cpf1). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA target sequence or cleavage site of the nickase on the first strand is separated from the guide RNA target sequence or cleavage site of the nickase on the second strand by at least 2, 3, 4, 5, 6, 7, 8, 9, 10, 15, 20, 25, 30, 40, 50, 75, 100, 250, 500, or 1,000 base pairs.

2. Antisense Oligonucleotides, Antisense RNAs, siRNAs, or shRNAs

Antisense oligonucleotides, antisense RNAs, small interfering RNAs (siRNAs), or short hairpin RNAs (shRNAs) can also be used to decrease expression of BANF1, PPP2CA, or ANKLE2. Such antisense RNAs, siRNAs, or shRNAs can be designed to target any region of a BANF1, PPP2CA, or ANKLE2 mRNA.

The term "antisense RNA" refers to a single-stranded RNA that is complementary to a messenger RNA strand transcribed in a cell. The term "small interfering RNA (siRNA)" refers to a typically double-stranded RNA molecule that induces the RNA interference (RNAi) pathway. These molecules can vary in length (generally between 18-30 base pairs) and contain varying degrees of complementarity to their target mRNA in the antisense strand. Some, but not all, siRNAs have unpaired overhanging bases on the 5' or 3' end of the sense strand and/or the antisense strand. The term "siRNA" includes duplexes of two separate strands, as well as single strands that can form hairpin structures comprising a duplex region. The double-stranded structure can be, for example, less than 20, 25, 30, 35, 40, 45, or 50 nucleotides in length. For example, the double-stranded structure can be from about 21-23 nucleotides in length, from about 19-25 nucleotides in length, or from about 19-23 nucleotides in length. The term "short hairpin RNA (shRNA)" refers to a single strand of RNA bases that self-hybridizes in a hairpin structure and can induce the RNA interference (RNAi) pathway upon processing. These molecules can vary in length (generally about 50-90 nucleotides in length, or in some cases up to greater than 250 nucleotides in length, e.g., for microRNA-adapted shRNA). shRNA molecules are processed within the cell to form siRNAs, which in turn can knock down gene expression. shRNAs can be incorporated into vectors. The term "shRNA" also refers to a DNA molecule from which a short, hairpin RNA molecule may be transcribed.

Antisense oligonucleotides and RNAi agents can also be used to decrease expression of BANF1, PPP2CA, or ANKLE2. Such antisense oligonucleotides or RNAi agents can be designed to target any region of a BANF1, PPP2CA, or ANKLE2 mRNA.

An "RNAi agent" is a composition that comprises a small double-stranded RNA or RNA-like (e.g., chemically modified RNA) oligonucleotide molecule capable of facilitating degradation or inhibition of translation of a target RNA, such as messenger RNA (mRNA), in a sequence-specific manner. The oligonucleotide in the RNAi agent is a polymer of linked nucleosides, each of which can be independently modified or unmodified. RNAi agents operate through the RNA interference mechanism (i.e., inducing RNA interference through interaction with the RNA interference pathway machinery (RNA-induced silencing complex or RISC) of mammalian cells). While it is believed that RNAi agents, as that term is used herein, operate primarily through the RNA interference mechanism, the disclosed RNAi agents are not bound by or limited to any particular pathway or mechanism of action. RNAi agents disclosed herein comprise a sense strand and an antisense strand, and include, but are not limited to, short interfering RNAs (siRNAs), double-stranded RNAs (dsRNA), micro RNAs (miRNAs), short hairpin RNAs (shRNA), and dicer substrates. The antisense strand of the RNAi agents described herein is at least partially complementary to a sequence (i.e., a succession or order of nucleobases or nucleotides, described with a succession of letters using standard nomenclature) in the target RNA.

Single-stranded antisense oligonucleotides (ASOs) and RNA interference (RNAi) share a fundamental principle in that an oligonucleotide binds a target RNA through Watson-Crick base pairing. Without wishing to be bound by theory, during RNAi, a small RNA duplex (RNAi agent) associates with the RNA-induced silencing complex (RISC), one strand (the passenger strand) is lost, and the remaining strand (the guide strand) cooperates with RISC to bind complementary RNA. Argonaute 2 (Ago2), the catalytic component of the RISC, then cleaves the target RNA. The guide strand is always associated with either the complementary sense strand or a protein (RISC). In contrast, an ASO must survive and function as a single strand. ASOs bind to the target RNA and block ribosomes or other factors, such as splicing factors, from binding the RNA or recruit proteins such as nucleases. Different modifications and target regions are chosen for ASOs based on the desired mechanism of action. A gapmer is an ASO oligonucleotide containing 2-5 chemically modified nucleotides (e.g. LNA or 2'-MOE) on each terminus flanking a central 8-10 base gap of DNA. After binding the target RNA, the DNA-RNA hybrid acts substrate for RNase H.

ASOs are DNA oligos, typically 15-25 bases long, designed in antisense orientation to the RNA of interest. Hybridization of the ASO to the target RNA mediates RNase H cleavage of the RNA, which can prevent protein translation of the mRNA. To increase nuclease resistance, phosphorothioate (PS) modifications can be added to the oligo. Phosphorothioate linkages also promote binding to serum proteins, which increases the bioavailability of the ASO and facilitates productive cellular uptake. In phosphorothioates, a sulfur atom replaces a non-bridging oxygen in the oligo phosphate backbone. ASOs can be chimeras comprising both DNA and modified RNA bases. The use of modified RNA, such as 2'-O-methoxy-ethyl (2'-MOE) RNA, 2'-O-methyl (2'OMe) RNA, or Affinity Plus Locked Nucleic Acid bases in chimeric antisense designs, increases both nuclease stability and affinity ($T_m$) of the antisense oligo to the target RNA. However, these modifications do not activate RNase H cleavage (i.e., ASOs fully composed of sugar-modified RNA-like nucleotides (such as 2'-MOE), however, do not support RNase H cleavage of the complementary RNA). Thus, one antisense strategy is a "gapmer" design that incorporates 2'-O-modified RNA or Affinity Plus Locked Nucleic Acid bases in chimeric antisense oligos that retain an RNase-H-activating domain. A standard gapmer retains a central region of PS-modified DNA bases sufficient to induce RNase H cleavage. These bases are flanked on both sides by blocks of 2' modifications that will increase binding affinity to the target. For example, gapmers can contain a central section of deoxynucleotides that allows the induction of RNase H cleavage, with the central part being flanked by blocks of 2'-O-alkyl modified ribonucleotides that protect the central section from nuclease degradation. Once delivered to cells, ASOs enter the nucleus and bind to their complementary, endogenous RNA target. Hybridization of the ASO gapmers to target RNA forms a DNA:RNA heteroduplex in the central region, which becomes a substrate for cleavage by the enzyme RNase H1.

Figure 40:
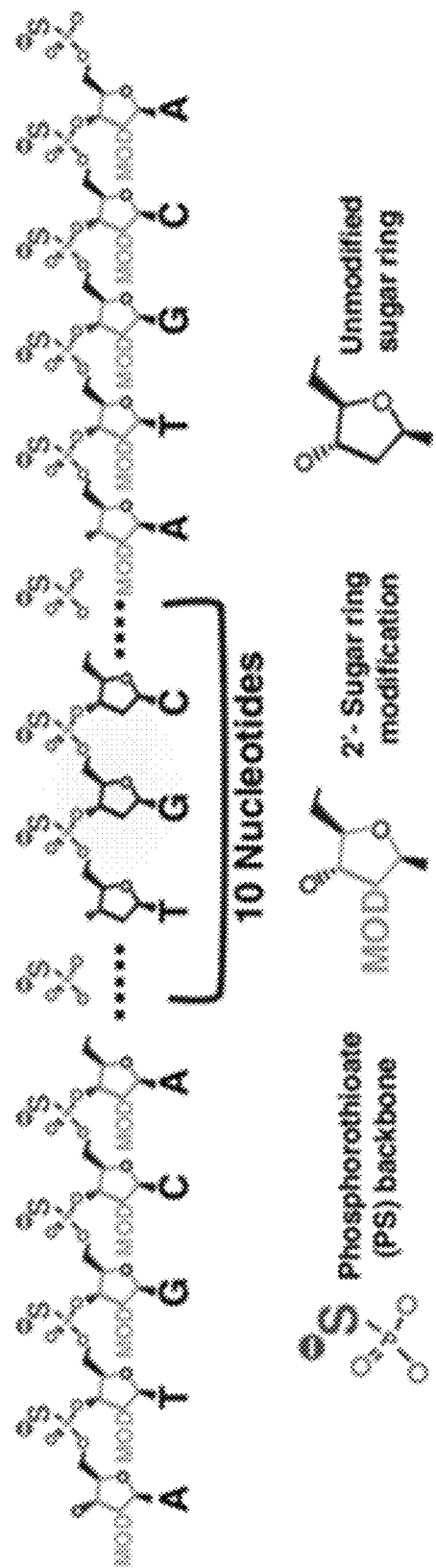
FIG. 40 shows a general schematic of ASO design in which ASOs were designed as 5-10-5 gapmers with a phosphorothioate backbone, 2' methoxyethyl modified bases used in each wing (5 nucleotides from both ends), and a 10 nucleotide core of unmodified DNA bases.

In one example, ASOs that are 5-10-5 gapmers are used containing 5' and 3' wings of 5 chemically modified nucleotides flanking a central 10 nucleotide core of DNA. In a specific example, ASOs that are 5-10-5 gapmers are used containing a phosphorothioate backbone, 2' methoxyethyl modified bases in the wings (5 nucleotides from both ends), and a 10 nucleotide core of unmodified DNA bases. See, e.g., FIG. 40.

In one example, an ASO targeting mBanf1 can comprise a modified version of the parent antisense RNA sequence set forth in any one of SEQ ID NOS: 215-236. In another example, an ASO targeting mBanf1 can comprise a modified version of the parent antisense RNA sequence set forth in any one of SEQ ID NOS: 215, 216, 220-223, 225, 230-232, 234, and 235. Such modifications can comprise, for example, one or more of the following: replacement of one or more RNA bases with one or more DNA bases, addition of one or more phosphorothioate linkages, or replacement of one or more bases with modified RNA bases such as 2'-O-methoxy-ethyl (2'-MOE) RNA, 2'-O-methyl (2'OMe) RNA, or Affinity Plus Locked Nucleic Acid. In one example, an ASO targeting mBanf1 can comprise the sequence set forth in any one of SEQ ID NOS: 105-126 or a modified version thereof. In another example, an ASO targeting mBanf1 can comprise the sequence set forth in any one of SEQ ID NOS: 105, 106, 110-113, 115, 120-122, 124, and 125 or a modified version thereof. Such modifications can comprise, for example, addition of one or more phosphorothioate linkages and/or replacement of one or more bases with modified RNA bases such as 2'-O-methoxy-ethyl (2'-MOE) RNA, 2'-O-methyl (2'OMe) RNA, or Affinity Plus Locked Nucleic Acid. In another example, an ASO targeting mBanf1 can comprise any of the sequences and/or modification patterns set forth in Table 13. In any of the above sequences, any "T" in the first 5 or last 5 nucleotides can be replaced with a "U."

In one example, an ASO targeting mPpp2ca can comprise a modified version of the parent antisense RNA sequence set forth in any one of SEQ ID NOS: 237-278. In another example, an ASO targeting mPpp2ca can comprise a modified version of the parent antisense RNA sequence set forth in any one of SEQ ID NOS: 240, 243, 246, 247, 260, 262, 263, 265, 268-270, 272, 275, and 276. Such modifications can comprise, for example, one or more of the following: replacement of one or more RNA bases with one or more DNA bases, addition of one or more phosphorothioate linkages, or replacement of one or more bases with modified RNA bases such as 2'-O-methoxy-ethyl (2'-MOE) RNA, 2'-O-methyl (2'OMe) RNA, or Affinity Plus Locked Nucleic Acid. In one example, an ASO targeting mPpp2ca can comprise the sequence set forth in any one of SEQ ID NOS: 127-168 or a modified version thereof. In another example, an ASO targeting mPpp2ca can comprise the sequence set forth in any one of SEQ ID NOS: 130, 133, 136, 137, 150, 152, 153, 155, 158-160, 162, 165, and 166 or a modified version thereof. Such modifications can comprise, for example, addition of one or more phosphorothioate linkages and/or replacement of one or more bases with modified RNA bases such as 2'-O-methoxy-ethyl (2'-MOE) RNA, 2'-O-methyl (2'OMe) RNA, or Affinity Plus Locked Nucleic Acid. In another example, an ASO targeting mPpp2ca can comprise any of the sequences and/or modification patterns set forth in Table 14. In any of the above sequences, any "T" in the first 5 or last 5 nucleotides can be replaced with a "U."

In one example, an ASO targeting mAnkle2 can comprise a modified version of the parent antisense RNA sequence set forth in any one of SEQ ID NOS: 279-324. In another example, an ASO targeting mAnkle2 can comprise a modified version of the parent antisense RNA sequence set forth in any one of SEQ ID NOS: 279, 281-283, 285, 287, 291-294, 297, 304, 307, 321, and 323. Such modifications can comprise, for example, one or more of the following: replacement of one or more RNA bases with one or more DNA bases, addition of one or more phosphorothioate linkages, or replacement of one or more bases with modified RNA bases such as 2'-O-methoxy-ethyl (2'-MOE) RNA, 2'-O-methyl (2'OMe) RNA, or Affinity Plus Locked Nucleic Acid. In one example, an ASO targeting mAnkle2 can comprise the sequence set forth in any one of SEQ ID NOS: 169-214 or a modified version thereof. In another example, an ASO targeting mAnkle2 can comprise the sequence set forth in any one of SEQ ID NOS: 169, 171-173, 175, 177, 181-184, 187, 194, 197, 211, and 213 or a modified version thereof. Such modifications can comprise, for example, addition of one or more phosphorothioate linkages and/or replacement of one or more bases with modified RNA bases such as 2'-O-methoxy-ethyl (2'-MOE) RNA, 2'-O-methyl (2'OMe) RNA, or Affinity Plus Locked Nucleic Acid. In another example, an ASO targeting mAnkle2 can comprise any of the sequences and/or modification patterns set forth in Table 15. In any of the above sequences, any "T" in the first 5 or last 5 nucleotides can be replaced with a "U."

III. Methods of Making Improved Tauopathy Models and Methods for Accelerating Tau Aggregation in a Tauopathy Model Methods of making the improved tauopathy models disclosed in detail elsewhere herein are also provided. Such methods can start with a preexisting tauopathy model (e.g., a transgenic cell, tissue, or animal comprising an exogenous human tau coding sequence). That is, such methods can be methods for accelerating or exacerbating tau aggregation in a preexisting tauopathy model (e.g., a tauopathy model non-human animal, a tauopathy model animal tissue, or a tauopathy model animal cell). For example, such methods can comprise introducing the one or more agents that reduce expression of one or more or all of BANF1, PPP2CA, and ANKLE2 into the preexisting tauopathy model cell(s), tissue, or animal (e.g., a non-human animal, an animal tissue, or a population of animal cells that comprises an exogenous human microtubule-associated protein tau coding sequence). Any of the tauopathy models discussed in more detail elsewhere herein can be used.

Various models of tauopathy have been developed. These include cellular/cell culture models (non-neuronal cell lines, neuronal cell lines such as PC12, SY5Y, and CN1.4 cells, primary neuronal cells), tissue models (e.g., brain slice cultures such as an organotypic brain slice culture), and whole animal transgenic models (e.g., *C. elegans*, *Drosophila*, zebrafish, or mouse). See, e.g., Hall et al. (2005) *Biochim. Biophys. Acta* 1739:224-239, Brandt et al. (2005) *Biochim. Biophys. Acta* 1739:331-354, and Lee et al. (2005) *Biochim. Biophys. Acta* 1739:251-259, each of which is herein incorporated by reference in its entirety for all purposes. Typically such models are transgenic models in which wild type or mutant human tau isoforms are overexpressed under the control of a variety of promoters to produce neurofibrillary pathology. The cell-based models have the advantage of greater accessibility to manipulation and flexibility, whereas the whole animal models (e.g., transgenic mouse models) are more complete and more directly relevant to human disease.

One specific tauopathy model is the PS19 (Tau P301S (Line PS19); PS19Tg; B6; C3-Tg(Prnp-MAPT*P301S) PS19Vle/J) mouse line. The genetic background of this strain is C57BL/6×C3H. PS19 transgenic mice express mutant human microtubule-associated protein tau, MAPT, driven by the mouse prion protein (Prnp) promoter. The transgene encodes the disease-associated P301S mutation and includes four microtubule-binding domains and one N-terminal insert (4R/1N). The transgene inserted at Chr3: 140354280-140603283 (Build GRCm38/mm10), causing a 249 Kb deletion that does not affect any known genes. See Goodwin et al. (2019) *Genome Res.* 29(3):494-505, herein incorporated by reference in its entirety for all purposes. Expression of the mutant human tau is fivefold higher than that of the endogenous mouse protein. See Yoshiyama et al. (2007) *Neuron* 53(3):337-351, herein incorporated by reference in its entirety for all purposes. PS19 mice develop neuronal loss and brain atrophy by eight months of age. They also develop widespread tau aggregates, known as neurofibrillary tangle-like inclusions, in the neocortex, amygdala, hippocampus, brain stem, and spinal cord. See Yoshiyama et al. (2007). Prior to the appearance of overt tau pathology by histological methods, the brains of these mice were shown to display tau seeding activity. That is, tau aggregates present in brain homogenate can elicit further tau aggregation, presumably via a prion-like mechanism. See Holmes (2014) *Proc. Natl. Acad. Sci. U.S.A.* 111(41):E4376-E4385, herein incorporated by reference in its entirety for all purposes.

Other such methods can comprise not only introducing the one or more agents that reduce expression of one or more or all of BANF1, PPP2CA, and ANKLE2 into a non-human animal, an animal tissue, or a population of animal cells but also introducing an exogenous microtubule-associated protein tau coding sequence (e.g., an exogenous human microtubule-associated protein tau coding sequence). Examples of such coding sequences are discussed in more detail elsewhere herein, such as in the section on improved tauopathy models. Any such sequences can be used.

The agent (and optionally the tau coding sequence) can be introduced by any known means. "Introducing" includes presenting to the cell or animal the agent (e.g., nucleic acid or protein) in such a manner that the sequence gains access to the interior of the cell(s) or cell(s) within the tissue or animal. The methods provided herein do not depend on a particular method for introducing an agent, only that the nucleic acid or protein gains access to the interior of a least one cell. Methods for introducing nucleic acids and proteins into various cell types are known and include, for example, stable transfection methods, transient transfection methods, and virus-mediated methods.

Molecules (e.g., Cas proteins or guide RNAs or RNAi agents or ASOs) introduced into the non-human animal or cell can be provided in compositions comprising a carrier increasing the stability of the introduced molecules (e.g., prolonging the period under given conditions of storage (e.g., $-20°$ C., $4°$ C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of molecule (e.g., a nucleic acid or protein) into a cell or non-human animal. Methods for introducing molecules into various cell types are known and include, for example, stable transfection methods, transient transfection methods, and virus-mediated methods.

Transfection protocols as well as protocols for introducing molecules (e.g., nucleic acids or proteins) into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. U.S.A.* 74 (4): 1590-4, and Kriegler, M (1991). Transfer and Expression: A Laboratory Manual. New York: W. H. Freeman and Company. pp. 96-97, each of which is herein incorporated by reference in its entirety for all purposes); dendrimers; or cationic polymers such as DEAE-dextran or polyethylenimine. Non-chemical methods include electroporation, sonoporation, and optical transfection. Particle-based transfection includes the use of a gene gun, or magnet-assisted transfection (Bertram (2006) *Current Pharmaceutical Biotechnology* 7, 277-28, herein incorporated by reference in its entirety for all purposes). Viral methods can also be used for transfection.

Introduction of molecules (e.g., nucleic acids or proteins) into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of molecules (e.g., nucleic acids or proteins) into a cell can also be accomplished by microinjection. Microinjection of an mRNA is preferably into the cytoplasm (e.g., to deliver mRNA directly to the translation machinery), while microinjection of a protein or a DNA encoding a protein is preferably into the nucleus. Alternatively, microinjection can be carried out by injection into both the nucleus and the cytoplasm: a needle can first be introduced into the nucleus and a first amount can be injected, and while removing the needle from the cell a second amount can be injected into the cytoplasm. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); Meyer et al. (2010) *Proc. Natl. Acad. Sci. U.S.A.* 107:15022-15026 and Meyer et al. (2012) *Proc. Natl. Acad. Sci. U.S.A.* 109:9354-9359, each of which is herein incorporated by reference in its entirety for all purposes.

Other methods for introducing molecules (e.g., nucleic acids or proteins) into a cell can include, for example, vector delivery, particle-mediated delivery, exosome-mediated delivery, lipid-nanoparticle-mediated delivery, cell-penetrating-peptide-mediated delivery, or implantable-device-mediated delivery. Methods of administering nucleic acids or proteins to a subject to modify cells in vivo are disclosed elsewhere herein. As specific examples, a molecule (e.g., nucleic acid or protein) can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

In one example, the agent (and optionally the tau coding sequence) can be introduced via viral transduction such as lentiviral transduction or adeno-associated viral transduction.

In some methods, components of a CRISPR/Cas system are introduced into a non-human animal or cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Introduction of nuclease agents can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include about $10^{12}$, about $10^{13}$, about $10^{14}$, about $10^{15}$, and about $10^{16}$ vector genomes/mL. Other exemplary viral titers (e.g., AAV titers) include about $10^{12}$, about $10^{13}$, about $10^{14}$, about $10^{15}$, and about $10^{16}$ vector genomes(vg)/kg of body weight.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8. Selectivity of AAV serotypes for gene delivery in neurons is discussed, for example, in Hammond et al. (2017) *PLoS One* 12(12):e0188830, herein incorporated by reference in its entirety for all purposes.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods can result in transient Cas expression, and the biodegradable lipids can improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, S024, S027, S031, or S033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) Cell Rep. 22(9):2227-2235 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. See, e.g., Finn et al. (2018) Cell Rep. 22(9):2227-2235 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino) propoxy)carbonyl)oxy)hexadecanoyl)oxy)propane-1,3-diyl (9Z,9'Z,12Z,12'Z)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl 4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-distearoylglycerol (PEG-DSPE), PEG-dilaurylglycamide, PEG-dimyristylglycamide, PEG-dipalmitoylglycamide, and PEG-distearoylglycamide, PEG-cholesterol (1-[8'-(Cholest-5-en-3 [beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

A specific example of using LNPs to deliver to the brain is disclosed in Nabhan et al. (2016) *Sci. Rep.* 6:20019, herein incorporated by reference in its entirety for all purposes.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyrus, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically. In a specific example, administration to an animal is by intrathecal injection or by intracranial injection (e.g., stereotactic surgery for injection in the hippocampus and other brain regions, or intracerebroventricular injection).

The frequency of administration and the number of dosages can depend on the half-life of the agent and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

Such methods can further comprise screening the cells, tissues, or animals to confirm the presence of the one or more agents (and optionally the tau coding sequence). Screening for cells, tissues, or animals comprising the agent (and optionally the tau coding sequence) can be performed by any known means.

As one example, reporter genes can be used to screen for cells that have the agent (or optionally the tau coding sequence). For example, the tau coding sequence can encode a tau protein fused to a reporter gene such as a fluorescent protein. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. For example, if the first reporter and the second reporter are fluorescent proteins (e.g., CFP and YFP), cells comprising these reporters can be selected by flow cytometry to select for dual-positive cells. The dual-positive cells can then be combined to generate a polyclonal line, or monoclonal lines can be generated from single dual-positive cells.

As another example, selection markers can be used to screen for cells that have the agent (or optionally the tau coding sequence). Exemplary selection markers include neomycin phosphotransferase ($neo^r$), hygromycin B phosphotransferase ($hyg^r$), puromycin-N-acetyltransferase (puror), blasticidin S deaminase (bsrr), xanthine/guanine phosphoribosyl transferase (gpt), or herpes simplex virus thymidine kinase (HSV-k).

The cells or tissues can then be seeded with tau aggregates by any suitable means. This can be done, for example, after about 1 day, about 2 days, about 3 days, about 4 days, about 5 days, about 6 days, about 1 week, about 2 weeks, or about 3 weeks in culture (e.g., about 1 week in culture) following introducing the one or more agents (and optionally the tau coding sequence). Alternatively, the cells or tissues can be seeded with tau aggregates prior to introducing the one or more agents (and optionally the tau coding sequence). For example, the cells or tissue can be treated with recombinant fibrillized tau (e.g., recombinant fibrillized tau repeat domain) to seed the aggregation of the tau repeat domain protein stably expressed by these cells. Tau cell-to-cell propagation may also result from tau aggregation activity secreted by aggregate-containing cells. For example, the cells or tissue can be cultured using conditioned medium harvested from cultured tau-aggregation-positive cells in which a tau repeat domain stably presents in an aggregated state. Conditioned medium refers to spent medium harvested from cultured cells. It contains metabolites, growth factors, and extracellular matrix proteins secreted into the medium by the cultured cells. As one example, conditioned medium can be generated by collecting medium that has been on confluent tau-aggregation-positive Agg[+] cells. The medium can have been on the confluent Agg[+] cells for about 12 hours, about 24 hours, about 2 days, about 3 days, about 4 days, about 5 days, about 6 days, about 7 days, about 8 days, about 9 days, or about 10 days. For example, the medium can have been on the confluent Agg[+] cells for about 1 to about 7, about 2 to about 6, about 3 to about 5, or about 4 days. Conditioned medium can then be applied to cells or tissue in combination with fresh medium. The ratio of conditioned medium to fresh medium can be, for example, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10. For example, the ratio of conditioned medium of fresh medium can be from about 5:1 to about 1:1, about 4:1 to about 2:1, or about 3:1. For example, it can comprise culturing the genetically modified population of cells in about 90% conditioned medium and about 10% fresh medium, about 85% conditioned medium and about 15% fresh medium, about 80% conditioned medium and about 20% fresh medium, about 75% conditioned medium and about 25% fresh medium, about 70% conditioned medium and about 30% fresh medium, about 65% conditioned medium and about 35% fresh medium, about 60% conditioned medium and about 40% fresh medium, about 55% conditioned medium and about 45% fresh medium, about 50% conditioned medium and about 50% fresh medium, about 45% conditioned medium and about 55% fresh medium, about 40% conditioned medium and about 60% fresh medium, about 35% conditioned medium and about 65% fresh medium, about 30% conditioned medium and about 70% fresh medium, about 25% conditioned medium and about 75% fresh medium, about 20% conditioned medium and about 80% fresh medium, about 15% conditioned medium and about 85% fresh medium, or about 10% conditioned medium and about 90% fresh medium. In one example, it can comprise culturing the genetically modified population of cells in a medium that comprises at least about 50% conditioned medium and no more than about 50% fresh medium. In a specific example, it can comprise culturing the genetically modified population of cells in about 75% conditioned medium and about 25% fresh medium.

The conditioned medium can be used without co-culturing. Conditioned medium without co-culturing has not been used in this context as a seeding agent before. However, conditioned medium is particularly useful for large-scale genome-wide screens because tau fibrils produced in vitro are a limited resource. In addition, conditioned medium is more physiologically relevant because it is produced by cells rather than in vitro. Use of conditioned medium as described herein provides a boost of tau seeding activity (e.g., ~0.1% as measured by FRET induction as disclosed elsewhere herein) to sensitize cells to tau aggregation.

One or more signs or symptoms of tauopathy can then be assessed by any suitable means. Examples of such signs and symptoms are discussed in more detail elsewhere herein and include, for example, tau hyperphosphorylation or tau aggregation. Other signs and symptoms can include, for example, increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, or decreased Ran GTPase-activating protein 1 (RanGAP1) nuclear-to-cytoplasmic ratio in neurons. The phospho-tau can be, for example, phospho-tau (S356) or phospho-tau AT8 (5202, T205). This can be done, for example, about 1 week, about 2 weeks, about 3 weeks, about 4 weeks, about 5 weeks, about 6 weeks, or longer after tau seeding or after introducing the one or more agents (and optionally the tau coding sequence). For example, the assessing can be done about 2 weeks to about 6 weeks or about 3 weeks to about 5 weeks after tau seeding or after introducing the one or more agents (and optionally the tau coding sequence).

IV. Methods of Testing Candidate Tauopathy Therapeutic Agents

Various methods are provided for identifying or assessing therapeutic candidates for the treatment of a tauopathy using the improved tauopathy models disclosed in detail elsewhere herein. Such methods can comprise, for example, administering a candidate agent to an improved tauopathy model as disclosed elsewhere herein (e.g., an animal, tissue, or cell as disclosed elsewhere herein), performing one or more assays to determine if the candidate agent has an effect on one or more signs or symptoms associated with the tauopathy, and identifying the candidate agent as a therapeutic candidate if it has an effect on the one or more signs or symptoms associated with the tauopathy.

Any candidate agent can be tested. Such candidates could comprise, for example, large molecules such as siRNAs, antibodies, or CRISPR/Cas gRNAs) or small molecules. The candidate agent can be administered to the non-human animal or non-human animal cell by any means by any suitable route.

Any assay that measure a sign or symptom associated with a tauopathy can be used. Examples of such signs and symptoms are disclosed elsewhere herein. As a first example, the sign or symptom can be tau hyperphosphorylation (e.g., AT8 staining as set forth in the examples). As a second example, the sign or symptom can be tau aggregation (e.g., thioflavin S staining as set forth in the examples). Other signs and symptoms can include, for example, increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, or decreased Ran GTPase-activating protein 1 (RanGAP1) nuclear-to-cytoplasmic ratio in neurons. The phospho-tau can be, for example, phospho-tau (S356) or phospho-tau AT8 (5202, T205).

The candidate agent can be administered in vivo to an animal, and the one or more assays can be performed in the animal. Alternatively, the candidate agent can be administered in vivo to the animal, and the one or more assays can be performed in vitro in cells isolated from the animal after administration of the candidate agent. Alternatively, the candidate agent can be administered in vitro to cells (e.g., neurons) or ex vivo to tissue (e.g., brain slices such as an organotypic brain slice culture), and the assays can be performed in vitro in the cells or ex vivo in the tissues.

Optionally, the cell or tissues can be seeded with tau aggregates by any suitable means before or after administering the candidate agent. For example, the cells or tissue can be treated with recombinant fibrillized tau (e.g., recombinant fibrillized tau repeat domain) to seed the aggregation of the tau repeat domain protein stably expressed by these cells. Tau cell-to-cell propagation may also result from tau aggregation activity secreted by aggregate-containing cells. For example, the cells or tissue can be cultured using conditioned medium harvested from cultured tau-aggregation-positive cells in which a tau repeat domain stably presents in an aggregated state. Conditioned medium refers to spent medium harvested from cultured cells. It contains metabolites, growth factors, and extracellular matrix proteins secreted into the medium by the cultured cells. As one example, conditioned medium can be generated by collecting medium that has been on confluent tau-aggregation-positive Agg[+] cells. The medium can have been on the confluent Agg[+] cells for about 12 hours, about 24 hours, about 2 days, about 3 days, about 4 days, about 5 days, about 6 days, about 7 days, about 8 days, about 9 days, or about 10 days. For example, the medium can have been on the confluent Agg[+] cells for about 1 to about 7, about 2 to about 6, about 3 to about 5, or about 4 days. Conditioned medium can then be applied to cells or tissue in combination with fresh medium. The ratio of conditioned medium to fresh medium can be, for example, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10. For example, the ratio of conditioned medium of fresh medium can be from about 5:1 to about 1:1, about 4:1 to about 2:1, or about 3:1. For example, it can comprise culturing the genetically modified population of cells in about 90% conditioned medium and about 10% fresh medium, about 85% conditioned medium and about 15% fresh medium, about 80% conditioned medium and about 20% fresh medium, about 75% conditioned medium and about 25% fresh medium, about 70% conditioned medium and about 30% fresh medium, about 65% conditioned medium and about 35% fresh medium, about 60% conditioned medium and about 40% fresh medium, about 55% conditioned medium and about 45% fresh medium, about 50% conditioned medium and about 50% fresh medium, about 45% conditioned medium and about 55% fresh medium, about 40% conditioned medium and about 60% fresh medium, about 35% conditioned medium and about 65% fresh medium, about 30% conditioned medium and about 70% fresh medium, about 25% conditioned medium and about 75% fresh medium, about 20% conditioned medium and about 80% fresh medium, about 15% conditioned medium and about 85% fresh medium, or about 10% conditioned medium and about 90% fresh medium. In one example, it can comprise culturing the genetically modified population of cells in a medium that comprises at least about 50% conditioned medium and no more than about 50% fresh medium. In a specific example, it can comprise culturing the genetically modified population of cells in about 75% conditioned medium and about 25% fresh medium.

The one or more signs or symptoms of tauopathy can then be assessed by any suitable means at any suitable time after seeding or after administering the candidate agent. This can be done, for example, about 1 week, about 2 weeks, about 3 weeks, about 4 weeks, about 5 weeks, about 6 weeks, or longer after tau seeding or after administering the candidate agent. For example, the assessing can be done about 2 weeks to about 6 weeks or about 3 weeks to about 5 weeks after tau seeding or after administering the candidate agent.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | DNA | Human BANF1 g1 Target Sequence |
| 2 | DNA | Human BANF1 g2 Target Sequence |
| 3 | DNA | Human BANF1 g3 Target Sequence |
| 4 | DNA | Human BANF1 g6 Target Sequence |
| 5 | DNA | Human PPP2CA g5 Target Sequence |
| 6 | DNA | Human PPP2CA g6 Target Sequence |
| 7 | DNA | Non-Targeted g1 Target Sequence (NT_0069) |
| 8 | DNA | Non-Targeted g3 Target Sequence (NT_0303) |
| 9 | DNA | Human VRK1 g3 Target Sequence |
| 10 | DNA | Human CDK5 g1 Target Sequence |
| 11 | DNA | Human PPP2R2A g1 Target Sequence |
| 12 | DNA | Human ANKLE2 g3 Target Sequence |
| 13 | DNA | Human EMD g2 Target Sequence |
| 14 | DNA | Human LEMD2 g3 Target Sequence |
| 15 | DNA | Human LEMD3 g1 Target Sequence |
| 16 | DNA | Human TMPO g5 Target Sequence |
| 17 | DNA | Non-Targeted NT_0071 Target Sequence |
| 18 | DNA | Mouse Banf1 g1 Target Sequence |
| 19 | DNA | Mouse Banf1 g2 Target Sequence |
| 20 | DNA | Mouse Banf1 g3 Target Sequence |
| 21 | DNA | Mouse Ppp2ca g1 Target Sequence |
| 22 | DNA | Mouse Ppp2ca g2 Target Sequence |
| 23 | DNA | Mouse Ppp2ca g3 Target Sequence |
| 24 | DNA | Mouse Ankle2 g1 Target Sequence |
| 25 | DNA | Mouse Ankle2 g2 Target Sequence |
| 26 | DNA | Mouse Ankle2 g3 Target Sequence |
| 27 | RNA | Human BANF1 g1 DNA-Targeting Segment |
| 28 | RNA | Human BANF1 g2 DNA-Targeting Segment |
| 29 | RNA | Human BANF1 g3 DNA-Targeting Segment |
| 30 | RNA | Human BANF1 g6 DNA-Targeting Segment |
| 31 | RNA | Human PPP2CA g5 DNA-Targeting Segment |
| 32 | RNA | Human PPP2CA g6 DNA-Targeting Segment |
| 33 | RNA | Non-Targeted g1 DNA-Targeting Segment (NT_0069) |
| 34 | RNA | Non-Targeted g3 DNA-Targeting Segment (NT_0303) |
| 35 | RNA | Human VRK1 g3 DNA-Targeting Segment |
| 36 | RNA | Human CDK5 g1 DNA-Targeting Segment |
| 37 | RNA | Human PPP2R2A g1 DNA-Targeting Segment |
| 38 | RNA | Human ANKLE2 g3 DNA-Targeting Segment |
| 39 | RNA | Human EMD g2 DNA-Targeting Segment |
| 40 | RNA | Human LEMD2 g3 DNA-Targeting Segment |
| 41 | RNA | Human LEMD3 g1 DNA-Targeting Segment |
| 42 | RNA | Human TMPO g5 DNA-Targeting Segment |
| 43 | RNA | Non-Targeted NT_0071 DNA-Targeting Segment |
| 44 | RNA | Mouse Banf1 g1 DNA-Targeting Segment |
| 45 | RNA | Mouse Banf1 g2 DNA-Targeting Segment |
| 46 | RNA | Mouse Banf1 g3 DNA-Targeting Segment |
| 47 | RNA | Mouse Ppp2ca g1 DNA-Targeting Segment |
| 48 | RNA | Mouse Ppp2ca g2 DNA-Targeting Segment |
| 49 | RNA | Mouse Ppp2ca g3 DNA-Targeting Segment |
| 50 | RNA | Mouse Ankle2 g1 DNA-Targeting Segment |
| 51 | RNA | Mouse Ankle2 g2 DNA-Targeting Segment |
| 52 | RNA | Mouse Ankle2 g3 DNA-Targeting Segment |
| 53 | DNA | hTau_huopt_WT Fwd Primer |
| 54 | DNA | hTau_huopt_WT Rev Primer |
| 55 | DNA | hTau_huopt_WT Probe |
| 56 | DNA | hTau_huopt_MUT Fwd Primer |
| 57 | DNA | hTau_huopt_MUT Rev Primer |
| 58 | DNA | hTau_huopt_MUT Probe |
| 59 | DNA | hTau_msopt_WT Fwd Primer |
| 60 | DNA | hTau_msopt_WT Rev Primer |
| 61 | DNA | hTau_msopt_WT Probe |
| 62 | DNA | hTau_msopt_MUT Fwd Primer |
| 63 | DNA | hTau_msopt_MUT Rev Primer |
| 64 | DNA | hTau_msopt_MUT Probe |
| 65 | RNA | crRNA Tail |
| 66 | RNA | TracrRNA |
| 67 | RNA | Guide RNA Scaffold V1 |
| 68 | RNA | Guide RNA Scaffold V2 |
| 69 | RNA | Guide RNA Scaffold V3 |
| 70 | RNA | Guide RNA Scaffold V4 |
| 71 | DNA | Guide RNA Target Sequence Plus PAM V1 |
| 72 | DNA | Guide RNA Target Sequence Plus PAM V2 |
| 73 | DNA | Guide RNA Target Sequence Plus PAM V3 |
| 74 | DNA | pSynapsin1-GFP |
| 75 | DNA | pSynapsin1-hTAU WT |
| 76 | DNA | pSynapsin1-hTAU WT-GFP |
| 77 | DNA | pSynapsin1-GFP-hTAU WT |
| 78 | DNA | pSynapsin1-hTAU 3MUT (A152T, P301L, S320F) |
| 79 | DNA | pSynapsin1-hTAU 3MUT (A152T, P301L, S320F)-GFP |
| 80 | DNA | pSynapsin1-GFP-hTAU 3MUT (A152T, P301L, S320F) |
| 81 | DNA | hTau-412 (1NR4) WT DNA |
| 82 | Protein | hTau-412 (1NR4) WT Protein |
| 83 | DNA | hTau-412 (1NR4) 3MUT DNA |
| 84 | Protein | hTau-412 (1NR4) 3MUT Protein |
| 85 | DNA | pLentiCRISPRv2 |
| 86 | DNA | Cas9 DNA |
| 87 | Protein | Cas9 Protein |
| 88 | Protein | Tau R1 Repeat Domain |
| 89 | Protein | Tau R2 Repeat Domain |
| 90 | Protein | Tau R3 Repeat Domain |
| 91 | Protein | Tau R4 Repeat Domain |
| 92 | DNA | Tau R1 Repeat Domain Coding Sequence |
| 93 | DNA | Tau R2 Repeat Domain Coding Sequence |
| 94 | DNA | Tau R3 Repeat Domain Coding Sequence |
| 95 | DNA | Tau R4 Repeat Domain Coding Sequence |
| 96 | Protein | Tau Four-Repeat Domain (R1-R4; amino acids 243-375 of full-length (P10636-8) Tau) |
| 97 | DNA | Coding Sequence for Tau Four-Repeat Domain (R1-R4; coding sequence for amino acids 243-375 of full-length (P10636-8) Tau) |
| 98 | Protein | Tau Four-Repeat Domain (R1-R4) with P301S Mutation |
| 99 | DNA | Coding Sequence for Tau Four-Repeat Domain (R1-R4) with P301S Mutation |
| 100 | RNA | TracrRNA V2 |
| 101 | RNA | TracrRNA V3 |
| 102 | RNA | Guide RNA Scaffold V5 |
| 103 | RNA | Guide RNA Scaffold V6 |
| 104 | RNA | Guide RNA Scaffold V7 |
| 105-126 | DNA | mBanf1 ASOs |
| 127-168 | DNA | mPpp2ca ASOs |
| 169-214 | DNA | mAnkle2 ASOs |
| 215-236 | RNA | mBanf1 Parent Antisense RNA Sequences |
| 237-278 | RNA | mPpp2ca Parent Antisense RNA Sequences |
| 279-324 | RNA | mAnkle2 Parent Antisense RNA Sequences |

EXAMPLES

Example 1. Development of Genome-Wide CRISPR/Cas9 Screening Platform to Identify Genetic Modifiers of Tau Aggregation Abnormal aggregation or fibrillization of proteins is a defining feature of many diseases, notably including a number of neurodegenerative diseases such as Alzheimer's disease (AD), Parkinson's disease (PD), frontotemporal dementia (FTD), amyotrophic lateral sclerosis (ALS), chronic traumatic encephalopathy (CTE), Creutzfeldt-Jakob disease (CJD), and others. In many of these diseases, the fibrillization of certain proteins into insoluble aggregates is not only a hallmark of disease, but has also been implicated as a causative factor of neurotoxicity. Furthermore, these diseases are characterized by propagation of aggregate pathology through the central nervous system following stereotypical patterns, a process which correlates with disease progression. The identification of genes and genetic pathways that modify the processes of abnormal protein aggregation, or cell-to-cell propagation of aggregates, are therefore of great value in better understanding neurodegenerative disease etiology as well as in devising strategies for therapeutic intervention.

To identify genes and pathways that modify the processes of abnormal tau protein aggregation, a platform was developed for performing genome-wide screens with CRISPR nuclease (CRISPRn) sgRNA libraries to identify genes that regulate the potential of cells to be "seeded" by tau disease-associated protein aggregates (i.e. genes which, when disrupted, cause cells to be more susceptible to tau aggregate formation when exposed to a source of tau fibrillized protein). The identification of such genes may elucidate the mechanisms of tau cell-to-cell aggregate propagation and genetic pathways that govern the susceptibility of neurons to form tau aggregates in the context of neurodegenerative diseases.

Figure 2:
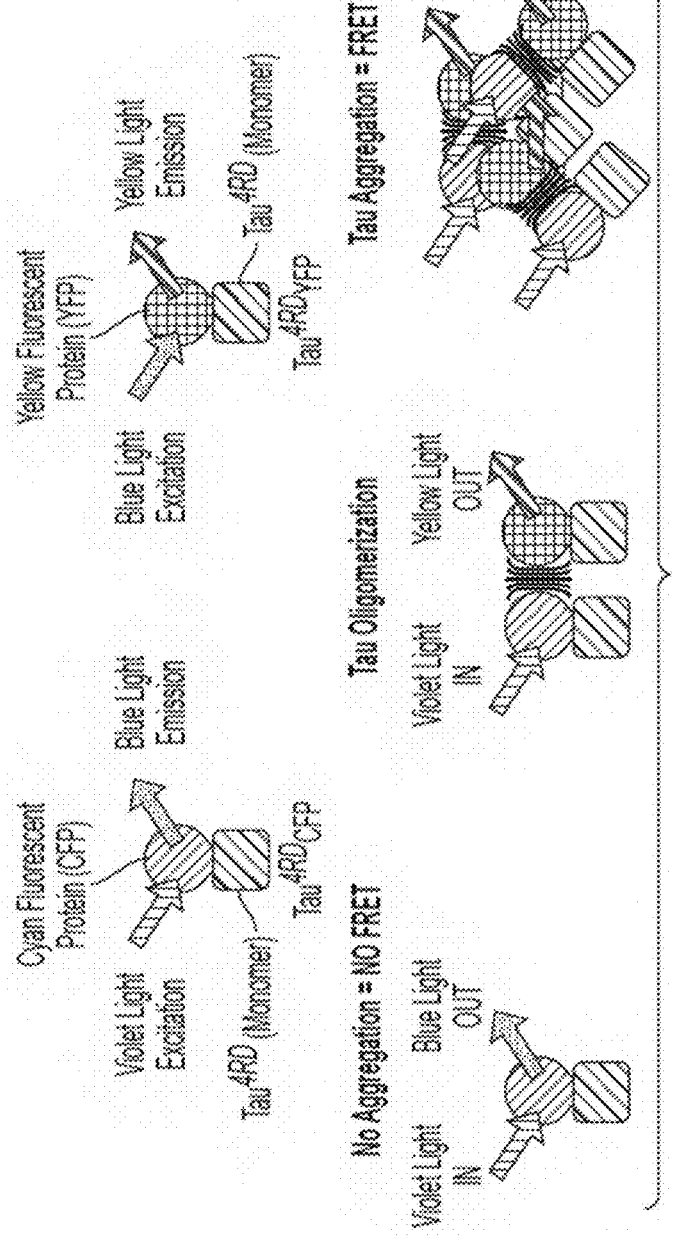
FIG. 2 shows a schematic of how aggregate formation is monitored by fluorescence resonance energy transfer (FRET) in tau biosensor cell lines. The tau$^{4RD}$-CFP protein is excited by violet light and emit blue light. The tau$^{4RD}$-YFP fusion protein is excited by blue light and emits yellow light. If there is no aggregation, excitation by violet light will not lead to FRET. If there is tau aggregation, excitation by violet light will lead to FRET and yellow light emission.

The screen employed a tau biosensor human cell line consisting of HEK293T cells stably expressing tau four-repeat domain, tau_4RD, comprising the tau microtubule binding domain (MBD) with the P301S pathogenic mutation, fused to either CFP or YFP. That is, the HEK293T cell lines contain two transgenes stably expressing disease-associated protein variants fused to the fluorescent protein CFP or the fluorescent protein YFP: $tau^{4RD}$-CFP/$tau^{4RD}$-YFP (TCY), wherein the tau repeat domain (4RD) comprises the P301S pathogenic mutation. See FIG. 1. In these biosensor lines, tau-CFP/tau-YFP protein aggregation produces a FRET signal, the result of a transfer of fluorescent energy from donor CFP to acceptor YFP. See FIG. 2. FRET-positive cells, which contain tau aggregates, can be sorted and isolated by flow cytometry. At baseline, unstimulated cells express the reporters in a stable, soluble state with minimal FRET signal. Upon stimulation (e.g., liposome transfection of seed particles), the reporter proteins form aggregates, producing a FRET signal. Aggregate-containing cells can be isolated by FACS. Stably propagating aggregate-containing cell lines, Agg[+], can be isolated by clonal serial dilution of Agg[−] cell lines.

Figure 3A:
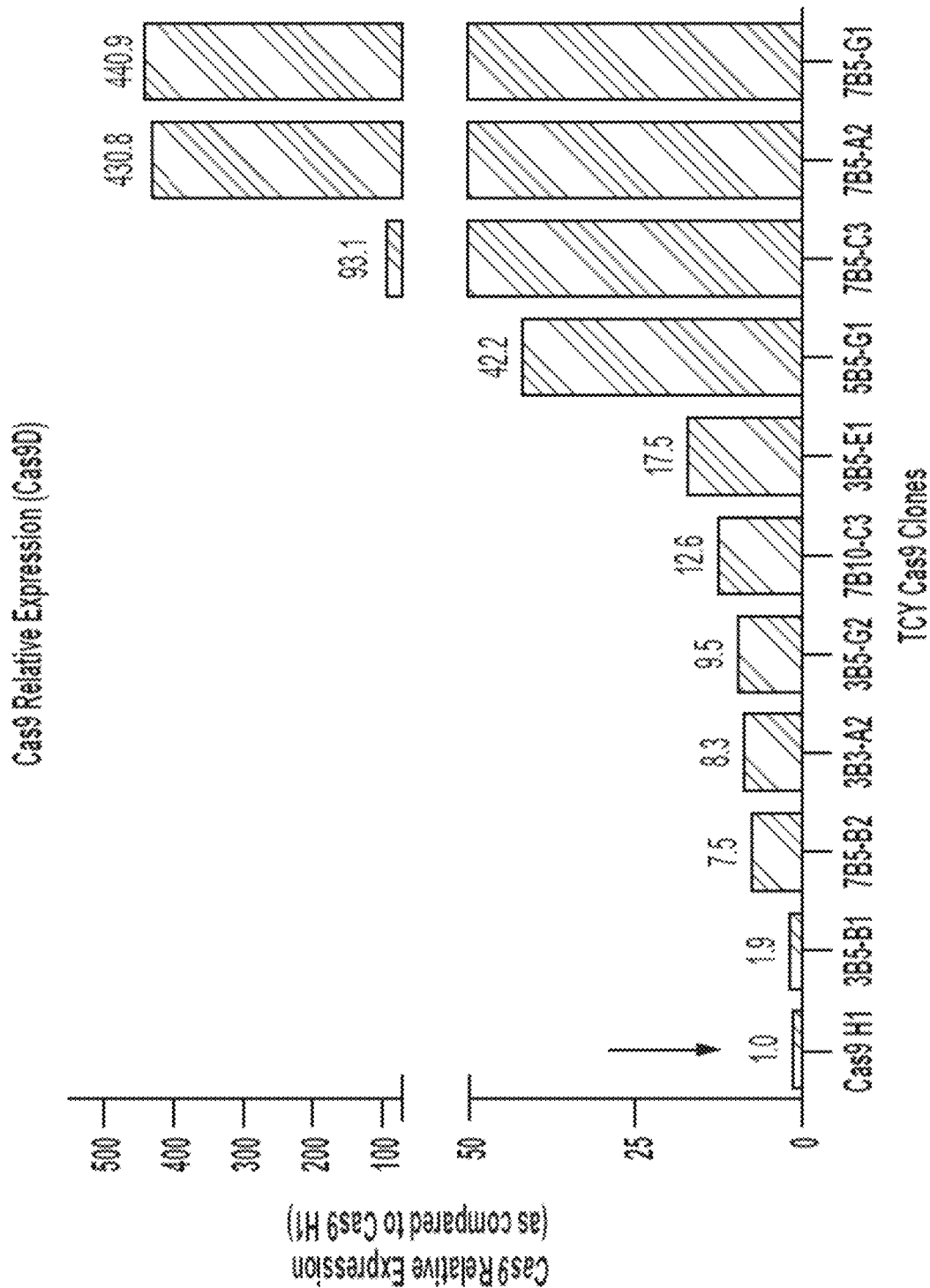
FIG. 3A shows relative Cas9 mRNA expression in tau$^{4RD}$-CFP/tau$^{4RD}$-YFP (TCY) biosensor cell clones transduced with lentiviral Cas9 expression constructs relative to clone Cas9H1, which is a control underperforming Cas9-expression TCY clone that was previously isolated.
Figure 3B:
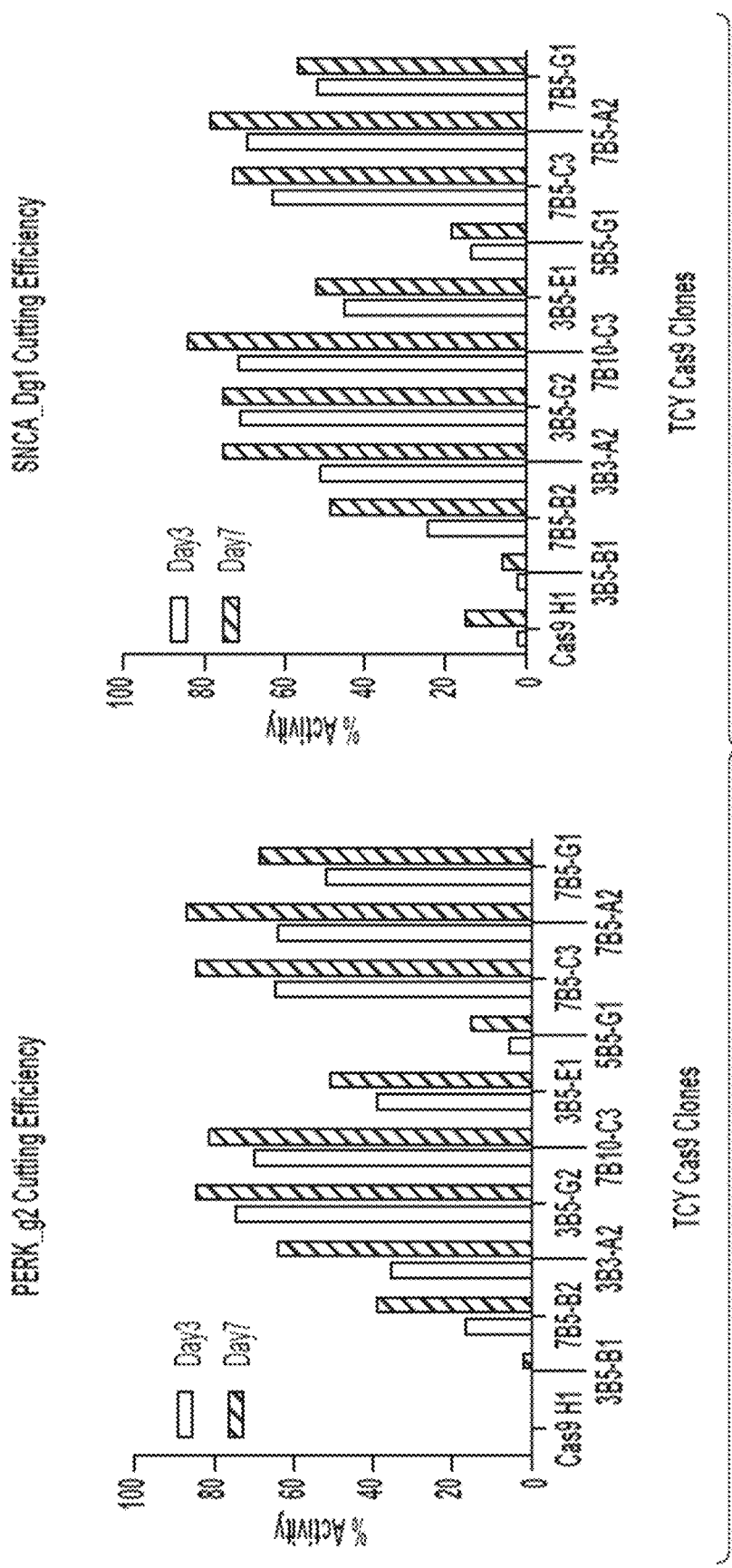
FIG. 3B shows cutting efficiency at the PERK locus and the SNCA locus in the Cas9 TCY clones three and seven days after transduction with sgRNAs targeting PERK and SNCA respectively.

Several modifications were made to this tau biosensor cell line to make it useful for genetic screening. First, these tau biosensor cells were modified by introducing a Cas9-expressing transgene (SpCas9) via a lentiviral vector. Clonal transgenic cell lines expressing Cas9 were selected with blasticidin and isolated by clonal serial dilution to obtain single-cell-derived clones. Clones were evaluated for level of Cas9 expression by qRT-PCR (FIG. 3A) and for DNA cleavage activity by digital PCR (FIG. 3B). Relative Cas9 expression levels are also shown in Table 3.

TABLE 3

Relative Cas9 Expression Levels.

| Clone Name | Cas9D Ct | | | | Cas9D AVG Ct | B2m AVG Ct | Cas9D − B2m delta Ct |
| --- | --- | --- | --- | --- | --- | --- | --- |
| | rep1 | rep2 | rep3 | rep4 | | | |
| 3B5-B1 | 26.22 | 26.31 | 26.36 | 26.45 | 26.33 | 22.01 | 4.33 |
| 3B5-G2 | 23.68 | 23.85 | 24.39 | 23.61 | 23.88 | 21.51 | 2.38 |
| 7B5-B2 | 23.63 | 23.60 | 24.12 | 23.50 | 23.71 | 21.38 | 2.34 |
| 3B3-A2 | 24.05 | 23.95 | 24.02 | 24.47 | 24.12 | 21.94 | 2.19 |
| 7B10-C3 | 22.58 | 22.71 | 22.67 | 23.20 | 22.79 | 21.19 | 1.59 |
| 3B5-E1 | 24.12 | 24.32 | 24.75 | 24.05 | 24.31 | 22.81 | 1.50 |
| 3B5-G1 | 21.16 | 21.14 | 21.09 | 21.43 | 21.20 | 21.35 | −0.15 |
| 7B5-C3 | 19.98 | 19.99 | 19.86 | 19.97 | 19.95 | 21.24 | −1.29 |
| 7B5-A2 | 18.84 | 18.74 | 19.33 | 18.99 | 18.97 | 22.10 | −3.12 |
| 7B5-G1 | 19.01 | 18.88 | 19.61 | 19.18 | 19.17 | 22.33 | −3.16 |

Specifically, Cas9 mutation efficiency was assessed by digital PCR 3 and 7 days after transduction of lentiviruses encoding gRNAs against two selected target genes. Cutting efficiency was limited by Cas9 levels in lower-expressing clones. A clone with an adequate level of Cas9 expression was needed to achieve maximum activity. Several derived clones with lower Cas9 expression were not able to cut target sequences efficiently, whereas clones with higher expression (including those used for screening) were able to generate mutations at target sequences in the genes PERK and SNCA with approximately 80% efficiency after three days in culture. Efficient cutting was observed already at 3 days after gRNA transduction with only marginal improvement after 7 days. Clone 7B10-C3 was selected as a high-performing clone to use for subsequent library screens.

Figure 5:
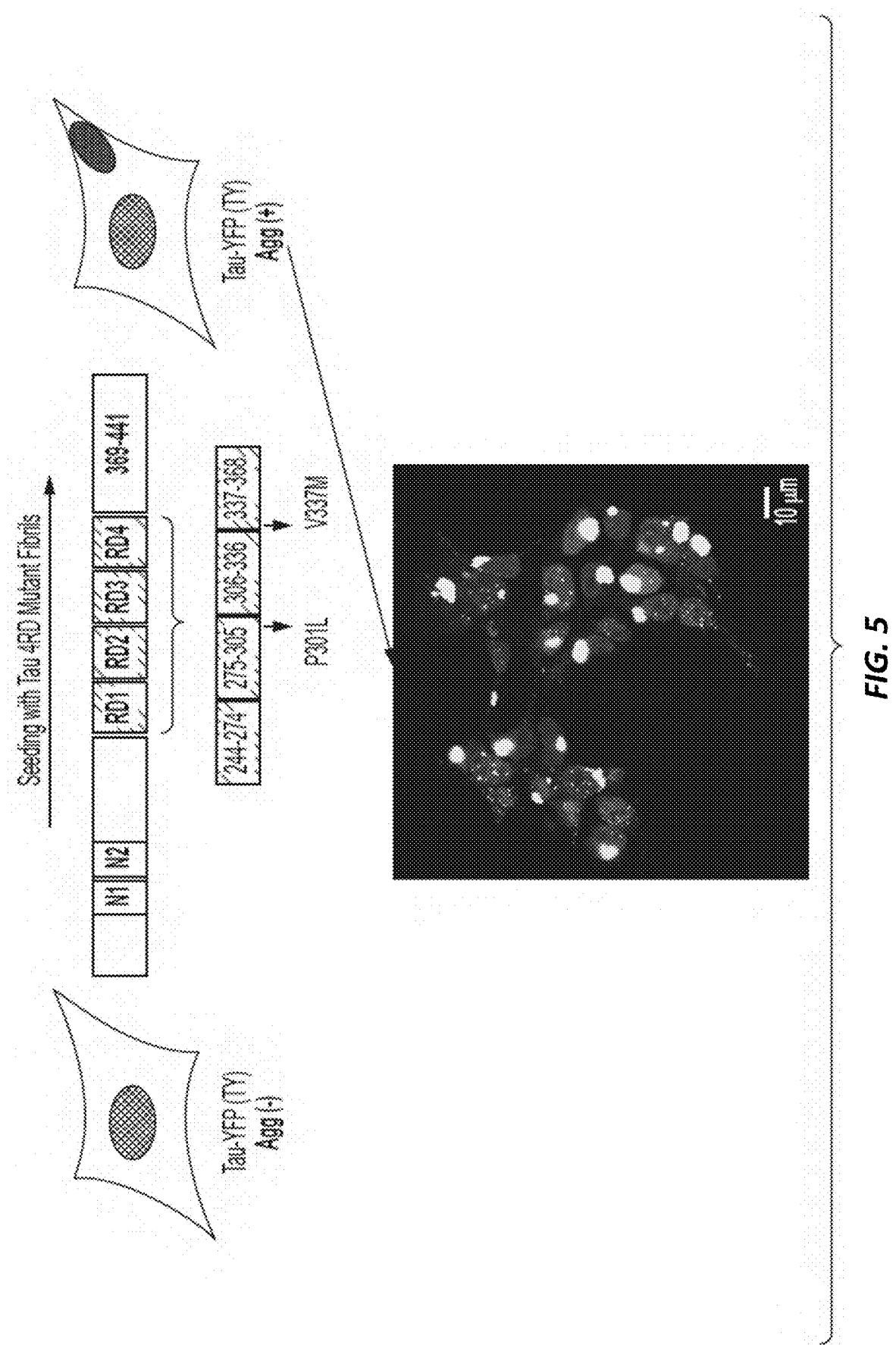
FIG. 5 is a schematic showing derivation of tau$^{4RD}$-YFP Agg[+] subclones containing stably propagating tau aggregates when tau$^{4RD}$-YFP cells are seeded with tau$^{4RD}$ fibrils. A fluorescence microscopy image showing the subclone with tau aggregates is also shown.
Figure 6:
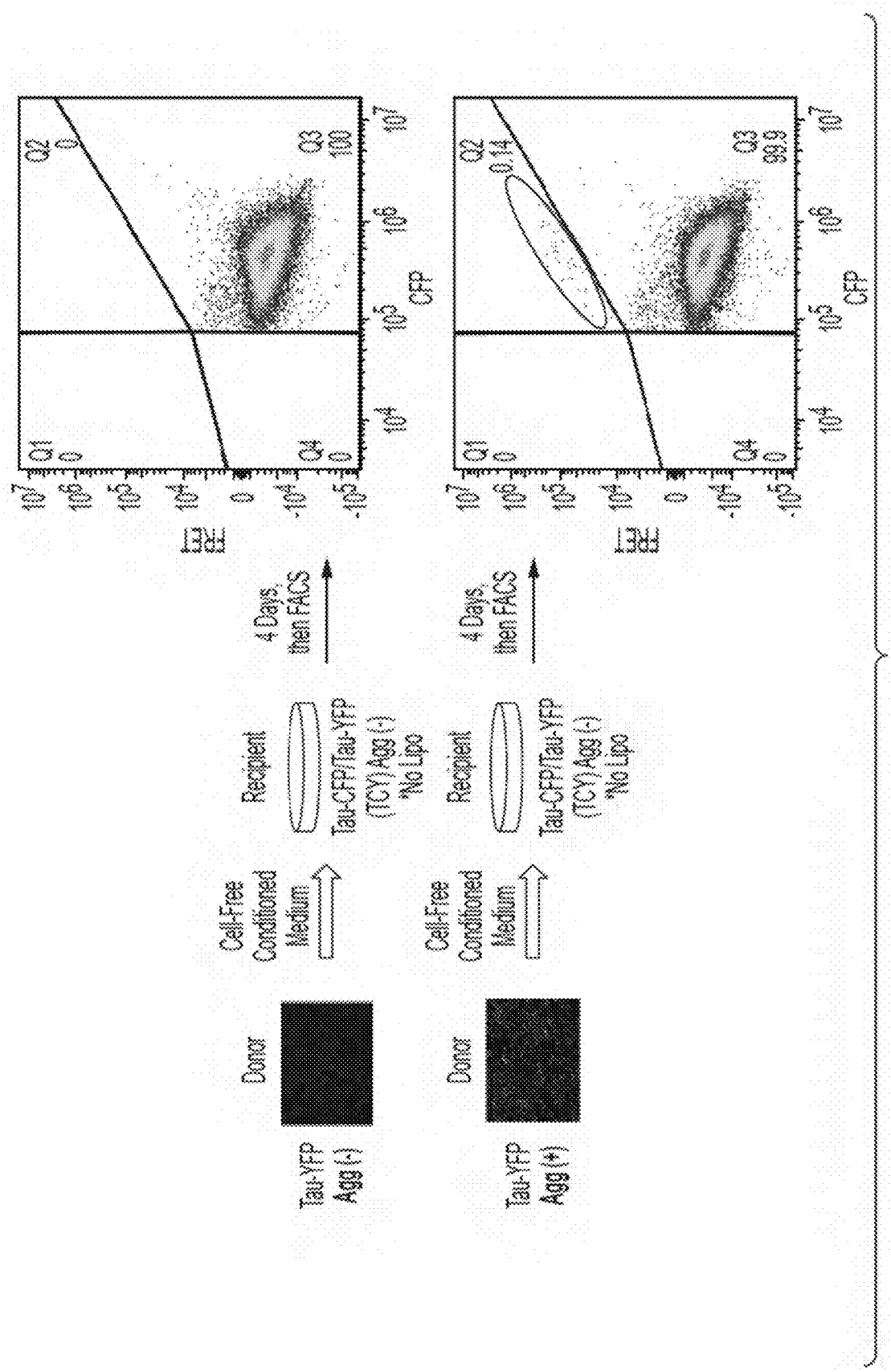
FIG. 6 is a schematic showing that conditioned medium from tau$^{4RD}$-YFP Agg[+] subclones collected after three days on confluent cells can provide a source of tau aggregation activity whereas medium from tau$^{4RD}$-YFP Agg[−] subclones does not. Conditioned medium was applied to recipient cells as 75% conditioned medium and 25% fresh medium. Fluorescence-activated cell sorting (FACS) analysis images are shown for each. The x-axis shows CFP (405 nm laser excitation), and the y-axis shows FRET (excitation from CFP emission). The upper right quadrant is FRET[+], the lower right quadrant is CFP[+], and the lower left quadrant is double-negative.

Second, reagents and a method were developed for sensitizing cells to tau seeding activity. Tau cell-to-cell propagation may result from tau aggregation activity secreted by aggregate-containing cells. To study cell propagation of tau aggregation, sub-clones were obtained of a tau-YFP cell line consisting of HEK293T cells stably expressing tau repeat domain, tau_4RD, comprising the tau microtubule binding domain (MBD) with the P301S pathogenic mutation, fused to YFP. See FIG. 5. Cells in which tau-YFP protein stably presents in an aggregated state (Agg[+]) were obtained by treating these tau-YFP cells with recombinant fibrillized tau mixed with lipofectamine reagent in order to seed the aggregation of the tau-YFP protein stably expressed by these cells. The "seeded" cells were then serially diluted to obtain single-cell-derived clones. These clones were then expanded to identify clonal cell lines in which tau-YFP aggregates stably persist in all cells with growth and multiple passages over time. One of these tau-YFP_Agg[+] clones, Clone_18, was used to produce conditioned medium by collecting medium that has been on confluent tau-YFP_Agg[+] cells for four days. Conditioned medium (CM) was then applied onto naïve biosensor tau-CFP/Tau-YFP cells at a ratio of 3:1 CM:fresh medium so that tau aggregation could be induced in a small percentage of these recipient cells. No lipofectamine was used. Lipofectamine was not used in order to have an assay that is as physiologic as possible, without tricking the recipient cells to force/increase tau aggregation using lipofectamine. As measured by using flow cytometry to assess the percentage of cells producing a FRET signal as a measure of aggregation, conditioned medium consistently induced FRET in approximately 0.1% of cells. See FIG. 6. In conclusion, tau-YFP_Agg[+] cells cannot produce a FRET signal, but they can provide a source of tau seeds.

Figure 4:
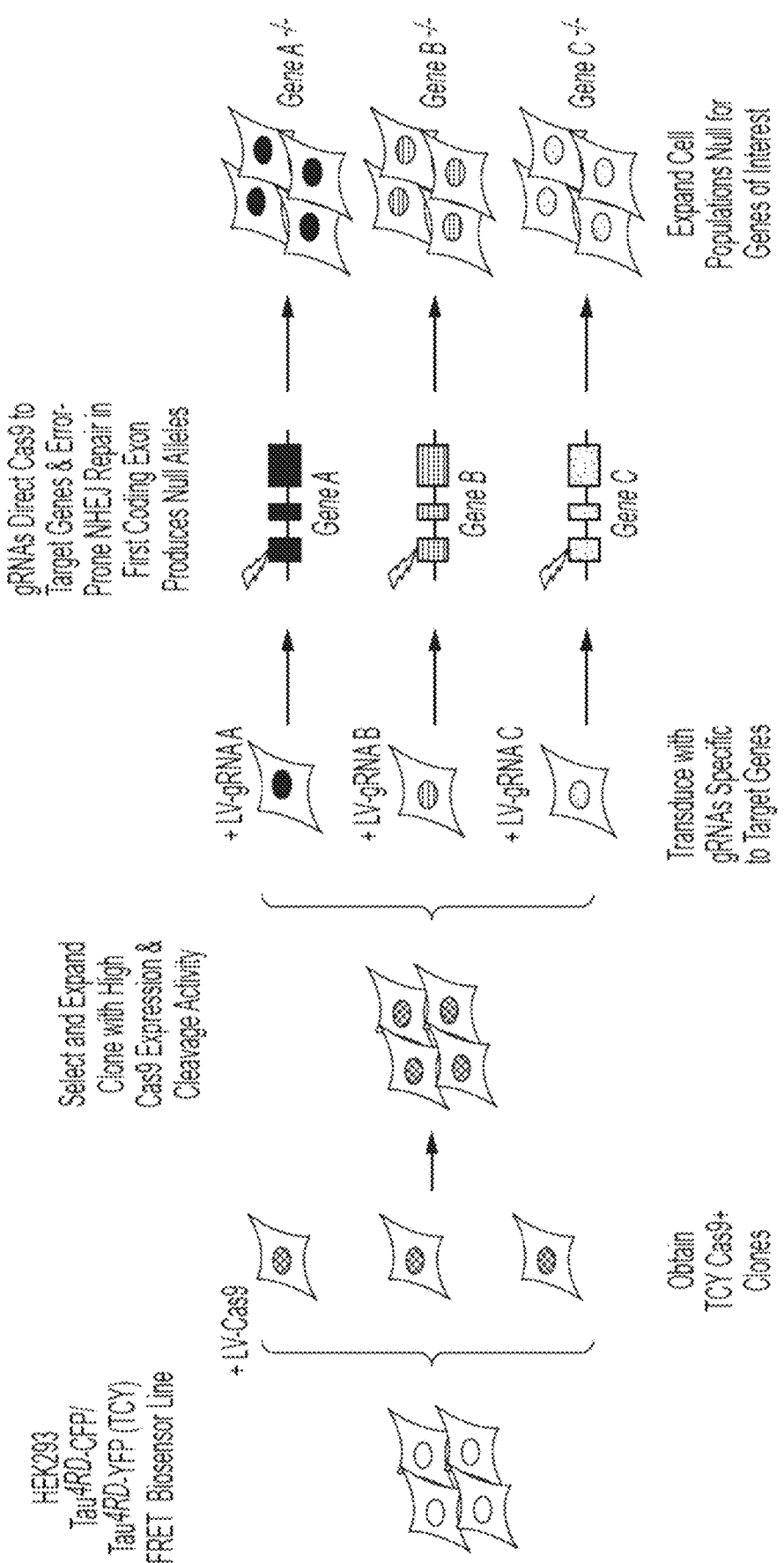
FIG. 4 shows a schematic of the strategy for disruption of target genes in Cas9 TCY biosensor cell using a genome-wide CRISPR/Cas9 sgRNA library.

Example 2. Genome-Wide CRISPR/Cas9 Screening to Identify Genetic Modifiers of Tau Aggregation To reveal modifier genes of tau aggregation as enriched sgRNAs in FRET(+) cells, the Cas9-expressing tau-CFP/tau-YFP biosensor cells without aggregates (Agg[−]) were transduced with two human genome-wide CRISPR sgRNA libraries using a lentiviral delivery approach to introduce knock-out mutations at each target gene. See FIG. 4. Each CRISPR sgRNA library targets 5' constitutive exons for functional knock-out with an average coverage of ~3 sgRNAs per gene (total of 6 gRNAs per gene in the two libraries combined). Read count distribution (i.e., the representation of each gRNA in the library) was normal and similar for each library. The sgRNAs were designed to avoid off-target effects by avoiding sgRNAs with two or fewer mismatches to off-target genomic sequences. The libraries cover 19,050 human genes and 1864 miRNA with 1000 non-targeting control sgRNAs. The libraries were transduced at a multiplicity of infection (MOI)<0.3 at a coverage of >300 cells per sgRNA. Tau biosensor cells were grown under puromycin selection to select cells with integration and expression of a unique sgRNA per cell. Puromycin selection began 24 h after transduction at 1 µg/mL. Five independent screening replicates were used in the primary screen.

Figure 7:
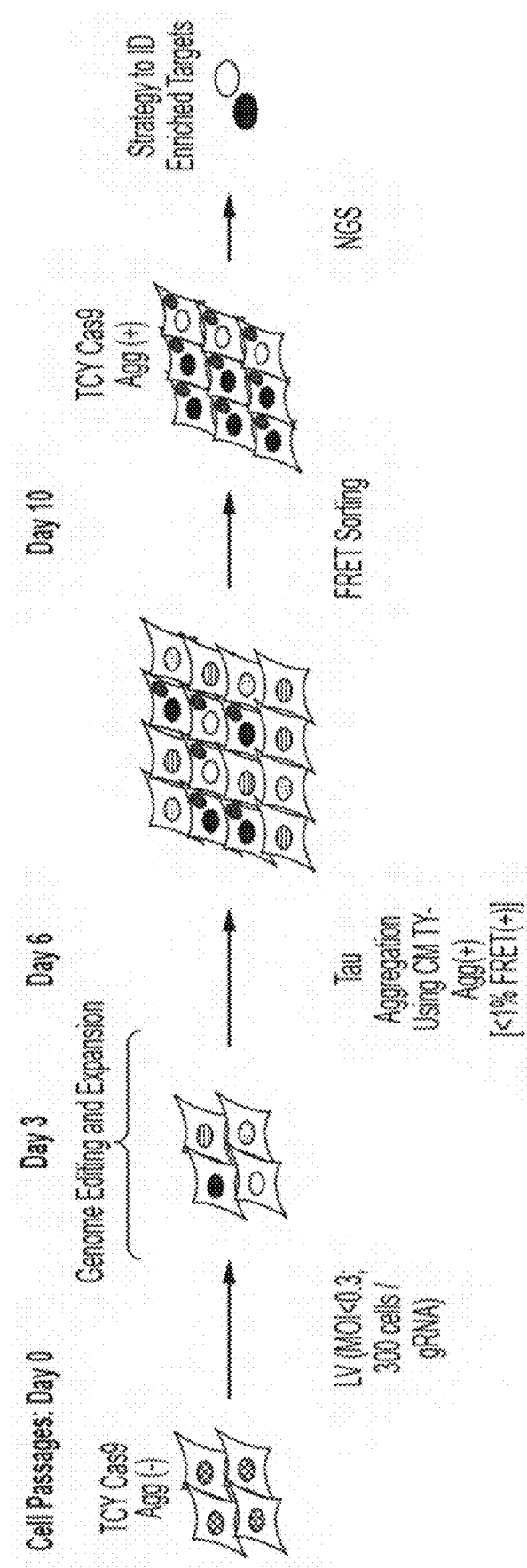
FIG. 7 is a schematic showing the strategy for a genome-wide CRISPR nuclease (CRISPRn) screen to identify modifier genes that promote tau aggregation.

Samples of the full, transduced cell population were collected upon cell passaging at Day 3 and Day 6 post-transduction. After the Day 6 passage, cells were grown in conditioned medium to sensitize them to the seeding activity. At Day 10, fluorescence-assisted cell sorting (FACS) was used to isolate specifically the sub-population of FRET [+] cells. See FIG. 7. The screening consisted of five replicated experiments. DNA isolation and PCR amplification of the integrated sgRNA constructs allowed a characterization by next generation sequencing (NGS) of the sgRNA repertoire at each time point.

Figure 8:
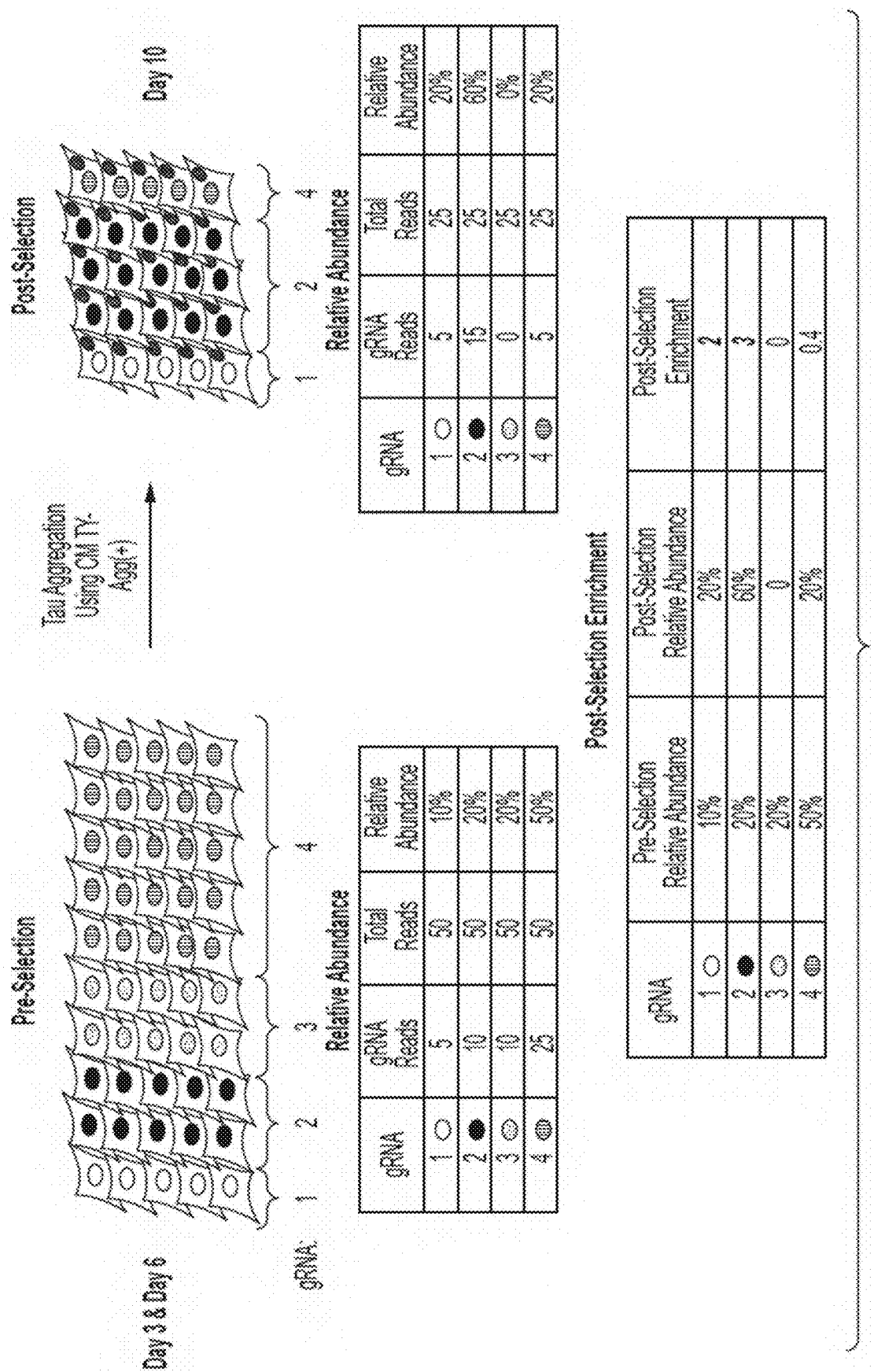
FIG. 8 is a schematic showing the concepts of abundance and enrichment for next-generation sequencing (NGS) analysis using the genome-wide CRISPRn screen.

Statistical analysis of the NGS data enabled identification of sgRNAs enriched in the Day 10 FRET[+] sub-population of the five experiments as compared to the sgRNAs repertoire at earlier time points Day 3 and Day 6. The concepts of relative abundance and enrichment for NGS analysis are exemplified in FIG. 8. The first strategy to identify potential tau modifiers was to use DNA sequencing to produce sgRNA read counts in each sample using the DESeq algorithm to find the sgRNAs that are more abundant in Day 10 vs. Day 3 or Day 10 vs. Day 6 but not in Day 6 vs. Day 3 (fold change (fc)≥1.5 and negative binomial test p<0.01). Fc≥1.5 means the ratio of (average of day 10 counts)/(average of day 3 or day 6 counts)≥1.5. P<0.01 means the chance that there is no statistical difference between Day 10 and Day 3 or Day 6 counts<0.01. The DESeq algorithm is a widely used algorithm for "differential expression analysis for sequence count data." See, e.g., Anders et al. (2010) *Genome Biology* 11:R106, herein incorporated by reference in its entirety for all purposes.

Specifically, two comparisons were used in each library to identify the significant sgRNAs: Day 10 vs. Day 3, and Day 10 vs. Day 6. For each of these four comparisons, the DESeq algorithm was used, and the cutoff threshold to be considered as significant was fold change≥1.5 as well as negative binomial test p<0.01. Once the significant guides were identified in each of these comparisons for each library, a gene was considered to be significant if it meets one of the two following criteria: (1) at least two sgRNAs corresponding to the that gene were considered to be significant in one comparison (either Day 10 vs. Day 3 or Day 10 vs. Day 6); and (2) at least one sgRNA was significant in both comparisons (Day 10 vs. Day 3 and Day 10 vs. Day 6). Using this algorithm, we identified five genes to be significant from the first library and four genes from the second library. See Table 4.

TABLE 4

Genes Identified Using Strategy #1.

| | Day 10 vs Day 3 | | Day 10 vs Day 6 | | Day 6 vs Day 3 |
|---|---|---|---|---|---|
| Gene | Significant gRNAs | Gene | Significant gRNAs | Gene | Significant gRNAs |
| Library #1 | | | | | |
| Target Gene 1 | 1 | Target Gene 1 | 1 | Target Gene 1 | 0 |
| BANF1 | 3 | BANF1 | 1 | BANF1 | 0 |
| Target Gene 15 | 1 | Target Gene 15 | 1 | Target Gene 15 | 0 |
| Target Gene 16 | 1 | Target Gene 16 | 1 | Target Gene 16 | 0 |
| Target Gene 17 | 2 | Target Gene 17 | 0 | Target Gene 17 | 0 |
| Library #2 | | | | | |
| BANF1 | 1 | BANF1 | 1 | BANF1 | 0 |
| Target Gene 18 | 1 | Target Gene 18 | 1 | Target Gene 18 | 0 |
| Target Gene 19 | 1 | Target Gene 19 | 1 | Target Gene 19 | 0 |
| Target Gene 20 | 1 | Target Gene 20 | 1 | Target Gene 20 | 0 |

However, the first strategy requires certain levels of read count homogeneity within each experiment group might be too stringent. For the same sgRNA, many factors could produce read count variability among the samples within each experiment group (Day 3, Day 6 or Day 10 samples), such as initial viral counts in the screening library, infection or gene editing efficiency, and relative growth rate post-gene editing. Thus, a second strategy was also used based on the positive occurrence (read count>30) of guides per gene in each sample at Day 10 (post-selection) instead of exact read count. Formal statistical p-value was calculated for positively observing a number of guides in the post-selection sample (n') given the library size (x), number of guides per gene (n), and the total number of positive guides in the post-selection sample (m) (the "number" refers to sgRNA type (i.e., unique guide RNA sequences), not read count) ($p_{n'}=nCn'*(x-n')C(m-n)/xCm$). The probability of n' guides or more for gene g to be present by change was calculated as:

$$p_g = \Sigma_{i=n'}^{n} p_i$$

The overall enrichment of read counts of a gene post-selection compared to pre-selection was used as additional parameter to identify positive genes: (Relative abundance=[read count of a gene]/[read count of all genes] and post-selection enrichment=[relative abundance post-selection]/[relative abundance pre-selection]).

More specifically, the second strategy is a new and more sensitive analysis method for CRISPR positive selection. The goal of CRISPR positive selection is to use DNA sequencing to identify genes for which perturbation by sgRNAs is correlated to the phenotype. To reduce the noise background, multiple sgRNAs for the same gene together with experiment replicates are usually used in these experiments. However, currently the commonly used statistical analysis methods, which require a certain degree of homogeneity/agreement among the sgRNAs for the same gene as well as among technical repeats, do not work well. This is because these methods cannot handle huge variation among sgRNAs and repeats for the same gene, due to many possible reasons (e.g., different infection or gene editing efficiency, initial viral counts in the screening library, and the presence of other sgRNAs with the same phenotype). In contrast, we developed a method that is robust to large variations. It is based on the positive occurrences of guides per gene in an individual experiment instead of the exact read count of each sgRNA. Formal statistical p-values are calculated for positively observing a number of sgRNAs over experiment repeats given the library size, number of sgRNAs per gene, and the totally number of positive sgRNAs in each experiment. Relative sgRNA sequence read enrichment before and after phenotype selection is also used as a parameter. Our method performs better than widely used methods up-to-date, including DESeq, MAGECK, and others. Specifically, this method includes the following steps:

(1) For each experiment, identifying any present guides in cells with positive phenotype.

(2) At the gene level, calculating the random chance of guides being present in each experiment: $nCn'*(x-n')C(m-n)/xCm$, where x is the variety of guides before phenotype selection, m is the variety of guides after phenotype selection, n is the variety of guides for a gene before phenotype selection, and n' is the variety of guides for the gene after phenotype selection. The overall chance of being present across multiple experiments is calculated by multiplying the above calculated possibility obtained from each experiment.

(3) Calculating the average enrichment of guides at gene level: Enrichment score=relative abundance post-selection/relative abundance pre-selection. Relative abundance=read count of guides for a gene/read count of all guides.

(4) Selecting genes significantly below the random chance of being present as well as above certain enrichment score.

Figure 9:
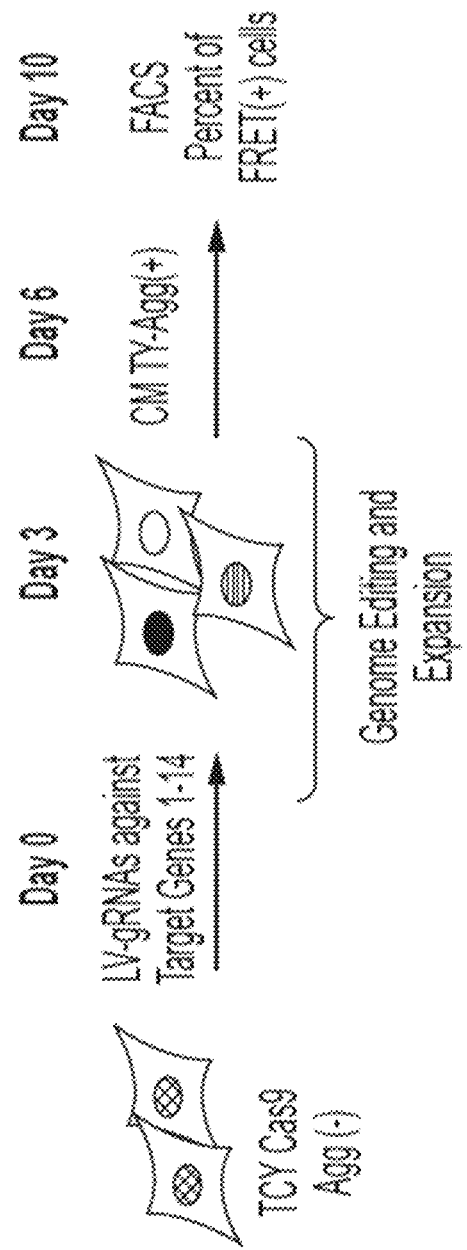
FIG. 9 shows a schematic for secondary screening for Target Genes 1-14 identified in the genome-wide screen for modifier genes that promote tau aggregation.
Figure 10:
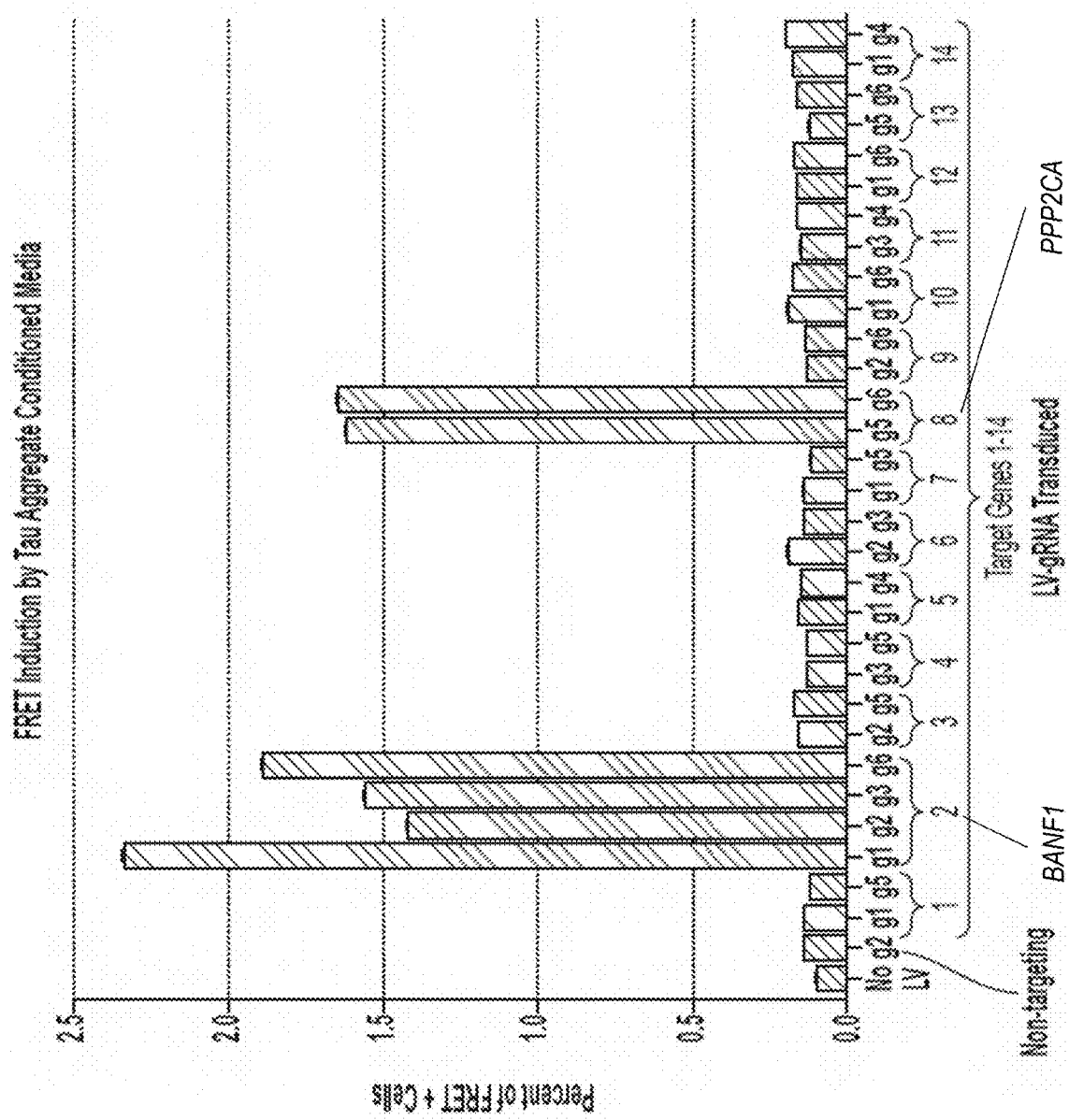
FIG. 10 is a graph showing FRET induction by tau aggregate conditioned medium in Cas9 TCY biosensor cells transduced with lentiviral expression constructs for sgRNAs targeting Target Genes 1-14. The secondary screen confirmed that Target Genes 2 (BANF1) and 8 (PPP2CA) modulate cell susceptibility to tau seeding/aggregation.
Figure 11:
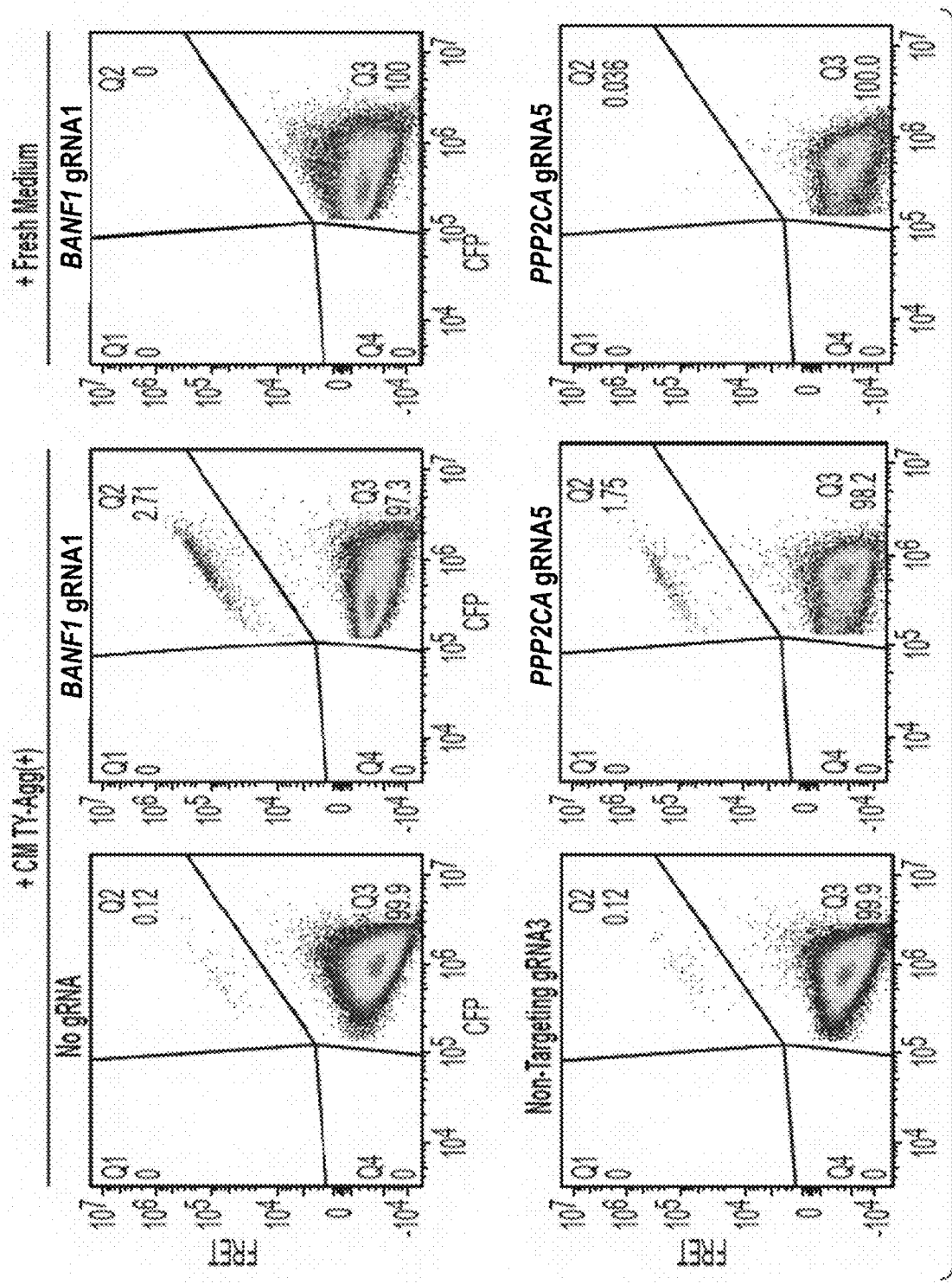
FIG. 11 shows FACS analysis images for Cas9 TCY biosensor cells transduced with lentiviral expression constructs for BANF1 gRNA1, PPP2CA gRNA5, a non-targeting gRNA, and no gRNA. The cells were cultured in conditioned medium or fresh medium. The x-axis shows CFP (405 nm laser excitation), and the y-axis shows FRET (excitation from CFP emission). The upper right quadrant is FRET[+], the lower right quadrant is CFP[+], and the lower left quadrant is double-negative. Disruption of BANF1 or PPP2CA increases the formation of tau aggregates in response to tau aggregate conditioned medium but not fresh medium.

Fourteen of the target genes identified by the two different approaches (either approach or both) as being enriched in the FRET[+] cells were selected as top candidates for further validation after visual inspection based on read counts data. See Table 5. Thirty individual sgRNAs were tested in secondary screens for validation. A schematic of the secondary screens is shown in FIG. 9, and the results are shown in FIG. 10. Disruption of either BANF1 or PPP2CA, by multiple tested sgRNAs, increased the susceptibility of a cell to form tau aggregates in response to a source of tau seeding activity (conditioned medium). The induction of FRET signal increased by 15-20 fold in cells with disruption of either of these two targets. The disruption of these two target genes increased the formation of tau aggregates in response to conditioned medium but not fresh medium. See FIG. 11.

TABLE 5

Targets Identified.

| Target Gene | sgRNA (Target Sequence) | SEQ ID NO (Target Sequence) | SEQ ID NO (DNA-Targeting Segment) |
|---|---|---|---|
| Target Gene 1 | g1-Lib-A | | |
| Target Gene 1 | g5-Lib-B | | |
| Target Gene 2 (BANF1) | g1-Lib-A (TTGCAGGCCTATGTTGTCCT) | 1 | 27 |
| Target Gene 2 (BANF1) | g2-Lib-A (GCTTCGGATGCCTTCGAGAG) | 2 | 28 |
| Target Gene 2 (BANF1) | g3-Lib-A (TTTCCTCCAGCTTCTTGCCC) | 3 | 29 |
| Target Gene 2 (BANF1) | g6-Lib-B (CGCCAACGCCAAGCAGTCCC) | 4 | 30 |
| Target Gene 3 | g2-Lib-A | | |
| Target Gene 3 | g5-Lib-B | | |
| Target Gene 4 | g3-Lib-A | | |
| Target Gene 4 | g5-Lib-B | | |
| Target Gene 5 | g1-Lib-A | | |
| Target Gene 5 | g4-Lib-B | | |
| Target Gene 6 | g2-Lib-A | | |
| Target Gene 6 | g5-Lib-B | | |
| Target Gene 7 | g1-Lib-A | | |
| Target Gene 7 | g5-Lib-B | | |
| Target Gene 8 (PPP2CA) | g5-Lib-B (GAGCTCTAGACACCAACGTG) | 5 | 31 |
| Target Gene 8 (PPP2CA) | g6-Lib-B (CAAGCAGCTGTCCGAGTCCC) | 6 | 32 |
| Target Gene 9 | g2-Lib-A | | |
| Target Gene 9 | g6-Lib-B | | |
| Target Gene 10 | g1-Lib-A | | |

TABLE 5-continued

Targets Identified.

| Target Gene | sgRNA (Target Sequence) | SEQ ID NO (Target Sequence) | SEQ ID NO (DNA-Targeting Segment) |
|---|---|---|---|
| Target Gene 10 | g6-Lib-B | | |
| Target Gene 11 | g3-Lib-A | | |
| Target Gene 11 | g4-Lib-B | | |
| Target Gene 12 | g1-Lib-A | | |
| Target Gene 12 | g6-Lib-B | | |
| Target Gene 13 | g5-Lib-B | | |
| Target Gene 13 | g6-Lib-B | | |
| Target Gene 14 | g1-Lib-A | | |
| Target Gene 14 | g4-Lib-B | | |

Figure 12:
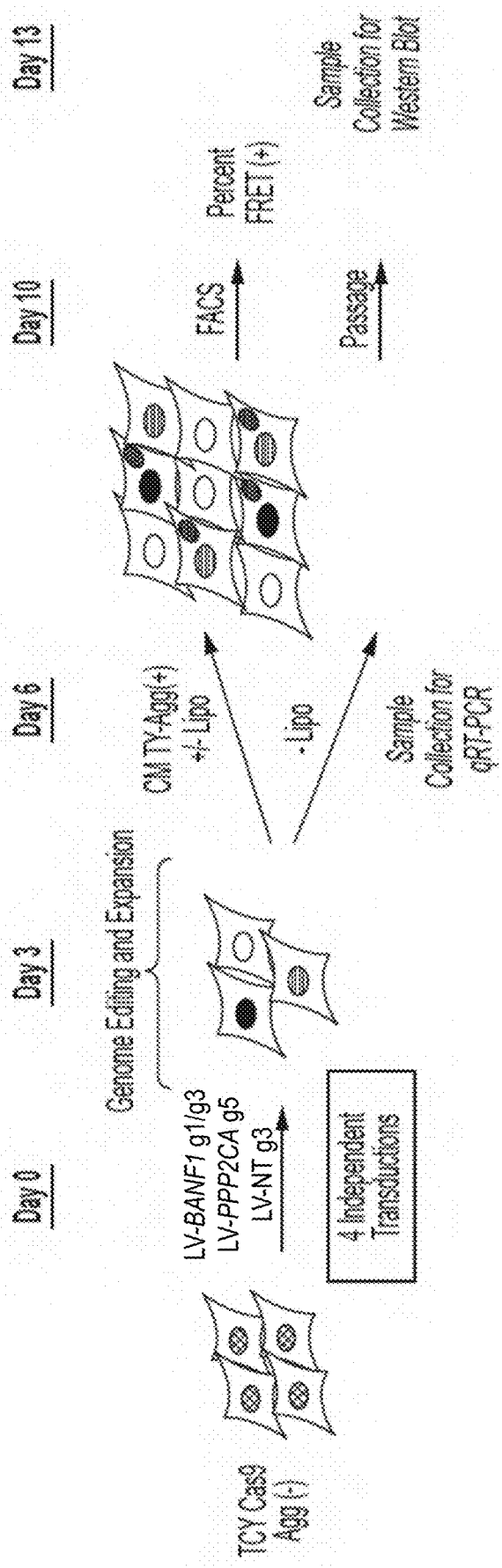
FIG. 12 shows a schematic for secondary screening in Cas9 TCY biosensor cells transduced with lentiviral expression constructs for sgRNAs targeting BANF1 and PPP2CA, including mRNA expression analysis, protein expression analysis, and FRET analysis. Two sgRNAs were used against BANF1 (g1 and g3), one sgRNA was used against PPP2CA (g5), and a non-targeting sgRNA (g3) was used as a non-targeting control.
Figure 13:
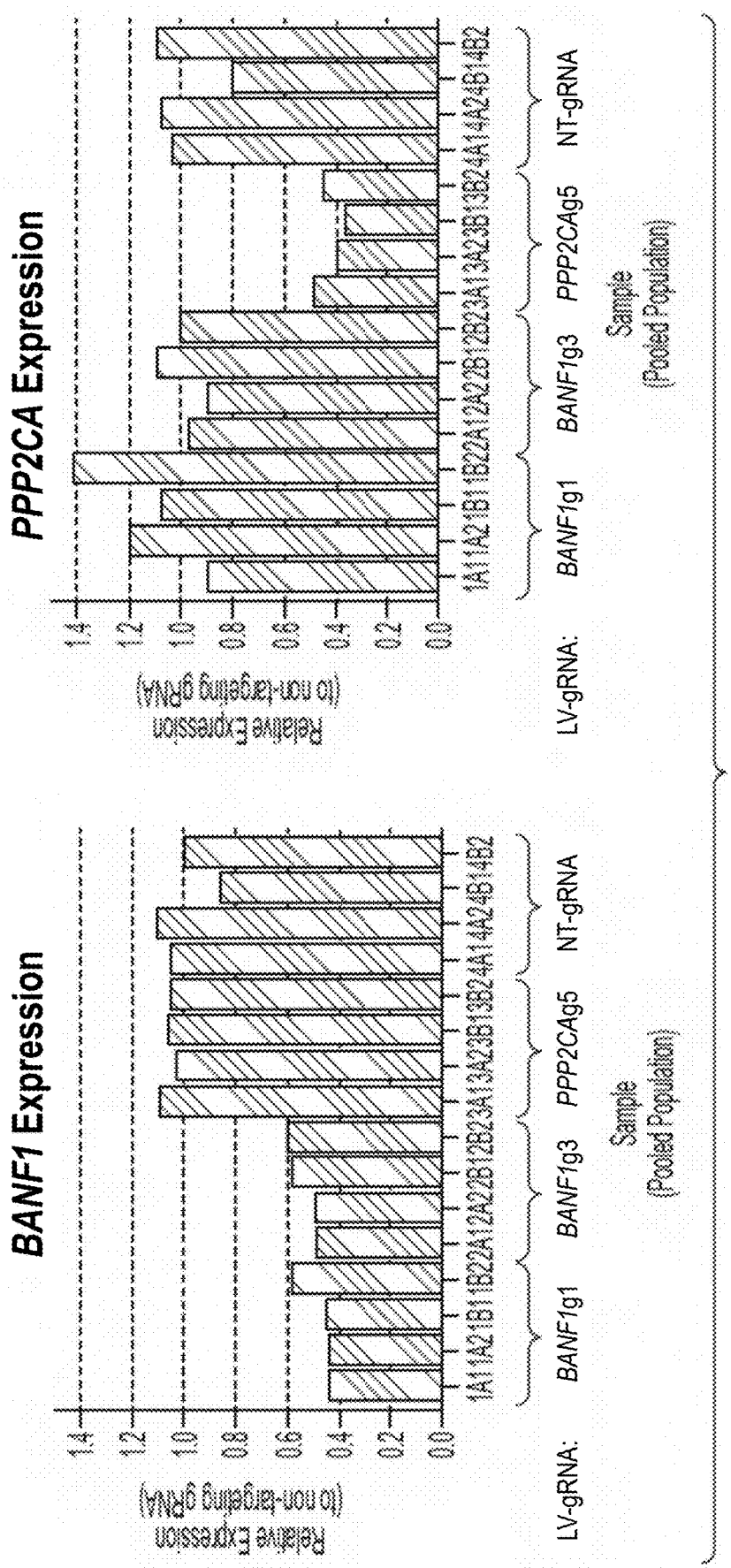
FIG. 13 shows relative expression of BANF1 and PPP2CA in Cas9 TCY biosensor cells as assessed by qRT-PCR at Day 6 following transduction with the lentiviral sgRNA expression constructs.
Figure 14:
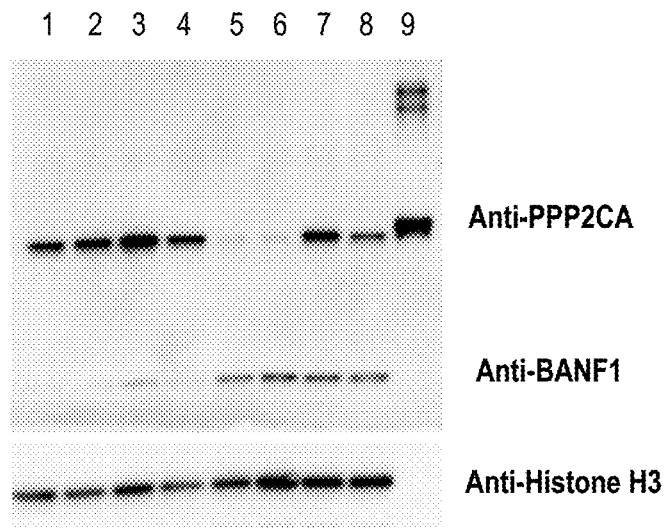
FIG. 14 shows expression of BANF1 protein and PPP2CA protein in Cas9 TCY biosensor cells as assessed by western blot at Day 13 following transduction with the lentiviral sgRNA expression constructs.
Figure 15:
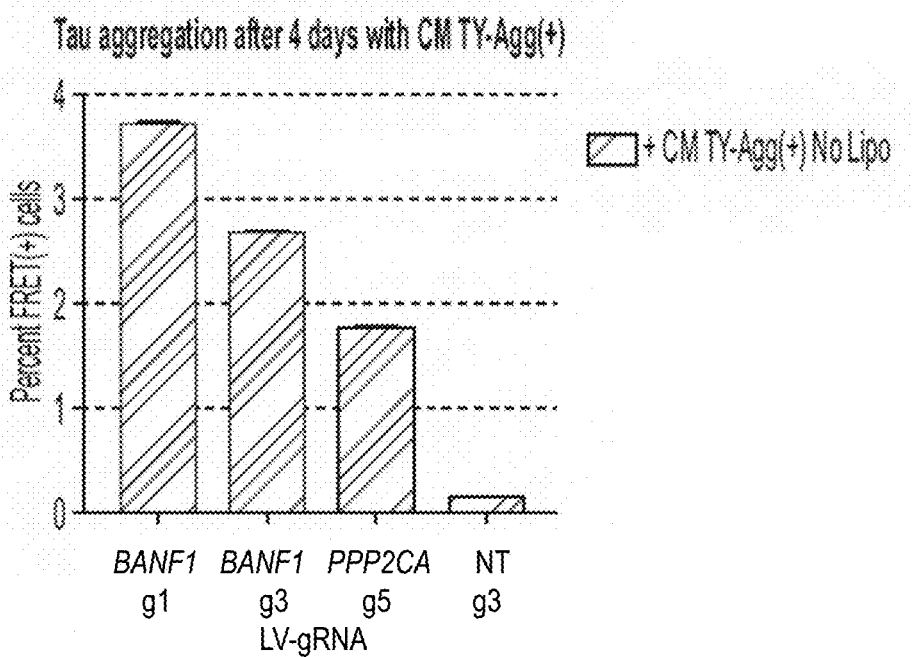
FIG. 15 shows tau aggregation as measured by percent FRET[+] cells in Cas9 TCY biosensor cells at Day 10 following transduction with the lentiviral sgRNA expression constructs. No lipofectamine was used.

Further experiments with BANF1 and PPP2CA were then performed to further validate that targeting of each gene promotes tau aggregation. See FIG. 12. Two different sgRNAs against BANF1 were tested and one sgRNA against PPP2CA were used. A non-targeting sgRNA was used as a negative control. Four independent lentiviral transductions were done for each guide RNA on Day 0. On Day 6, tau seeding with conditioned medium was performed with or without lipofectamine and samples were collected for qRT-PCR. The qRT-PCR data are shown in FIG. 13. Each of the two sgRNAs targeting BANF1 reduced BANF1 mRNA expression, and the gRNA targeting PPP2CA reduced PPP2CA expression. On Day 10, FACS analysis was done to assess induction of FRET signal. Tau aggregation was increased by each of the two sgRNAs targeting BANF1 and the gRNA targeting PPP2CA. See FIG. 15. On Day 13, samples were collected for western blot analysis. The western blot results are shown in FIG. 14. The antibodies used are shown in Table 6. Similar to the qRT-PCR experiments assessing mRNA expression, expression of barrier-to-autointegration factor (BANF1) protein was reduced by the two sgRNAs targeting BANF1, and expression of serine/threonine-protein phosphatase 2A catalytic subunit alpha (PPP2CA) protein was reduced by the sgRNA targeting PPP2CA.

TABLE 6

Antibodies for Western Blots.

| Target | Provider | Catalog # | Dilution for WB |
|---|---|---|---|
| BANF1 | abcam | ab129074 | 1:1,000 |
| PPP2CA | proteintech | 13482-1-AP | 1:1,000 |
| phopho-tau S356 | abcam | ab75603 | 1:1,000 |
| phospho-tau S262 | abcam | ab131354 | 1:10,000 |
| Histone H3 | proteintech | 17168-1-AP | 1:10,000 |
| Total tau | dako | A0024 | 1:150,000 |

Figure 16:
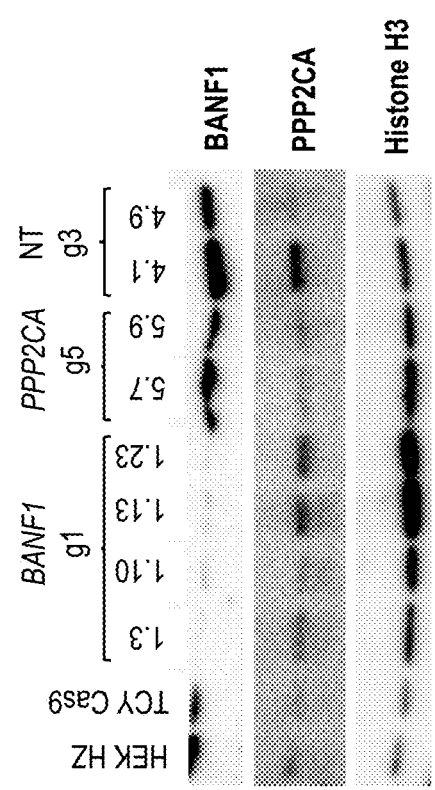
FIG. 16 shows expression of BANF1 and PPP2CA in the knockdown Cas9 TCY cell clones as assessed by western blot.

Further validation of BANF1 and PPP2CA as modifiers of tau aggregation was done by isolating individual BANF1 knockdown clones and individual PPP2CA knockdown clones for validation. Cas9-expressing tau-CFP/tau-YFP biosensor cells without aggregates (Agg[−]) were transduced with lentivirus expressing BANF1 sgRNA 1, PPP2CA sgRNA 5, or a non-targeting sgRNA. Serial clonal dilution was then undertaken to select individual clones. Levels of BANF1 mRNA and PPP2CA mRNA were assessed by qRT-PCR (TaqMan qRT-PCR assays obtained from ThermoFisher, Assay IDs Hs00427805_g1 and Hs00427260_m1), and levels of barrier-to-autointegration factor (BANF1) protein and serine/threonine-protein phosphatase 2A catalytic subunit alpha (PPP2CA) protein were assessed by western blot. Each BANF1 sgRNA clone had reduced BANF1 mRNA expression (data not shown) and barrier-to-autointegration factor (BANF1) protein expression (FIG. 16), and each PPP2CA sgRNA clone had reduced PPP2CA mRNA expression (data not shown) and serine/threonine-protein phosphatase 2A catalytic subunit alpha (PPP2CA) protein expression (FIG. 16).

Figure 17:
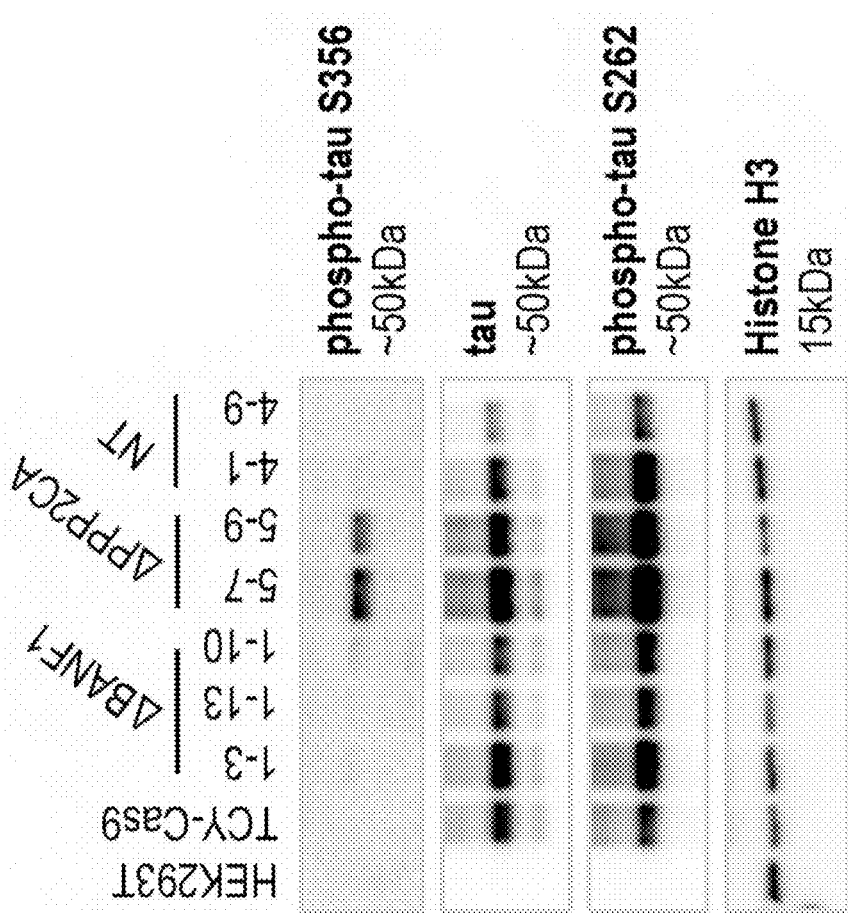
FIG. 17 shows expression of tau in the knockdown Cas9 TCY cell clones as assessed by western blot and phosphorylation of tau at positions S262 and S356 in those clones as assessed by western blot.

Tau expression and tau phosphorylation were also assessed in each clone by western blot. PPP2CA knockdown increased by phospho-tau and tau levels. See FIG. 17.

Figure 18:
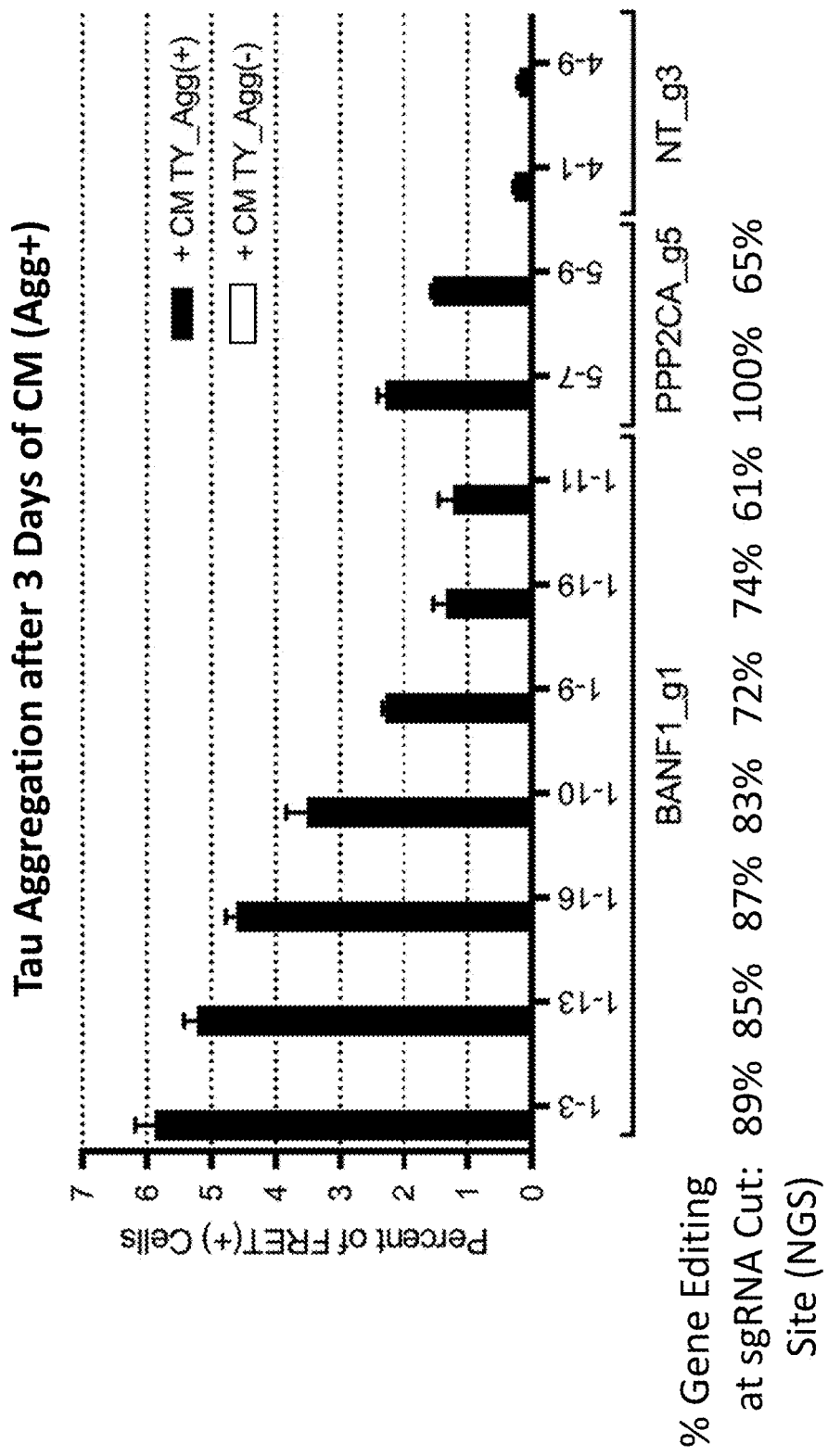
FIG. 18 shows tau aggregation in the BANF1 and PPP2CA knockdown Cas9 TCY cell clones as assessed by FRET.

Next, each clone was seeded with conditioned medium for 3 days and FRET analysis was done to assess tau aggregation. The knockdown clones validate BANF1 and PPP2CA as modifiers of tau aggregation. See FIG. 18. FRET enhancement directly correlated with the extent of gene editing in the BANF1 and PPP2CA mutant clones.

The individual clones were then further characterized by next-generation sequencing to determine what modifications were made that the BANF1 and PPP2CA loci. The modifications are summarized in Table 7 below. Almost all of the mutant clones contain some percentage of wild type alleles. The percentage of FRET(+) cells (tau aggregation activity) correlated with the percentage of insertions/deletions caused by non-homologous end joining at the cleavage sites (i.e., tau aggregation was inversely correlated with the percentage of wild type alleles—the lower the percentage of wild type alleles, the higher the percentage of Fret(+) cells). See FIG. 16 and Table 7.

TABLE 7

Characterization of BANF1 and PPP2CA Clones.

| Gene (Target) | Clone | Amplicon Sequenced | WT | INDEL 1 | INDEL 2 |
|---|---|---|---|---|---|
| BANF1 | MP1-3 | PPP2CA_g5 | 98.80% | | |
| | | BANF1_g1 | 11.30% | 49.9% (+1 bp) | 33.9% (Δ16 bp) |
| | MP1-10 | PPP2CA_g5 | 98.60% | | |
| | | BANF1_g1 | 16.50% | 79.1% (+1 bp) | |
| | MP1-13 | PPP2CA_g5 | 98.80% | | |
| | | BANF1_g1 | 14.90% | 35.9% (Δ6 bp) | 44.3% (+1 bp) |
| | MP1-23 | PPP2CA_g5 | 98.70% | | |
| | | BANF1_g1 | 20.20% | 71.4% (+1 bp) | |
| PPP2CA | MP5-7 | PPP2CA_g5 | 0.00% | 54.8% (Δ3 bp + 6 bp) | 29.7% (C→T) |
| | | BANF1_g1 | 99.5%% | | |
| | MP5-9 | PPP2CA_g5 | 34.80% | 55.0% (Δ20 bp) | 6.8% (+1 bp) |
| | | BANF1_g1 | 99.30% | | |

Figure 23:
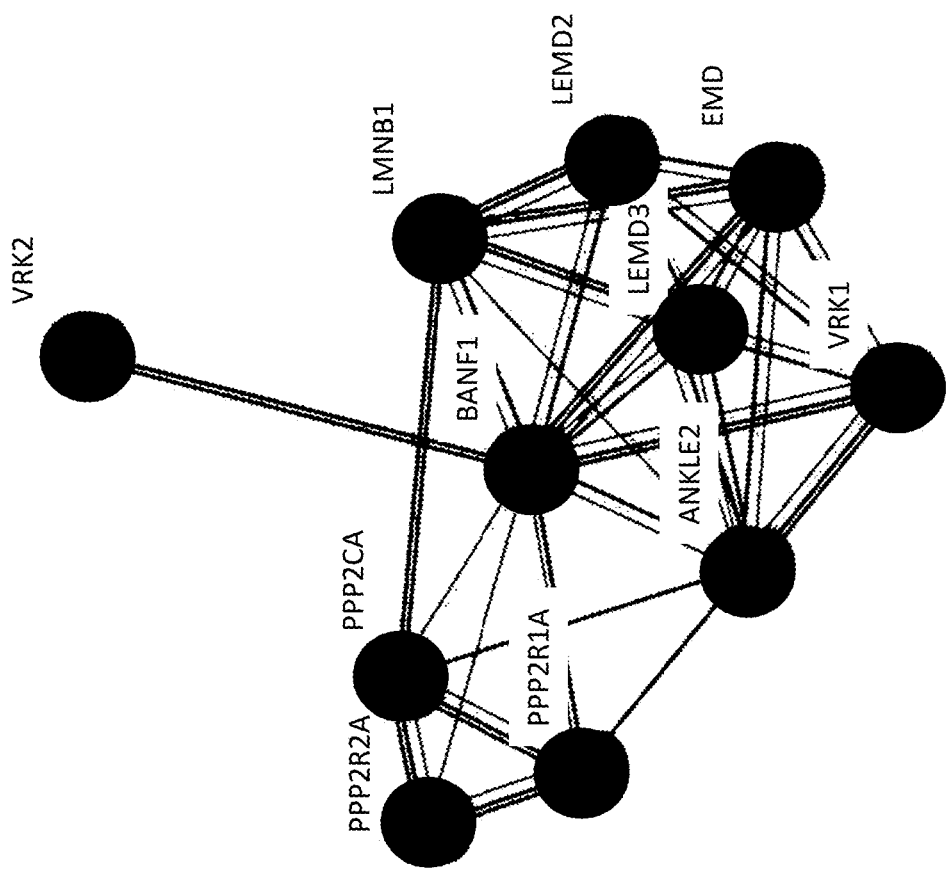
FIG. 23 shows a BANF1/PPP2CA interactome.

We studied whether BANF1 and PPP2CA were involved in the same biological pathways or functions using String, a software program based on protein-protein interaction network. See Szklarczyk et al. (2015) *Nucleic Acids Res.* 43(database issue):D447-D452, herein incorporated by reference in its entirety for all purposes. Using BANF1 and PPP2CA as input, we found a "catalysis" relationship between BANF1 and PPP2CA based on Reactome Pathways. See FIG. 23. BANF1 also interacts with several proteins that play important roles in the biology of the nuclear envelope. These targets were tested as potential modifiers of tau aggregation.

Cas9-expressing tau biosensor cells were transduced with lentiviral vectors containing sgRNAs targeting these genes of interest. The target sequences for these sgRNAs are provided in Table 8. Antibiotic selection began 24 hours later. After a week in culture, conditioned medium (CM) collected after 3 days on confluent tau-YFP (Agg[+]) was applied to transduced cells as 75% CM/25% fresh medium and evaluated for seeding activity, as a percent of FRET[+] cells. Specific target knock down was assessed by qRT-PCR. As expected, disruption of BANF1 or PPP2CA enhanced tau aggregation. Disruption of ANKLE2 also enhanced tau aggregation. See FIG. 19. ANKLE2 is the only LEM domain protein to be both localized to the endoplasmic reticulum and to the inner nuclear membrane.

Figure 19:
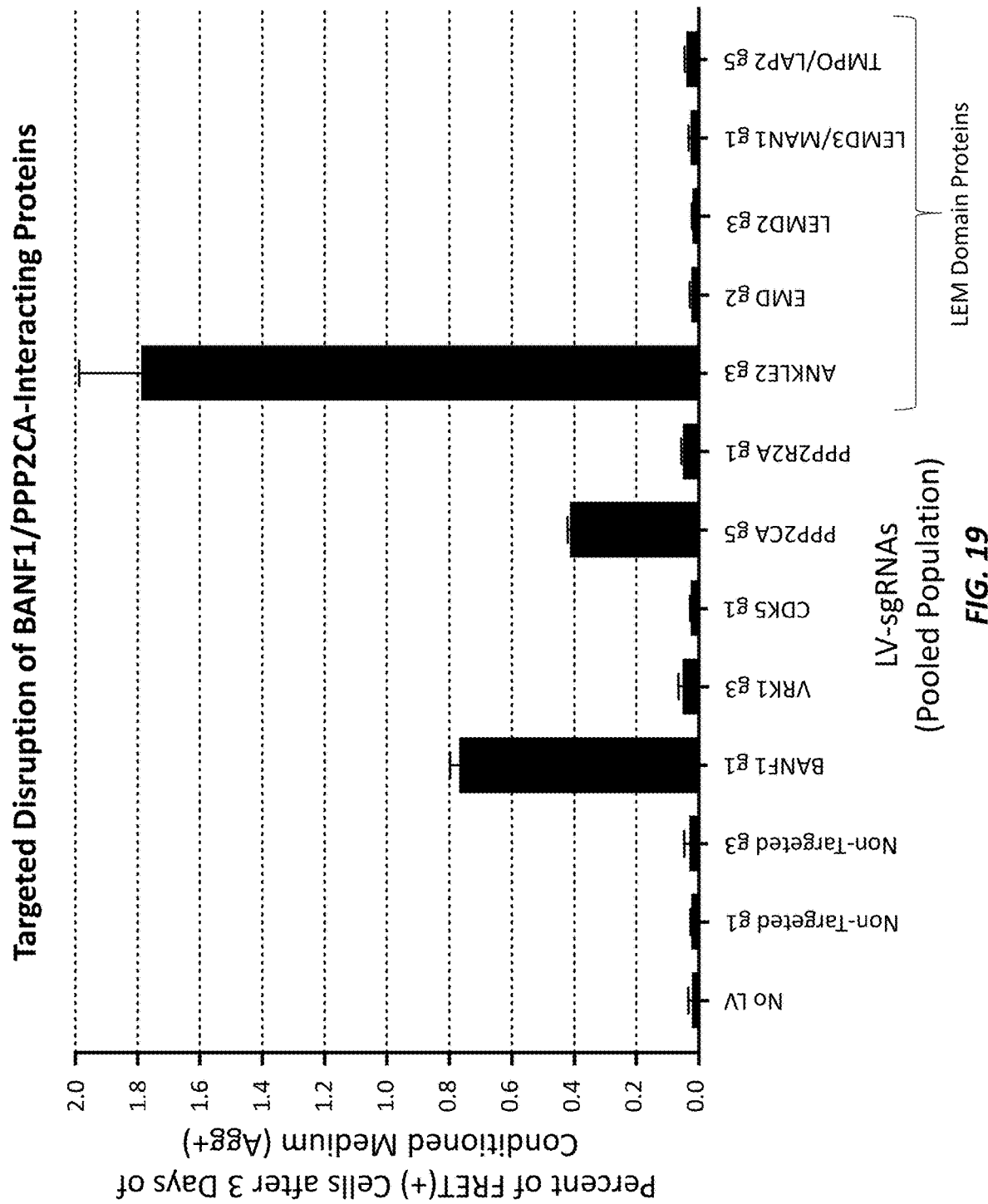
FIG. 19 shows tau aggregation in BANF1, VRK1, CDK5, PPP2CA, PPP2R2A, ANKLE2, EMD, LEMD2, LEMD3/MAN1, and TMPO/LAP2 knockdown Cas9 TCY cell clones as assessed by FRET.
Figure 20:
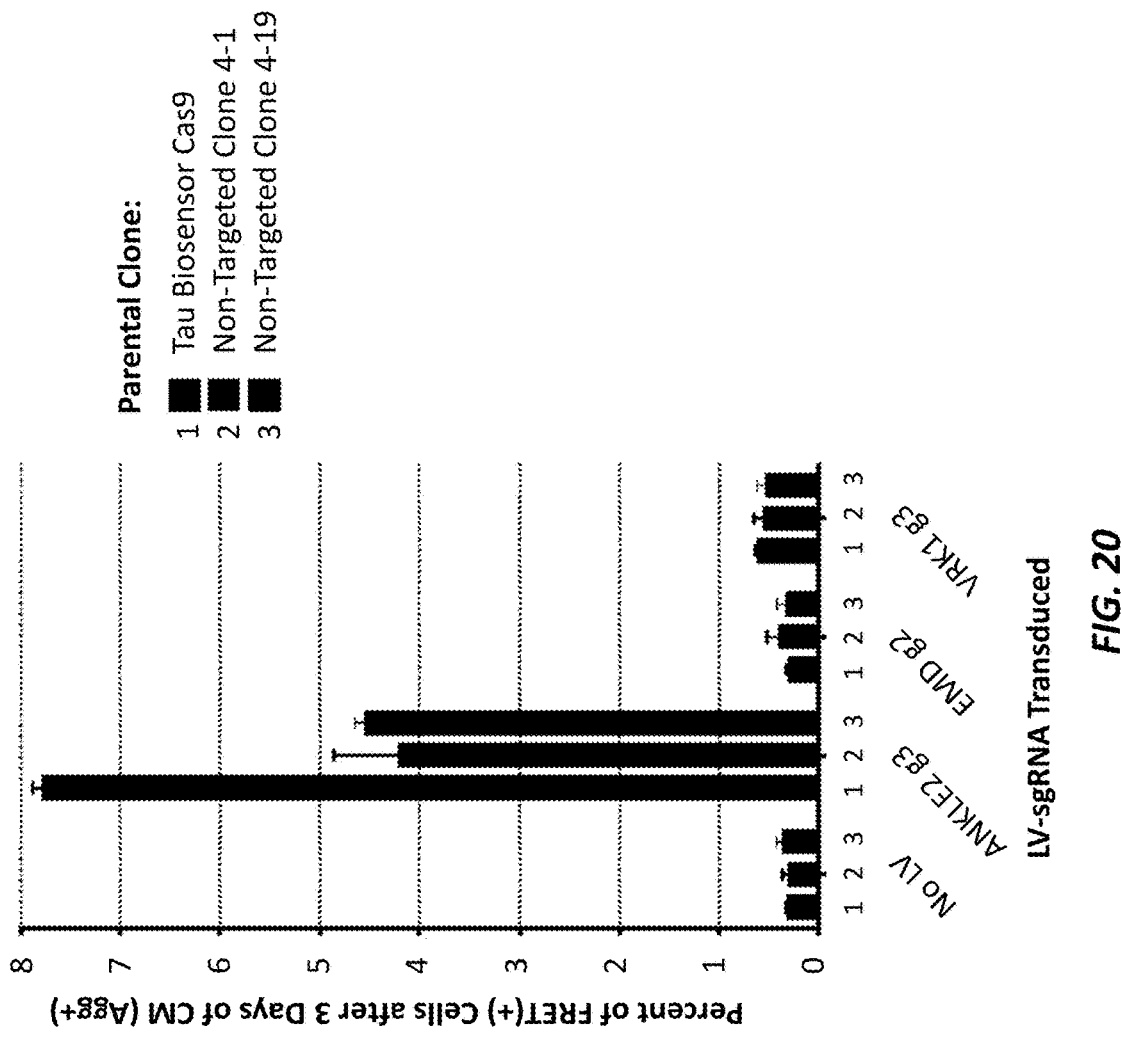
FIG. 20 shows tau aggregation as measured by percent FRET[+] cells in Cas9 TCY biosensor cells at following transduction with the lentiviral sgRNA expression constructs targeting ANKLE2, EMD, or VRK1.

TABLE 8 sgRNA Target Sequences Used in FIG. 19 and FIG. 20.

| Target Gene | Target Sequence | SEQ ID NO (Target Sequence) | SEQ ID NO (sgRNA DNA-Targeting Segment) |
|---|---|---|---|
| Non Targeted g1 | CTTCGACGCCATCGTGCTCA | 7 | 33 |
| Non Targeted g3 | CGCCTCTCACGTGTAGGCTT | 8 | 34 |
| BANF1 g1 | TTGCAGGCCTATGTTGTCCT | 1 | 27 |
| VRK1 g3 | TTTAAGGAACCCAGTGACAA | 9 | 35 |
| CDK5 g1 | GGCCTTGAACACAGTTCCGT | 10 | 36 |
| PPP2CA g5 | GAGCTCTAGACACCAACGTG | 5 | 31 |
| PPP2R2A g1 | TAGAGTTGTCATCTTTCAAC | 11 | 37 |
| ANKLE2 g3 | AAGGAGCCGCCCCTGTACTA | 12 | 38 |
| EMD g2 | TCCGGCCAGGATCAACTCGT | 13 | 39 |
| LEMD2 g3 | TACTTACGGCTATATATTCT | 14 | 40 |
| LEMD3 g1 | AAGAACGCTTTCTGTTCAAG | 15 | 41 |
| TMPO g5 | GTGAAATACGGAGTGAATCC | 16 | 42 |

Genes in the BANF1/PPP2CA interacting network were then further assessed. In particular, ANKLE2, EMD, and VRK1 were assessed. To assess genes in the BANF1/PPP2CA interacting network, sgRNAs targeting ANKLE2, EMD, or VRK1 were tested in non-targeted clones 4-1 and 4-19. The percent of FRET[+] cells was assessed after 3 days of conditioned media. Disruption of genes in the BANF1/PPP2CA-interacting network revealed ANKLE2 as a modifier of tau aggregation (see FIG. 20) and VRK1 as an enhancer of BANF1-induced aggregation (data not shown).

This provided further support for a link between tau aggregation and the BANF1/PPP2CA pathway that regulates the integrity of the nuclear envelope. Consistent with this, lamin staining revealed abnormal nuclear envelopes in BANF1 and ANKLE2 knockdown dCas9-KRAB-expressing tau biosensor cell clones relative to a non-targeted clone, and similar results were observed in BANF1 and ANKLE2 mutant Cas9-expressing tau biosensor cell clones relative to a non-targeted clone (data not shown). BANF1 interacts with the two major components of the nuclear lamina, Lamin A/C and Lamin B1. Studies have recently linked abnormal morphology of the nuclear lamina to the neurodegenerative process in FTD and AD. Disruption of the lamin nucleoskeleton causes heterochromatin relaxation and neuronal cell death in a *Drosophila* model of tauopathy. Lamin pathology is conserved in post-mortem AD brains. Following transduction of dCas9-KRAB-expressing tau biosensor cells, we isolated knockdown clones of BANF1 and ANKLE2. Lamin staining revealed abnormal nuclear envelope in these BANF1 and ANKLE2 knockdown clones relative to a clone transduced and selected for a non-targeted sgRNA (data not shown). The marked abnormalities of nuclear lamina shape are similar to those reported recently in FTD neurons.

Abnormalities in nuclear pore complexes (NPCs) and the resulting nucleocytoplasmic transport (NCT) defects contribute to pathogenesis in mouse models of tauopathy. Disruptions of the NPC and functional nuclear transport may be also present in cells containing hyperphosphorylated tau in human neurons, as well as in mouse and cellular models of tauopathy. Nuclear pore and nuclear envelope defects may present a common mechanism of neurodegeneration in ALS/FTD and Huntington's disease.

Immunostaining for GTP-binding nuclear protein Ran (Ran), Ran GTPase-activating protein 1 (RanGAP1), and regulator of chromosome condensation (RCC1) can be used to interrogate disruptions of NCT in cells. A Ran protein gradient is important for an active transport through the NPC. Most Ran protein is inside the nucleus, which mostly contains Ran-GTP. RanGAP1 localizes to the cytoplasmic side of NPCs and converts Ran-GTP to Ran-GDP. RCC1 localizes to the nucleus and converts Ran-GDP into Ran-GTP.

To determine subcellular localizations, neurons are stained for tau, phospho-tau, Ran, RanGAP1, RCC1, nuclear pore complex protein Nup98-Nup96 (Nup98) (that interacts with phospho-tau), and nuclear pore glycoprotein p62 (Nup62) (core component of the NPC that can form hydrogel) as well as TAR DNA-binding protein 43 (TDP-43) (N-term), RNA-binding protein FUS (FUS), and heterogeneous nuclear ribonucleoprotein A1 (HNRNPA1). Mislocalization of TDP-43, HNRNPA1, and FUS from the nucleus to the cytoplasm is linked to ALS/FTD.

This validation confirmed the value of the primary screening approach in the identification of genes that can regulate the susceptibility of cells to tau seeding when exposed to an external source of tau seeding activity. Targets identified through the screening could be therefore relevant targets in the cell-to-cell propagation of tau pathology in the context of neurodegenerative disease and will be further explored. The genome-wide screen for modifiers of tau aggregation in the FRET biosensor cell lines identified multiple targets involved in the integrity of the nuclear envelope (BANF1, PPP2CA, and ANKLE2). BANF1 and ANKLE2 mutant clones exhibited marked abnormalities of nuclear lamina shape similar to those reported in both FTD neurons and Alzheimer's disease post-mortem neurons.

Example 3. Targeting Ankle2, Banf1, and Ppp2ca in Mouse Cells

In order to validate putative tau modifier genes in mouse models of tauopathy, it was first necessary to validate CRISPR tools that could modify the expression of these genes in mouse cells. sgRNAs targeting the mouse genes Ankle2, Banf1, and Ppp2ca, as well as non-targeted (NT) control sgRNAs that do not match any genomic sequence were tested in mouse ES cells. The expression of these genes was assessed afterwards by qRT-PCR (using TaqMan assays from Thermo Fischer, normalized to expression of the housekeeping gene Drosha.

In the first experiment, the following sgRNA-containing plasmids (obtained from GenScript) were packaged into lentivirus (LV) and transduced into a Cas9-ready mouse ES cell line (2600A-A3) in which Cas9 expression is driven from the Rosa26 locus. The sgRNA target sequences are provided in Table 9.

TABLE 9

Mouse sgRNA Target Sequences.

| sgRNA | Target Sequence | SEQ ID NO (Target Sequence) | SEQ ID NO (sgRNA DNA-Targeting Segment) | Vector |
| --- | --- | --- | --- | --- |
| NT_0303 | CGCCTCTCACGTGTAGGCTT | 8 | 34 | pLentiGuide-Puro |
| NT_0071 | ATAGCCGCCGCTCATTACTT | 17 | 43 | pLentiGuide-Puro |
| NT_0069 | CTTCGACGCCATCGTGCTCA | 7 | 33 | pLentiGuide-Puro |
| Banf1 g1 | ATGAAGACCTCTTCCGAGAA | 18 | 44 | pLentiGuide-Puro |
| Banf1 g2 | ATCCCGGCCAGGCTCCCCAC | 19 | 45 | pLentiGuide-Puro |
| Banf1 g3 | TTGGTGACGTCCTGAGCAAG | 20 | 46 | pLentiGuide-Puro |
| Ppp2ca g1 | CCGAGCACTCGATCGCCTAC | 21 | 47 | pLentiGuide-Puro |
| Ppp2ca g2 | ACATCGAACCTCTTGAACGT | 22 | 48 | pLentiGuide-Puro |
| Ppp2ca g3 | GGGATATCTCCTCGGGGAGC | 23 | 49 | pLentiGuide-Puro |

Figure 21A:
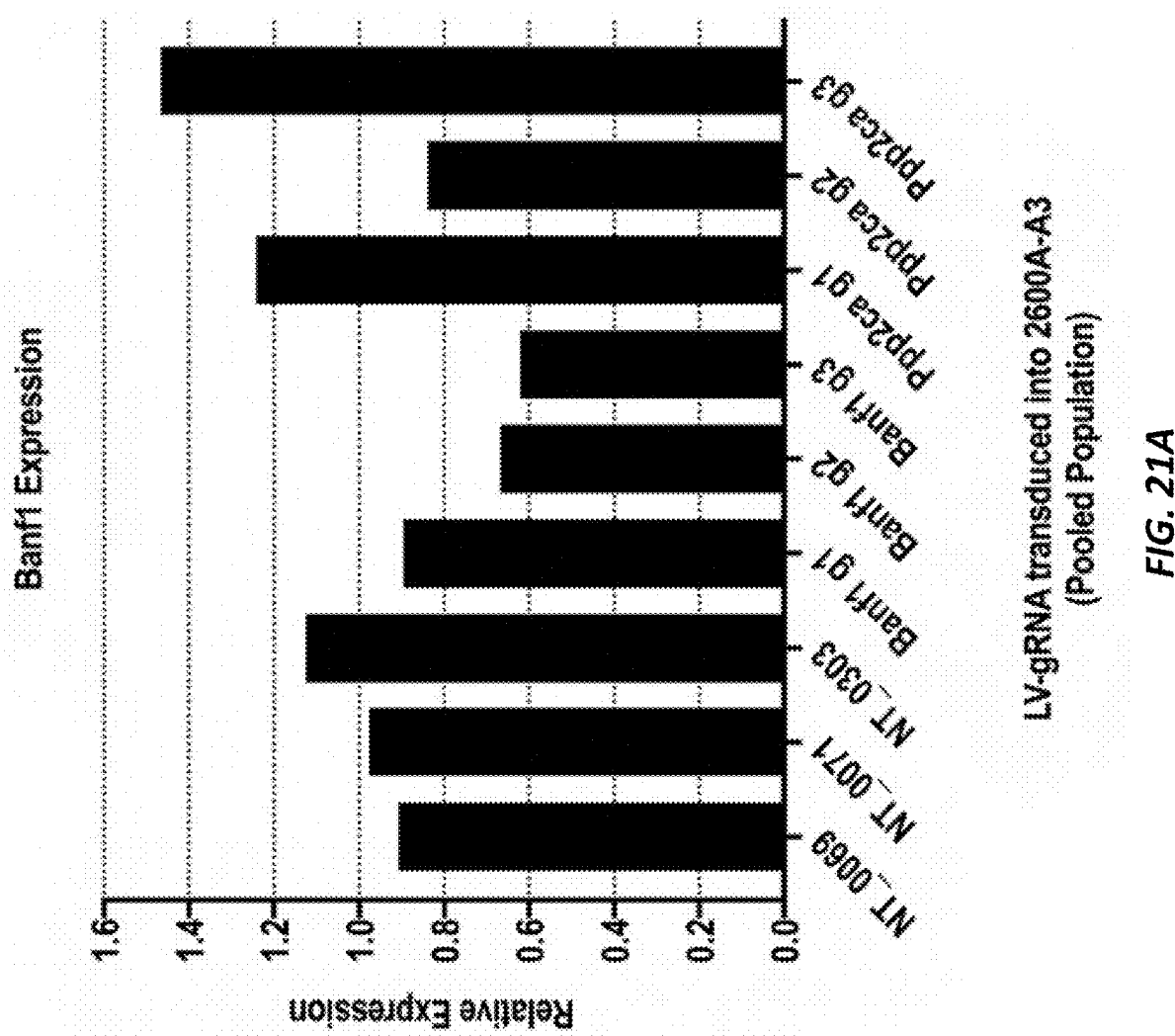
FIG. 21A shows relative expression of Banf1 in Cas9-ready mouse embryonic stem cells as assessed by qRT-PCR following transduction with the lentiviral sgRNA expression constructs.
Figure 21B:
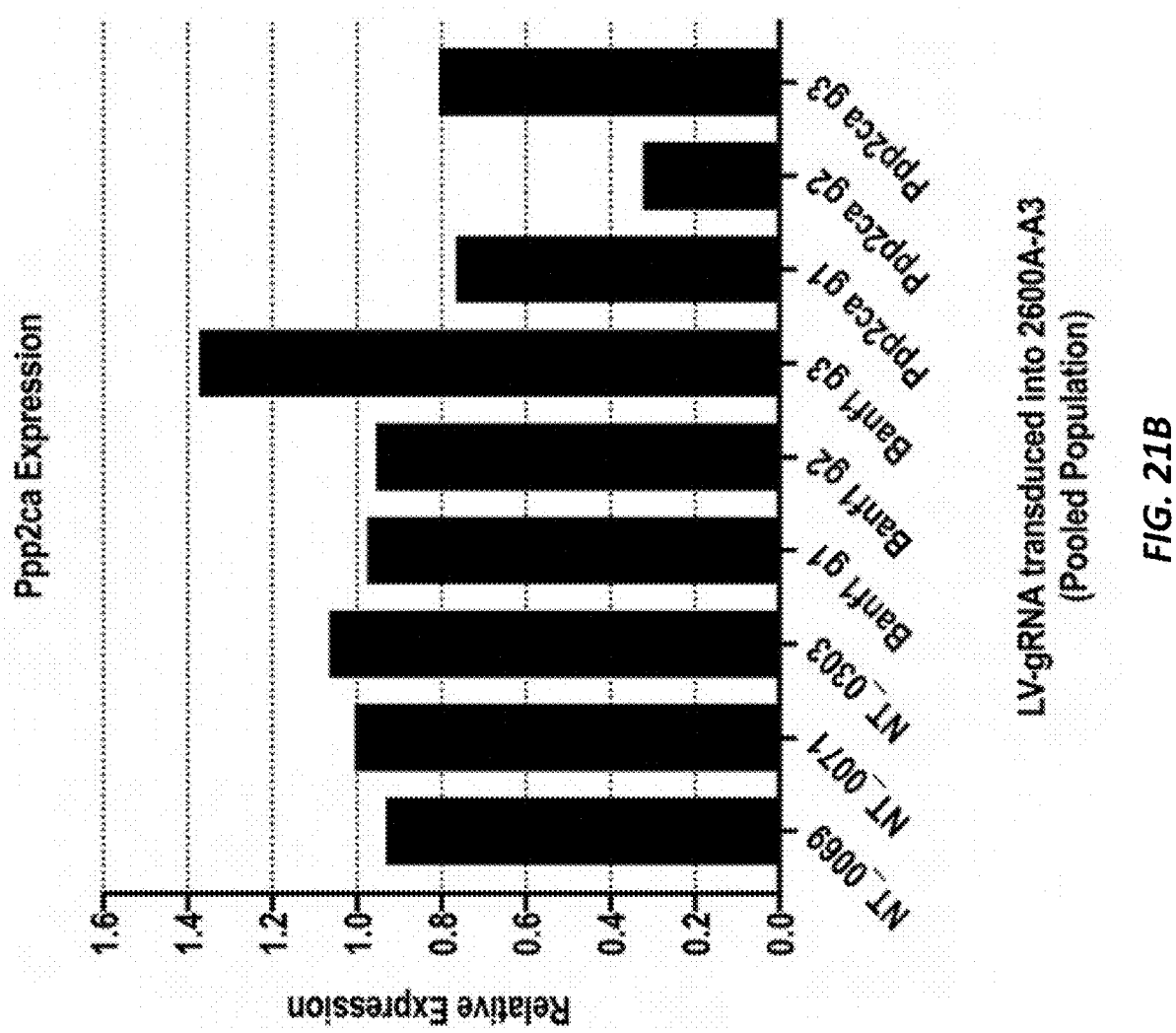
FIG. 21B shows relative expression of Ppp2ca in Cas9-ready mouse embryonic stem cells as assessed by qRT-PCR following transduction with the lentiviral sgRNA expression constructs.

Expression was selected for by puromycin selection (1.5 μg/mL). Mouse ES cells were transduced with individual LVs at an MOI of 600 in the presence of polybrene (64 μg/mL). Cells were grown without feeders under puromycin selection for 10 days. RNA was collected from the cells, and expression of target genes was assessed by qRT-PCR. In this experiment, targeting cells with Banf1 g2 or Banf1 g3 caused a specific reduction of Banf1 expression by approximately 35% relative to NT controls. See FIG. 21A. Likewise, targeting cells with Ppp2ca g2 caused a specific reduction of Ppp2ca expression by approximately 65% relative to NT controls. See FIG. 21B.

To further assess the sgRNAs targeting these mouse genes, the following plasmids (obtained from GenScript) were packaged into LV and transduced in F1H4 mouse ES cells, which are wild type mouse ES cells on a hybrid genetic background (50% C57BL/6NTac 50% 129S6/SvEvTac). The pLentiCRISPR-v2 plasmid constructs contain both Cas9 coding sequence and the sequence for the specific sgRNA in a single "all-in-one" (AIO) vector, with expression of both Cas9 and sgRNA selectable by puromycin. As an additional negative control, sgRNAs targeting Banf1 or Ppp2ca in the pLentiGuide-puro vector (containing the sgRNA but lacking Cas9) were also used. The vectors are shown in Table 10.

Figure 22A:
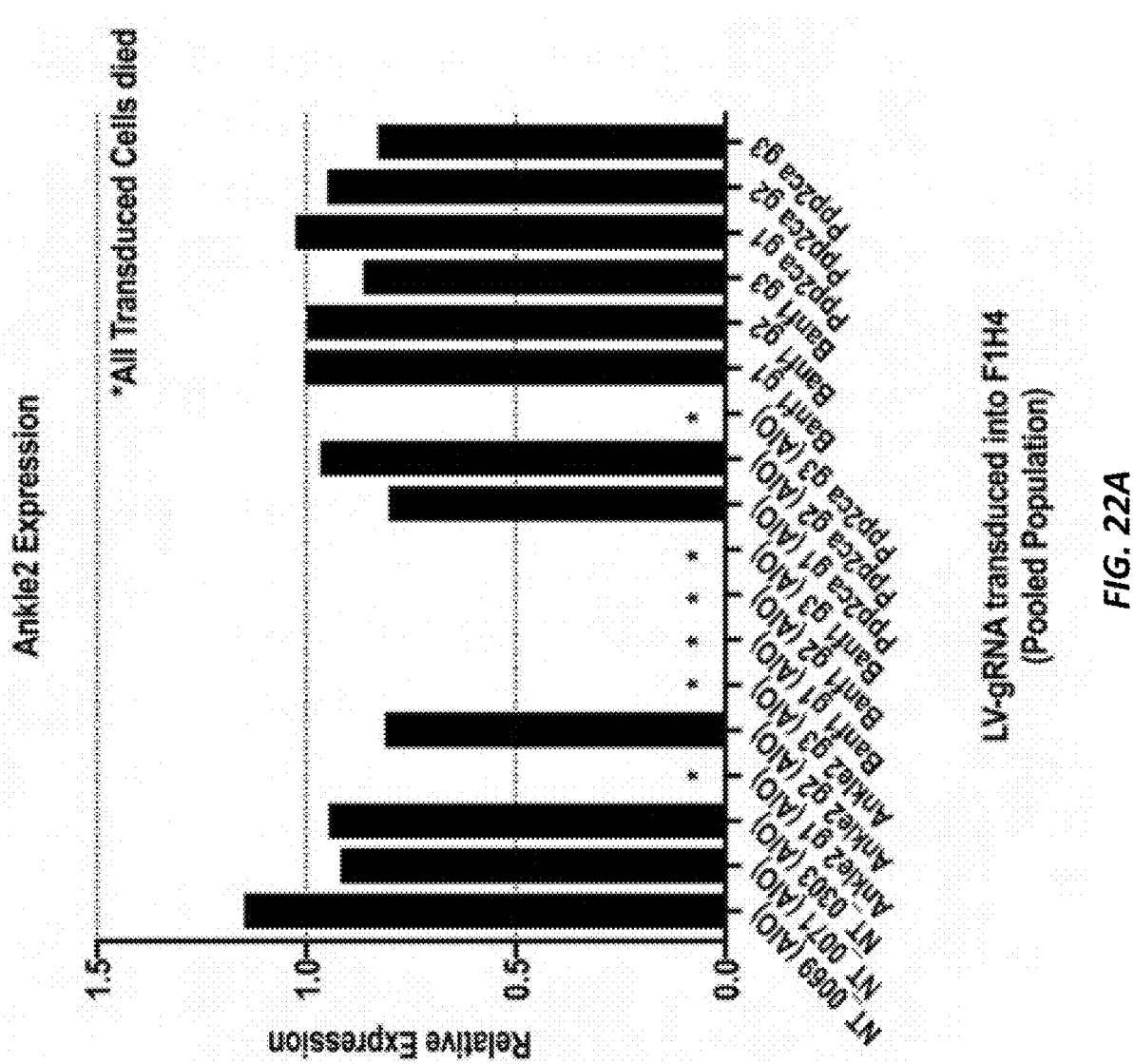
FIG. 22A shows relative expression of Ankle2 in F1H4 mouse embryonic stem cells as assessed by qRT-PCR following transduction with the lentiviral sgRNA expression constructs (all-in-one (AIO) construct including Cas9, or sgRNA alone).
Figure 22B:
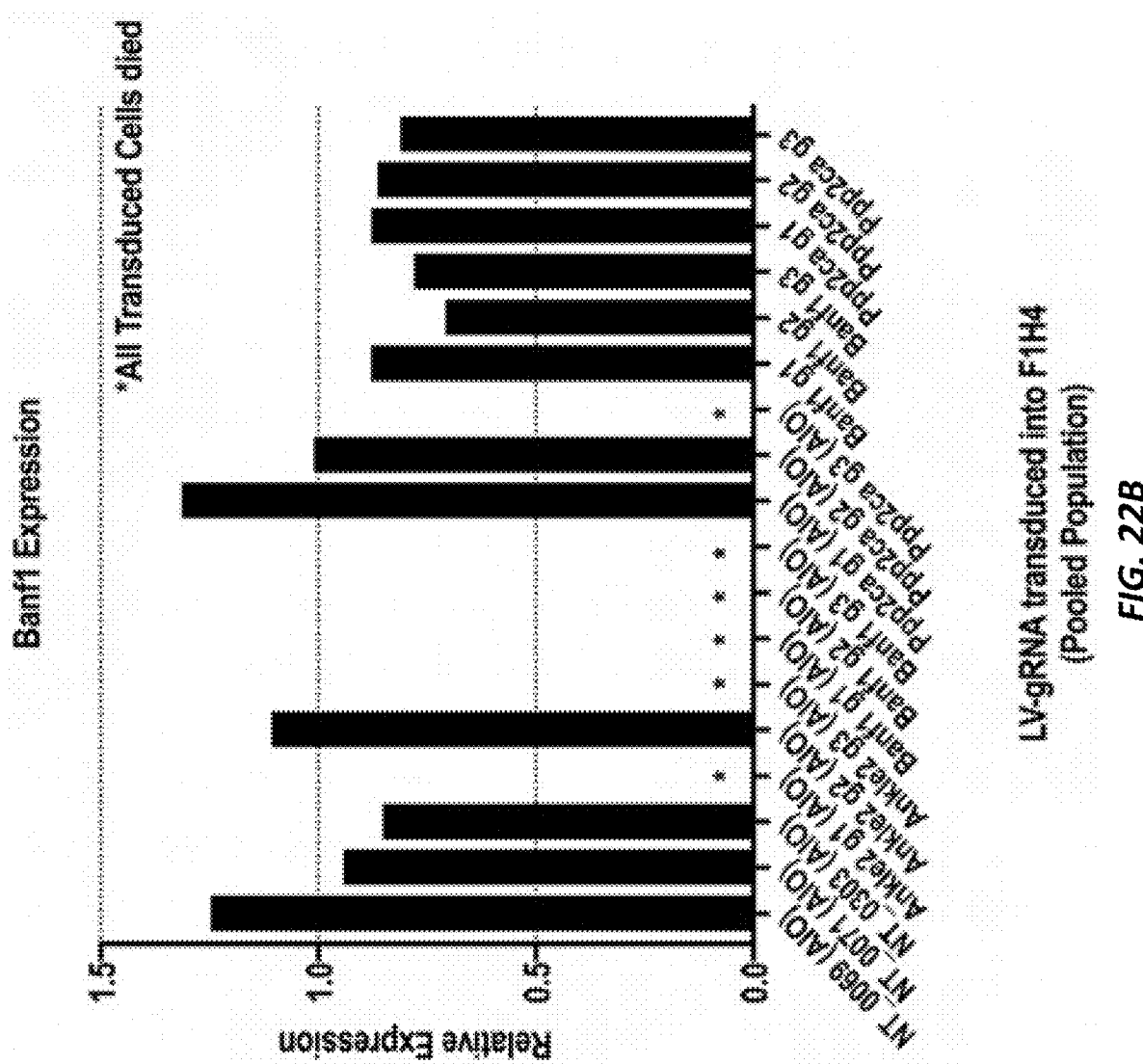
FIG. 22B shows relative expression of Banf1 in F1H4 mouse embryonic stem cells as assessed by qRT-PCR following transduction with the lentiviral sgRNA expression constructs (all-in-one (AIO) construct including Cas9, or sgRNA alone).
Figure 22C:
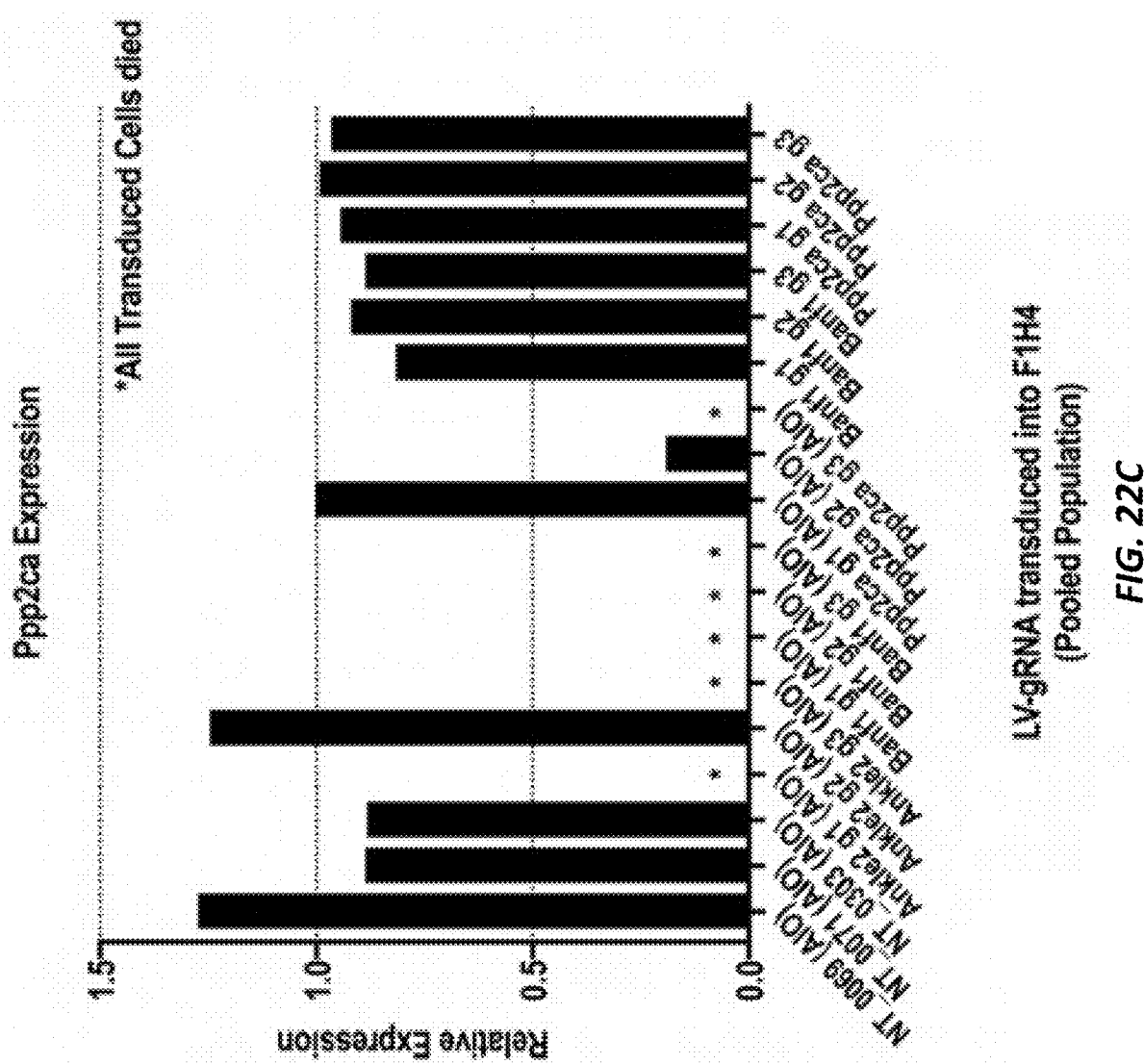
FIG. 22C shows relative expression of Ppp2ca in F1H4 mouse embryonic stem cells as assessed by qRT-PCR following transduction with the lentiviral sgRNA expression constructs (all-in-one (AIO) construct including Cas9, or sgRNA alone).

In this experiment, mouse ES cells were again transduced with LV at an MOI of 600 in the presence of polybrene, grown for 10 days under puromycin selection. RNA was extracted, and qRT-PCR analysis was performed (TaqMan qRT-PCR assays obtained from ThermoFisher, Assay IDs Mm01205802_m1, Mm01231514_g1, and Mm00479816_m1). Confirming the result in the previous experiment, Ppp2ca g2 again cause a specific sharp reduction in Ppp2ca expression, in this case >80%, confirming the specific effect of this sgRNA. See FIG. 22C. More dramatically, in this experiment, selection for the expression of several sgRNAs (Ankle2 g1, Ankle2 g3, Banf1 g1, Banf1 g2, Banf1 g3, and Ppp2ca g3) caused widespread cell death and loss of all cells, such that RNA collection was not possible. See FIGS. 22A-22C. Notably, transduction with NT control sgRNAs in the all-in-one vector did not cause cell death, indicating that expression of Cas9 from this construct is not inherently toxic to cells. Moreover, expression of Banf1 and Ppp2ca-targeting sgRNAs in the pLentiGuide-puro vector (lacking Cas9) likewise did not cause cell death. Therefore, we concluded that the Cas9-mediated activity of these sgRNAs causing specific disruption of their target genes was the cause of cell death in these cells, indicating the sgRNAs were likely efficacious in hitting their targets. This outcome was not completely surprising, as it has been reported that BANF1 and PPP2CA are essential for the viability and/or pluripotency of ES cells.

TABLE 10

Mouse sgRNA Target Sequences.

| sgRNA | Target Sequence | SEQ ID NO (Target Sequence) | SEQ ID NO (sgRNA DNA-Targeting Segment) | Vector |
| --- | --- | --- | --- | --- |
| NT 0303 | CGCCTCTCACGTGTAGGCTT | 8 | 34 | pLentiCRISPR-v2 |
| NT 0071 | ATAGCCGCCGCTCATTACTT | 17 | 43 | pLentiCRISPR-v2 |
| NT 0069 | CTTCGACGCCATCGTGCTCA | 7 | 33 | pLentiCRISPR-v2 |
| Banf1 g1 | ATGAAGACCTCTTCCGAGAA | 18 | 44 | pLentiCRISPR-v2 |
| Banf1 g2 | ATCCCGGCCAGGCTCCCCAC | 19 | 45 | pLentiCRISPR-v2 |
| Banf1 g3 | TTGGTGACGTCCTGAGCAAG | 20 | 46 | pLentiCRISPR-v2 |
| Ppp2ca g1 | CCGAGCACTCGATCGCCTAC | 21 | 47 | pLentiCRISPR-v2 |
| Ppp2ca g2 | ACATCGAACCTCTTGAACGT | 22 | 48 | pLentiCRISPR-v2 |
| Ppp2ca g3 | GGGATATCTCCTCGGGGAGC | 23 | 49 | pLentiCRISPR-v2 |
| Ankle2 g1 | GATACAGGTCAACAACGTAG | 24 | 50 | pLentiCRISPR-v2 |
| Ankle2 g2 | TTCGACAGCTTTCCGCAGCT | 25 | 51 | pLentiCRISPR-v2 |
| Ankle2 g3 | CCAGAACCAATTAGATATCG | 26 | 52 | pLentiCRISPR-v2 |
| Banf1 g1 | ATGAAGACCTCTTCCGAGAA | 18 | 44 | pLentiGuide-puro |
| Banf1 g2 | ATCCCGGCCAGGCTCCCCAC | 19 | 45 | pLentiGuide-puro |
| Banf1 g3 | TTGGTGACGTCCTGAGCAAG | 20 | 46 | pLentiGuide-puro |
| Ppp2ca g1 | CCGAGCACTCGATCGCCTAC | 21 | 47 | pLentiGuide-puro |
| Ppp2ca g2 | ACATCGAACCTCTTGAACGT | 22 | 48 | pLentiGuide-puro |
| Ppp2ca g3 | GGGATATCTCCTCGGGGAGC | 23 | 49 | pLentiGuide-puro |

Example 4. Improving Models of Tauopathy

Tau inclusions are a pathological hallmark of tauopathies including AD, progressive supranuclear palsy, corticobasal degeneration, Pick's disease, and frontotemporal dementia with parkinsonism linked to chromosome 17 (FTDP-17). Tau inclusions are comprised of numerous forms of aggregated, post-translationally modified tau including highly phosphorylated, cleaved, and acetylated species. We next set out to develop new screening platforms that recapitulate tau hyperphosphorylation and tau aggregation ex vivo in neurons derived from human induced pluripotent stem (iPS) cells (e.g., iCELL GABA neurons), neurons derived from mouse embryonic stem (ES) cells, and primary mouse neurons (isolated mouse cortical neurons). For human iPS-derived neurons, human iPS-derived neurons that are already post-mitotic and ready for use are used. The cells are thawed and plated following established protocols for iCELL® GABANeurons.

First, several constructs were generated to express human tau cDNA (1N4R) under the control of a human synapsin1 promoter. These constructs were codon optimized for use with human or mouse neurons. Seven constructs were generated: (1) pSynapsin1-GFP (SEQ ID NO: 74); (2) pSynapsin1-hTAU WT (SEQ ID NO: 75); (3) pSynapsin1-hTAU WT-GFP (SEQ ID NO: 76); (4) pSynapsin1-GFP-hTAU WT (SEQ ID NO: 77); (5) pSynapsin1-hTAU 3MUT (A152T, P301L, S320F) (SEQ ID NO: 78); (6) pSynapsin1-hTAU 3MUT (A152T, P301L, S320F)-GFP (SEQ ID NO: 79); and (7) pSynapsin1-GFP-hTAU 3MUT (A152T, P301L, S320F) (SEQ ID NO: 80). The synapsin 1 gene promoter confers neuron-specific expression. These constructs can be packaged in a Lentivirus or in an Adeno-Associated Virus for delivery. DNA and protein sequences for the wild type Tau 1N4R are set forth in SEQ ID NOS: 81 and 82, respectively. DNA and protein sequences for the 3MUT Tau 1N4R (A152T, P301L, S320F) are set forth in SEQ ID NOS: 83 and 84, respectively.

TaqMan assays were designed to detect specifically the transgenic expression of human tau cDNA in human or mouse neurons. Quantitative reverse transcription Polymerase Chain reaction (qRT-PCR) was performed to detect transgenic human TAU using specific primers and probes to detect codon optimized sequences of wild type (WT) and mutant (MUT) TAU cDNA. Total RNA was isolated using Direct-zol RNA Miniprep plus kit according to the manufacturer's protocol (Zymo Research). Total RNA was treated with DNase using Turbo DNA-free kit according to the manufacturer's protocol (Invitrogen) and diluted to 20 ng/μL. Reverse transcription (RT) and PCR were performed in a one-step reaction with Quantitect Probe RT-PCR kit (Qiagen). The qRT-PCR reaction contained 2 μL RNA and 8 μL mixture containing RT-PCR Master mix, ROX dye, RT-mix, and gene specific primer-probe mix to make a final volume of 10 μL. After reverse transcription, the PCR reaction solution was reconstituted to a final volume of 8 μL containing 3 μL cDNA and 5 μL of PCR mixture, probe and gene specific primers. Unless otherwise noted, final primer and probe concentrations were 0.5 μM and 0.25 μM, respectively. qPCR qRT-PCR was performed on a ViiA™ 7 Real-Time PCR Detection System (ThermoFisher). PCR reactions were done in quadruplicates at 95° C. 10 min and 95° C. 3 s, 60° C. 30 s with RT-step at 45° C. 10 min followed by 95° C. 10 min and 2-step cycling 95° C. 5 s, 60° C. 30 s for 45 cycles in an optical 384-well plate. The sequences of the primers and probes used in each analysis are provided in Table 11 below.

TABLE 11

Primers and Probes for Human Tau.

| Assay | Forward primer | Reverse primer | Probe |
|---|---|---|---|
| hTau_huopt_WT | AGAATCTGAAGCATCAACCGG (SEQ ID NO: 53) | GGTTTGTAAACGATCTGCACTG (SEQ ID NO: 54) | AATATCAAGCACGTCCCTGGAGGC (SEQ ID NO: 55) |
| hTau_huopt_MUT | CCGAAAATCTCAAGCATCAGC (SEQ ID NO: 56) | ACACAATCTGTACGCTTCCG (SEQ ID NO: 57) | TGCACGTTAGACAGGTCCAGCTTC (SEQ ID NO: 58) |
| hTau_msopt_WT | GGCGGTAAGGTCCAAATTATAAAC (SEQ ID NO: 59) | GGTTTGTAAACGATCTGAACGG (SEQ ID NO: 60) | AATGTCCAAAGCAAGTGTGGCAGC (SEQ ID NO: 61) |
| hTau_msopt_MUT | GGTAGTACAGAGAACCTGAAGC (SEQ ID NO: 62) | CTTTGCTCCCACATTTGCTC (SEQ ID NO: 63) | CGGTGGTGGTAAGGTCCAGATCAT (SEQ ID NO: 64) |

Neurons are plated in a 6-well plate (~300,000 cells per well) to perform biochemical assays and in a 96-well plate (~15,000 neurons per well) to immunostain followed by high-content imaging, and image analysis. Neurons are transduced with the human tau constructs alone or in combination with the all-in-one virus (SEQ ID NO: 85) that expresses the Cas9 transgene under a specific promoter (for example, the EF1 alpha promoter) as well as BANF1, PPP2CA, ANKLE2, or non-targeted sgRNAs (for example, under the control of a U6 promoter). DNA and protein sequences for the Cas9 are set forth in SEQ ID NOS: 86 and 87, respectively.

After about a week in culture, cells are exposed to 50% conditioned medium tau-YFP (Agg[+]) and maintained in culture. Cells in 96-well plates are finally fixed and immunostained with specific antibodies to detect the following: tau hyperphosphorylation and tau aggregation (AT8 and S356 antibodies to detect tau hyperphosphorylation, with subcellular localization (axonal, somatodendritic compartments)); abnormal morphology of the nuclear lamina and impaired nucleocytoplasmic transport (lamin A/C, lamin B1, FUS, TDP-43, HNRPA1, NPC, and NPT); and cell survival (DAPI/NeuN/MAP2) in cells transduced with BANF1, PPP2CA, or ANKLE2 sgRNAs as compared to non-targeted sgRNAs. Thioflavin S is also used to stain and visualize β-amyloid structures. Neuronal function (neurite retraction, loss of synapses, aberrant calcium homeostasis, and imbalanced neurotransmitter release) is also assessed. A high-content imager Phenix Opera (96-well format) is used for the cell survival assay (DAPI/NeuN/MAP2), the phospho-tau assay (AT8, S356), and the thioflavin S assay. Cells in 6-well plates are collected to perform cell fractionation assay and reveal the presence of insoluble and mislocalized tau.

We then set out to develop new screening platforms that recapitulate tau hyperphosphorylation and tau aggregation ex vivo in mouse brain slice cultures. Brain slice assays are well-known. See, e.g., Polleux et al. (2002) *Sci. STKE* 2002(136) p19 (doi: 10.1126/stke.2002.136.p19), herein incorporated by reference in its entirety for all purposes.

Brain slice cultures of mouse neonates are transduced with all-in-one lentivirus or adeno-associated virus (inducing the expression of Cas9 as well as specific sgRNAs) or antisense oligonucleotide (ASO) and are exposed to conditioned medium tau-YFP (Agg[+]) and maintained in culture. Finally, slices are fixed to reveal tau hyperphosphorylation and tau aggregation as described above. Slices are also collected to reveal the presence of insoluble tau.

We then set out to develop a screening platform that recapitulates tau hyperphosphorylation and tau aggregation in vivo. Adult PS19 mice (6-8 weeks) are injected by intracranial (stereotactic surgery for injection in the hippocampus and other brain regions or intracerebroventricular injection) or intrathecal (in the spinal cord) injection with: (1) lipid nanoparticle (LNP) with Cas9 mRNA and sgRNA; (2) LNP with siRNA; (3) lentivirus (LV) all-in-one (Cas9+sgRNA); (4) adeno-associated virus (AAV) all-in-one (Cas9+sgRNA); or (5) antisense oligonucleotide (ASO). PS19 mice (available atjax.org/strain/008169, herein incorporated by reference in its entirety for all purposes) are used.

sgRNAs, siRNAs, and antisense oligonucleotides target the genes Banf1, Ppp2ca, Ankle2, or consist of non-targeted control sequences. Animals are sacrificed to reveal tau hyperphosphorylation (AT8 staining) and tau aggregation as described above after sectioning and staining of the brain. Brains are also collected to reveal the presence of insoluble and mislocalized tau (thioflavin S staining).

Figure 24A:
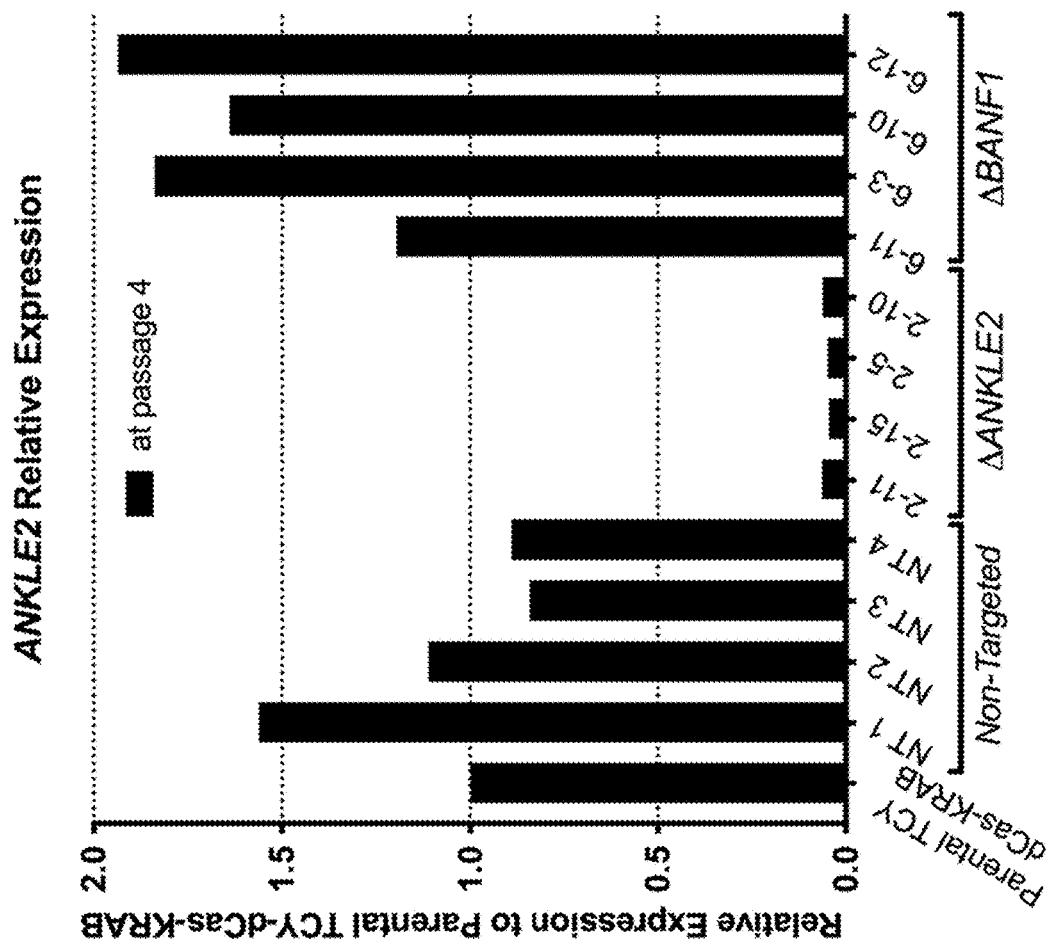
FIG. 24A shows ANKLE2 relative expression in tau-CFP/tau-YFP (TCY) dCas-KRAB clones (targeted knockdown of BANF1 or ANKLE2 or non-targeted).
Figure 24B:
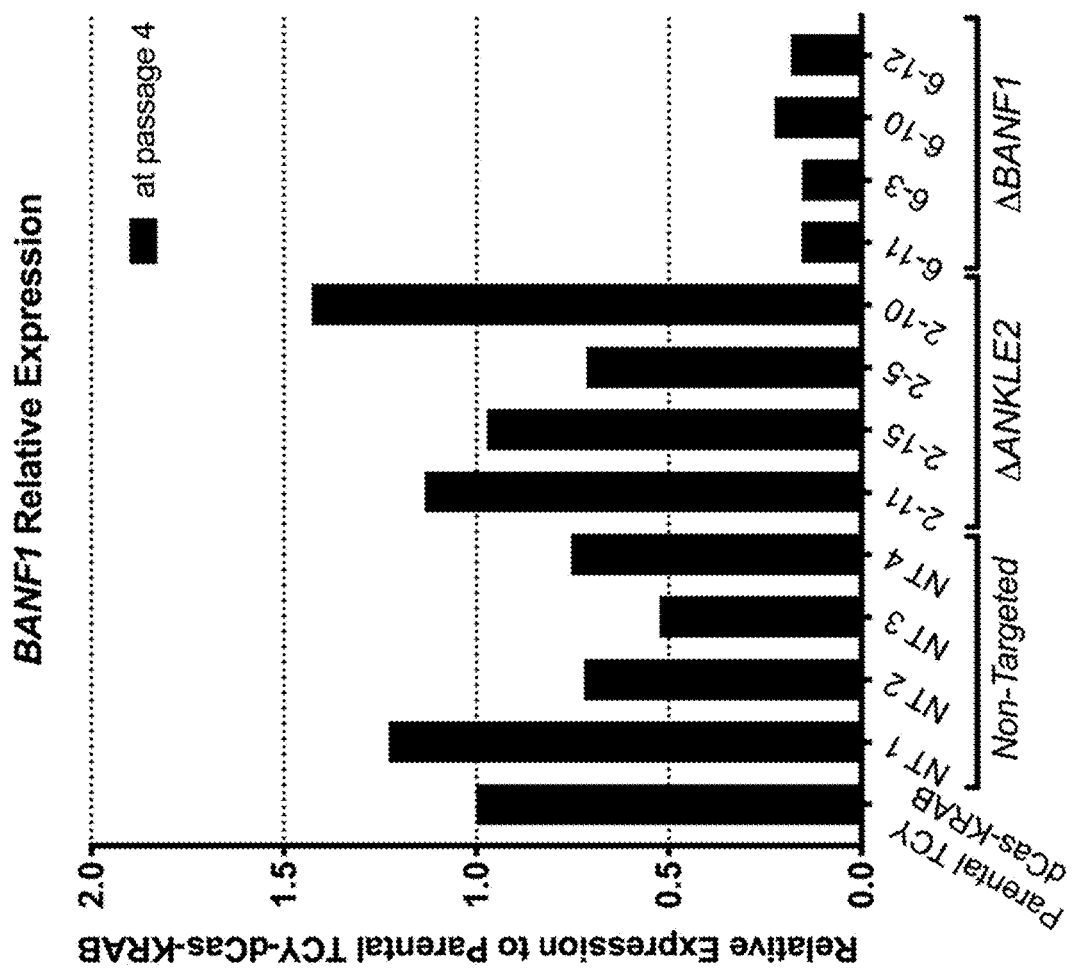
FIG. 24B shows BANF1 relative expression in tau-CFP/tau-YFP (TCY) dCas-KRAB clones (targeted knockdown of BANF1 or ANKLE2 or non-targeted).
Figure 25:
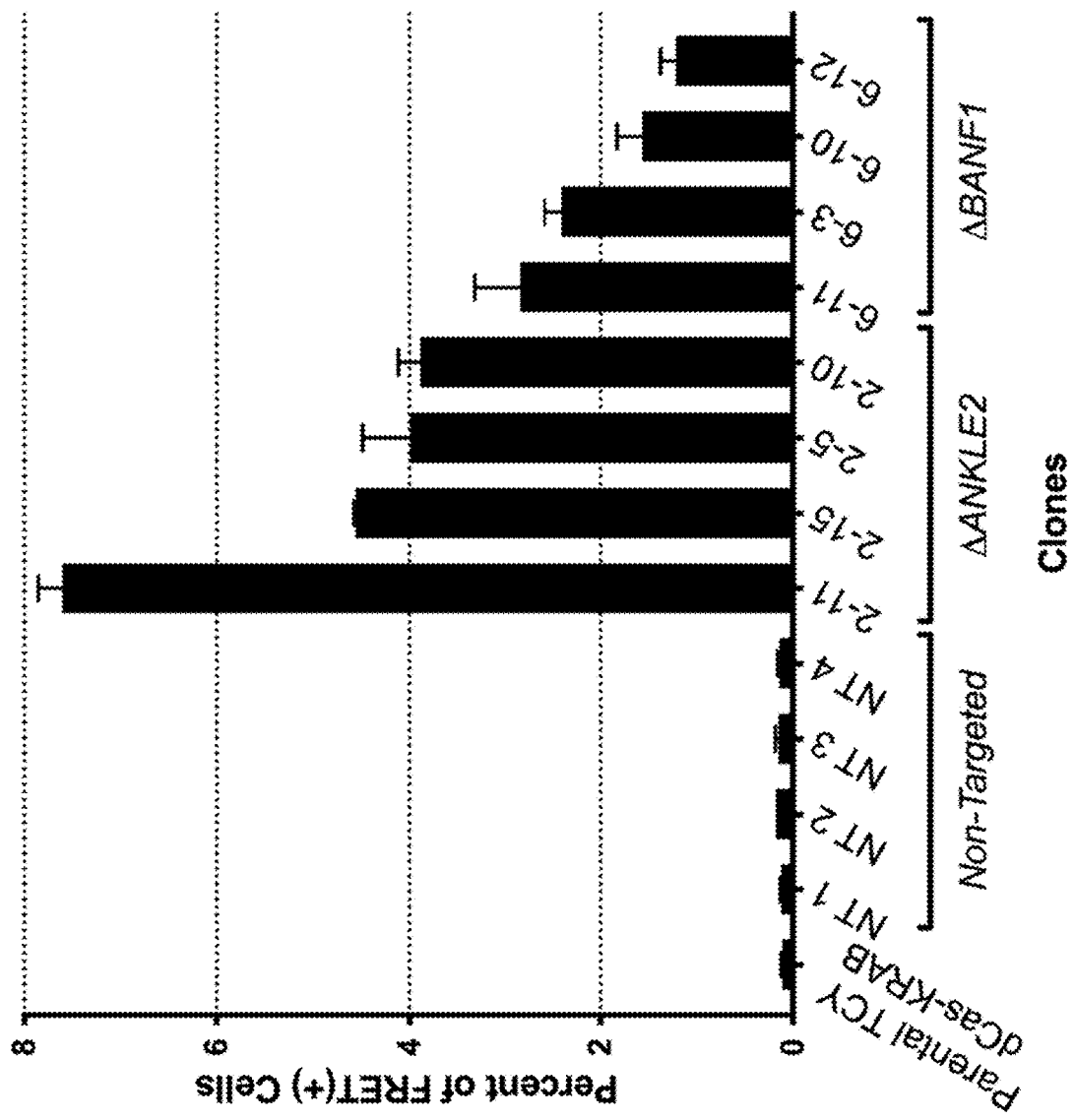
FIG. 25 shows tau aggregation as measured by percent FRET[+] cells in tau-CFP/tau-YFP (TCY) dCas-KRAB clones (targeted knockdown of BANF1 or ANKLE2) treated with conditioned medium tau-YFP Agg[+] for three days.

As BANF1/PPP2CA/ANKLE2 are essential in mitotic cells, we hypothesized that a knockdown strategy would allow us to better understand this novel link to tau aggregation. We introduced the dCas9-KRAB CRISPRi system of transcriptional repression in tau biosensor cells and transduced specific sgRNAs, targeted to promoter regions immediately preceding transcriptional start sites. See FIGS. 24A and 24B. We isolated ΔBANF1 and ΔANKLE2 knockdown clones by clonal serial dilution that can induce tau aggregation after treatment with conditioned medium tau-YFP (Agg[+]). See FIG. 25. This showed that CRISPRi dCas9-KRAB ΔBANF1 and ΔANKLE2 targeted knockdown clones can induce tau aggregation.

Figure 26:
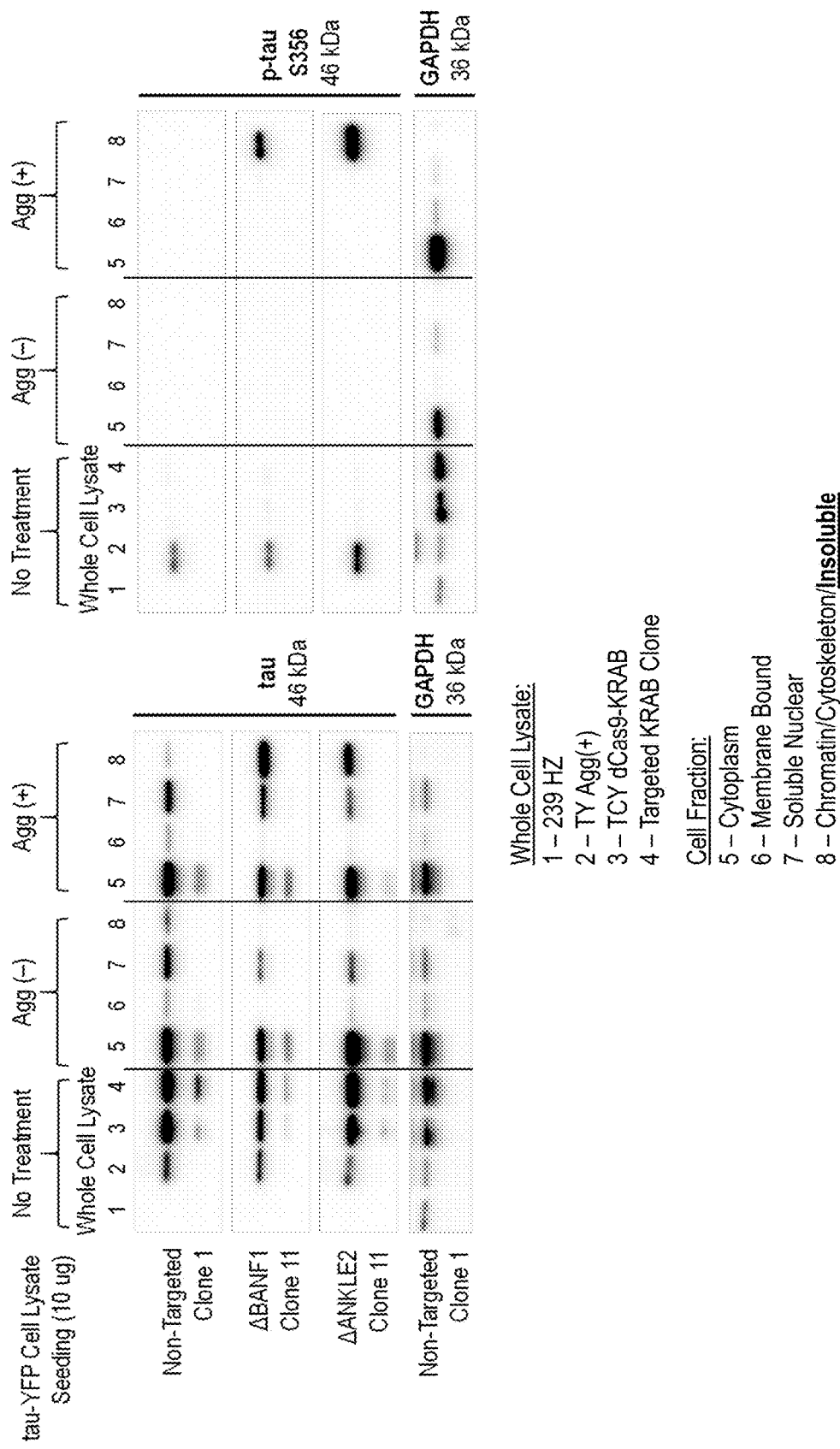
FIG. 26 shows cell fractionation of ΔBANF1 and ΔANKLE2 clones enables detection of tau and phospho-tau (serine 356) in the insoluble fraction after two days with tau-YFP Agg[+] cell lysate.

We next performed a cell fractionation of ΔBANF1 and ΔANKLE2 clones that enabled detection of tau and phospho-tau (serine 356) in the insoluble fraction after two days with tau-YFP Agg[+] cell lysate, providing functional evidence of a link between ΔBANF1 and ΔANKLE2 clones with tau insolubility and phosphorylation at serine 356. See FIG. 26.

Figure 27:
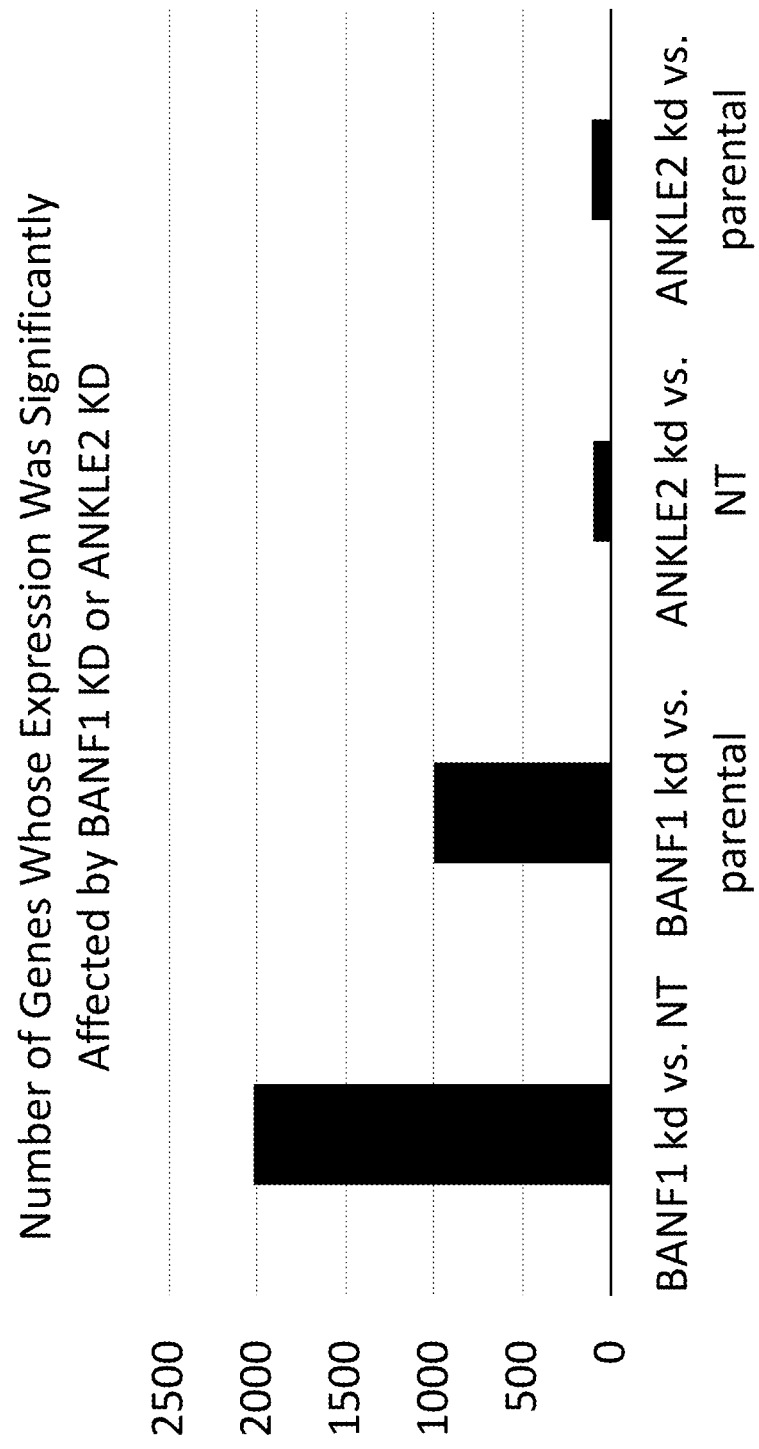
FIG. 27 shows the gene list size of significant genes (fold change greater than or equal to 1.5) in four comparisons by RNA-seq analysis (BANF1 KD vs. non-targeted control, BANF1 KD vs. parental, ANKLE2 KD vs. non-targeted control, and ANKLE2 KD vs. parental).

We also collected RNA from ΔBANF1 and ΔANKLE2 clones as well as two control groups (non-targeted and parental). RNA-seq analysis characterized significant differences in the ΔBANF1 and ΔANKLE2 knockdown clones versus the two control groups. RNA-seq analysis of the CRISPRi knockdown clones revealed that ΔBANF1 knockdown samples are more different from samples of ΔANKLE2 or non-targeted groups. See FIG. 27. We validated 10 transcriptional differences between these groups (data not shown). These ten target genes had reduced expression in both ΔBANF1 and ΔANKLE2 knockdown clones.

Figure 28:
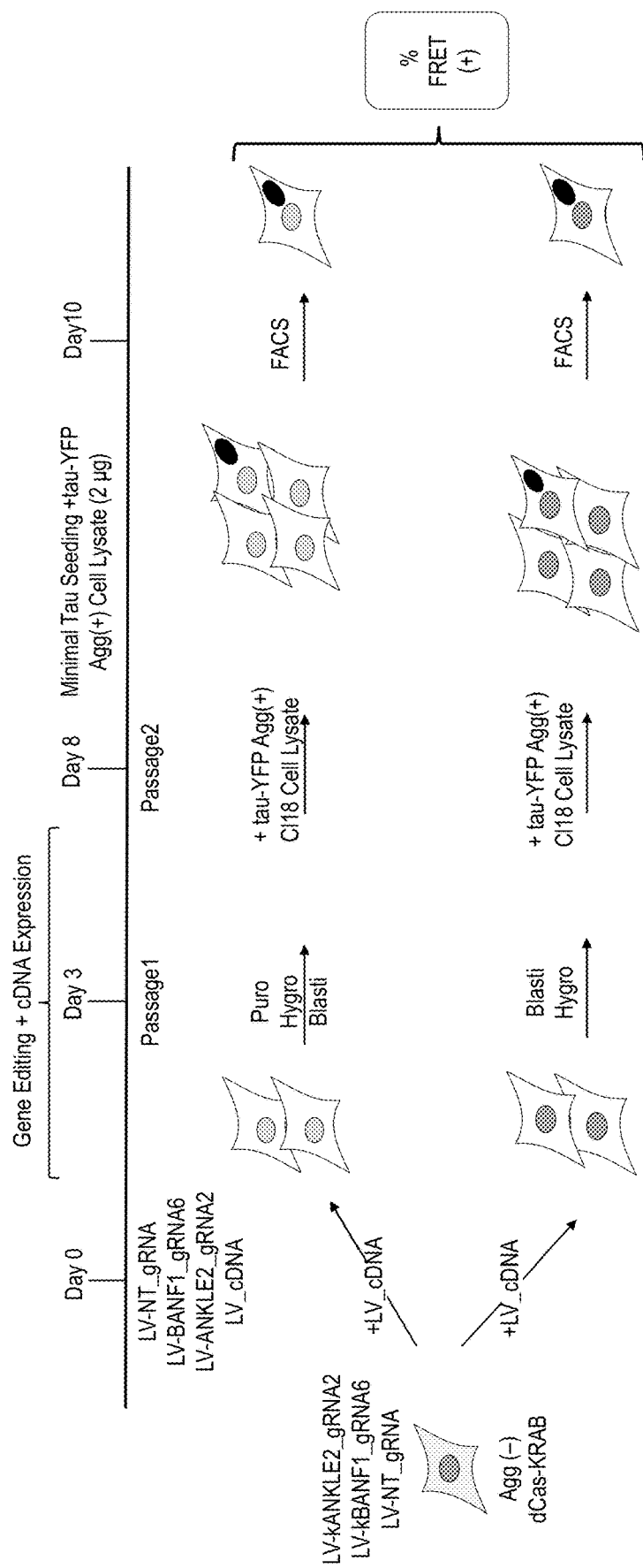
FIG. 28 shows a schematic for testing cDNA complementation for rescue of increased tau aggregation in ΔBANF1 and ΔANKLE2 knockdown cells.

We then took a cDNA complementation approach by adding BANF1 cDNA (with luciferase cDNA as a control). A schematic of the cDNA complementation experimental design is shown in FIG. 28.

Figure 29:
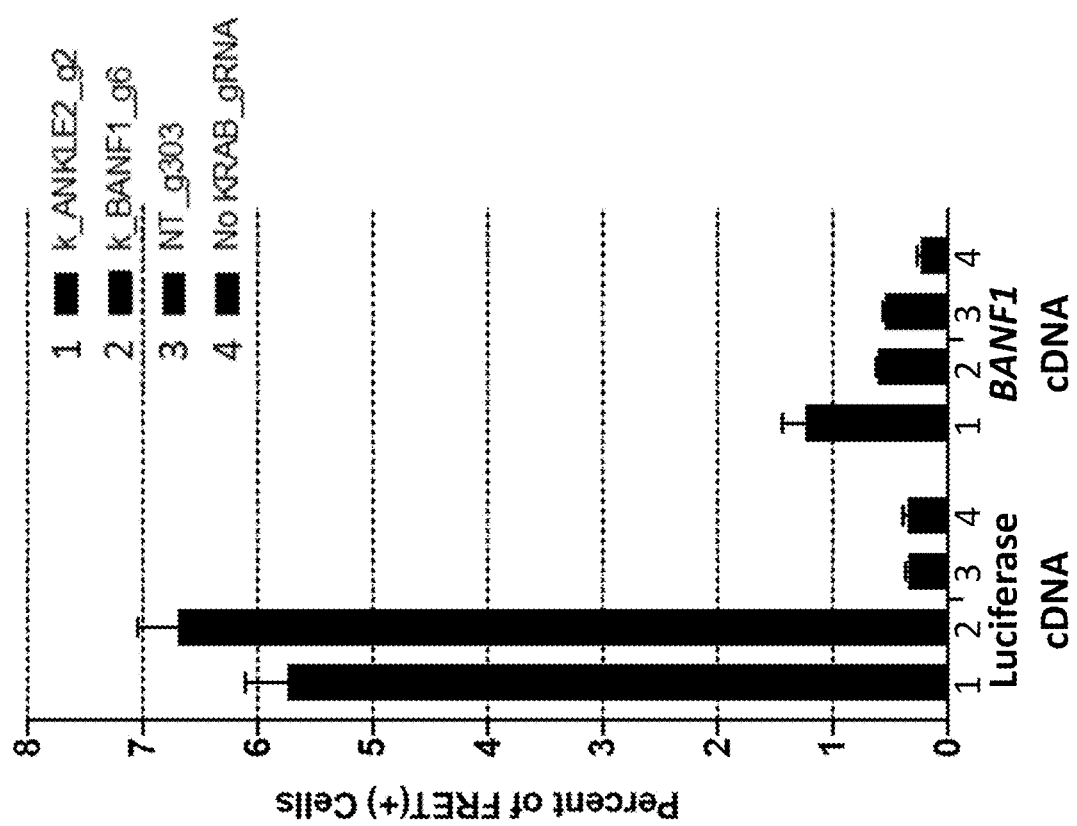
FIG. 29 shows tau aggregation as measured by percent FRET[+] cells following cDNA complementation of tau-CFP/tau-YFP dCas-KRAB ΔBANF1 and ΔANKLE2 knockdown cells treated with tau-YFP Agg[+] cell lysate (2 μg) for 2 days. No_KRAB_gRNA refers to negative control samples in which no gRNA was administered.

BANF1 cDNAs was subcloned in pLVX-EF1a plasmid and packaged for lentiviral transduction of cDNA in ΔBANF1 knockdown cells, ΔANKLE2 knockdown cells, and non-targeted control cells. Specifically, the cDNA was tested for rescue of increased tau aggregation in ΔBANF1 and ΔANKLE2 knockdown cells. cDNA-expressing cells were treated with tau-YFP Agg[+] cell lysate for two days. We showed that BANF1 cDNA can rescue tau aggregation in both ΔBANF1 and ΔANKLE2 knockdown cells, providing another functional link between BANF1/ANKLE2 and tau aggregation. See FIG. 29.

We next used primary cultures of mouse cortical neurons to study in post-mitotic cells the effect of ΔBANF1 and ΔANKLE2 mutations on tau phosphorylation, misfolding, and insolubility. Cortical neurons were transduced with an All_In_One Lentivirus (AIO_LV, LV_Cas9_sgRNA) that expresses both Cas9 and an sgRNA (Banf1_g3, Ankle2_g3, or Ppp2ca_g2) that was previously validated for efficacy in mouse ESC. Mouse primary cortical neurons were transduced two days after plating with AIO_LV and maintained for 14 days in culture for fluorescent immuno-staining and western-blot studies (using WES technology by Protein Simple). For immunofluorescence, C57BL/6 mouse primary cortical neurons (commercially available) were plated at Day 0 at a density of 25,000 neurons per well in 96-well poly-D lysine coated plates. At Day2, neurons were transduced at a multiplicity of infection of 40,000 viral genome per neuron with an AIO_LV for Banf1_g3 or Ankle2_g3 or Ppp2ca_g2 or non-targeted_gRNA control. Culture medium was changed every 3-4 days. At Day16, neurons were fixed with a solution of paraformaldehyde (PFA) at 4% and studied by fluorescent immunostaining. For the western blot study, 400,000 neurons were plated in a poly-D lysine 6-well and transduced with AIO-LV (25,000 VG per neuron). Culture medium was changed every 3-4 days. Neurons were collected after 14 days in culture and prepared for protein study.

After 14 days, we also collected AIO_LV transduced neurons to determine the extent of gene editing (INDEL %). We found gene editing to be consistently higher using the Banf1_g3 sgRNA than with the Ankle2_g3. See Table 12.

TABLE 12

Gene Editing.

| | AIO-LV | Gene Editing (INDEL %) | |
|---|---|---|---|
| XP | Transduced | Banf1 Amplicon | Ankle2 Amplicon |
| XP1 | NT | 0.22 | 0.04 |
| | Banf1_g3 | 68.77 | 0.08 |
| | Ankle2_g3 | 0.83 | 15.5 |
| XP2 | NT | 6.99 | 0.13 |
| | Banf1_g3 | 78.59 | 0.23 |
| | Ankle2_g3 | 0.33 | 32.07 |
| XP3 | NT | 9.5 | 0.09 |
| | Banf1_g3 | 70.61 | 0.37 |
| | Ankle2_g3 | 0.22 | 39.3 |

For the fluorescent immunostaining study, we focused on abnormal phenotypes that have been linked to tauopathies, such as tau hyper-phosphorylation (in the somatodendritic domain), nuclear pore complex integrity (Nup98 mislocalization), and nucleocytoplasmic transport impairment (Ran/RanGAP1 nuclear/cytoplasmic ratio decrease).

We used an automated and unbiased imaging analysis approach combining the Opera Phenix high-content confocal imager (Perkin Elmer) with the Harmony software (Perkin Elmer) for the image data analysis. For each experiment, an average of six biological replicates was performed, approximately 70 fields were imaged in each well and analyzed per biological replicate, and fluorescence-conjugated secondary antibodies used for labeling primary antibody. Secondary antibodies were conjugated with Alexa-488 nm (green), -568 nm (Orange) and -647 nm (Far Red). 4',6-Diamidino-2-phenylindole (DAPI) was used for nuclear staining.

For each field, first the number of DAPI$^+$ neurons was counted. Second, the fluorescent intensity of microtubule associated protein-2 (Map2), a neuronal marker of the somatodendritic domain, was used to segment the cytoplasm including the somatodendritic domain and count the number of healthy neurons. Third, the fluorescent intensity of different cellular markers (phospho-tau S356, phospho-tau AT8 (S202, T205), total tau, Nup98, LaminB1, Ran, RanGAP1) was determined in several cellular compartments including the cytoplasm, the nucleus as well as a perinuclear region surrounding the nucleus. Fourth, the mean fluorescent intensity in each well (biological replicate), including the average over all cells of all fields in each well, was calculated.

We developed image analysis methods to quantify the biomarker intensity in the following combination: phospho-tau and total tau; phospho-tau and LaminB1 or Nuclear Pore Complex (NPC); and the nuclear/cytoplasmic ratio of Nup98, Ran and RanGAP1, and phospho-tau intensity.

Figures 30A, 30B:
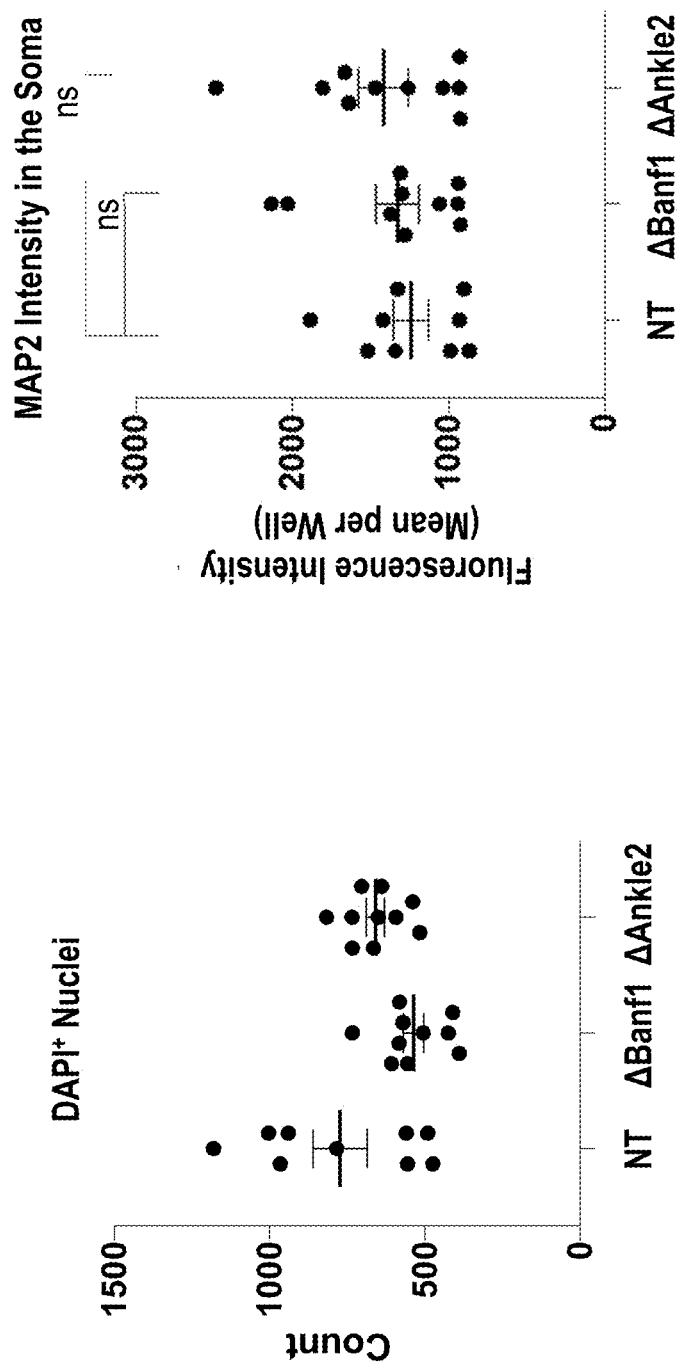
FIG. 30A shows the count of DAPI+ nuclei in non-targeted mouse primary cortical neurons and in ΔBANF1 and ΔANKLE2 mutant cortical neurons.
FIG. 30B shows MAP2 intensity in the soma as measured by fluorescence intensity in non-targeted mouse primary cortical neurons and in ΔBANF1 and ΔANKLE2 mutant cortical neurons. Two-tailed unpaired Student's t test was used (ns=not significant; error bar represents s.e.m.).

ΔBanf1 and ΔAnkle2 mutant mouse cortical neurons showed a similar Map2 somatodendritic staining intensity as non-targeted cortical neurons. See FIGS. 30A and 30B. This indicated that disruption of Banf1 and Ankle2 does not affect neuronal survival in post-mitotic cortical neurons after 14 days.

Figure 31A:
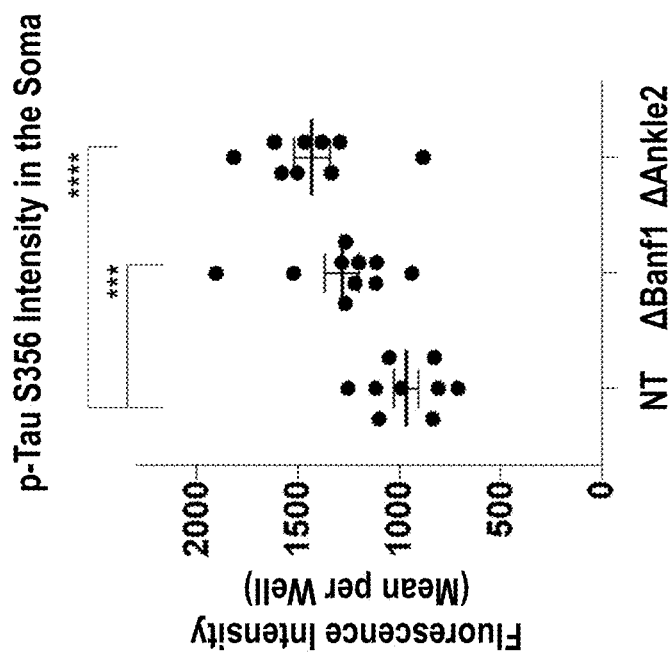
FIG. 31A shows phospho-Tau S356 intensity in the soma (as measured by fluorescence intensity) in non-targeted mouse primary cortical neurons and in ΔBANF1 and ΔANKLE2 mutant cortical neurons.
Figure 31B:
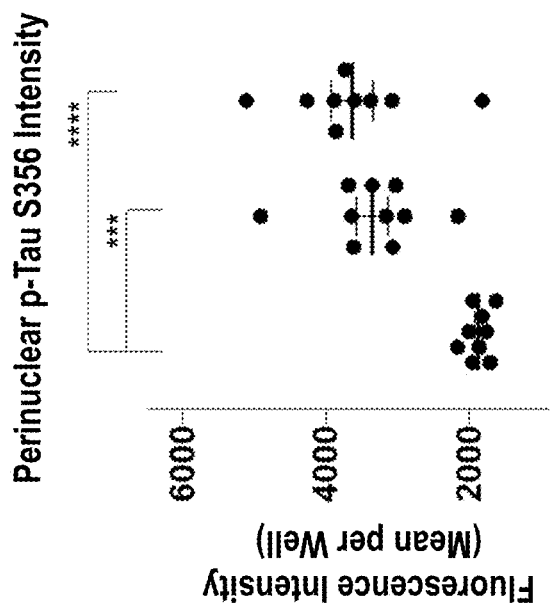
FIG. 31B shows perinuclear phospho-Tau S356 intensity (as measured by fluorescence intensity) in non-targeted mouse primary cortical neurons and in ΔBANF1 and ΔANKLE2 mutant cortical neurons. Two-tailed unpaired Student's t test was used (*=p<0.004**=p<0.0001; error bar represents s.e.m.).
Figure 35B:
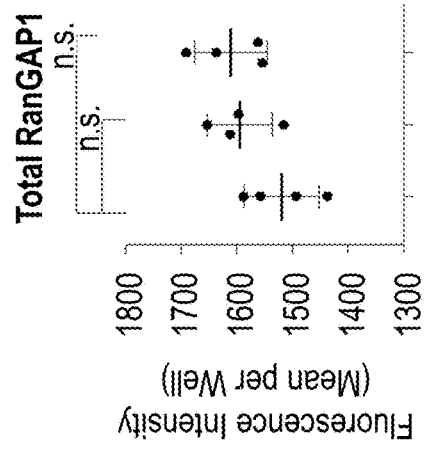
FIG. 35B shows the total RanGAP1 levels in non-targeted mouse primary cortical neurons and in ΔBANF1 and ΔANKLE2 mutant cortical neurons.
Figure 35D:
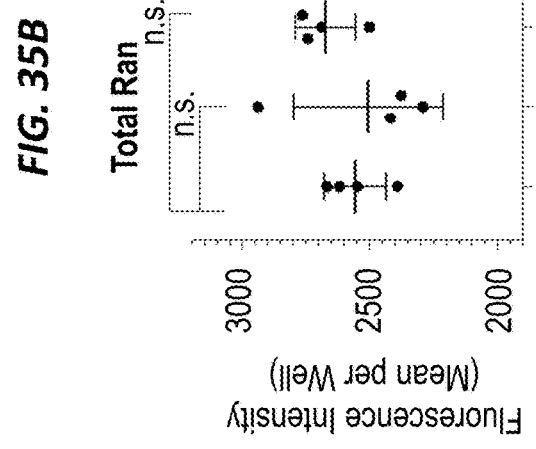
FIG. 35D shows the total Ran levels in non-targeted mouse primary cortical neurons and in ΔBANF1 and ΔANKLE2 mutant cortical neurons. Two-tailed unpaired Student's t test was used (**=p<0.002—ns, not significant; error bar represents s.e.m.).
Figure 35A:
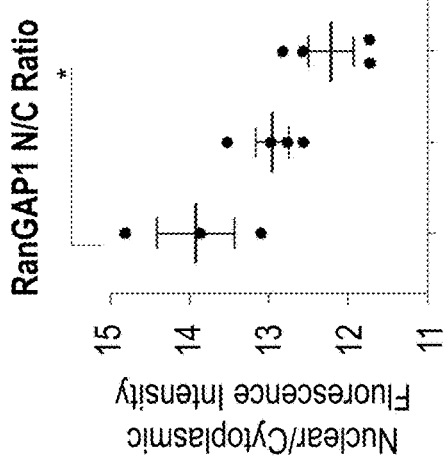
FIG. 35A shows the RanGAP1 nuclear/cytoplasmic ratio in non-targeted mouse primary cortical neurons and in ΔBANF1 and ΔANKLE2 mutant cortical neurons.
Figure 35C:
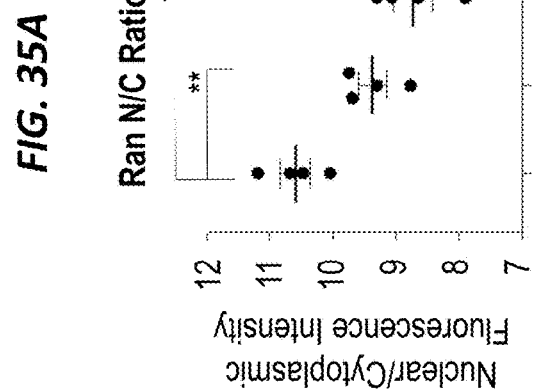
FIG. 35C shows the Ran nuclear/cytoplasmic ratio in non-targeted mouse primary cortical neurons and in ΔBANF1 and ΔANKLE2 mutant cortical neurons.

Phospho-tau (serine 356) staining was increased in the somatodendritic compartment of ΔBanf1 (p value<0.004) and ΔAnkle2 (p value<0.001) mutant cortical neurons compared to non-targeted cortical neurons. See FIG. 31A. This is reminiscent of observations in Alzheimer's disease, where the protein tau forms hyper-phosphorylated aggregates in the somatodendritic domain. Notably, we found the increased phospho-tau staining intensity to be particularly pronounced in the perinuclear region. See FIG. 31B. Data were expressed as means±standard errors of the means (SEM), and the number of biological replicates for each experimental condition was indicated as a dot. Data were analyzed by an unpaired Student's t test when making comparisons between two samples (i.e., ΔBanf1 vs. non-targeted cortical neurons).

As a control experiment, we determined that total tau staining intensity is not increased in the somatodendritic compartment of ΔBanf1 and ΔAnkle2 mutant compared to non-targeted cortical neurons. See FIGS. 32A-32C.

As shown in FIGS. 33A-33E, phospho-tau AT8 (S202, T205) staining is increased in the somatodendritic compartment of ΔBanf1 and ΔAnkle2 mutant neurons compared to non-targeted cortical neurons.

Pathological tau can impair nuclear import and export in tau-overexpressing transgenic mice and in human AD brain tissue. phospho-tau disrupts nuclear pore complex diffusion barrier function. The nuclear pore complex protein nucleoporin Nup98 accumulates in the cell bodies of some tangle-bearing neurons and can facilitate tau aggregation in vitro.

We looked at the subcellular localization of Nup98 and found it was enriched in the soma of ΔBanf1 and ΔAnkle2 mutant compared to non-targeted cortical neurons. Nup98 nuclear/cytoplasmic ratio was decreased. See FIGS. 34A-34D.

In addition, decreased Ran and RanGAP1 nuclear/cytoplasmic ratio provides evidence of an impaired nuclear pore complex active transport in ΔBanf1 and ΔAnkle2 mutant compared to non-targeted cortical neurons. See FIGS. 35A-35D.

Mouse primary cortical neurons were transduced two days after plating with AIO_LV_NT, AIO_LV_Banf1_g3 and AIO_LV_Ppp2ca_g2 and maintained for 14 days in culture for fluorescent phospho-tau immunostaining (at serine 356 and serine 202/threonine 205, also known as AT8 antibody) as well as misfolded tau detection. We used the PROTEOSTAT® Aggresome detection kit by ENZO as a robust and quantitative method to detect misfolded protein aggregates and aggresomes, that has been optimized for antibody co-localization studies with the Aggresome Detection Reagent (ADR). The PROTEOSTAT® dye specifically intercalates into the cross-beta spine of quaternary protein structures typically found in misfolded and aggregated proteins, which will inhibit the dye's rotation and lead to a strong fluorescence. At day 16, neurons were fixed with a solution of paraformaldehyde (PFA) at 4% and studied for Fluorescent immunostaining. Increased phosphorylation of tau on serine 356 in the somatodendritic compartment of ΔBanf1 (p-value<0.026) and ΔPpp2ca (p-value<0.0087) was revealed in mutant cortical neurons compared to non-targeted cortical neurons. See FIG. 38D. Notably, we found the increased phospho-tau staining intensity to be particularly pronounced in a cytoplasmic region just around the nucleus that we defined as the perinuclear region (ΔBanf1 p-value<0.002 and ΔPpp2ca p-value<0.04). See FIG. 38B. Similarly, increased phospho-tau (serine 202/threonine 205) in the perinuclear region of ΔBanf1 (p-value<0.026) and ΔPpp2ca (p-value<0.0087) was observed in mutant cortical neurons compared to non-targeted cortical neurons. See FIGS. 39B and 39D. Data were expressed as means±standard errors of the means (SEM), and the number of biological replicates for each experimental condition was indicated as a dot. Data were analyzed by an unpaired Student's t test when making comparisons between two samples (i.e., ΔBanf1 vs. non-targeted cortical neurons). The increase in tau phosphorylation on serine 356 (Pearson correlation (ρ)=0.85—R squared=0.72 for ΔBanf1; ρ=0.92—R squared=0.85 for ΔPpp2ca) as well as on serine 202 and threonine 205 (ρ=0.86—R squared=0.74 for ΔBanf1; ρ=0.94—R squared=0.89 for ΔPpp2ca) correlates with an increased detection of misfolded tau in the soma of mutant neurons as compared to non-targeted. See FIGS. 38A-38F and 39A-39F. Correlation analysis was done using the Pearson parametric test. A P value of <0.05 was taken as significant. We have now confirmed that disruption of Banf1, Ankle2 or Ppp2ca can increase the phosphorylation as well as misfolding of tau.

Figure 37C:
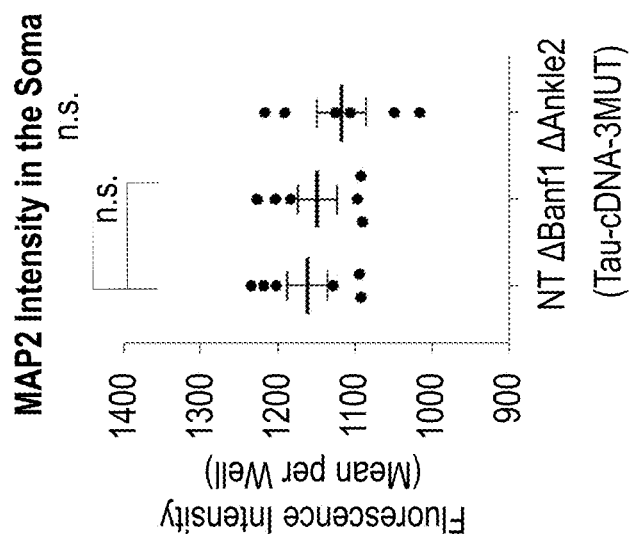
FIG. 37C shows MAP2 intensity in the soma (as measured by fluorescence intensity) in non-targeted mouse primary cortical neurons and in ΔBANF1 and ΔANKLE2 mutant cortical neurons when tau-cDNA 3MUT was added. Two-tailed unpaired Student's t test was used (ns=not significant; error bar represents s.e.m.).
Figure 37B:
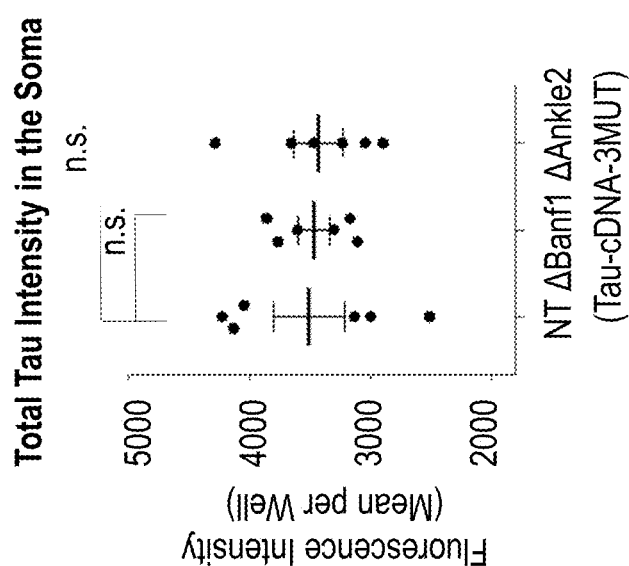
FIG. 37B shows total tau intensity in the soma (as measured by fluorescence intensity) in non-targeted mouse primary cortical neurons and in ΔBANF1 and ΔANKLE2 mutant cortical neurons when tau-cDNA 3MUT was added.
Figure 37A:
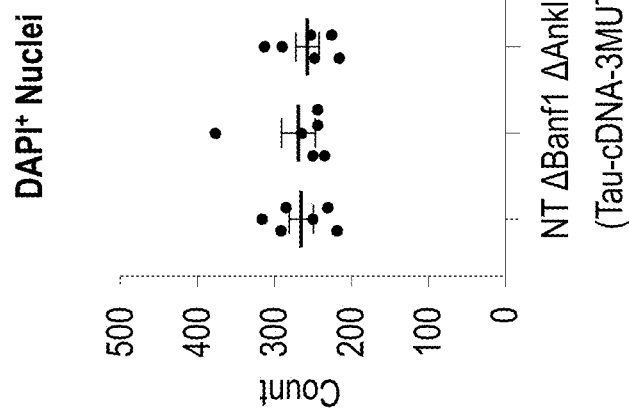
FIG. 37A shows the count of DAPI+ nuclei in non-targeted mouse primary cortical neurons and in ΔBANF1 and ΔANKLE2 mutant cortical neurons when tau-cDNA 3MUT was added.

Experiments were next done using tau seeding in mutant cortical neurons using brain cell lysate from mice transduced with tau cDNA 3MUT or P301S. Phospho-tau (serine 356) staining was increased in the somatodendritic domain of ΔBanf1 and ΔAnkle2 mutant compared to non-targeted cortical neurons when tau-cDNA 3MUT was added. See FIGS. 36A-36D. However, total tau staining was not increased in the somatodendritic domain of ΔBanf1 and ΔAnkle2 mutant compared to non-targeted cortical neurons when tau-cDNA 3MUT was added. See FIGS. 37A-37C.

Organotypic brain slice cultures are then used to validate Banf1, Ankle2, and Ppp2ca as genetic modifiers of tau aggregation. Organotypic brain slice cultures are prepared from wild-type C57BL/6 mice and are transduced with LV-All-In-One (AIO) constructs including Cas9_Banf1_g3, Cas9_Ankle2_g3, Cas9_Ppp2ca_g2, and Cas9_non-targeted_g3 at $10^{10}$ VG at day 0. Alternatively, organotypic brain slice cultures are prepared from wild-type C57BL/6 mice and are transduced with ASOs targeting Ankle2, Ppp2ca, or Banf1 at day 0. At day 14, samples are collected for NGS analysis (INDEL %), phospho-tau staining (S356 and AT8), and ThS staining for misfolded tau.

Stereotactic AIO-LV injection in mouse hippocampus was then used to validate Banf1, Ankle2, and Ppp2ca as genetic modifiers of tau aggregation. A total of 24 C57BL/6 wild-type animals were injected (NT, AIO Cas9_Banf1, AIO Cas9_Ankle2, and AIO Cas9_Ppp2ca). Two animals (for each condition) were taken down 7 days post-injection. NGS revealed significant editing (as INDELs %~>15%; data not shown). Later, animals are taken down for western blot analysis (phospho-tau, misfolded tau, total tau) and for tau seeding assay of hippocampus lysates in tau biosensor cells. Stereotactic AIO-LV injection of dCas9-KRAB plus gRNAs targeting Banf1, Ankle2, or Ppp2ca in mouse hippocampus is then used to validate Banf1, Ankle2, and Ppp2ca as genetic modifiers of tau aggregation.

Stereotactic injection of ASOs in mouse hippocampus is then used to validate Banf1, Ankle2, and Ppp2ca as genetic modifiers of tau aggregation. Examples of ASOs targeting mouse Banf1 are set forth in Table 13. Examples of ASOs targeting mouse Ppp2ca are set forth in Table 14. Examples of ASOs targeting mouse Ankle2 are set forth in Table 15. Parent antisense RNA sequence used to design the ASOs in Tables 13-15 are shown in Table 16.

TABLE 13 mBanf1 ASOs.

| ID | Unmodified | Modified | SEQ ID NO |
|---|---|---|---|
| 320 | TGGGAGGTTGTCATCGTGAT | /52MOErT/*/i2MOErG/*/i2MOErG/*/i2MOErG/*/i2MOErA/*G*G*T*T*G*T*C*A*T*C*/i2MOErG/*/i2MOErT/*/i2MOErG/*/i2MOErA/*/32MOErT/ | 105 |
| 408 | CAGCCTCTTGCTCAGGACGT | /52MOErC/*/i2MOErA/*/i2MOErG/*/i2MOErC/*/i2MOErC/*T*C*T*T*G*C*T*C*A*G*/i2MOErG/*/i2MOErA/*/i2MOErC/*/i2MOErG/*/32MOErT/ | 106 |
| 436 | CATAAGCCTTGTCAAAGCCC | /52MOErC/*/i2MOErA/*/i2MOErT/*/i2MOErA/*/i2MOErA/*G*C*C*T*T*G*T*C*A*A*/i2MOErA/*/i2MOErG/*/i2MOErC/*/i2MOErC/*/32MOErC/ | 107 |
| 442 | GGACCACATAAGCCTTGTCA | /52MOErG/*/i2MOErG/*/i2MOErA/*/i2MOErC/*/i2MOErC/*A*C*A*T*A*A*G*C*C*T*/i2MOErT/*/i2MOErG/*/i2MOErT/*/i2MOErC/*/32MOErA/ | 108 |
| 472 | CATCTTTCTTTAGCACCAGA | /52MOErC/*/i2MOErA/*/i2MOErT/*/i2MOErC/*/i2MOErT/*T*T*C*T*T*T*A*G*C*A*/i2MOErC/*/i2MOErC/*/i2MOErA/*/i2MOErG/*/32MOErA/ | 109 |
| 478 | GGTCTTCATCTTTCTTTAGC | /52MOErG/*/i2MOErG/*/i2MOErT/*/i2MOErC/*/i2MOErT/*T*C*A*T*C*T*T*T*C*T*/i2MOErT/*/i2MOErT/*/i2MOErA/*/i2MOErG/*/32MOErC/ | 110 |
| 492 | CCATTCTCGGAAGAGGTCTT | /52MOErC/*/i2MOErC/*/i2MOErA/*/i2MOErT/*/i2MOErT/*C*T*C*G*G*A*A*G*A*G*/i2MOErG/*/i2MOErT/*/i2MOErC/*/i2MOErT/*/32MOErT/ | 111 |
| 496 | TCAGCCATTCTCGGAAGAGG | /52MOErT/*/i2MOErC/*/i2MOErA/*/i2MOErG/*/i2MOErC/*C*A*T*T*C*T*C*G*G*A*/i2MOErA/*/i2MOErG/*/i2MOErA/*/i2MOErG/*/32MOErG/ | 112 |
| 506 | CATGTATCCTTCAGCCATTC | /52MOErC/*/i2MOErA/*/i2MOErT/*/i2MOErG/*/i2MOErT/*A*T*C*C*T*T*C*A*G*C*/i2MOErC/*/i2MOErA/*/i2MOErT/*/i2MOErT/*/32MOErC/ | 113 |
| 524 | TGCTTGGCATTGGCACCACA | /52MOErT/*/i2MOErG/*/i2MOErC/*/i2MOErT/*/i2MOErT/*G*G*C*A*T*T*G*C*C*A*/i2MOErC/*/i2MOErC/*/i2MOErA/*/i2MOErC/*/32MOErA/ | 114 |
| 528 | GGACTGCTTGGCATTGGCAC | /52MOErG/*/i2MOErG/*/i2MOErA/*/i2MOErC/*/i2MOErT/*G*C*T*T*G*G*C*A*T*T*/i2MOErG/*/i2MOErG/*/i2MOErC/*/i2MOErA/*/32MOErC/ | 115 |
| 550 | GAAGGCACCCAAAGCAGTCC | /52MOErG/*/i2MOErA/*/i2MOErA/*/i2MOErG/*/i2MOErG/*C*A*C*C*C*A*A*A*G*C*/i2MOErA/*/i2MOErG/*/i2MOErT/*/i2MOErC/*/32MOErC/ | 116 |
| 552 | TCGAAGGCACCCAAAGCAGT | /52MOErT/*/i2MOErC/*/i2MOErG/*/i2MOErA/*/i2MOErA/*G*G*C*A*C*C*C*A*A*A*/i2MOErG/*/i2MOErC/*/i2MOErA/*/i2MOErG/*/32MOErT/ | 117 |

TABLE 13-continued mBanf1 ASOs.

| ID | Unmodified | Modified | SEQ ID NO |
|---|---|---|---|
| 554 | TCTCGAAGGCACCCAAAGCA | /52MOErT/*/i2MOErC/*/i2MOErT/*/i2MOErC/*/i2MOErG/*A*A*G*G*C*A*C*C*C*A/i2MOErA/*/i2MOErA/*/i2MOErG/*/i2MOErC/*/32MOErA/ | 118 |
| 556 | ATTCTCGAAGGCACCCAAAG | /52MOErA/*/i2MOErT/*/i2MOErT/*/i2MOErC/*/i2MOErT/*C*G*A*A*G*G*C*A*C*C/i2MOErC/*/i2MOErA/*/i2MOErA/*/i2MOErA/*/32MOErG/ | 119 |
| 560 | CACCATTCTCGAAGGCACCC | /52MOErC/*/i2MOErA/*/i2MOErC/*/i2MOErC/*/i2MOErA/*T*T*C*T*C*G*A*A*G*G*/i2MOErC/*/i2MOErA/*/i2MOErC/*/i2MOErC/*/32MOErC/ | 120 |
| 562 | CACACCATTCTCGAAGGCAC | /52MOErC/*/i2MOErA/*/i2MOErC/*/i2MOErA/*/i2MOErC/*C*A*T*T*C*T*C*G*A*A/i2MOErG/*/i2MOErG/*/i2MOErC/*/i2MOErA/*/32MOErC/ | 121 |
| 564 | ATCACACCATTCTCGAAGGC | /52MOErA/*/i2MOErT/*/i2MOErC/*/i2MOErA/*/i2MOErC/*A*C*C*A*T*T*C*T*C*G/i2MOErA/*/i2MOErA/*/i2MOErG/*/i2MOErG/*/32MOErC/ | 122 |
| 584 | AGAGAACACTACAAGAAGGC | /52MOErA/*/i2MOErG/*/i2MOErA/*/i2MOErG/*/i2MOErA/*A*C*A*C*T*A*C*A*A*G/i2MOErA/*/i2MOErA/*/i2MOErG/*/i2MOErG/*/32MOErC/ | 123 |
| 630 | TGCAGACTCTGGAAACTGTG | /52MOErT/*/i2MOErG/*/i2MOErC/*/i2MOErA/*/i2MOErG/*A*C*T*C*T*G*G*A*A*A/i2MOErC/*/i2MOErT/*/i2MOErG/*/i2MOErT/*/32MOErG/ | 124 |
| 714 | CCATAGACCCTGGAGTACAT | /52MOErC/*/i2MOErC/*/i2MOErA/*/i2MOErT/*/i2MOErA/*G*A*C*C*C*T*G*G*A*G/i2MOErT/*/i2MOErA/*/i2MOErC/*/i2MOErA/*/32MOErT/ | 125 |
| 758 | GAAACGATCCCAGAAAGATT | /52MOErG/*/i2MOErA/*/i2MOErA/*/i2MOErA/*/i2MOErC/*G*A*T*C*C*C*A*G*A*A/i2MOErA/*/i2MOErG/*/i2MOErA/*/i2MOErT/*/32MOErT/ | 126 |

*denotes phosphorothioate bond; 2MOEr denotes 2' Methoxyethyl modified bases; i denotes internal bases; 5/3 denotes bases at the 5' and 3' end

TABLE 14 mPpp2ca ASOs.

| ID | Unmodified | Modified | SEQ ID NO |
|---|---|---|---|
| 1 | GGGACTCGGCTTTCTGTAAT | /52MOErG/*/i2MOErG/*/i2MOErG/*/i2MOErA/*/i2MOErC/*T*C*G*G*C*T*T*T*C*T/i2MOErG/*/i2MOErT/*/i2MOErA/*/i2MOErA/*/32MOErT/ | 127 |
| 221 | CAACTTCTCGTCCATGATGC | /52MOErC/*/i2MOErA/*/i2MOErA/*/i2MOErC/*/i2MOErT/*T*C*T*C*G*T*C*C*A*T/i2MOErG/*/i2MOErA/*/i2MOErT/*/i2MOErG/*/32MOErC/ | 128 |
| 253 | TGCTCGATCCACTGGTCCAG | /52MOErT/*/i2MOErG/*/i2MOErC/*/i2MOErT/*/i2MOErC/*G*A*T*C*C*A*C*T*G*G/i2MOErT/*/i2MOErC/*/i2MOErC/*/i2MOErA/*/32MOErG/ | 129 |
| 281 | CTCGGAGAGCTGCTTGCACT | /52MOErC/*/i2MOErT/*/i2MOErC/*/i2MOErG/*/i2MOErG/*A*G*A*G*C*T*G*C*T*T/i2MOErG/*/i2MOErC/*/i2MOErA/*/i2MOErC/*/32MOErT/ | 130 |
| 293 | CTTGACCTGGGACTCGGAGA | /52MOErC/*/i2MOErT/*/i2MOErT/*/i2MOErG/*/i2MOErA/*C*C*T*G*G*G*A*C*T*C/i2MOErG/*/i2MOErG/*/i2MOErA/*/i2MOErG/*/32MOErA/ | 131 |
| 309 | CCTTCTCGCAGAGGCTCTTG | /52MOErC/*/i2MOErC/*/i2MOErT/*/i2MOErT/*/i2MOErC/*T*C*G*C*A*G*A*G*G*C/i2MOErT/*/i2MOErC/*/i2MOErT/*/i2MOErT/*/32MOErG/ | 132 |

TABLE 14-continued mPpp2ca ASOs.

| ID | Unmodified | Modified | SEQ ID NO |
|---|---|---|---|
| 325 | GTCAGGATTTCTTTAGCCTT | /52MOErG/*/i2MOErT/*/i2MOErC/*/i2MOErA/*/i2MOErG/*G*A* T*T*T*C*T*T*A*/i2MOErG/*/i2MOErC/*/i2MOErC/*/i2MOErT/*/ 32MOErT/ | 133 |
| 357 | GACATCGAACCTCTTGAACG | /52MOErG/*/i2MOErA/*/i2MOErC/*/i2MOErA/*/i2MOErT/*C*G* A*A*C*C*T*C*T*T*/i2MOErG/*/i2MOErA/*/i2MOErA/*/i2MOErC/*/ 32MOErG/ | 134 |
| 365 | AGTGACTGGACATCGAACCT | /52MOErA/*/i2MOErG/*/i2MOErT/*/i2MOErG/*/i2MOErA/*C*T* G*G*A*C*A*T*C*G*/i2MOErA/*/i2MOErA/*/i2MOErC/*/i2MOErC/*/ 32MOErT/ | 135 |
| 381 | GTACATCTCCACACACAGTG | /52MOErG/*/i2MOErT/*/i2MOErA/*/i2MOErC/*/i2MOErA/*T*C* T*C*C*A*C*A*C*A*/i2MOErC/*/i2MOErA/*/i2MOErG/*/i2MOErT/*/ 32MOErG/ | 136 |
| 449 | CAGGTAATTTGTATCTGGTG | /52MOErC/*/i2MOErA/*/i2MOErG/*/i2MOErG/*/i2MOErT/*A*A* T*T*T*G*T*A*T*C*/i2MOErT/*/i2MOErG/*/i2MOErG/*/i2MOErT/*/ 32MOErG/ | 137 |
| 461 | GTCTCCCATAAACAGGTAAT | /52MOErG/*/i2MOErT/*/i2MOErC/*/i2MOErT/*/i2MOErC/*C*C* A*T*A*A*A*C*A*G*/i2MOErG/*/i2MOErT/*/i2MOErA/*/i2MOErA/*/ 32MOErT/ | 138 |
| 533 | CTCTCGGTAACGAACCTTAA | /52MOErC/*/i2MOErT/*/i2MOErC/*/i2MOErT/*/i2MOErC/*G*G* T*A*A*C*G*A*A*C*/i2MOErC/*/i2MOErT/*/i2MOErT/*/i2MOErA/*/ 32MOErA/ | 139 |
| 541 | GTGATGCGCTCTCGGTAACG | /52MOErG/*/i2MOET/*/i2MOErG/*/i2MOErA/*/i2MOErT/*G*C* G*C*T*C*T*C*G*G*/i2MOErT/*/i2MOErA/*/i2MOErA/*/i2MOErC/*/ 32MOErG/ | 140 |
| 557 | ATTCCCTCGGAGTATGGTGA | /52MOErA/*/i2MOErT/*/i2MOErT/*/i2MOErC/*/i2MOErC/*C*T* C*G*G*A*G*T*A*T*/i2MOErG/*/i2MOErG/*/i2MOErT/*/i2MOErG/*/ 32MOErA/ | 141 |
| 565 | CTCTCGTGATTCCCTCGGAG | /52MOErC/*/i2MOErT/*/i2MOErC/*/i2MOErT/*/i2MOErC/*G*T* G*A*T*T*C*C*C*T*/i2MOErC/*/i2MOErG/*/i2MOErG/*/i2MOErA/*/ 32MOErG/ | 142 |
| 593 | GAACCCATAAACCTGTGTGA | /52MOErG/*/i2MOErA/*/i2MOErA/*/i2MOErC/*/i2MOErC/*C*A* T*A*A*A*C*C*T*G*/i2MOErT/*/i2MOErG/*/i2MOErT/*/i2MOErG/*/ 32MOErA/ | 143 |
| 601 | TCGTCGTAGAACCCATAAAC | /52MOErT/*/i2MOErC/*/i2MOErG/*/i2MOErT/*/i2MOErC/*G*T* A*G*A*A*C*C*C*A*/i2MOErT/*/i2MOErA/*/i2MOErA/*/i2MOErA/*/ 32MOErC/ | 144 |
| 653 | AAGGTCTGTGAAGTATTTCC | /52MOErA/*/i2MOErA/*/i2MOErG/*/i2MOErG/*/i2MOErT/*C*T* G*T*G*A*A*G*T*A*/i2MOErT/*/i2MOErT/*/i2MOErT/*/i2MOErC/*/ 32MOErC/ | 145 |
| 673 | GTGAGAGGAAGATAGTCAAA | /52MOErG/*/i2MOErT/*/i2MOErG/*/i2MOErA/*/i2MOErG/*A*G* G*A*A*G*A*T*A*G*/i2MOErT/*/i2MOErC/*/i2MOErA/*/i2MOErA/*/ 32MOErA/ | 146 |
| 681 | CCAAGGCAGTGAGAGGAAGA | /52MOErC/*/i2MOErC/*/i2MOErA/*/i2MOErA/*/i2MOErG/*G*C* A*G*T*G*A*G*A*G*/i2MOErG/*/i2MOErA/*/i2MOErA/*/i2MOErG/*/ 32MOErA/ | 147 |
| 713 | ACCACCGTGTAGACAGAAGA | /52MOErA/*/i2MOErC/*/i2MOErC/*/i2MOErA/*/i2MOErC/*C*G* T*G*T*A*G*A*C*A*/i2MOErG/*/i2MOErA/*/i2MOErA/*/i2MOErG/*/ 32MOErA/ | 148 |
| 737 | CAGTGTGTCTATGGATGGTG | /52MOErC/*/i2MOErA/*/i2MOErG/*/i2MOErT/*/i2MOErG/*T*G* T*C*T*A*T*G*G*A*/i2MOErT/*/i2MOErG/*/i2MOErG/*/i2MOErT/*/ 32MOErG/ | 149 |
| 757 | TCGAGTGCTCGGATGTGATC | /52MOErT/*/i2MOErC/*/i2MOErG/*/i2MOErA/*/i2MOErG/*T*G* C*T*C*G*G*A*T*G*/i2MOErT/*/i2MOErG/*/i2MOErA/*/i2MOErT/*/3 2MOErC/ | 150 |

TABLE 14-continued mPpp2ca ASOs.

| ID | Unmodified | Modified | SEQ ID NO |
|---|---|---|---|
| 797 | GTCACACATTGGACCCTCAT | /52MOErG/*/i2MOErT/*/i2MOErC/*/i2MOErA/*/i2MOErC/*A*C* A*T*G*G*A*C*C/i2MOErC/*/i2MOErT/*/i2MOErC/*/i2MOErA/*/ 32MOErT/ | 151 |
| 829 | CCACCACGGTCATCTGGATC | /52MOErC/*/i2MOErC/*/i2MOErA/*/i2MOErC/*/i2MOErC/*A*C* G*G*T*C*A*T*C*T/i2MOErG/*/i2MOErG/*/i2MOErA/*/i2MOErT/*/ 32MOErC/ | 152 |
| 869 | GCCAAAGGTATAACCAGCTC | /52MOErG/*/i2MOErC/*/i2MOErC/*/i2MOErA/*/i2MOErA/*A*G* G*T*A*T*A*A*C*C/i2MOErA/*/i2MOErG/*/i2MOErC/*/i2MOErT/*/ 32MOErC/ | 153 |
| 909 | TGAGGCCATTGGCATGATTA | /52MOErT/*/i2MOErG/*/i2MOErA/*/i2MOErG/*/i2MOErG/*C*C* A*T*T*G*G*C*A*T/i2MOErG/*/i2MOErA/*/i2MOErT/*/i2MOErT/*/ 32MOErA/ | 154 |
| 921 | TGGACACCAACGTGAGGCCA | /52MOErT/*/i2MOErG/*/i2MOErG/*/i2MOErA/*/i2MOErC/*A*C* C*A*A*C*G*T*G*A/i2MOErG/*/i2MOErG/*/i2MOErC/*/i2MOErC/*/ 32MOErA/ | 155 |
| 953 | GTTATATCCCTCCATCACCA | /52MOErG/*/i2MOErT/*/i2MOErT/*/i2MOErA/*/i2MOErT/*A*T* C*C*C*T*C*C*A*T/i2MOErC/*/i2MOErA/*/i2MOErC/*/i2MOErC/*/ 32MOErA/ | 156 |
| 961 | TGGCACCAGTTATATCCCTC | /52MOErT/*/i2MOErG/*/i2MOErG/*/i2MOErC/*/i2MOErA/*C*C* A*G*T*T*A*T*A*T/i2MOErC/*/i2MOErC/*/i2MOErC/*/i2MOErT/*/ 32MOErC/ | 157 |
| 973 | ACGTTCCGGTCATGGCACCA | /52MOErA/*/i2MOErC/*/i2MOErG/*/i2MOErT/*/i2MOErT/*C*C* G*G*T*C*A*T*G*G/i2MOErC/*/i2MOErA/*/i2MOErC/*/i2MOErC/*/ 32MOErA/ | 158 |
| 981 | TTGTTACTACGTTCCGGTCA | /52MOErT/*/i2MOErT/*/i2MOErG/*/i2MOErT/*/i2MOErT/*A*C* T*A*C*G*T*T*C*C/i2MOErG/*/i2MOErG/*/i2MOErT/*/i2MOErC/*/ 32MOErA/ | 159 |
| 1005 | AGCAATAGTTTGGAGCACTG | /52MOErA/*/i2MOErG/*/i2MOErC/*/i2MOErA/*/i2MOErA/*T*A* G*T*T*T*G*G*A*G/i2MOErC/*/i2MOErA/*/i2MOErC/*/i2MOErT/*/ 32MOErG/ | 160 |
| 1017 | TACCACAACGATAGCAATAG | /52MOErT/*/i2MOErA/*/i2MOErC/*/i2MOErC/*/i2MOErA/*C*A* A*C*G*A*T*A*G*C/i2MOErA/*/i2MOErA/*/i2MOErT/*/i2MOErA/*/ 32MOErG/ | 161 |
| 1025 | AGCTTGGTTACCACAACGAT | /52MOErA/*/i2MOErG/*/i2MOErC/*/i2MOErT/*/i2MOErT/*G*G* T*T*A*C*C*A*C*A/i2MOErA/*/i2MOErC/*/i2MOErG/*/i2MOErA/*/ 32MOErT/ | 162 |
| 1049 | AGTGTCGTCAAGTTCCATGA | /52MOErA/*/i2MOErG/*/i2MOErT/*/i2MOErG/*/i2MOErT/*C*G* T*C*A*A*G*T*T*C/i2MOErC/*/i2MOErA/*/i2MOErT/*/i2MOErG/*/ 32MOErA/ | 163 |
| 1081 | GCTGGGTCAAACTGCAAGAA | /52MOErG/*/i2MOErC/*/i2MOErT/*/i2MOErG/*/i2MOErG/*G*T* C*A*A*A*C*T*G*C/i2MOErA/*/i2MOErA/*/i2MOErG/*/i2MOErA/*/ 32MOErA/ | 164 |
| 1173 | ACGGTTCATGGCAATACTGT | /52MOErA/*/i2MOErC/*/i2MOErG/*/i2MOErG/*/i2MOErT/*T*C* A*T*G*G*C*A*A*T/i2MOErA/*/i2MOErC/*/i2MOErT/*/i2MOErG/*/ 32MOErT/ | 165 |
| 1181 | GTCAATATACGGTTCATGGC | /52MOErG/*/i2MOErT/*/i2MOErC/*/i2MOErA/*/i2MOErA/*T*A* T*A*C*G*T*T*C/i2MOErA/*/i2MOErT/*/i2MOErG/*/i2MOErG/*/ 32MOErC/ | 166 |
| 1205 | TGTTGCTCTTCCCATTTCCA | /52MOErT/*/i2MOErG/*/i2MOErT/*/i2MOErT/*/i2MOErG/*C*T* C*T*T*C*C*C*A*T/i2MOErT/*/i2MOErT/*/i2MOErC/*/i2MOErC/*/ 32MOErA/ | 167 |

TABLE 14-continued mPpp2ca ASOs.

| ID | Unmodified | Modified | SEQ ID NO |
|---|---|---|---|
| 1265 | TTTGGTCCGTGTGAAAACAA | /52MOET/*/i2MOErT/*/i2MOErT/*/i2MOErG/*/i2MOErG/*T*C*C*G*T*G*T*G*A*A*/i2MOErA/*/i2MOErA/*/i2MOErC/*/i2MOErA/*/32MOErA/ | 168 |

*denotes phosphorothioate bond; 2MOEr denotes 2' Methoxyethyl modified bases; i denotes internal bases; 5/3 denotes bases at the 5' and 3' end

TABLE 15 mAnkle2 ASOs.

| ID | Unmodified | Modified | SEQ ID NO |
|---|---|---|---|
| 445 | CAAGAGTTTCAGTCGAGCCA | /52MOErC/*/i2MOErA/*/i2MOErA/*/i2MOErG/*/i2MOErA/*G*T*T*T*C*A*G*T*C*G*/i2MOErA/*/i2MOErG/*/i2MOErC/*/i2MOErC/*/32MOErA/ | 169 |
| 457 | GTCATCTGGATTCAAGAGTT | /52MOErG/*/i2MOErT/*/i2MOErC/*/i2MOErA/*/i2MOErT/*C*T*G*G*A*T*T*C*A*A*/i2MOErG/*/i2MOErA/*/i2MOErG/*/i2MOErT/*/32MOErT/ | 170 |
| 637 | AGTCCTTGAGGTGCCCTGGA | /52MOErA/*/i2MOErG/*/i2MOErT/*/i2MOErC/*/i2MOErC/*T*T*G*A*G*G*T*G*C*C*/i2MOErC/*/i2MOErT/*/i2MOErG/*/i2MOErG/*/32MOErA/ | 171 |
| 673 | GGCCTGCTGAGTTTGTTTCC | /52MOErG/*/i2MOErG/*/i2MOErC/*/i2MOErC/*/i2MOErT/*G*C*T*G*A*G*T*T*T*G*/i2MOErT/*/i2MOErT/*/i2MOErT/*/i2MOErC/*/32MOErC/ | 172 |
| 721 | AGGGTTCAAGCCCACACTGT | /52MOErA/*/i2MOErG/*/i2MOErG/*/i2MOErG/*/i2MOErT/*T*C*A*A*G*C*C*C*A*C*/i2MOErA/*/i2MOErC/*/i2MOErT/*/i2MOErG/*/32MOErT/ | 173 |
| 757 | TGGGTGGACACTGGATGCTA | /52MOErT/*/i2MOErG/*/i2MOErG/*/i2MOErG/*/i2MOErT/*G*G*A*C*A*C*T*G*G*A*/i2MOErT/*/i2MOErG/*/i2MOErC/*/i2MOErT/*/32MOErA/ | 174 |
| 793 | GTGGTTGTCATTCCTGGTAG | /52MOErG/*/i2MOErT/*/i2MOErG/*/i2MOErG/*/i2MOErT/*T*G*T*C*A*T*T*C*C*T*/i2MOErG/*/i2MOErG/*/i2MOErT/*/i2MOErA/*/32MOErG/ | 175 |
| 865 | AGGGCCATCCTCATATACTG | /52MOErA/*/i2MOErG/*/i2MOErG/*/i2MOErG/*/i2MOErC/*C*A*T*C*C*T*C*A*T*A*/i2MOErT/*/i2MOErA/*/i2MOErC/*/i2MOErT/*/32MOErG/ | 176 |
| 877 | CTCATGTCTCACAGGGCCAT | /52MOErC/*/i2MOErT/*/i2MOErC/*/i2MOErA/*/i2MOErT/*G*T*C*T*C*A*C*A*G*G*/i2MOErG/*/i2MOErC/*/i2MOErC/*/i2MOErA/*/32MOErT/ | 177 |
| 1033 | TAAGGGCGTAGTTTTGTTGG | /52MOErT/*/i2MOErA/*/i2MOErA/*/i2MOErG/*/i2MOErG/*G*C*G*T*A*G*T*T*T*T*/i2MOErG/*/i2MOErT/*/i2MOErT/*/i2MOErG/*/32MOErG/ | 178 |
| 1105 | TTCAGCCAGGCACAAGCCAT | /52MOErT/*/i2MOErT/*/i2MOErC/*/i2MOErA/*/i2MOErG/*C*C*A*G*G*C*A*C*A*A*/i2MOErG/*/i2MOErC/*/i2MOErC/*/i2MOErA/*/32MOErT/ | 179 |
| 1141 | GTAACTGTTTGCTCGTTCTT | /52MOErG/*/i2MOErT/*/i2MOErA/*/i2MOErA/*/i2MOErC/*T*G*T*T*T*G*C*T*C*G*/i2MOErT/*/i2MOErT/*/i2MOErC/*/i2MOErT/*/32MOErT/ | 180 |
| 1333 | GGAAGCCTGGTTCTCTTTGG | /52MOErG/*/i2MOErG/*/i2MOErA/*/i2MOErA/*/i2MOErG/*C*C*T*G*G*T*T*C*T*C*/i2MOErT/*/i2MOErT/*/i2MOErT/*/i2MOErG/*/32MOErG/ | 181 |
| 1381 | ACGCATAAACTCAGGGTTCT | /52MOErA/*/i2MOErC/*/i2MOErG/*/i2MOErC/*/i2MOErA/*T*A*A*A*C*T*C*A*G*G*/i2MOErG/*/i2MOErT/*/i2MOErT/*/i2MOErC/*/32MOErT/ | 182 |

TABLE 15-continued mAnkle2 ASOs.

| ID | Unmodified | Modified | SEQ ID NO |
|---|---|---|---|
| 1405 | CATGTTGTCATCTGGGTACA | /52MOErC/*/i2MOErA/*/i2MOErT/*/i2MOErG/*/i2MOErT/*T*G* T*C*A*T*C*T*G*G/i2MOErG/*/i2MOErT/*/i2MOErA/*/i2MOErC/*/ 32MOErA/ | 183 |
| 1441 | GTCAACAACGTAGAGGATGC | /52MOErG/*/i2MOErT/*/i2MOErC/*/i2MOErA/*/i2MOErA/*C*A* A*C*G*T*A*G*A*G/i2MOErG/*/i2MOErA/*/i2MOET/*/i2MOErG/*/ 32MOErC/ | 184 |
| 1681 | CAGGAGTGGCACATAGTAGT | /52MOErC/*/i2MOErA/*/i2MOErG/*/i2MOErG/*/i2MOErA/*G*T* G*G*C*A*C*A*T*A/i2MOErG/*/i2MOErT/*/i2MOErA/*/i2MOErG/*/ 32MOErT/ | 185 |
| 1753 | AGTATTTGAGGCTTCAGCTT | /52MOErA/*/i2MOErG/*/i2MOErT/*/i2MOErA/*/i2MOErT/*T*T* G*A*G*G*C*T*T*C/i2MOErA/*/i2MOErG/*/i2MOErC/*/i2MOErT/*/ 32MOErT/ | 186 |
| 1813 | AGGTCCCACGAAAGCTCTCA | /52MOErA/*/i2MOErG/*/i2MOErG/*/i2MOErT/*/i2MOErC/*C*C* A*C*G*A*A*A*G*C/i2MOErT/*/i2MOErC/*/i2MOErT/*/i2MOErC/*/ 32MOErA/ | 187 |
| 1837 | ATCTTCTGCTTTGGATGGAC | /52MOErA/*/i2MOErT/*/i2MOErC/*/i2MOErT/*/i2MOErT/*C*T* G*C*T*T*T*G*G*A/i2MOErT/*/i2MOErG/*/i2MOErG/*/i2MOErA/*/ 32MOErC/ | 188 |
| 1873 | TTTCTTTCGAGGTGGAGTTT | /52MOErT/*/i2MOErT/*/i2MOErT/*/i2MOErC/*/i2MOErT/*T*T*C *G*A*G*G*T*G*G/i2MOErA/*/i2MOErG/*/i2MOErT/*/i2MOErT/*/ 32MOErT/ | 189 |
| 1921 | AATGCCTCGTTCTGGGTCAG | /52MOErA/*/i2MOErA/*/i2MOErT/*/i2MOErG/*/i2MOErC/*C*T* C*G*T*T*C*T*G*G/i2MOErG/*/i2MOErT/*/i2MOErC/*/i2MOErA/*/ 32MOErG/ | 190 |
| 1933 | TCCAACTCTCTCAATGCCTC | /52MOErT/*/i2MOErC/*/i2MOErC/*/i2MOErA/*/i2MOErA/*C*T* C*T*C*T*C*A*A*T/i2MOErG/*/i2MOErC/*/i2MOErC/*/i2MOErT/*/ 32MOErC/ | 191 |
| 1981 | TTCCCAGTATTCAACCCAGG | /52MOErT/*/i2MOErT/*/i2MOErC/*/i2MOErC/*/i2MOErC/*A*G* T*A*T*T*C*A*A*C/i2MOErC/*/i2MOErC/*/i2MOErA/*/i2MOErG/*/ 32MOErG/ | 192 |
| 1993 | ACATCCCAGAAATTCCCAGT | /52MOErA/*/i2MOErC/*/i2MOErA/*/i2MOErT/*/i2MOErC/*C*C* A*G*A*A*A*T*T*C*/i2MOErC/*/i2MOErC/*/i2MOErA/*/i2MOE rG/*/32MOErT/ | 193 |
| 2101 | GCAGCCTTCATTTTCTCGTA | /52MOErG/*/i2MOErC/*/i2MOErA/*/i2MOErG/*/i2MOErC/*C*T* T*C*A*T*T*T*T*C/i2MOErT/*/i2MOErC/*/i2MOErG/*/i2MOEr T/*/32MOErA/ | 194 |
| 2137 | CTTTCCACTGCCAAAATCTG | /52MOErC/*/i2MOErT/*/i2MOErT/*/i2MOErT/*/i2MOErC/*C*A* C*T*G*C*C*A*A*A*/i2MOErA/*/i2MOErT/*/i2MOErC/*/i2MOEr T/*/32MOErG/ | 195 |
| 2161 | CACGGAGATGGAGTTGCTGT | /52MOErC/*/i2MOErA/*/i2MOErC/*/i2MOErG/*/i2MOErG/*A*G* A*T*G*G*A*G*T*T/i2MOErG/*/i2MOErC/*/i2MOErT/*/i2MOEr G/*/32MOErT/ | 196 |
| 2245 | GGGCTGACTCTGACTTGGAA | /52MOErG/*/i2MOErG/*/i2MOErG/*/i2MOErC/*/i2MOErT/*G*A* C*T*C*T*G*A*C*T/i2MOErT/*/i2MOErG/*/i2MOErG/*/i2MOEr A/*/32MOErA/ | 197 |
| 2269 | AGAGGTTTGGAACTTATCAG | /52MOErA/*/i2MOErG/*/i2MOErA/*/i2MOErG/*/i2MOErG/*T*T* T*G*G*A*A*C*T*T*/i2MOErA/*/i2MOErT/*/i2MOErC/*/i2MOEr A/*/32MOErG/ | 198 |
| 2329 | AGTTCCAACTGAGGTTTCTC | /52MOErA/*/i2MOErG/*/i2MOErT/*/i2MOErT/*/i2MOErC/*C*A* A*C*T*G*A*G*G*T/i2MOErT/*/i2MOErT/*/i2MOErC/*/i2MOEr T/*/32MOErC/ | 199 |
| 2569 | GTCACTGTCTGCTGCACCCT | /52MOErG/*/i2MOErT/*/i2MOErC/*/i2MOErA/*/i2MOErC/*T*G* T*C*T*G*C*T*G*C*/i2MOErA/*/i2MOErC/*/i2MOErC/*/i2MOEr C/*/32MOErT/ | 200 |

TABLE 15-continued mAnkle2 ASOs.

| ID | Unmodified | Modified | SEQ ID NO |
|---|---|---|---|
| 2581 | AGATGCCAGCAAGTCACTGT | /52MOErA/*/i2MOErG/*/i2MOErA/*/i2MOErT/*/i2MOErG/*C*C*A*G*C*A*A*G*T*C*/i2MOErA/*/i2MOErC/*/i2MOErT/*/i2MOErG/*/32MOErT/ | 201 |
| 2629 | AGTGTTGGTCCTGACTTGCT | /52MOErA/*/i2MOErG/*/i2MOErT/*/i2MOErG/*/i2MOErT/*T*G*G*T*C*C*T*G*A*C*/i2MOErT/*/i2MOErT/*/i2MOErG/*/i2MOErC/*/32MOErT/ | 202 |
| 2713 | GAGTATAGGTTCCAGACCAG | /52MOErG/*/i2MOErA/*/i2MOErG/*/i2MOErT/*/i2MOErA/*T*A*G*G*T*T*C*C*A*G*/i2MOErA/*/i2MOErC/*/i2MOErC/*/i2MOErA/*/32MOErG/ | 203 |
| 2737 | GGTGGAATCTACCGTGGCAG | /52MOErG/*/i2MOErG/*/i2MOErT/*/i2MOErG/*/i2MOErG/*A*A*T*C*T*A*C*C*G*T*/i2MOErG/*/i2MOErG/*/i2MOErC/*/i2MOErA/*/32MOErG/ | 204 |
| 2773 | TTTTGATGGTTCCTCTCCAG | /52MOErT/*/i2MOErT/*/i2MOErT/*/i2MOErT/*/i2MOErG/*A*T*G*G*T*T*C*C*T*C*/i2MOErT/*/i2MOErC/*/i2MOErC/*/i2MOErA/*/32MOErG/ | 205 |
| 2809 | CGCACACTCAAGAGCTGCTA | /52MOErC/*/i2MOErG/*/i2MOErC/*/i2MOErA/*/i2MOErC/*A*C*T*C*A*A*G*A*G*C*/i2MOErT/*/i2MOErG/*/i2MOErC/*/i2MOErT/*/32MOErA/ | 206 |
| 2833 | TGGGTACAGACCAGGGTCAA | /52MOErT/*/i2MOErG/*/i2MOErG/*/i2MOErG/*/i2MOErT/*A*C*A*G*A*C*C*A*G*G*/i2MOErG/*/i2MOErT/*/i2MOErC/*/i2MOErA/*/32MOErA/ | 207 |
| 2881 | GTCTGAGGGCGAGTAGCACA | /52MOErG/*/i2MOErT/*/i2MOErC/*/i2MOErT/*/i2MOErG/*A*G*G*G*C*G*A*G*T*A*/i2MOErG/*/i2MOErC/*/i2MOErA/*/i2MOErC/*/32MOErA/ | 208 |
| 2917 | CTTCCCTTTGAGTGCAGGAC | /52MOErC/*/i2MOErT/*/i2MOErT/*/i2MOErC/*/i2MOErC/*C*T*T*T*G*A*G*T*G*C*/i2MOErA/*/i2MOErG/*/i2MOErG/*/i2MOErA/*/32MOErC/ | 209 |
| 2953 | ATGAGAGCAATCGAGATCCA | /52MOErA/*/i2MOErT/*/i2MOErG/*/i2MOErA/*/i2MOErG/*A*G*C*A*A*T*C*G*A*G*/i2MOErA/*/i2MOErT/*/i2MOErC/*/i2MOErC/*/32MOErA/ | 210 |
| 3025 | GCCAGAAGAGGAGGAGGTGT | /52MOErG/*/i2MOErC/*/i2MOErC/*/i2MOErA/*/i2MOErG/*A*A*G*A*G*G*A*G*G*A*/i2MOErG/*/i2MOErG/*/i2MOErT/*/i2MOErG/*/32MOET/ | 211 |
| 3061 | CCCATGTGCTGGACTGTAGC | /52MOErC/*/i2MOErC/*/i2MOErC/*/i2MOErA/*/i2MOErT/*G*T*G*C*T*G*A*C*T*/i2MOErG/*/i2MOErT/*/i2MOErA/*/i2MOErG/*/32MOErC/ | 212 |
| 3133 | ATGAATCCCAGGAGTAAGCT | /52MOErA/*/i2MOErT/*/i2MOErG/*/i2MOErA/*/i2MOErA/*T*C*C*C*A*G*G*A*G*T*/i2MOErA/*/i2MOErA/*/i2MOErG/*/i2MOErC/*/32MOErT/ | 213 |
| 3409 | CTCACTTGTCTATGCCTTTG | /52MOErC/*/i2MOErT/*/i2MOErC/*/i2MOErA/*/i2MOErC/*T*T*G*T*C*T*A*T*G*C*/i2MOErC/*/i2MOErT/*/i2MOErT/*/i2MOErT/*/32MOErG/ | 214 |

*denotes phosphorothioate bond; 2MOEr denotes 2' Methoxyethyl modified bases; i denotes internal bases; 5/3 denotes bases at the 5' and 3' end

TABLE 16

Parent Antisense RNA Sequences for Design of mBanf1, mPpp2ca, and mAnkle2 ASOs.

| ASO ID | Parent Antisense RNA Sequence | SEQ ID NO |
|---|---|---|
| Banf1_320 | UGGGAGGUUGUCAUCGUGAU | 215 |
| Banf1_408 | CAGCCUCUUGCUCAGGACGU | 216 |
| Banf1_436 | CAUAAGCCUUGUCAAAGCCC | 217 |
| Banf1_442 | GGACCACAUAAGCCUUGUCA | 218 |
| Banf1_472 | CAUCUUUCUUUAGCACCAGA | 219 |
| Banf1_478 | GGUCUUCAUCUUUCUUUAGC | 220 |
| Banf1_492 | CCAUUCUCGGAAGAGGUCUU | 221 |
| Banf1_496 | UCAGCCAUUCUCGGAAGAGG | 222 |
| Banf1_506 | CAUGUACCUUCAGCCAUUC | 223 |
| Banf1_524 | UGCUUGGCAUUGGCACCACA | 224 |
| Banf1_528 | GGACUGCUUGGCAUUGGCAC | 225 |
| Banf1_550 | GAAGGCACCCAAAGCAGUCC | 226 |
| Banf1_552 | UCGAAGGCACCCAAAGCAGU | 227 |
| Banf1_554 | UCUCGAAGGCACCCAAAGCA | 228 |
| Banf1_556 | AUUCUCGAAGGCACCCAAAG | 229 |
| Banf1_560 | CACCAUUCUCGAAGGCACCC | 230 |
| Banf1_562 | CACACCAUUCUCGAAGGCAC | 231 |
| Banf1_564 | AUCACACCAUUCUCGAAGGC | 232 |
| Banf1_584 | AGAGAACACUACAAGAAGGC | 233 |
| Banf1_630 | UGCAGACUCUGGAAACUGUG | 234 |
| Banf1_714 | CCAUAGACCCUGGAGUACAU | 235 |
| Banf1_758 | GAAACGAUCCCAGAAAGAUU | 236 |
| Ppp2ca_1 | GGGACUCGGCUUUCUGUAAU | 237 |
| Ppp2ca_221 | CAACUUCUCGUCCAUGAUGC | 238 |
| Ppp2ca_253 | UGCUCGAUCCACUGGUCCAG | 239 |
| Ppp2ca_281 | CUCGGAGAGCUGCUUGCACU | 240 |
| Ppp2ca_293 | CUUGACCUGGGACUCGGAGA | 241 |
| Ppp2ca_309 | CCUUCUCGCAGAGGCUCUUG | 242 |
| Ppp2ca_325 | GUCAGGAUUUCUUUAGCCUU | 243 |
| Ppp2ca_357 | GACAUCGAACCUCUUGAACG | 244 |
| Ppp2ca_365 | AGUGACUGGACAUCGAACCU | 245 |
| Ppp2ca_381 | GUACAUCUCCACACACAGUG | 246 |
| Ppp2ca_449 | CAGGUAAUUGUAUCUGGUG | 247 |
| Ppp2ca_461 | GUCUCCCAUAAACAGGUAAU | 248 |
| Ppp2ca_533 | CUCUCGGUAACGAACCUUAA | 249 |
| Ppp2ca_541 | GUGAUGCGCUCUCGGUAACG | 250 |
| Ppp2ca_557 | AUUCCCUCGGAGUAUGGUGA | 251 |
| Ppp2ca_565 | CUCUCGUGAUUCCCUCGGAG | 252 |
| Ppp2ca_593 | GAACCCAUAAACCUGUGUGA | 253 |
| Ppp2ca_601 | UCGUCGUAGAACCCAUAAAC | 254 |
| Ppp2ca_653 | AAGGUCUGUGAAGUAUUCC | 255 |
| Ppp2ca_673 | GUGAGAGGAAGAUAGUCAAA | 256 |
| Ppp2ca_681 | CCAAGGCAGUGAGAGGAAGA | 257 |
| Ppp2ca_713 | ACCACCGUGUAGACAGAAGA | 258 |
| Ppp2ca_737 | CAGUGUGUCUAUGGAUGGUG | 259 |
| Ppp2ca_757 | UCGAGUGCUCGGAUGUGAUC | 26 |
| Ppp2ca_797 | GUCACACAUUGGACCCUCAU | 261 |
| Ppp2ca_829 | CCACCACGGUCAUCUGGAUC | 262 |
| Ppp2ca_869 | GCCAAAGGUAUAACCAGCUC | 263 |
| Ppp2ca_909 | UGAGGCCAUUGGCAUGAUUA | 264 |
| Ppp2ca_921 | UGGACACCAACGUGAGGCCA | 265 |
| Ppp2ca_953 | GUUAUAUCCCUCCAUCACCA | 266 |
| Ppp2ca_961 | UGGCACCAGUUAUAUCCCUC | 267 |
| Ppp2ca_973 | ACGUUCCGGUCAUGGCACCA | 268 |
| Ppp2ca_981 | UUGUUACUACGUUCCGGUCA | 269 |
| Ppp2ca_1005 | AGCAAUAGUUUGGAGCACUG | 270 |
| Ppp2ca_1017 | UACCACAACGAUAGCAAUAG | 271 |
| Ppp2ca_1025 | AGCUUGGUUACCACAACGAU | 272 |
| Ppp2ca_1049 | AGUGUCGUCAAGUUCCAUGA | 273 |
| Ppp2ca_1081 | GCUGGGUCAAACUGCAAGAA | 274 |
| Ppp2ca_1173 | ACGGUUCAUGGCAAUACUGU | 275 |
| Ppp2ca_1181 | GUCAAUAUACGGUUCAUGGC | 276 |
| Ppp2ca_1205 | UGUUGCUCUUCCCAUUUCCA | 277 |
| Ppp2ca_1265 | UUUGGUCCGUGUGAAAACAA | 278 |
| Ankle2_445 | CAAGAGUUUCAGUCGAGCCA | 279 |
| Ankle2_457 | GUCAUCUGGAUUCAAGAGUU | 280 |
| Ankle2_637 | AGUCCUUGAGGUGCCCUGGA | 281 |
| Ankle2_673 | GGCCUGCUGAGUUUGUUUCC | 282 |
| Ankle2_721 | AGGGUUCAAGCCCACACUGU | 283 |
| Ankle2_757 | UGGGUGGACACUGGAUGCUA | 284 |
| Ankle2_793 | GUGGUUGUCAUUCCUGGUAG | 285 |
| Ankle2_865 | AGGGCCAUCCUCAUAUACUG | 286 |
| Ankle2_877 | CUCAUGUCUCACAGGGCCAU | 287 |
| Ankle2_1033 | UAAGGGCGUAGUUUUGUUGG | 288 |

TABLE 16-continued

Parent Antisense RNA Sequences for Design of mBanf1, mPpp2ca, and mAnkle2 ASOs.

| ASO ID | Parent Antisense RNA Sequence | SEQ ID NO |
|---|---|---|
| Ankle2_1105 | UUCAGCCAGGCACAAGCCAU | 289 |
| Ankle2_1141 | GUAACUGUUUGCUCGUUCUU | 290 |
| Ankle2_1333 | GGAAGCCUGGUUCUCUUUGG | 291 |
| Ankle2_1381 | ACGCAUAAACUCAGGGUUCU | 292 |
| Ankle2_1405 | CAUGUUGUCAUCUGGGUACA | 293 |
| Ankle2_1441 | GUCAACAACGUAGAGGAUGC | 294 |
| Ankle2_1681 | CAGGAGUGGCACAUAGUAGU | 295 |
| Ankle2_1753 | AGUAUUUGAGGCUUCAGCUU | 296 |
| Ankle2_1813 | AGGUCCCACGAAAGCUCUCA | 297 |
| Ankle2_1837 | AUCUUCUGCUUUGGAUGGAC | 298 |
| Ankle2_1873 | UUUCUUUCGAGGUGGAGUUU | 299 |
| Ankle2_1921 | AAUGCCUCGUUCUGGGUCAG | 300 |
| Ankle2_1933 | UCCAACUCUCUCAAUGCCUC | 301 |
| Ankle2_1981 | UUCCCAGUAUUCAACCCAGG | 302 |
| Ankle2_1993 | ACAUCCCAGAAAUUCCCAGU | 303 |
| Ankle2_2101 | GCAGCCUUCAUUUCUCGUA | 304 |
| Ankle2_2137 | CUUUCCACUGCCAAAAUCUG | 305 |
| Ankle2_2161 | CACGGAGAUGGAGUUGCUGU | 306 |
| Ankle2_2245 | GGGCUGACUCUGACUUGGAA | 307 |
| Ankle2_2269 | AGAGGUUUGGAACUUAUCAG | 308 |
| Ankle2_2329 | AGUUCCAACUGAGGUUUCUC | 309 |
| Ankle2_2569 | GUCACUGUCUGCUGCACCCU | 310 |
| Ankle2_2581 | AGAUGCCAGCAAGUCACUGU | 311 |
| Ankle2_2629 | AGUGUUGGUCCUGACUUGCU | 312 |
| Ankle2_2713 | GAGUAUAGGUUCCAGACCAG | 313 |
| Ankle2_2737 | GGUGGAAUCUACCGUGGCAG | 314 |
| Ankle2_2773 | UUUUGAUGGUUCCUCUCCAG | 315 |
| Ankle2_2809 | CGCACACUCAAGAGCUGCUA | 316 |
| Ankle2_2833 | UGGGUACAGACCAGGGUCAA | 317 |
| Ankle2_2881 | GUCUGAGGGCGAGUAGCACA | 318 |
| Ankle2_2917 | CUUCCCUUUGAGUGCAGGAC | 319 |
| Ankle2_2953 | AUGAGAGCAAUCGAGAUCCA | 320 |
| Ankle2_3025 | GCCAGAAGAGGAGGAGGUGU | 321 |
| Ankle2_3061 | CCCAUGUGCUGGACUGUAGC | 322 |
| Ankle2_3133 | AUGAAUCCCAGGAGUAAGCU | 323 |
| Ankle2_3409 | CUCACUUGUCUAUGCCUUUG | 324 |

Figure 41A:
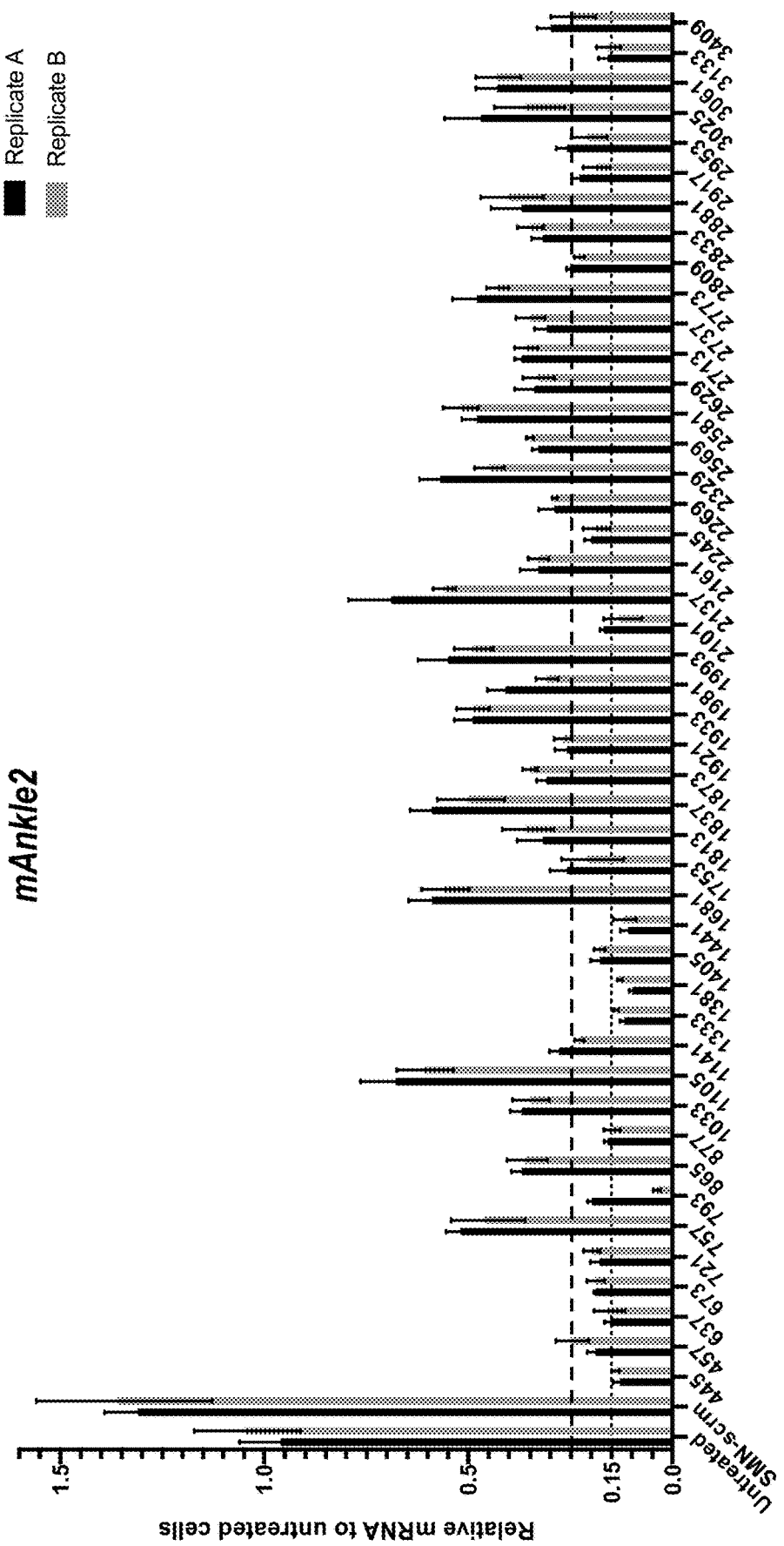
FIGS. 41A-41C show qPCR results from screening mAnkle2 ASOs in mouse NSC34 cells 72 hours after transfection with the ASOs. Knockdown in total mRNA of the target was compared to untreated cells.
Figure 41B:
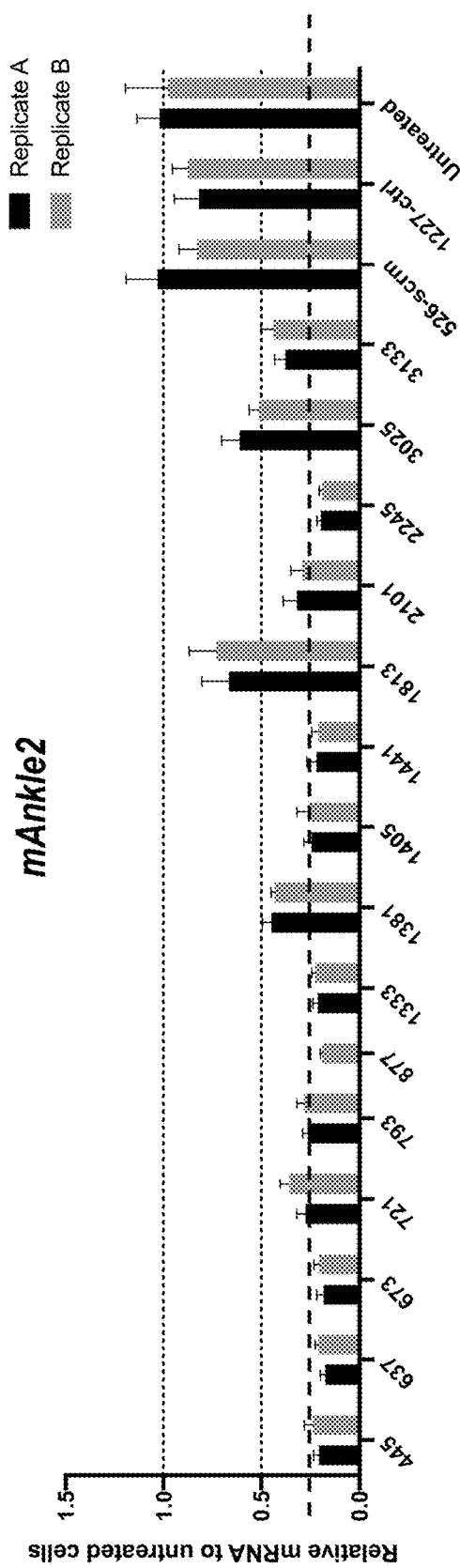
Figure 41C:
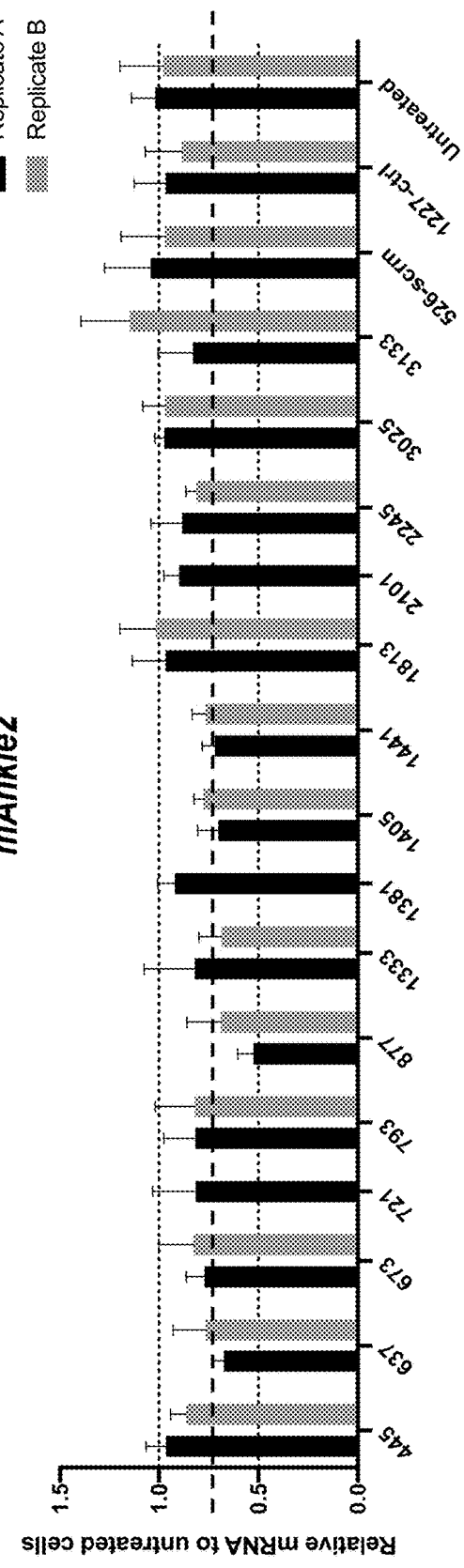
Figure 42A:
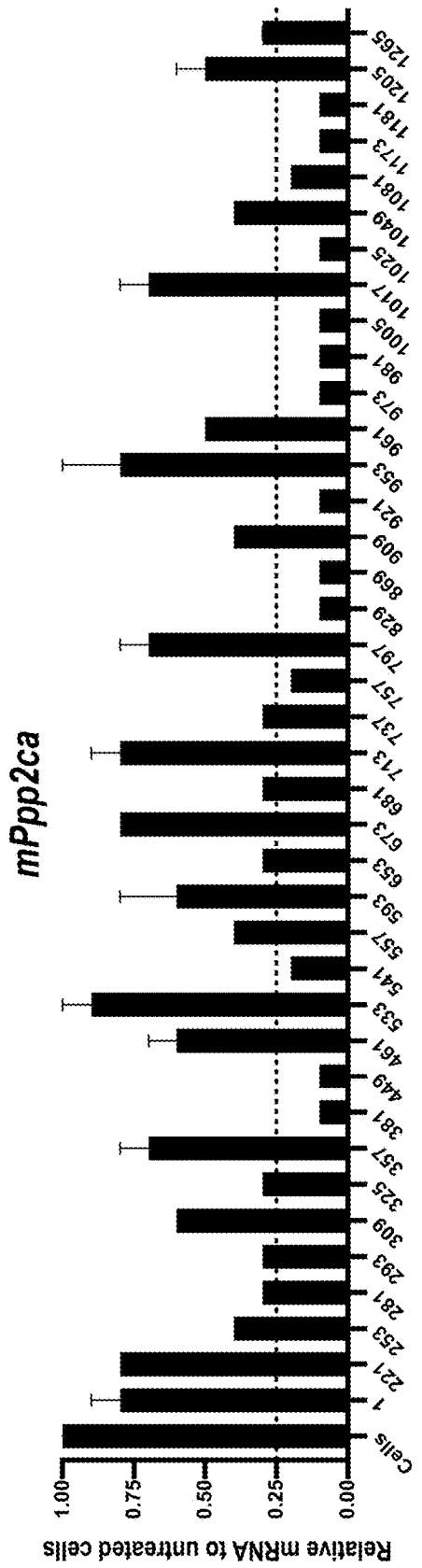
FIGS. 42A-42C show qPCR results from screening mPpp2ca ASOs in mouse NSC34 cells 72 hours after transfection with the ASOs. Knockdown in total mRNA of the target was compared to untreated cells.
Figure 42B:
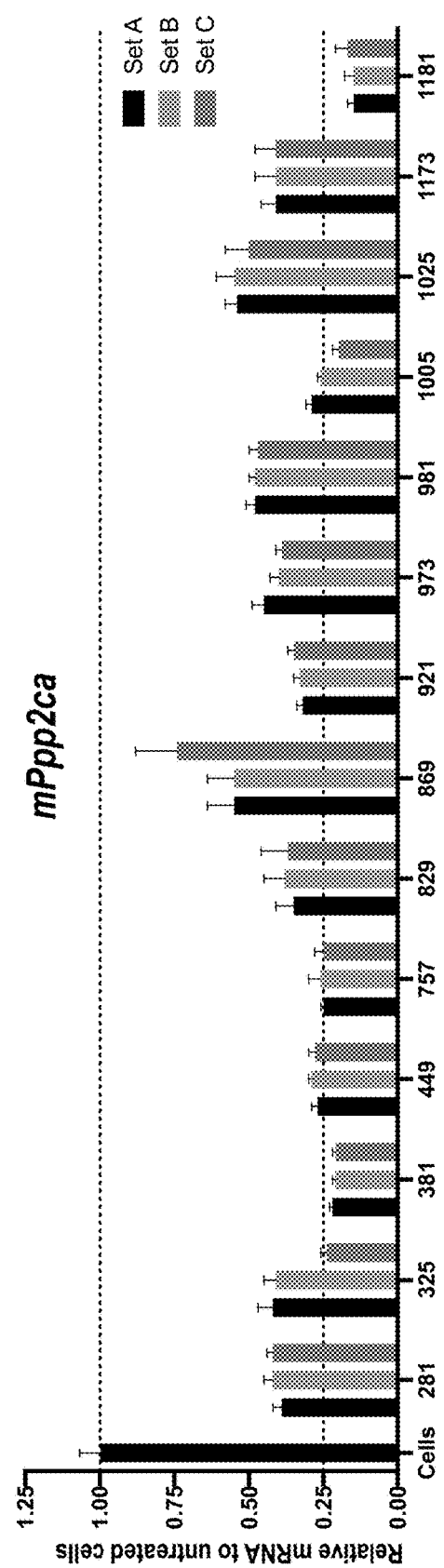
Figure 42C:
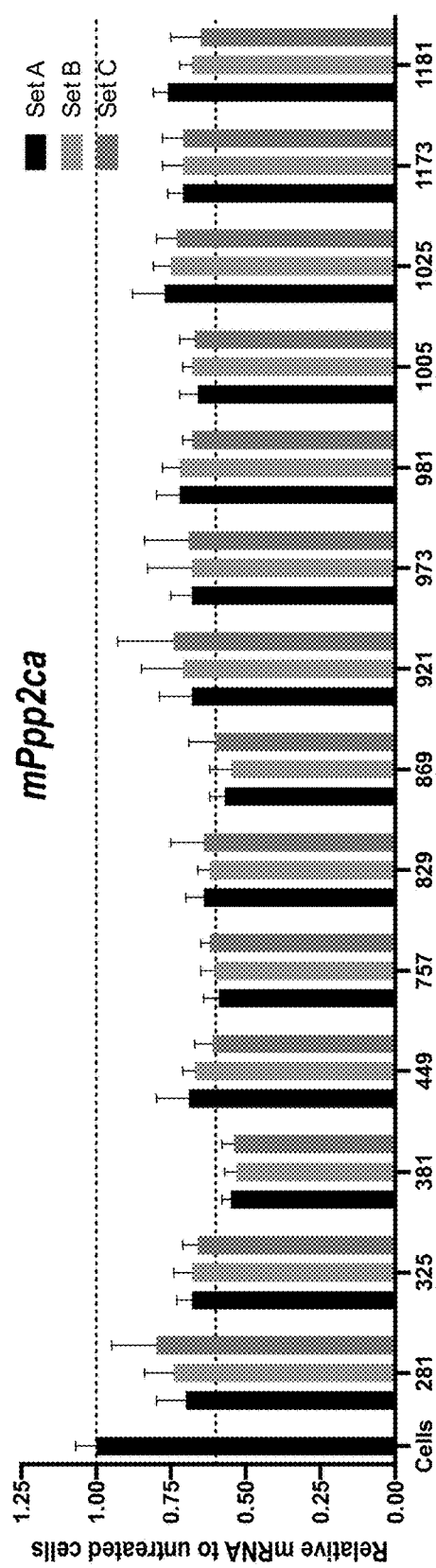
Figure 43:
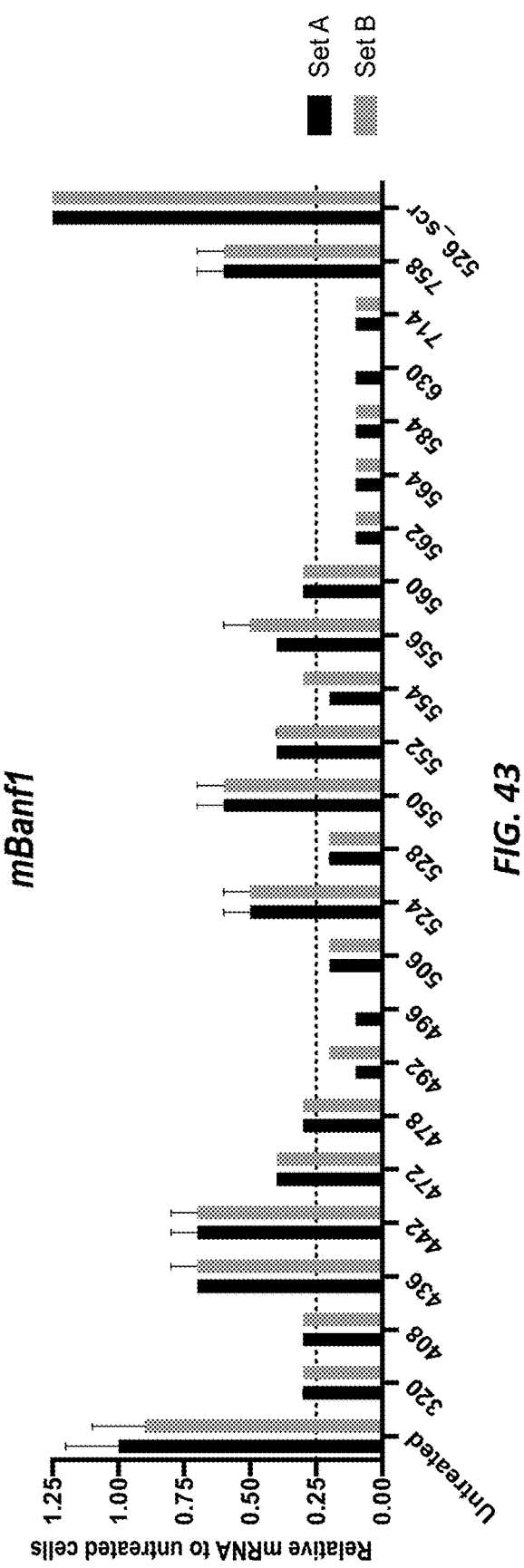
FIG. 43 show qPCR results from screening mBanf1 ASOs in mouse NSC34 cells 72 hours after transfection with the ASOs at a concentration of 100 nM (two replicates). Knockdown in total mRNA of the target was compared to untreated cells. Dotted line indicates 75% knockdown.

All ASOs were designed as 5-10-5 gapmers with phosphorothioate backbones. 2'MethoxyEthyl modified bases were used in the wings (5 nucleotides from both ends), and the 10 nucleotide core had unmodified DNA bases. See FIG. 40. Primary screens were first carried out in NSC34 cells at 100 nM ASO concentration. All ASOs were transfected using lipofectamine RNAiMAx, and cells were incubated for 72 hours before harvesting the RNA for TaqMan qPCR. Knockdown in total mRNA of the target was compared with untreated cells. Based on primary screen data, hits were selected for a second screen at 50 nM and 5 nM. Transfection and TaqMan qPCR analysis was carried out in a similar manner as the primary screen. Results for the primary screen for mAnkle2 are shown in FIG. 41A, and results for the secondary screens for mAnkle2 are shown in FIGS. 41B and 41C. Results for the primary screen for mPpp2ca are shown in FIG. 42A, and results for the secondary screens for mPpp2ca are shown in FIGS. 42B and 42C. Results for the primary screen for mBanf1 are shown in FIG. 43. As shown in these results, ASOs targeting Banf1 or Ankle2 or Ppp2ca have been validated in NSC34 cells and show a >75% reduction in expression.

In conclusion, we have developed three approaches to validate Banf1, Ankle2, and Ppp2ca as modifiers of tau aggregation in vitro (primary culture of mouse cortical neurons), ex vivo (organotypic brain slice culture), and in vivo (stereotactic injection of the hippocampus). We propose that disruption of Banf1, Ankle2, and/or Ppp2ca can be used for the development of new mouse model of tauopathies

We claim:

1. A non-human animal comprising:
   (a) a microtubule-associated protein tau coding sequence in one or more cells; and
   (b) (i) a genetic modification in one or more or all of BANF1, PPP2CA, and ANKLE2 that reduces expression of the one or more or all of BANF1, PPP2CA, and ANKLE2, respectively, in the one or more cells and/or (ii) one or more agents that reduce expression of one or more or all of BANF1, PPP2CA, and ANKLE2 in the one or more cells,
   wherein the microtubule-associated protein tau coding sequence is an exogenous human microtubule-associated protein tau coding sequence and/or wherein the microtubule-associated protein tau comprises a tauopathy-associated mutation.

2. The non-human animal of claim 1, wherein the one or more cells are neuronal cells.

3. The non-human animal of claim 1, wherein the microtubule-associated protein tau coding sequence is an exogenous human microtubule-associated protein tau coding sequence.

4. The non-human animal of claim 3, wherein the exogenous human microtubule-associated protein tau coding sequence is genomically integrated.

5. The non-human animal of claim 3, wherein the exogenous human microtubule-associated protein tau coding sequence comprises a complementary DNA (cDNA) sequence.

6. The non-human animal of claim 3, wherein the exogenous human microtubule-associated protein tau coding sequence is codon-optimized for expression in the non-human animal.

7. The non-human animal of claim 3, wherein the exogenous human microtubule-associated protein tau coding sequence is operably linked to a heterologous promoter.

8. The non-human animal of claim 7, wherein the heterologous promoter is a mouse prion protein promoter.

9. The non-human animal of claim 7, wherein the heterologous promoter is a neuron-specific promoter.

10. The non-human animal of claim 9, wherein the neuron-specific promoter is a synapsin-1 promoter.

11. The non-human animal of claim 1, wherein the microtubule-associated protein tau comprises a tauopathy-associated mutation.

12. The non-human animal of claim 11, wherein the tauopathy-associated mutation comprises a P301S mutation.

13. The non-human animal of claim 11, wherein the microtubule-associated protein tau comprises the sequence set forth in SEQ ID NO: 98.

14. The non-human animal of claim 11, wherein the tauopathy-associated mutation comprises an A152T/P301L/S320F triple mutation.

15. The non-human animal of claim 11, wherein the microtubule-associated protein tau coding sequence comprises the sequence set forth in SEQ ID NO: 83 or the microtubule-associated protein tau comprises the sequence set forth in SEQ ID NO: 84.

16. The non-human animal of claim 1, wherein the non-human animal comprises the genetic modification in the one or more or all of BANF1, PPP2CA, and ANKLE2 that reduces expression of the one or more or all of BANF1, PPP2CA, and ANKLE2, respectively, in the one or more cells.

17. The non-human animal of claim 1, wherein the non-human animal comprises the one or more agents that reduce expression of the one or more or all of BANF1, PPP2CA, and ANKLE2 in the one or more cells.

18. The non-human animal of claim 17, wherein the one or more agents comprise a nuclease agent targeting BANF1, PPP2CA, or ANKLE2 or a nucleic acid encoding the nuclease agent.

19. The non-human animal of claim 18, wherein the nuclease agent is a Zinc Finger Nuclease (ZFN), a Transcription Activator-Like Effector Nuclease (TALEN), or a Clustered Regularly Interspaced Short Palindromic Repeats (CRISPR)-associated (Cas) protein and a guide RNA.

20. The non-human animal of claim 19, wherein the nuclease agent is the Cas protein and the guide RNA.

21. The non-human animal of claim 20, wherein the Cas protein is a Cas9 protein.

22. The non-human animal of claim 20, wherein the Cas protein is a catalytically active Cas protein.

23. The non-human animal of claim 17, wherein the one or more agents comprise a transcriptional repressor targeting BANF1, PPP2CA, or ANKLE2 or a nucleic acid encoding the transcriptional repressor.

24. The non-human animal of claim 23, wherein the transcriptional repressor comprises a guide RNA and a catalytically inactive Cas protein fused to a transcriptional repressor domain, wherein the transcriptional repressor domain is a Krüppel associated box (KRAB) domain.

25. The non-human animal of claim 20, wherein the guide RNA targets mouse Banf1 and comprises any one of the sequences set forth in SEQ ID NOS: 44-46 or the guide RNA targets human BANF1 and comprises any one of the sequences set forth in SEQ ID NOS: 27-30.

26. The non-human animal of claim 20, wherein the guide RNA targets mouse Ppp2ca and comprises any one of the sequences set forth in SEQ ID NOS: 47-49 or the guide RNA targets human PPP2CA and comprises any one of the sequences set forth in SEQ ID NOS: 31-32.

27. The non-human animal of claim 20, wherein the guide RNA targets mouse Ankle2 and comprises any one of the sequences set forth in SEQ ID NOS: 50-52 or the guide RNA targets human ANKLE2 and comprises the sequence set forth in SEQ ID NO: 38.

28. The non-human animal of claim 17, wherein the one or more agents comprise an antisense oligonucleotide or an RNAi agent targeting BANF1, PPP2CA, or ANKLE2 or a nucleic acid encoding the antisense oligonucleotide or the RNAi agent.

29. The non-human animal of claim 28, wherein the antisense oligonucleotide comprises the sequence set forth in any one of SEQ ID NOS: 105-324 or a modified version thereof.

30. The non-human animal of claim 29, wherein the antisense oligonucleotide comprises the sequence set forth in any one of SEQ ID NOS: 105, 106, 110-113, 115, 120-122, 124, 125, 130 133, 136, 137, 150, 152, 153, 155, 158-160, 162, 165, 166, 169, 171-173, 175, 177, 181-184, 187, 194, 197, 211, 213, 215, 216, 220-223, 225, 230-232, 234, 235, 240, 243, 246, 247, 260 262, 263, 265, 268-270, 272, 275, 276, 279, 281-283, 285, 287, 291-294, 297, 304, 307, 321, and 323 or a modified version thereof.

31. The non-human animal of claim 29, wherein the antisense oligonucleotide comprises one or more phosphorothioate linkages and/or one or more 2'-methoxyethyl modified bases.

32. The non-human animal of claim 31, wherein the antisense oligonucleotide is a 5-10-5 gapmer comprising a phosphorothioate backbone, a 5' wing of 2'-methoxyethyl modified bases, a central 10-nucleotide core of DNA, and a 3' wing of 2'-methoxyethyl modified bases.

33. The non-human animal of claim 1, wherein at least one sign or symptom of tauopathy is increased in the non-human animal relative to a non-human animal that does not comprise the genetic modification in the one or more or all of BANF1, PPP2CA, and ANKLE2 or does not comprise the one or more agents that reduce expression of one or more or all of BANF1, PPP2CA, and ANKLE2.

34. The non-human animal of claim 33, wherein the at least one sign or symptom comprises tau hyperphosphorylation or tau aggregation.

35. The non-human animal of claim 33, wherein the at least one sign or symptom comprises increased tau and/or phospho-tau in an insoluble fraction following cell fractionation, increased phospho-tau in the somatodendritic compartment of neurons, increased phospho-tau in the perinuclear region of neurons, decreased nuclear pore complex protein Nup98-Nup96 (Nup98) nuclear-to-cytoplasmic ration in neurons, decreased GTP-binding nuclear protein Ran (Ran) nuclear-to-cytoplasmic ratio in neurons, or decreased Ran GTPase-activating protein 1 (RanGAP1) nuclear-to-cytoplasmic ratio in neurons.

36. The non-human animal of claim 1, wherein the genetic modification in one or more or all of BANF1, PPP2CA, and ANKLE2 is in one or more neuronal cells and/or wherein the one or more agents that reduce expression of one or more or all of BANF1, PPP2CA, and ANKLE2 are in one or more neuronal cells, wherein the one or more neuronal cells are in the hippocampus.

37. The non-human animal of claim 1, wherein the non-human animal is a mouse or a rat.

38. The non-human animal of claim 37, wherein the non-human animal is the mouse.

39. The non-human animal of claim 38, wherein the mouse is a PS19 transgenic mouse further comprising the genetic modification in the one or more or all of BANF1, PPP2CA, and ANKLE2 that reduces expression of the one or more or all of BANF1, PPP2CA, and ANKLE2, respectively, in the one or more cells and/or further comprising the one or more agents that reduce expression of one or more or all of BANF1, PPP2CA, and ANKLE2 in the one or more cells.

40. A method for assessing a therapeutic candidate for the treatment of a tauopathy, comprising:
 (a) administering a candidate agent to the non-human animal of claim 1;
 (b) performing one or more assays to determine if the candidate agent has an effect on one or more signs or symptoms associated with the tauopathy; and
 (c) identifying the candidate agent that has an effect on the one or more signs or symptoms associated with the tauopathy as a therapeutic candidate.

41. A method of making the non-human animal of claim 1, comprising:
 (a) introducing the one or more agents that reduce expression of one or more or all of BANF1, PPP2CA, and ANKLE2 into a non-human animal that comprises the microtubule-associated protein tau coding sequence; and
 (b) screening the non-human animal to confirm the presence of the one or more agents.

42. A method of making the non-human animal of claim 1, comprising:
 (a) introducing into a non-human animal:
  (i) an exogenous human microtubule-associated protein tau coding sequence; and
  (ii) the one or more agents that reduce expression of one or more or all of BANF1, PPP2CA, and ANKLE2; and
 (b) screening the non-human animal to confirm the presence of the one or more agents and the exogenous human microtubule-associated protein tau coding sequence.

* * * * *

SEQUENCE LISTING

```
Sequence total quantity: 324
SEQ ID NO: 1            moltype = DNA  length = 20
FEATURE                 Location/Qualifiers
source                  1..20
                        mol_type = other DNA
                        organism = Homo sapiens
SEQUENCE: 1
ttgcaggcct atgttgtcct                                               20

SEQ ID NO: 2            moltype = DNA  length = 20
FEATURE                 Location/Qualifiers
source                  1..20
                        mol_type = other DNA
                        organism = Homo sapiens
```

-continued

```
SEQUENCE: 2
gcttcggatg ccttcgagag                                               20

SEQ ID NO: 3           moltype = DNA  length = 20
FEATURE                Location/Qualifiers
source                 1..20
                       mol_type = other DNA
                       organism = Homo sapiens
SEQUENCE: 3
tttcctccag cttcttgccc                                               20

SEQ ID NO: 4           moltype = DNA  length = 20
FEATURE                Location/Qualifiers
source                 1..20
                       mol_type = other DNA
                       organism = Homo sapiens
SEQUENCE: 4
cgccaacgcc aagcagtccc                                               20

SEQ ID NO: 5           moltype = DNA  length = 20
FEATURE                Location/Qualifiers
source                 1..20
                       mol_type = other DNA
                       organism = Homo sapiens
SEQUENCE: 5
gagctctaga caccaacgtg                                               20

SEQ ID NO: 6           moltype = DNA  length = 20
FEATURE                Location/Qualifiers
source                 1..20
                       mol_type = other DNA
                       organism = Homo sapiens
SEQUENCE: 6
caagcagctg tccgagtccc                                               20

SEQ ID NO: 7           moltype = DNA  length = 20
FEATURE                Location/Qualifiers
misc_feature           1..20
                       note = Synthetic
source                 1..20
                       mol_type = other DNA
                       organism = synthetic construct
SEQUENCE: 7
cttcgacgcc atcgtgctca                                               20

SEQ ID NO: 8           moltype = DNA  length = 20
FEATURE                Location/Qualifiers
misc_feature           1..20
                       note = Synthetic
source                 1..20
                       mol_type = other DNA
                       organism = synthetic construct
SEQUENCE: 8
cgcctctcac gtgtaggctt                                               20

SEQ ID NO: 9           moltype = DNA  length = 20
FEATURE                Location/Qualifiers
source                 1..20
                       mol_type = other DNA
                       organism = Homo sapiens
SEQUENCE: 9
tttaaggaac ccagtgacaa                                               20

SEQ ID NO: 10          moltype = DNA  length = 20
FEATURE                Location/Qualifiers
source                 1..20
                       mol_type = other DNA
                       organism = Homo sapiens
SEQUENCE: 10
ggccttgaac acagttccgt                                               20

SEQ ID NO: 11          moltype = DNA  length = 20
FEATURE                Location/Qualifiers
source                 1..20
                       mol_type = other DNA
                       organism = Homo sapiens
SEQUENCE: 11
tagagttgtc atcttctcaac                                              20
```

```
SEQ ID NO: 12              moltype = DNA   length = 20
FEATURE                    Location/Qualifiers
source                     1..20
                           mol_type = other DNA
                           organism = Homo sapiens
SEQUENCE: 12
aaggagccgc ccctgtacta                                                    20

SEQ ID NO: 13              moltype = DNA   length = 20
FEATURE                    Location/Qualifiers
source                     1..20
                           mol_type = other DNA
                           organism = Homo sapiens
SEQUENCE: 13
tccggccagg atcaactcgt                                                    20

SEQ ID NO: 14              moltype = DNA   length = 20
FEATURE                    Location/Qualifiers
source                     1..20
                           mol_type = other DNA
                           organism = Homo sapiens
SEQUENCE: 14
tacttacggc tatatattct                                                    20

SEQ ID NO: 15              moltype = DNA   length = 20
FEATURE                    Location/Qualifiers
source                     1..20
                           mol_type = other DNA
                           organism = Homo sapiens
SEQUENCE: 15
aagaacgctt tctgttcaag                                                    20

SEQ ID NO: 16              moltype = DNA   length = 20
FEATURE                    Location/Qualifiers
source                     1..20
                           mol_type = other DNA
                           organism = Homo sapiens
SEQUENCE: 16
gtgaaatacg gagtgaatcc                                                    20

SEQ ID NO: 17              moltype = DNA   length = 20
FEATURE                    Location/Qualifiers
misc_feature               1..20
                           note = Synthetic
source                     1..20
                           mol_type = other DNA
                           organism = synthetic construct
SEQUENCE: 17
atagccgccg ctcattactt                                                    20

SEQ ID NO: 18              moltype = DNA   length = 20
FEATURE                    Location/Qualifiers
source                     1..20
                           mol_type = other DNA
                           organism = Mus musculus
SEQUENCE: 18
atgaagacct cttccgagaa                                                    20

SEQ ID NO: 19              moltype = DNA   length = 20
FEATURE                    Location/Qualifiers
source                     1..20
                           mol_type = other DNA
                           organism = Mus musculus
SEQUENCE: 19
atcccggcca ggctccccac                                                    20

SEQ ID NO: 20              moltype = DNA   length = 20
FEATURE                    Location/Qualifiers
source                     1..20
                           mol_type = other DNA
                           organism = Mus musculus
SEQUENCE: 20
ttggtgacgt cctgagcaag                                                    20

SEQ ID NO: 21              moltype = DNA   length = 20
FEATURE                    Location/Qualifiers
source                     1..20
                           mol_type = other DNA
                           organism = Mus musculus
```

```
SEQUENCE: 21
ccgagcactc gatcgcctac                                              20

SEQ ID NO: 22           moltype = DNA   length = 20
FEATURE                 Location/Qualifiers
source                  1..20
                        mol_type = other DNA
                        organism = Mus musculus
SEQUENCE: 22
acatcgaacc tcttgaacgt                                              20

SEQ ID NO: 23           moltype = DNA   length = 20
FEATURE                 Location/Qualifiers
source                  1..20
                        mol_type = other DNA
                        organism = Mus musculus
SEQUENCE: 23
gggatatctc ctcggggagc                                              20

SEQ ID NO: 24           moltype = DNA   length = 20
FEATURE                 Location/Qualifiers
source                  1..20
                        mol_type = other DNA
                        organism = Mus musculus
SEQUENCE: 24
gatacaggtc aacaacgtag                                              20

SEQ ID NO: 25           moltype = DNA   length = 20
FEATURE                 Location/Qualifiers
source                  1..20
                        mol_type = other DNA
                        organism = Mus musculus
SEQUENCE: 25
ttcgacagct ttccgcagct                                              20

SEQ ID NO: 26           moltype = DNA   length = 20
FEATURE                 Location/Qualifiers
source                  1..20
                        mol_type = other DNA
                        organism = Mus musculus
SEQUENCE: 26
ccagaaccaa ttagatatcg                                              20

SEQ ID NO: 27           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 27
ttgcaggcct atgttgtcct                                              20

SEQ ID NO: 28           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 28
gcttcggatg ccttcgagag                                              20

SEQ ID NO: 29           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 29
tttcctccag cttcttgccc                                              20

SEQ ID NO: 30           moltype = RNA   length = 20
FEATURE                 Location/Qualifiers
misc_feature            1..20
                        note = Synthetic
source                  1..20
                        mol_type = other RNA
```

-continued

```
                          organism = synthetic construct
SEQUENCE: 30
cgccaacgcc aagcagtccc                                                     20

SEQ ID NO: 31             moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 31
gagctctaga caccaacgtg                                                     20

SEQ ID NO: 32             moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 32
caagcagctg tccgagtccc                                                     20

SEQ ID NO: 33             moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 33
cttcgacgcc atcgtgctca                                                     20

SEQ ID NO: 34             moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 34
cgcctctcac gtgtaggctt                                                     20

SEQ ID NO: 35             moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 35
tttaaggaac ccagtgacaa                                                     20

SEQ ID NO: 36             moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 36
ggccttgaac acagttccgt                                                     20

SEQ ID NO: 37             moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 37
tagagttgtc atctttcaac                                                     20

SEQ ID NO: 38             moltype = RNA   length = 20
FEATURE                   Location/Qualifiers
misc_feature              1..20
                          note = Synthetic
source                    1..20
```

```
                        mol_type = other RNA
                        organism = synthetic construct
SEQUENCE: 38
aaggagccgc ccctgtacta                                                    20

SEQ ID NO: 39           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 39
tccggccagg atcaactcgt                                                    20

SEQ ID NO: 40           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 40
tacttacggc tatatattct                                                    20

SEQ ID NO: 41           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 41
aagaacgctt tctgttcaag                                                    20

SEQ ID NO: 42           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 42
gtgaaatacg gagtgaatcc                                                    20

SEQ ID NO: 43           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 43
atagccgccg ctcattactt                                                    20

SEQ ID NO: 44           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 44
atgaagacct cttccgagaa                                                    20

SEQ ID NO: 45           moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 45
atcccggcca ggctccccac                                                    20

SEQ ID NO: 46           moltype = RNA   length = 20
FEATURE                 Location/Qualifiers
misc_feature            1..20
                        note = Synthetic
```

```
source                      1..20
                            mol_type = other RNA
                            organism = synthetic construct
SEQUENCE: 46
ttggtgacgt cctgagcaag                                                   20

SEQ ID NO: 47               moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 47
ccgagcactc gatcgcctac                                                   20

SEQ ID NO: 48               moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 48
acatcgaacc tcttgaacgt                                                   20

SEQ ID NO: 49               moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 49
gggatatctc ctcggggagc                                                   20

SEQ ID NO: 50               moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 50
gatacaggtc aacaacgtag                                                   20

SEQ ID NO: 51               moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 51
ttcgacagct ttccgcagct                                                   20

SEQ ID NO: 52               moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 52
ccagaaccaa ttagatatcg                                                   20

SEQ ID NO: 53               moltype = DNA   length = 21
FEATURE                     Location/Qualifiers
misc_feature                1..21
                            note = Synthetic
source                      1..21
                            mol_type = other DNA
                            organism = synthetic construct
SEQUENCE: 53
agaatctgaa gcatcaaccg g                                                 21

SEQ ID NO: 54               moltype = DNA   length = 22
FEATURE                     Location/Qualifiers
misc_feature                1..22
```

-continued

```
                       note         = Synthetic
source                 1..22
                       mol_type     = other DNA
                       organism     = synthetic construct
SEQUENCE: 54
ggtttgtaaa cgatctgcac tg                                                  22

SEQ ID NO: 55          moltype = DNA   length = 24
FEATURE                Location/Qualifiers
misc_feature           1..24
                       note         = Synthetic
source                 1..24
                       mol_type     = other DNA
                       organism     = synthetic construct
SEQUENCE: 55
aatatcaagc acgtccctgg aggc                                                24

SEQ ID NO: 56          moltype = DNA   length = 21
FEATURE                Location/Qualifiers
misc_feature           1..21
                       note         = Synthetic
source                 1..21
                       mol_type     = other DNA
                       organism     = synthetic construct
SEQUENCE: 56
ccgaaaatct caagcatcag c                                                   21

SEQ ID NO: 57          moltype = DNA   length = 20
FEATURE                Location/Qualifiers
misc_feature           1..20
                       note         = Synthetic
source                 1..20
                       mol_type     = other DNA
                       organism     = synthetic construct
SEQUENCE: 57
acacaatctg tacgcttccg                                                     20

SEQ ID NO: 58          moltype = DNA   length = 24
FEATURE                Location/Qualifiers
misc_feature           1..24
                       note         = Synthetic
source                 1..24
                       mol_type     = other DNA
                       organism     = synthetic construct
SEQUENCE: 58
tgcacgttag acaggtccag cttc                                                24

SEQ ID NO: 59          moltype = DNA   length = 24
FEATURE                Location/Qualifiers
misc_feature           1..24
                       note         = Synthetic
source                 1..24
                       mol_type     = other DNA
                       organism     = synthetic construct
SEQUENCE: 59
ggcggtaagg tccaaattat aaac                                                24

SEQ ID NO: 60          moltype = DNA   length = 22
FEATURE                Location/Qualifiers
misc_feature           1..22
                       note         = Synthetic
source                 1..22
                       mol_type     = other DNA
                       organism     = synthetic construct
SEQUENCE: 60
ggtttgtaaa cgatctgaac gg                                                  22

SEQ ID NO: 61          moltype = DNA   length = 24
FEATURE                Location/Qualifiers
misc_feature           1..24
                       note         = Synthetic
source                 1..24
                       mol_type     = other DNA
                       organism     = synthetic construct
SEQUENCE: 61
aatgtccaaa gcaagtgtgg cagc                                                24

SEQ ID NO: 62          moltype = DNA   length = 22
FEATURE                Location/Qualifiers
```

```
                        misc_feature            1..22
                                                note = Synthetic
                        source                  1..22
                                                mol_type = other DNA
                                                organism = synthetic construct
                        SEQUENCE: 62
                        ggtagtacag agaacctgaa gc                                          22

SEQ ID NO: 63           moltype = DNA   length = 20
                        FEATURE                 Location/Qualifiers
                        misc_feature            1..20
                                                note = Synthetic
                        source                  1..20
                                                mol_type = other DNA
                                                organism = synthetic construct
                        SEQUENCE: 63
                        ctttgctccc acatttgctc                                             20

SEQ ID NO: 64           moltype = DNA   length = 24
                        FEATURE                 Location/Qualifiers
                        misc_feature            1..24
                                                note = Synthetic
                        source                  1..24
                                                mol_type = other DNA
                                                organism = synthetic construct
                        SEQUENCE: 64
                        cggtggtggt aaggtccaga tcat                                        24

SEQ ID NO: 65           moltype = RNA   length = 16
                        FEATURE                 Location/Qualifiers
                        misc_feature            1..16
                                                note = Synthetic
                        source                  1..16
                                                mol_type = other RNA
                                                organism = synthetic construct
                        SEQUENCE: 65
                        gttttagagc tatgct                                                 16

SEQ ID NO: 66           moltype = RNA   length = 67
                        FEATURE                 Location/Qualifiers
                        misc_feature            1..67
                                                note = Synthetic
                        source                  1..67
                                                mol_type = other RNA
                                                organism = synthetic construct
                        SEQUENCE: 66
                        agcatagcaa gttaaaataa ggctagtccg ttatcaactt gaaaaagtgg caccgagtcg  60
                        gtgcttt                                                           67

SEQ ID NO: 67           moltype = RNA   length = 77
                        FEATURE                 Location/Qualifiers
                        misc_feature            1..77
                                                note = Synthetic
                        source                  1..77
                                                mol_type = other RNA
                                                organism = synthetic construct
                        SEQUENCE: 67
                        gttttagagc tagaaatagc aagttaaaat aaggctagtc cgttatcaac ttgaaaagt   60
                        ggcaccgagt cggtgct                                                77

SEQ ID NO: 68           moltype = RNA   length = 82
                        FEATURE                 Location/Qualifiers
                        misc_feature            1..82
                                                note = Synthetic
                        source                  1..82
                                                mol_type = other RNA
                                                organism = synthetic construct
                        SEQUENCE: 68
                        gttggaacca ttcaaaacag catagcaagt taaataagg ctagtccgtt atcaacttga   60
                        aaaagtggca ccgagtcggt gc                                          82

SEQ ID NO: 69           moltype = RNA   length = 76
                        FEATURE                 Location/Qualifiers
                        misc_feature            1..76
                                                note = Synthetic
                        source                  1..76
                                                mol_type = other RNA
                                                organism = synthetic construct
                        SEQUENCE: 69
```

```
gttttagagc tagaaatagc aagttaaaat aaggctagtc cgttatcaac ttgaaaaagt    60
ggcaccgagt cggtgc                                                    76

SEQ ID NO: 70           moltype = RNA  length = 86
FEATURE                 Location/Qualifiers
misc_feature            1..86
                        note = Synthetic
source                  1..86
                        mol_type = other RNA
                        organism = synthetic construct
SEQUENCE: 70
gtttaagagc tatgctggaa acagcatagc aagtttaaat aaggctagtc cgttatcaac    60
ttgaaaaagt ggcaccgagt cggtgc                                         86

SEQ ID NO: 71           moltype =    length =
SEQUENCE: 71
000

SEQ ID NO: 72           moltype =    length =
SEQUENCE: 72
000

SEQ ID NO: 73           moltype =    length =
SEQUENCE: 73
000

SEQ ID NO: 74           moltype = DNA  length = 9099
FEATURE                 Location/Qualifiers
misc_feature            1..9099
                        note = Synthetic
misc_feature            1..635
                        note = LTR
misc_feature            636..653
                        note = PBS
misc_feature            685..822
                        note = PackagingSignal
misc_feature            1303..1536
                        note = RRE
misc_feature            2028..2151
                        note = cPPT
misc_feature            2185..2668
                        note = hSynapsin promoter
misc_feature            2675..2686
                        note = MCS
misc_feature            2687..3403
                        note = GFP
misc_feature            3415..3420
                        note = MCS
misc_feature            3421..4019
                        note = IRES
misc_feature            4020..5054
                        note = HygR
misc_feature            5068..5659
                        note = WPRE
misc_feature            5862..6498
                        note = LTR
misc_feature            6967..7640
                        note = pUCorigin
misc_feature            7785..8781
                        note = AmpR
source                  1..9099
                        mol_type = other DNA
                        organism = synthetic construct
SEQUENCE: 74
tggaagggct aattcactcc caaagaagac aagatatcct tgatctgtgg atctaccaca    60
cacaaggcta cttccctgat tagcagaact acacaccagg gccagggrtc agatatccac   120
tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtggcccgag   300
agctgcatcc ggagtacttc aagaactgct gatatcgagc ttgctacaag gactttccg    360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta gagatccctc   600
agacccttt agtcagtgtg gaaaatctct agcagtggcg cccgaacagg acttgaaag    660
cgaaagggaa accagaggag ctctctcgac gcaggactcg gcttgctgaa gcgcgcacgg   720
caagaggcga gggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaaatataa attaaaacat atagtatggg   900
```

```
caagcaggga gctagaacga ttcgcagtta atcctggcct gttagaaaca tcagaaggct   960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagaggaag agcaaaacaa aagtaagacc accgcacagc  1140
aagcggccgg ccgctgatct tcagacctgg aggaggaagt atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag cagctccagg caagaatcct  1500
ggctgtggaa agatacctaa aggatcaaca gctcctgggg atttgggggt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtggaa ttggtttaac ataacaaatt ggctgtggta  1800
tataaaatta ttcataatga tagtaggagg cttggtaggt ttaagaatag ttttgctgt  1860
actttctata gtgaatagag ttaggcaggg atattcacca ttatcgtttc agacccacct  1920
cccaacccg aggggacccg acaggcccga aggaatagaa gaagaaggtg gagagagaga  1980
cagagacaga tccattcgat tagtgaacgg atctcgacgg tatcgccttt aaaagaaaag  2040
gggggattgg ggggtacagt gcaggggaaa gaatagtaga cataatagca acagacatac  2100
aaactaaaga attacaaaaa caaattacaa aaattcaaaa ttttcgggtt tattacaggg  2160
acagcagaga tccagtttat cgatctgcag aagggcctgc gtatgagtgc aagtgggttt  2220
taggaccagg atgaggcggg gtgggggtgc ctacctgacg accgacccg acccactgga  2280
caagcaccca accccattc cccaaattgc gcatccccta tcagagaggg ggagggaaa   2340
caggatgcgg cgaggcgcgt gcgcactgcc agcttcagca ccgcggacag tgccttcgcc  2400
cccgcctggc ggcgcgcgcc accgccgcct cagcactgag ggcgcgctga cgtcactcgc  2460
cggtcccccg caaactcccc ttcccggcca ccttggtcgc gtccgcgccg ccgccgccc   2520
agccggaccg caccacgcga ggcgcgagat aggggggcac gggcgcgacc atctgcgctg  2580
cggcgccggc gactcagcgc tgcctcagtc tgcggtgggc agcggaggag tcgtgtcgtg  2640
cctgagagcg cagggatcta tttccggtga attcctcaga actagtatgg tgagcaaggg  2700
cgaggagctg ttcaccgggg tggtgcccat cctggtcgag ctggacgcg acgtaaacgg  2760
ccacaagttc agcgtgtccg gcgagggcga gggcgatgcc acctacggca agctgaccct  2820
gaagttcatc tgcaccaccg gcaagctgcc cgtgccctgg cccaccctcg tgaccaccct  2880
gacctacggc gtgcagtgct tcagccgcta ccccgaccac atgaagcagc acgacttctt  2940
caagtccgcc atgcccgaag gctacgtcca ggagcgcacc atcttcttca aggacgacgg  3000
caactacaag acccgcgccg aggtgaagtt cgagggcgac accctggtga accgcatcga  3060
gctgaagggc atcgacttca aggaggacgg caacatcctg gggcacaagc tggagtacaa  3120
ctacaacagc cacaacgtct atatcatggc cgacaagcag aagaacggca tcaaggtgaa  3180
cttcaagatc cgccacaaca tcgaggacgg cagcgtgcag ctcgccgaca ctaccagca   3240
gaacaccccc atcggcgacg gccccgtgct gctgcccgac aaccactacc tgagcaccca  3300
gtccgccctg agcaaagacc ccaacgaaaa gcgcgatcac atggtcctgc tggagttcgt  3360
gaccgccgcc gggatcactc tcggcatgga cgagctgtac aagtaagcgg ccgcggatcc  3420
cgcccctctc cctcccccc cctaacgtt actggccgaa gccgcttgga ataaggccgg  3480
tgtgcgtttg tctatatgtt attttccacc atattgccgt cttttggcaa tgtgagggcc  3540
cggaaacctg gccctgtctt cttgacgagc attcctaggg gtcttccccc tctgccaaa   3600
ggaatgcaag gtctgttgaa tgtcgtgaag gaagcagttc ctctggaagc ttcttgaaga  3660
caaacaacgt ctgtagcgac cctttgcagg cagcggaacc cccacctgg cgacaggtgc   3720
ctctgcggcc aaaagccacg tgtataagat acacctgcaa aggcggcaca acccagtgtc  3780
cacgttgtga gttggatagt tgtggaaaga gtcaaatggc tctcctcaag cgtattcaac  3840
aaggggctga aggatgccca gaaggtaccc cattgtatgg gatctgatct ggggcctcgg  3900
tgcacatgct ttacatgtgt ttagtcgagg ttaaaaaaac gtctaggccc cccgaaccac  3960
ggggacgtgg ttttccttg aaaaacacga tgataagctt gccacaaccc gtaccaaaga   4020
tggatagatc cggaaagcct gaactcaccg cgacgtctgt cgagaagttt ctgatcgaaa  4080
agttcgacag cgtctccgac ctgatgcagc tctcggaggg cgaagaatct cgtgctttca  4140
gcttcgatgt aggagggcgt ggatatgtcc tgcgggtaaa tagctgcgcc gatggtttct  4200
acaaagatcg ttatgtttat cggcactttg catcggccgc gctccgattc cggaagtgc   4260
ttgacattgg ggaattcagc gagagcctga cctattgcat ctcccgccgt gcacagggtg  4320
tcacgttgca agacctgcct gaaaccgaac tgcccgctgt tctgcagccg gtcgcggagg  4380
ccatggatga tcgcgtgcg gccgatctta gccagacgag cgggttcggc ccattcggac   4440
cgcaaggaat cggtcaatac actacatggc gtgatttcat atgcgcgatt gctgatccac  4500
atgtgtcatca ctggcaaact gtgatggacg acaccgtcag tgcgtccgtc gcgcaggctc  4560
tcgatgagct gatgctttgg gccgaggact gccccgaagt ccggcacctc gtgcacgcgg  4620
atttcggctc caacaatgtc ctgacggaca atggccgcat aacagcggtc attgactgga  4680
gcgaggcgat gttcggggat tcccaatacg aggtcgccaa catcttcttc tggaggccgt  4740
ggttggcttg tatggagcag cagacgcgct acttcgagcg gaggcatccg gagcttcag   4800
gatcgccgcg gctccgggcg tatatgctcc gcattggtct tgaccaactc tatcagagct  4860
tggttgacgg caatttcgat gatgcagctt gggcgcaggg tcgatgcgac gcaatcgtcc  4920
gatccggagc cgggactgtc gggcgtacac aaatcgcccg cagaagcgcg gccgtctgga  4980
ccgatggctg tgtagaagta ctcgccgata gtggaaaccg acgccccagc actcgtccga  5040
gggcaaagga atagcgcgt ctggaacaat caacctctgg attacaaaat ttgtgaaaga   5100
ttgactggta ttcttaacta tgttgctcct tttacgctat gtggatacgc tgctttaatg  5160
cctttgtatc atgctattgc ttcccgtatg gctttcattt tctcctcctt gtataaatcc  5220
tggttgctgt ctctttatga ggagttgtgg cccgttgtca ggcaacgtgg cgtggtgtgc  5280
actgtgtttg ctgacgcaac ccccactggt tggggcattg ccaccacctg tcagctcctt  5340
tccgggactt tcgctttccc cctccctatt gccacgcgg aactcatcgc cgcctgcctt   5400
gcccgctgct ggacagggc tcggctgttg ggcactgaca attccgtggt gttgtcgggg  5460
aagctgacgt ccttttccatg gctgctgccc tgtgttgcca cctggattct gcgcgggacg  5520
tccttctgct acgtcccttc ggccctcaat ccagcggacc ttccttcccg cggcctgctg  5580
ccggctctgc ggcctcttcc gcgtcttcgc cttcgccctc agacgagtcg gatctccctt  5640
```

```
tgggccgcct cccgcctgg aattaattct gcagtcgaga cctagaaaaa catggagcaa  5700
tcacaagtag caatacagca gctaccaatg ctgattgtgc ctggctagaa gcacaagagg  5760
aggaggaggt gggttttcca gtcacacctc aggtaccttt aagaccaatg acttacaagg  5820
cagctgtaga tcttagccac tttttaaaag aaaagagggg actggaaggg ctaattcact  5880
cccaacgaag acaagatatc cttgatctgt ggatctacca cacacaaggc tacttccctg  5940
attagcagaa ctacacacca gggccagggg tcagatatcc actgacctt ggatggtgct  6000
acaagctagt accagttgag ccagataagg tagaagaggc caataaagga gagaacacca  6060
gcttgttaca ccctgtgagc ctgcatggga tggatgaccc ggagagagaa gtgttagagt  6120
ggaggtttga cagccgccta gcatttcatc acgtggcccg agagctgcat ccggagtact  6180
tcaagaactg ctgatatcga gcttgctaca agggactttc cgctgggac tttccaggga  6240
ggcgtggcct gggcgggact ggggagtggc gagccctcag atcctgcata taagcagctg  6300
ctttttgcct gtactgggtc tctctggtta accagatct gagcctggga gctctctggc  6360
taactaggga acccactgct taagcctcaa taaagcttgc cttgagtgct tcaagtagtg  6420
tgtgcccgtc tgttgtgtga ctctggtaac tagagatccc tcagaccctt ttagtcagtg  6480
tggaaaatct ctagcagtag tagttcatgt catcttatta ttcagtattt taacttgca  6540
aagaaatgaa tatcagagag tgagaggcct tgacattgct agcgtttacc gtcgacctct  6600
agctagagct tggcgtaatc atggtcatag ctgtttcctg tgtgaaattg ttatccgctc  6660
acaattccac acaacatacg agccggaagc ataaagtgta aagcctgggg tgcctaatga  6720
gtgagctaac tcacattaat tgcgttgcgc tcactgcccg ctttccagtc gggaaacctg  6780
tcgtgccagc tgcattaatg aatcggccaa cgcgcgggga gaggcggttt gcgtattggg  6840
cgctcttccg cttcctcgct cactgactcg ctgcgctcgg tcgttcggct gcggcgagcg  6900
gtatcagctc actcaaaggc ggtaatacgg ttatccacag aatcaggggga taacgcagga  6960
aagaacatgt gagcaaaagg ccagcaaaag gccaggaacc gtaaaaaggc cgcgttgctg  7020
gcgtttttcc ataggctccg ccccctgac gagcatcaca aaatcgacg ctcaagtcag  7080
aggtggcgaa acccgacagg actataaaga taccaggcgt ttccccctgg aagctccctc  7140
gtgcgctctc ctgttccgac cctgccgctt accggatacc tgtccgcctt tctccccttcg  7200
ggaagcgtgg cgctttctca tagctcacgc tgtaggtatc tcagttcggt gtaggtcgtt  7260
cgctccaagc tgggctgtgt gcacgaaccc cccgttcagc ccgaccgctg cgccttatcc  7320
ggtaactatc gtcttgagtc aacccgta agacacgact tatcgccact ggcagcagcc  7380
actggtaaca ggattagcag agcgaggtat gtaggcggtg ctacagagtt cttgaagtgg  7440
tggcctaact acggctacac tagaagaaca gtatttggta tctgcgctct gctgaagcca  7500
gttaccttcg gaaaaagagt tggtagctct tgatccggca acaaaccac cgctggtagc  7560
ggtggttttt tgtttgcaa gcagcagatt acgcgcagaa aaaaggatc tcaagaagat  7620
cctttgatct tttctacggg gtctgacgct cagtggaacg aaaactcacg ttaagggatt  7680
ttggtcatga gattatcaaa aaggatcttc acctagatct tttaaatta aaaatgaagt  7740
tttaaatcaa tctaaagtat atatgagtaa acttggtctg acagttacca atgcttaatc  7800
agtgaggcac ctatctcagc gatctgtcta tttcgttcat ccatagttgc ctgactcccc  7860
gtcgtgtaga taactacgat acgggagggc ttaccatctg gccccagtgc tgcaatgata  7920
ccgcgagacc cacgctcacc ggctccagat ttatcagcaa taaaccagcc agccggaagg  7980
gccgagcgca gaagtggtcc tgcaacttta tccgcctcca tccagtctat taattgttgc  8040
cgggaagcta gagtaagtag ttcgccagtt aatagtttgc gcaacgttgt tgccattgct  8100
acaggcatcg tggtgtcacg ctcgtcgttt ggtatggctt cattcagctc cggttcccaa  8160
cgatcaaggc gagttacatg atcccccatg ttgtgcaaaa aagcggttag ctccttcggt  8220
cctccgatcg ttgtcagaag taagttggcc gcagtgttat cactcatggt tatggcagca  8280
ctgcataatt ctcttactgt catgccatcc gtaagatgct tttctgtgac tggtgagtac  8340
tcaaccaagt cattctgaga atagtgtatg cggcgaccga gttgctcttg cccggcgtca  8400
atacgggata ataccgcgcc acatagcaga actttaaaag tgctcatcat tggaaaacgt  8460
tcttcgggc gaaaactctc aaggatctta ccgctgttga tccagttc gatgtaaccc  8520
actcgtgcac ccaactgatc ttcagcatct tttactttca ccagcgtttc tgggtgagca  8580
aaaacaggaa ggcaaaatgc cgcaaaaaag ggaataaggg cgacacgaaa atgttgaata  8640
ctcatactct tccttttca atattattga agcatttatc agggttattg tctcatgagc  8700
ggatacatat ttgaatgtat ttagaaaaat aaacaaatag gggttccgcg cacatttccc  8760
cgaaaagtgc cacctgacgt cgacggatcg ggagatcaac ttgtttattg cagcttataa  8820
tggttacaaa taaagcaata gcatcacaaa tttcacaaat aaagcatttt ttcactgca  8880
ttctagttgt ggtttgtcca aactcatcaa tgtatcttat catgtctgga tcaactggat  8940
aactcaagct aaccaaaatc atcccaaact tcccacccca taccctatta ccactgccaa  9000
ttacctgtgg tttcatttac tctaaacctg tgattcctct gaattatttt cattttaaag  9060
aaattgtatt tgttaaatat gtactacaaa cttagtagt                         9099
```

SEQ ID NO: 75        moltype = DNA   length = 9636
FEATURE              Location/Qualifiers
misc_feature         1..9636
                     note = Synthetic
misc_feature         1..635
                     note = LTR
misc_feature         636..653
                     note = PBS
misc_feature         685..822
                     note = Packaging§ignal
misc_feature         1303..1536
                     note = RRE
misc_feature         2028..2151
                     note = cPPT
misc_feature         2185..2668
                     note = hSynapsin promoter
misc_feature         2681..3919
                     note = hTau-412 (1N4R) WT
misc_feature         3926..3957
                     note = MCS

```
misc_feature        3958..4556
                    note = IRES
misc_feature        4557..5591
                    note = HygR
misc_feature        5605..6196
                    note = WPRE
misc_feature        6399..7035
                    note = LTR
misc_feature        7504..8177
                    note = pUCorigin
misc_feature        8322..9318
                    note = AmpR
source              1..9636
                    mol_type = other DNA
                    organism = synthetic construct
SEQUENCE: 75
tggaagggct aattcactcc caaagaagac aagatatcct tgatctgtgg atctaccaca   60
cacaaggcta cttccctgat tagcagaact acacaccagg gccagggtc agatatccac   120
tgaccttggg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtggcccgag  300
agctgcatcc ggagtacttc aagaactgct gatatcgagc ttgctacaag ggactttccg  360
ctggggactt tccagggagg cgtggcctgg gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agacccttt agtcagtgtg aaaatctct agcagtggcg cccgaacagg gacttgaaag   660
cgaaagggaa accagaggag ctctctcgac gcaggactcg gcttgctgaa gcgcgcacgg  720
caagaggcga ggggcggcga ctggtgagta cgccaaaaat tttgactagc ggaggctaga  780
aggagagaga tgggtgcgag agcgtcagta ttaagcgggg gagaattaga tcgcgatggg  840
aaaaaattcg gttaaggcca gggggaaaga aaaaatataa attaaaacat atagtatggg  900
caagcaggga gctagaacga ttcgcagtta atcctggcct gttagaaaca tcagaaggct  960
gtagacaaat actgggacag ctacaaccat cccttcagac aggatcagaa gaacttagat 1020
cattatataa tacagtagca accctctatt gtgtgcatca aaggatagag ataaaagaca 1080
ccaaggaagc tttagacaag atagaggaag agcaaaacaa agtaagacca accgcacagc 1140
aagcggccgg ccgctgatct tcagacctgg aggaggagat gagggaca attggagaag  1200
tgaattatat aaatataaag tagtaaaaat tgaaccatta ggagtagcac ccaccaaggc 1260
aaagagaaga gtggtgcaga gagaaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag ttttgctgt  1860
actttctata gtgaatagag ttaggcaggg atattcacca ttatcgtttc agacccacct 1920
cccaaccccg aggggaccg acaggcccga aggaatagaa gaagaaggtg gagagagaga 1980
cagagacaga tccattcgat tagtgaacgg atctcgacgg tatcgccttt aaaagaaaag 2040
gggggattgg ggggtacagt gcaggggaaa gaatagtaga cataatagca acagacatac 2100
aaactaaaga attacaaaaa caaattacaa aaattcaaaa ttttcgggtt tattacaggg 2160
acagcagaga tccagtttat cgatctgcag agggccctgc gtatgagtgc aagtgggttt 2220
taggaccagg atgaggcggg gtgggggtgc ctacctgacg accgacccg acccactgga  2280
caagcaccca acccccattc cccaaattgc gcatccccta tcagagaggg ggaggggaaa 2340
caggatgcgg cgaggcgcgt gcgcactgcc agcttcagca ccgcggacag tgccttcgcc 2400
cccgcctggc ggcgcgcgcc accgccgcct cagcactgaa ggcgcgctga cgtcactcgc 2460
cggtcccccg caaactcccc ttcccggcca ccttggtcgc gtccgcgccg ccgccggccc 2520
agccggaccg caccacgcga ggcgcgagat agggggggcac gggcgcgacc atctgcgctg 2580
cggcgcggc gactcagcgc tgcctcagtc tgcggtgggc agcggaggag tcgtgtcgtg 2640
cctgagagcg cagggatcta tttccggtga attcgccacc atggctgagc ccgacagga  2700
gttcgaggta atgaggatc acgcaggac gtatggtctg ggagacagga aggatcaagg 2760
cggctatacg atgcaccagg atcaggaggg cgataccgat gcgggcctca aagagtcccc 2820
gcttcaaaca ccaactgagg atgggagtga ggagccagaa agtgacgca gcgacgcaa  2880
atcaacccct actgccgaag cggaggaggc cgggatcgga gatacaccat ctctcgaaga 2940
cgaagctgct ggccacgtga cgcaagcacg aatggtgtcc aaaagcaaag acggtacagg 3000
ttctgacgac aaaaaggcga aggggcaga tgggaaaact aaaatcgcca cgccccgggg 3060
tgcggcgccg cctgggcaga aagggcaagc aaatgcgacg cgaataccg ccaagacgcc  3120
tccggctcct aagaccccac catcatctgg tgaacctgct aaaagcgggg atcgaagcgg 3180
ttattcatca ccgggtagtc cgggtacgcc aggctctagg agcagaactc cttcactgcc 3240
cacgccccc acgcgcgaac ctaagaaagt ggcagtggtg cgaacacccc caaaagccc   3300
ctcaagtgca aaatcacggc tccagactgc acccgtaccg atgcccgatc tcaaaaacgt 3360
gaaatctaag ataggtagta cagagaatct gaagcatcaa ccgggaggtg gaaagtgca  3420
gattatcaat aagaaacttg acctgagtaa cgttcaatcc aagtgtggat caaagataa  3480
tatcaagcac gtccctggag gcggttcagt gcagatcgtt tacaaacctg ttgatcttag 3540
caaggtgact tccaagtgcg ggtctctggg caacattcat cacaaacctg gtgagggca  3600
agttgaggtc aaaagcgaaa agctcgactt caaagatcga gttcagagca agataggcag 3660
ccttgataat attacccatg tccccggcgg agggaacaag aagattgaga ctcataagtt 3720
gacgttcaga gaaaatgcta aagcgaaaac ggatcatggc gcagaaatag tttataaatc 3780
```

```
tcctgtggtc agtggtgaca cttcacccag gcacctctca aacgtgtcat caacgggctc  3840
aatcgacatg gtggattctc cccaactcgc aacacttgct gatgaggtaa gtgccagcct  3900
cgcaaagcaa ggactctaaa attcgctcga gactagttct agagcggccg cggatcccgc  3960
ccctctccct cccccccccc taacgttact ggccgaagcc gcttggaata aggccggtgt  4020
gcgtttgtct atatgttatt ttccaccata ttgccgtctt ttggcaatgt gagggcccgg  4080
aaacctggcc ctgtcttctt gacgagcatt cctaggggtc tttcccctct cgccaaagga  4140
atgcaaggtc tgttgaatgt cgtgaaggaa gcagttcctc tggaagcttc ttgaagacaa  4200
acaacgtctg tagcgaccct ttgcaggcag cggaaccccc cacctggcga caggtgcctc  4260
tgcggccaaa agccacgtgt ataagataca cctgcaaagg cggcacaacc ccagtgccac  4320
gttgtgagtt ggatagttgt ggaaagagtc aaatggctct cctcaagcgt attcaacaag  4380
gggctgaagg atgcccagaa ggtacccat tgtatgggat ctgatctggg gcctcggtgc  4440
acatgcttta catgtgttta gtcgaggtta aaaaaacgtc taggccccccc gaaccacggg  4500
gacgtggttt tcctttgaaa aacacgatga taagcttgcc acaaccgtta ccaaagatgg  4560
atagatccgg aaagcctgaa ctcaccgcga cgtctgtcga gaagtttctg atcgaaaagt  4620
tcgacagcgt ctccgacctg atgcagctct cggagggcga agaatctcgt gctttcagct  4680
tcgatgtagg agggcgtgga tatgtcctgc gggtaaatag ctgcgccgat ggtttctaca  4740
aagatcgtta tgtttatcgg cactttgcat cggccgcgct cccgattccg gaagtgcttg  4800
acattgggga attcagcgag agcctgacct attgcatctc ccgccgtgca cagggtgtca  4860
cgttgcaaga cctgcctgaa accgaactgc ccgctgttct gcagccggtc gcggaggcca  4920
tggatgcgat cgctgcggcc gatcttagcc agacgagcgg gttcggccca ttcggaccgc  4980
aaggaatcgg tcaatacact acatggcgtg atttcatatg cgcgattgct gatccccatg  5040
tgtatcactg gcaaactgtg atggacgaca ccgtcagtgc gtccgtcgcg caggctctcg  5100
atgagctgat gctttgggcc gaggactgcc ccgaagtccg gcacctcgtg cacgcggatt  5160
tcggctccaa caatgtcctg acggacaatg gccgcataac agcggtcatt gactggagcg  5220
aggcgatgtt cggggattcc caatacgagg tcgccaacat cttcttctgg aggccgtggt  5280
tggcttgtat ggagcagcag acgcgctact tcgagcggag gcatccggag cttgcaggat  5340
cgccgcggct ccgggcgtat atgctccgca ttggtcttga ccaactctat cagagcttgg  5400
ttgacggcaa tttcgatgat gcagcttggg cgcagggtcg atgcgacgca atcgtccgat  5460
ccggagccgg gactgtcggg cgtacacaaa tcgcccgcag aagcgcggcc gtctggaccg  5520
atggctgtgt agaagtactc gccgatagtg gaaaccgacg ccccagcact cgtccgaggg  5580
caaaggaata gacgcgtctg gaacaatcaa cctctggatt acaaaatttg tgaaagattg  5640
actggtattc ttaactatgt tgctcctttt acgctatgtg gatacgctgc tttaatgcct  5700
ttgtatcatg ctattgcttc ccgtatggct ttcattttct cctccttgta taaatcctgg  5760
ttgctgtctc tttatgagga gttgtggccc gttgtcaggc aacgtggcgt ggtgtgcact  5820
gtgtttgctg acgcaacccc cactggttgg ggcattgcca ccacctgtca gctccttccc  5880
gggacttttcg ctttccccct ccctattgcc acggcggaac tcatcgccgc ctgccttgcc  5940
cgctgctgga caggggctcg gctgttgggc actgacaatt ccgtggtgtt gtcggggaag  6000
ctgacgtcct ttccatggct gctcgcctgt gttgccacct ggattctgcg cgggacgtcc  6060
ttctgctacg tccccttcgg cctcaatcca gcggaccttc cttcccgcgg cctgctgccg  6120
gctctgcggc ctcttccgcg tcttcgcctt cgccctcaga cgagtcggat ctccctttgg  6180
gccgcctccc cgcctggaat taattctgca gtcgagacct agaaaaacat ggagcaatca  6240
caagtagcaa tacagcagct accaatgctg attgtgcctg gctagaagca caagaggagg  6300
aggaggtggg ttttccagtc acacctcagg taccttttaag accaatgact tacaaggcag  6360
ctgtagatct tagccacttt ttaaaagaaa agagggggact ggaagggcta attcactccc  6420
aacgaagaca agatatcctt gatctgtgga tctaccacac acaaggctac ttccctgatt  6480
agcagaacta cacaccaggg ccaggggtca gatatccact gacctttgga tggtgctaca  6540
agctagtacc agttgagcca gataaggtag aagaggccaa taaaggagag aacaccagct  6600
tgttacaccc tgtgagcctg catgggatgg atgacccgga gagagaagtg ttagagtgga  6660
ggtttgacag ccgcctagca tttcatcacg tggcccgaga gctgcatccg gagtacttca  6720
agaactgctg atatcgagct tgctacaagg actttccgc tggggacttt ccagggaggc  6780
gtggcctggg cgggactggg gagtggcgag ccctcagatc ctgcatataa gcagctgctt  6840
tttgcctgta ctgggtctct ctggttagac cagatctgag cctgggagct ctctggctaa  6900
ctagggaacc cactgcttaa gcctcaataa agcttgcctt gagtgcttca agtagtgtgt  6960
gcccgtctgt tgtgtgactc tggtaactag agatccctca gacccttta gtcagtgtgg  7020
aaaatctcta gcagtagtag ttcatgtcat cttattattc agtatttata acttgcaaag  7080
aaatgaatat cagagagtga gaggccttga cattgctagc gtttaccgtc gacctctagc  7140
tagagcttgg cgtaatcatg gtcatagctg tttcctgtgt gaaattgtta tccgctcaca  7200
attccacaca acatacgagc cggaagcata agtgtaaagc ctggggtgc ctaatgagtg  7260
agctaactca cattaattgc gttgcgctca ctgcccgctt tccagtcggg aaacctgtcg  7320
tgccagctgc attaatgaat cggccaacgc gcggggagag gcggtttgcg tattgggcgc  7380
tcttccgctt cctcgctcac tgactcgctg cgctcggtcg ttcggctgcg gcgagcggta  7440
tcagctcact caaaggcggt aatacggtta tccacagaat caggggataa cgcaggaaag  7500
aacatgtgag caaaaggcca gcaaaaggcc aggaaccgta aaaaggccgc gttgctggcg  7560
ttttttccata ggctccgccc cctgacgag catcacaaaa atcgacgctc aagtcagagg  7620
tggcgaaacc cgacaggact ataaagatac caggcgtttc ccctggaag ctccctcgtg  7680
cgctctcctg ttccgaccct gccgcttacc ggatacctgt ccgcctttct cccttcggga  7740
agcgtggcgc tttctcatag ctcacgctgt aggtatctca gttcggtgta ggtcgttcgc  7800
tccaagctgg gctgtgtgca cgaaccccc gttcagcccg accgctgcgc cttatccggt  7860
aactatcgtc ttgagtccaa cccggtaaga cacgacttat cgccactggc agcagccact  7920
ggtaacagga ttagcagagc gaggtatgta ggcggtgcta cagagttctt gaagtggtgg  7980
cctaactacg gctacactag aagaacagta tttggtatct gcgctctgct gaagccagtt  8040
accttcggaa aaagagttgg tagctcttga tccggcaaac aaaccaccgc tggtagcggt  8100
ggttttttttg tttgcaagca gcagattacg cgcagaaaaa aaggatctca agaagatcct  8160
ttgatctttt ctacggggtc tgacgctcag tggaacgaaa actcacgtta agggattttg  8220
gtcatgagat tatcaaaaag gatcttcacc tagatccttt taaattaaaa atgaagtttt  8280
aaatcaatct aaagtatata tgagtaaact tggtctgaca gttaccaatg cttaatcagt  8340
gaggcaccta tctcagcgat ctgtctattt cgttcatcca tagttgcctg actccccgtc  8400
gtgtagataa ctacgatacg ggagggctta ccatctggcc ccagtgctgc aatgataccg  8460
cgagacccac gctcaccggc tccagattta tcagcaataa accagccagc cggaagggcc  8520
```

```
gagcgcagaa gtggtcctgc aactttatcc gcctccatcc agtctattaa ttgttgccgg   8580
gaagctagag taagtagttc gccagttaat agtttgcgca acgttgttgc cattgctaca   8640
ggcatcgtgg tgtcacgctc gtcgtttggt atggcttcat tcagctccgg ttcccaacga   8700
tcaaggcgag ttacatgatc ccccatgttg tgcaaaaaag cggttagctc cttcggtcct   8760
ccgatcgttg tcagaagtaa gttggccgca gtgttatcac tcatggttat ggcagcactg   8820
cataattctc ttactgtcat gccatccgta agatgctttt ctgtgactgg tgagtactca   8880
accaagtcat tctgagaata gtgtatgcgg cgaccgagtt gctcttgccc ggcgtcaata   8940
cgggataata ccgcgccaca tagcagaact ttaaaagtgc tcatcattgg aaaacgttct   9000
tcggggcgaa aactctcaag gatcttaccg ctgttgagat ccagttcgat gtaacccact   9060
cgtgcaccca actgatcttc agcatctttt actttcacca gcgtttctgg gtgagcaaaa   9120
acaggaaggc aaaatgccgc aaaaaaggga ataagggcga cacggaaatg ttgaatactc   9180
atactcttcc ttttcaata ttattgaagc atttatcagg gttattgtct catgagcgga   9240
tacatatttg aatgtattta gaaaaataaa caaataggggt ttccgcgcac atttccccga   9300
aaagtgccac ctgacgtcga cggatcggga gatcaacttg tttattgcag cttataatgg   9360
ttacaaataa agcaatagca tcacaaattt cacaaataaa gcatttttt cactgcattc   9420
tagttgtggt ttgtccaaac tcatcaatgt atcttatcat gtctggatca actgatcaac   9480
tcaagctaac caaaatcatc ccaaacttcc caccccatac cctattacca ctgccaatta   9540
cctgtggttt catttactct aaacctgtga ttcctctgaa ttattttcat tttaaagaaa   9600
ttgtatttgt taaatatgta ctacaaactt agtagt                               9636
```

```
SEQ ID NO: 76           moltype = DNA  length = 10350
FEATURE                 Location/Qualifiers
misc_feature            1..10350
                        note = Synthetic
misc_feature            1..635
                        note = LTR
misc_feature            636..653
                        note = PBS
misc_feature            685..822
                        note = Packaging§ignal
misc_feature            1303..1536
                        note = RRE
misc_feature            2028..2151
                        note = cPPT
misc_feature            2185..2668
                        note = hSynapsin promoter
misc_feature            2681..3916
                        note = hTau-412 (1N4R) WT
misc_feature            3917..4630
                        note = eGFP
misc_feature            4640..4671
                        note = MCS
misc_feature            4672..5270
                        note = IRES
misc_feature            5271..6305
                        note = HygR
misc_feature            6319..6910
                        note = WPRE
misc_feature            7113..7749
                        note = LTR
misc_feature            8218..8891
                        note = pUCørigin
misc_feature            9036..10032
                        note = AmpR
source                  1..10350
                        mol_type = other DNA
                        organism = synthetic construct
SEQUENCE: 76
tggaagggct aattcactcc caaagaagac aagatatcct tgatctgtgg atctaccaca     60
cacaaggcta cttccctgat tagcagaact acacaccagg ccagggggtc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtggcccgag    300
agctgcatcc ggagtacttc aagaactgct gatatcgagc ttgctacaag ggactttccg    360
ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca ggggggaaga aaaaatataa attaaaacat atagtatggg    900
caagcaggga gctaaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aaggatagag ataaagacac   1080
ccaaggaagc tttagacaag atagaggaag agcaaaacaa aagtaagacc accgcacagc   1140
aagcggccgc ccgctgatct tcagacctgg aggaggagat atgagggaca attggagaag   1200
tgaattatat aaatataaag tagtaaaaat tgaaccatta ggagtagcac ccaccaaggc   1260
```

```
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc   1440
gcaacagcat ctgttgcaac tcacagtctg gggcatcaag cagctccagg caagaatcct   1500
ggctgtggaa agatacctaa aggatcaaca gctcctgggg atttggggtt gctctggaaa   1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtggaa ttggtttaac ataacaaatt ggctgtggta   1800
tataaaatta ttcataatga tagtaggagg cttggtaggt ttaagaatag tttttgctgt   1860
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcagggggaaa gaatagtaaa cataatagca acagacatac   2100
aaactaaaga attacaaaaa caaattacaa aaattcaaaa ttttcgggtt tattacaggg   2160
acagcagaga tccagtttat cgatctgcag agggccctgc gtatgagtgc aagtgggttt   2220
taggaccagg atgaggcggg gtgggggtgc ctacctgacg accgaccccg acccactgga   2280
caagcaccca acccccattc cccaaattgc gcatcccta tcagagaggg ggaggggaaa   2340
caggatgcgg cgaggcgcgt gcgcactgcc agcttcagca ccgcggacag tgccttcgcc   2400
cccgcctggc ggcgcgcgcc accgccgcct cagcactgaa ggcgcgctga cgtcactcgc   2460
cggtcccccg caaactcccc ttcccggcca ccttggtcgc gtccgcgccg ccgccggccc   2520
agccggaccg caccacgcga ggcgcgagat aggggggcac ggcgcgaccc atctgcgctg   2580
cggcgccggc gactcagcgc tgcctcagtc tgccggtgggc agcggaggag tcgtgtcgtg   2640
cctgagagcg cagggatcta tttccggtga attcgccacc atggctgagc cccgacagga   2700
gttcgaggta atgaggatc acgcagggac gtatggtctg ggagacagga aggatcaagg   2760
cggctatacg atgcaccagg atcaggaggg cgataccgat gcgggcctca aagagtcccc   2820
gcttcaaaca ccaactgagg atgggagtga ggagccagga agtgagacaa gcgacgcgaa   2880
atcaacccct actgccgaag cggaggaggc cgggatcgga gatacaccat ctctcgaaga   2940
cgaagctgct ggccacgtga cgcaagcacg aatggtgtcc aaaagcaaag acggtacagg   3000
ttctgacgac aaaaaggcga aggggtgcaga tgggaaaact aaaatcgcca cgccccgggg   3060
tgcggcgccg cctgggcaga aagggcaagc aaatgcgacg cgaatacctg ccaagacgcc   3120
tccggctcct aagaccccac catcatctgg tgaaccgcct aaaagcgggg atcgaagcgg   3180
ttattcatca ccgggtagtc cgggtacgcc aggctctagg agcagaactc cttcactgcc   3240
cacgccccccc acgcgcgaac ctaagaaagt ggcagtggtg cgaacacccc caaaagccc   3300
ctcaagtgca aaatcacggc tccagactgc accgtaccg atgcccgatc tcaaaaacgt   3360
gaaatctaag ataggtagta cagagaatct gaagcatcaa ccgggaggtg gaaaggtgca   3420
gattatcaat aagaaacttg acctgagtaa cgttcaatcc aagtgtggat caaaagataa   3480
tatcaagcac gtccctggag gcggttcagt gcagatcgtt tacaaacctg ttgatcttag   3540
caaggtgact tccaagtgcg ggtctctggg caacattcat cacaaacctg gtggagggca   3600
agttgaggtc aaaagcgaaa agctcgactt caaagatcga gttcagagca agataggcag   3660
ccttgataat attaccatg tccccggcgg agggaacaag aagattgaga ctcataagtt   3720
gacgttcaga gaaaatgcta aagcgaaaac ggatcatggc gcagaaatag tttataaatc   3780
tcctgtgtc agtggtgaca cttcacccag gcacctctca aacgtgtcat caacgggctc   3840
aatcgacatg gtggattctc cccaactcgc aacacttgct gatgaggtaa gtgccagcct   3900
cgcaaagcaa ggactcgtga gcaagggcga ggagctgttc accggggtgg tgcccatcct   3960
ggtcgagctg gacggcgacg taaacggcca caagttcagc gtgtccggcg agggcgaggg   4020
cgatgccacc tacggcaagc tgaccctgaa gttcatctgc accaccggca agctgcccgt   4080
gccctggccc accctcgtga ccaccctgac ctacggcgtg cagtgcttca gccgctaccc   4140
cgaccacatg aagcagcacg acttcttcaa gtccgccatg cccgaaggct acgtccagga   4200
gcgcaccatc ttcttcaagg acgacggcaa ctacaagacc cgcgccgagg tgaagttcga   4260
gggcgacacc ctggtgaacc gcatcgagct gaagggcatc gacttcaagg aggacggcaa   4320
catcctgggg cacaagctgg agtacaacta caacagccac aacgtctata tcatggccga   4380
caagcagaag aacggcatca aggtgaactt caagatccgc cacaacatcg aggacggcag   4440
cgtgcagctc gccgaccact accagcagaa cacccccatc ggcgacggcc ccgtgctgct   4500
gcccgacaac cactacctga gcacccagtc cgccctgagc aaagacccca acgagaagcg   4560
cgatcacatg gtcctgctgg agttcgtgac cgccgccggg atcactctcg gcatggacga   4620
gctgtacaag tgaaattcgc tcgagactag ttctagagcg gccgcggatc ccgcccctct   4680
ccctcccccc cccctaacgt tactggccga agccgcttgg aataaggccg gtgtgcgttt   4740
gtctatatgt tattttccac catattgccg tcttttggca atgtgagggc ccggaaacct   4800
ggccctgtct tcttgacgag cattcctagg ggtctttccc ctctcgccaa aggaatgcaa   4860
ggtctgttga atgtcgtgaa ggaagcagtt cctctggaag cttcttgaag acaaacaacg   4920
tctgtagcga cccctttgcag gcagcggaac ccccaccctg cgcacaggtg cctctgcggc   4980
caaaagccac gtgtataaga tacacctgca aaggcggcac aaccccagtg ccacgttgtg   5040
agttggatag ttgtggaaag agtcaaatgg ctctcctcag cgtattcaa caaggggctg   5100
aaggatgccc agaaggtacc ccattgtatg ggatctgatc tggggcctcg gtgcacatgc   5160
tttacatgtg tttagtcgag gttaaaaaaa cgtctaggcc cccgaaccca cggggacgtg   5220
gttttccttt gaaaaacacg atgataagct tgccacaacc cgtaccaaag atggatagat   5280
ccggaaagcc tgaactcacc gcgacgtctg tcgagaagtt tctgatcgaa aagttcgaca   5340
gcgtctccga tctgatgcag ctctcggagg gcgaagaatc tcgtgctttc agcttcgatg   5400
taggagggcg tggatatgtc ctgcgggtaa atagctgcgc cgatggtttc tacaaagatc   5460
gttatgttta tcggcacttt gcatcggccg cgctcccgat tccggaagtg cttgacattg   5520
gggaattcag cgagagcctg acctattgca tctcccgccg tgcacagggt gtcacgttgc   5580
aagacctgcc tgaaaccgaa ctgcccgctg ttctgcagcc ggtcgcggag gccatggatg   5640
cgatctgcgc ggcgatctt agccagacga cgggttgtca ccattccaag caaggaa   5700
tcggtcaata cactacatgg cgtgatttca tatgcgcgat tgctgatccc catgtgtatc   5760
actggcaaac tgtgatggac gacaccgtca gtgcgtccgt cgcgcaggct ctcgatgagc   5820
tgatgctttg gccgaggac tgccccgaag tccggcacct cgtgcacgcg gatttcggct   5880
ccaacaatgt cctgacggac aatggccgca taacagcggg cattgactgg agcgaggcga   5940
tgttcgggga ttcccaatac gaggtcgcca acatcttctt ctggaggccg tggttggctt   6000
```

```
gtatggagca gcagacgcgc tacttcgagc ggaggcatcc ggagcttgca ggatcgccgc  6060
ggctccgggc gtatatgctc cgcattggtc ttgaccaact ctatcagagc ttggttgacg  6120
gcaatttcga tgatgcagct tgggcgcagg tcgatgcga cgcaatcgtc cgatccggag   6180
ccgggactgt cgggcgtaca caaatcgccc gcagaagcgc ggccgtctgg accgatggct  6240
gtgtagaagt actcgccgat agtggaaacc gacgcccag cactcgtccg agggcaaagg   6300
aatagacgcg tctggaacaa tcaacctctg gattacaaaa tttgtgaaag attgactggt  6360
attcttaact atgttgctcc ttttacgcta tgtggatacg ctgctttaat gccttttgtat 6420
catgctattg cttcccgtat ggctttcatt ttctcctcct tgtataaatc ctggttgctg  6480
tctcttttatg aggagttgtg gcccgttgtc aggcaacgtg gcgtggtgtg cactgtgttt  6540
gctgacgcaa cccccactgg ttggggcatt gccaccacct gtcagctcct ttccgggact  6600
ttcgctttcc ccctccctat tgccacggcg gaactcatcg ccgcctgcct tgcccgctgc  6660
tggacagggg ctcggctgtt gggcactgac aattccgtgg tgttgtcggg gaagctgacg  6720
tcctttccat ggctgctcgc ctgtgttgcc acctggattc tgcgcgggac gtcctctgc   6780
tacgtcccctt cggccctcaa tccagcggac cttccttccc gcggcctgcc gccggctctg  6840
cggcctcttc cgcgtcttcg ccttcgcccc cagacgagtc ggatctccct ttgggccgcc  6900
tccccgcctg gaattaattc tgcagtcgag acctagaaaa acatgcagca atcacaagta  6960
gcaatacagc agctaccaat gctgattgtg cctggctaga agcacaagag gaggaggagg  7020
tgggttttcc agtcacacct caggtacctt taagaccaat gacttacaag gcagctgtag  7080
atcttagcca ctttttaaaa gaaaagaggg gactggaagg gctaattcac tcccaacgaa  7140
gacaagatat ccttgatctg tggatctacc acacacaagg ctacttccct gattagcaga  7200
actacacacc agggccaggg gtcagatatc cactgacctt tggatggtgc tacaagctag  7260
taccagttga gccagataag gtagaagagg ccaataaagg agagaaccac agcttgttac  7320
accctgtgag cctgcatggg atggatgacc cggagagaga agtgttagag tggaggtttg  7380
acagccgcct agcatttcat cacgtggccc gagagctgca tccggagtac ttcaagaact  7440
gctgatatcg agcttgctac aagggacttt ccgctgggga cttccagggg aggcgtggcc  7500
tgggcgggta tggggagtgg cgagccctca gatcctgcat ataagcagct gcttttttgcc  7560
tgtactgggt ctctctggtt agaccagatc tgagcctggg agctctctgg ctaactaggg  7620
aacccactgc ttaagcctca ataaagcttg ccttgagtgc ttcaagtagt gtgtgcccgt  7680
ctgttgtgtg actctggtaa ctagagatcc ctcagaccct tttagtcagt gtggaaaatc  7740
tctacagta gtagttcatg tcatcttatt attcagtatt tataacttgc aaagaaatga  7800
atatcagaga gtgagaggcc ttgacattgc tagcgtttac cgtcgacctc tagctagagc  7860
ttggcgtaat catggtcata gctgtttcct gtgtgaaatt gttatccgct cacaattcca  7920
cacaacatac gagccggaag cataaagtgt aaagcctggg gtgcctaatg agtgagctaa  7980
ctcacattaa ttgcgttgcg ctcactgccc gctttccagt cgggaaacct gtcgtgccag  8040
ctgcattaat gaatcggcca acgcgcgggg agaggcggtt tgcgtattgg gcgctcttcc  8100
gcttcctcgc tcactgactc gctgcgctcg gtcgttcggc tgcggcgagc ggtatcagct  8160
cactcaaagg cggtaatacg gttatccaca gaatcagggg ataacgcagg aaagaacatg  8220
tgagcaaaag gccagcaaaa ggccaggaac cgtaaaaagg ccgcgttgct ggcgtttttc  8280
cataggctcc gcccccctga cgagcatcac aaaaatcgac gctcaagtca gaggtggcga  8340
aacccgacag gactataaag ataccaggcg tttccccctg gaagctccct cgtgcgctct  8400
cctgttccga ccctgccgct taccggatac ctgtccgcct ttctcccttc gggaagcgtg  8460
gcgctttctc atagctcacg ctgtaggtat ctcagttcgg tgtaggtcgt tcgctccaag  8520
ctgggctgtg tgcacgaacc cccgttcag cccgaccgct gcgccttatc cggtaactat   8580
cgtcttgagt ccaacccggt aagacacgac ttatcgccac tggcagcagc cactggtaac  8640
aggattagca gagcgaggta tgtaggcggt gctacagagt tcttgaagtg gtggcctaac  8700
tacggctaca ctagaagaac agtatttggt atctgcgctc tgctgaagcc agttaccttc  8760
ggaaaaagag ttggtagctc ttgatccggc aaacaaacca ccgctggtag cggtggtttt  8820
tttgtttgca agcagcagat tacgcgcaga aaaaaaggat ctcaagaaga tcctttgatc  8880
ttttctacgg ggtctgacgc tcagtggaac gaaaactcac gttaagggat tttggtcatg  8940
agattatcaa aaaggatctt cacctagatc cttttaaatt aaaaatgaag ttttaaatca  9000
atctaaagta tatatgagta aacttggtct gacagttacc aatgcttaat cagtgaggca  9060
cctatctcag cgatctgtct atttcgttca tccatagttg cctgactccc cgtcgtgtag  9120
ataactacga tacgggaggg cttaccatct ggccccagtg ctgcaatgat accgcgagac  9180
ccacgctcac cggctccaga tttatcagca ataaaccagc cagccggaag ggccgagcgc  9240
agaagtggtc ctgcaacttt atccgcctcc atccagtcta ttaattgttg ccgggaagct  9300
agagtaagta gttcgccagt taatagtttg cgcaacgttg ttgccattgc tacaggcatc  9360
gtggtgtcac gctcgtcgtt tggtatggct tcattcagct ccggttccca acgatcaagg  9420
cgagttacat gatcccccat gttgtgcaaa aaagcggtta gctccttcgg tcctccgatc  9480
gttgtcagaa gtaagttggc cgcagtgtta tcactcatgg ttatggcagc actgcataat  9540
tctcttactg tcatgccatc cgtaagatgc ttttctgtga ctggtgagta ctcaaccaag  9600
tcattctgag aatagtgtat gcggcgaccg agttgctctt gcccggcgtc aatacgggat  9660
aataccgcgc cacatagcag aactttaaaa gtgctcatca ttggaaaacg ttcttcgggg  9720
cgaaaactct caaggatctt accgctgttg agatccagtt cgatgtaacc cactcgtgca  9780
cccaactgat cttcagcatc ttttactttc accagcgttt ctgggtgagc aaaaacagga  9840
aggcaaaatg ccgcaaaaaa gggaataagg gcgacacgga aatgttgaat actcatactc  9900
ttcctttttc aatattattg aagcatttat cagggttatt gtctcatgag cggatacata  9960
tttgaatgta tttagaaaaa taaacaaata ggggttccgc gcacatttcc ccgaaaagtg 10020
ccacctgacg tcgacggatc gggagatcaa cttgtttatt gcagcttata atggttacaa 10080
ataaagcaat agcatcacaa atttcacaaa taaagcattt ttttcactgc attctagttg 10140
tggtttgtcc aaactcatca atgtatctta tcatgtctgg atcaactgga taactcaagc 10200
taaccaaaat catcccaaac ttcccacccc atccctatt accactgcca attacctgtg  10260
gtttcattta ctctaaacct gtgattcctc tgaattattt tcatttttaaa gaaattgtat 10320
ttgttaaata tgtactacaa acttagtagt                                   10350
```

SEQ ID NO: 77        moltype = DNA   length = 10350
FEATURE              Location/Qualifiers
misc_feature         1..10350
                     note = Synthetic
misc_feature         1..635

```
                   note = LTR
misc_feature       636..653
                   note = PBS
misc_feature       685..822
                   note = Packaging§ignal
misc_feature       1303..1536
                   note = RRE
misc_feature       2028..2151
                   note = cPPT
misc_feature       2185..2668
                   note = hSynapsin promoter
misc_feature       2681..3397
                   note = eGFP
misc_feature       3398..4633
                   note = hTau-412 (1NR4) WT
misc_feature       4640..4671
                   note = MCS
misc_feature       4672..5270
                   note = IRES
misc_feature       5271..6305
                   note = HygR
misc_feature       6319..6910
                   note = WPRE
misc_feature       7113..7749
                   note = LTR
misc_feature       8218..8891
                   note = pUCørigin
misc_feature       9036..10032
                   note = AmpR
source             1..10350
                   mol_type = other DNA
                   organism = synthetic construct
SEQUENCE: 77
tggaagggct aattcactcc caaagaagac aagatatcct tgatctgtgg atctaccaca    60
cacaaggcta cttccctgat tagcagaact acacaccagg ccagggggtc agatatccac   120
tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtggcccgag   300
agctgcatcc ggagtacttc aagaactgct gatatcgagc ttgctacaag ggactttccg   360
ctggggactt tccagggagg cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata aagcttgcct   540
tgagtgcttc aagtagtgtg tgcccgtctg ttgtgtgact ctggtaacta agatccctc    600
agacccttt agtcagtgtg gaaaatctct agcagtggcg cccgaacagg gacttgaaag   660
cgaaagggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatgga   840
aaaaaattcg gttaaggcca ggggggaaaga aaaaatataa attaaaacat atagtatggg   900
caagcaggga gctagaacga ttcgcagtta atcctggcct gttagaaaca tcagaaggct   960
gtagacaaat actgggacag ctacaaccat cccttcagac aggatcagaa gaacttagat  1020
cattatataa tacagtagca accctctatt gtgtgcataa aggatagag ataaaagaca  1080
ccaaggaagc tttagacaag atagaggaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag cagctccagg caagaatcct  1500
ggctgtggaa agatacctaa aggatcaaca gctcctgggg atttgggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtgaa ttggtttaac ataacaaatt ggctgtggta  1800
tataaaatta ttcataatga tagtaggagg cttggtaggt ttaagaatag ttttttgctgt  1860
actttctata gtgaatagag ttaggcaggg atattcacca ttatcgtttc agacccacct  1920
cccaaccccg aggggacccg acaggcccga aggaatagaa gaagaaggtg gagagagaga  1980
cagagacaga tccattcgat tagtgaacgg atctcgacgg tatcgccttt aaaagaaaag  2040
gggggattgg ggggtacagt gcagggggaaa gaatagtaga cataatagca acagacatac  2100
aaactaaaga attacaaaaa caaattacaa aaattcgggtt tattacgagg  2160
acagcagaga tccagtttat cgatctgcag agggccctgc gtatgagtgc aagtgggttt  2220
taggaccagg atgaggcggg gtgggggtgc ctacctgacg accgaccccg acccactgga  2280
caagcaccca accccattc cccaaattgc gcatccccta tcagagaggg ggaggggaaa  2340
caggatgcgc cgaggcgcgt gcgcactgcc agcttcagca ccgcggacag tgccttcgcc  2400
ccggcctggc ggcgcgcgcc accgccgcct cagcactgaa ggcgcgctga cgtcactcgc  2460
cggtcccccg caaactcccc ttccggggcca ccttggtcgc gtccgcgccg ccgccgccc  2520
agccggaccg caccacgcga ggcgcagagat aggggggcac gggcgcgacc atctgcgctg  2580
cggcgccggc gactcagcgc tgcctcagtc tgcggtgggc agcggaggag tcgtgtcgtg  2640
cctgagagcg cagggatcta tttccggtga attcgccacc atggtgagca agggcgagga  2700
gctgttcacc ggggtggtgc ccatcctggt cgagctggac ggcgacgtaa acggccacaa  2760
```

```
gttcagcgtg tccggcgagg gcgagggcga tgccacctac ggcaagctga ccctgaagtt   2820
catctgcacc accggcaagc tgcccgtgcc ctggcccacc ctcgtgacca ccctgaccta   2880
cggcgtgcag tgcttcagcc gctaccccga ccacatgaag cagcacgact tcttcaagtc   2940
cgccatgccc gaaggctacg tccaggagcg caccatcttc ttcaaggacg acggcaacta   3000
caagacccgc gccgaggtga agttcgaggg cgacaccctg gtgaaccgca tcgagctgaa   3060
gggcatcgac ttcaaggagg acggcaacat cctggggcac aagctggagt acaactacaa   3120
cagccacaac gtctatatca tggccgacaa gcagaagaac ggcatcaagg tgaacttcaa   3180
gatccgccac aacatcgagg acggcagcgt gcagctcgcc gaccactacc agcagaacac   3240
ccccatcggc gacggccccg tgctgctgcc cgacaaccac tacctgagca cccagtccgc   3300
cctgagcaaa gaccccaacg agaagcgcga tcacatggtc ctgctggagt tcgtgaccgc   3360
cgccgggatc actctcggca tggacgagct gtacaaggct gagccccgac aggagttcga   3420
ggtaatggag gatcacgcag ggacgtatgg tctgggagac aggaaggatc aaggcggcta   3480
tacgatgcac caggatcagg agggcgatac cgatgcgggc ctcaaagagt cccgcttca   3540
aacaccaact gaggatggga gtgaggagcc aggaagtgag acaagcgacg cgaaatcaac   3600
ccctactgcc gaagcggagg aggccgggat cggagataca ccatctctcg aagacgaagc   3660
tgctggccac gtgacgcaag cacgaatggt gtccaaaagc aaagacggta caggttctga   3720
cgacaaaaag gcgaaggggg cagatgggaa aactaaaatc gccacgcccc ggggtgcggc   3780
gccgcctggg cagaaagggc aagcaaatgc gacgcgaata cctgccaaga cgcctccggc   3840
tcctaagacc ccaccatcat ctggtgaacc gcctaaaagc ggggatcgaa gcggttattc   3900
atcaccgggt agtccgggta cgccaggctc taggagcaga actccttcac tgcccacgcc   3960
ccccacgcgc gaacctaaga agtggcagt ggtgcgaaca ccccaaaaa gcccctcaag   4020
tgcaaaatca cggctccaga ctgcacccgt accgatgccc gatctcaaaa acgtgaaatc   4080
taagataggt agtacagaga atctgaagca tcaaccggga ggtggaaagg tgcagattat   4140
caataagaaa cttgacctga gtaacgttca atccaagtgt ggatcaaaag ataatatcaa   4200
gcacgtccct ggaggcggtt cagtgcagat cgtttacaaa cctgttgatc ttagcaaggt   4260
gacttccaag tgcgggtctc tgggcaacat tcatcacaaa cctggtggag ggcaagttga   4320
ggtcaaaagc gaaagctcg acttcaaaga tcgagttcag agcaagatag gcagccttga   4380
taatattacc catgtccccg gcggagggaa caagaagatt gagactcata agttgacgtt   4440
cagagaaaat gctaaagcga aaacggatca tggcgcagaa atagtttata aatctcctgt   4500
ggtcagtggt gacacttcac ccaggcacct ctcaaacgtg tcatcaacgg gctcaatcga   4560
catggtggat tctccccaac tcgcaacact tgctgatgag gtaagtgcca gcctcgcaaa   4620
gcaaggactc taaaattcgc tcgagactag ttctagagcg gccgcggatc ccgcccctct   4680
ccctccccc ccctaacgt tactggccga agccgcttgg aataaggccg gtgtgcgttt   4740
gtctatatgt tattttccac catattgccg tcttttggca atgtgagggc ccggaaacct   4800
ggccctgtct tcttgacgag cattcctagg ggtctttccc ctctcgccaa aggaatgcaa   4860
ggtctgttga atgtcgtgaa ggaagcagtt cctctggaag cttcttgaag acaaacaacg   4920
tctgtagcga cccttttgcag gcagcggaac ccccacctg gcgacaggtg cctctgcggc   4980
caaaagccac gtgtataaga tacacctgca aaggcggcac aacccagtg ccacgttgtg   5040
agttggatag ttgtggaaag agtcaaatgg ctctcctcaa gcgtattcaa caagggcctg   5100
aaggatgccc agaaggtacc ccattgtatg ggatctgatc tggggcctcg gtgcacatgc   5160
tttacatgtg tttagtcgag gttaaaaaaa cgtctaggcc ccccgaacca cggggacgtg   5220
gttttccttt gaaaaacacg atgataagct tgccacaacc cgtaccaaag atggatagat   5280
ccggaaagcc tgaactcacc gcgacgtctg tcgagaagtt tctgatcgaa aagttcgaca   5340
gcgtctccga cctgatgcag ctctcggagg gcgaagaatc tcgtgctttc agcttcgatg   5400
taggagggcg tggatatgtc ctgcgggtaa atagctgcgc cgatggtttc tacaaagatc   5460
gttatgttta tcggcacttt gcatcggccg cgctcccgat tccggaagtg cttgacattg   5520
gggaattcag cgagagcctg acctattgca tctcccgccg tgcacagggt gtcacgttgc   5580
aagacctgcc tgaaaccgaa ctgcccgctg ttctgcagcc ggtcgcggag gccatgatg   5640
cgatcgctgc ggccgatctt agccagacga gcgggttcgg cccattcgga ccgcaaggaa   5700
tcggtcaata cactacatgg cgtgatttca tatgcgcgat tgctgatccc catgtgtatc   5760
actgcaaac tgtgatggac gacaccgtca gtgcgtccgt cgcgcaggct ctcgatgagc   5820
tgatgctttg gccgaggac tgccccgaag tccggcacct cgtgcacgcg gatttcggct   5880
ccaacaatgt cctgacggac aatggccgca taacagcggt cattgactgg agcgaggcga   5940
tgttcgggga ttcccaatac gaggtcgcca acatcttctt ctggaggccg tggttggctt   6000
gtatggagca gcagacgcgc tacttcgagc ggaggcatcc ggagcttgca ggatcgccgc   6060
ggctccgggc gtatatgctc cgcattggtc ttgaccaact ctatcagagc ttggttgacg   6120
gcaatttcga tgatgcagct tgggcgcagg gtcgatgcga cgcaatcgtc cgatccggag   6180
ccgggactgt cgggcgtaca caatcgcccg cagaagcgc ggccgtctgg accgatggct   6240
gtgtagaagt actcgccgat agtggaaacc gacgccccag cactcgtccg agggcaaagg   6300
aatagacgcg tctggaacaa tcaacctctg gattacaaaa tttgtgaaag attgactagt   6360
attcttaact atgttgctcc ttttacgcta tgtggatacg ctgctttaat gcctttgtat   6420
catgctattg cttcccgtat ggctttcatt ttctcctcct tgtataaatc ctggttgctg   6480
tctctttatg aggagttgtg gcccgttgtc aggcaacgtg gcgtggtgtg cactgtgttt   6540
gctgacgcaa ccccccactgg ttgggcatt gccaccacct tccgggact   6600
ttcgctttcc cctcccctat gccacggcg gaactcatcg ccgcctgcct gcccgctgc   6660
tggacagggg ctcggctgtt gggcactgac aattccgtgg tgttgtcggg gaagctgacg   6720
tcctttccat ggctgctcgc ctgtgttgcc acctggattc tgcgcgggac gtccttctgc   6780
tacgtcccctt cggcctcttca tccagcggac cttcttccc gcggcctgct gccggctctg   6840
cggcctcttc cgcgtcttcg ccttcgccct cagacgagtc ggatctccct ttgggccgcc   6900
tccccgcctg gaattaattc tgcagtcgag acctagaaaa acatgaggca atcacaagta   6960
gcaatacagc agctaccaat gctgattgtg cctggctaga agcacaagag gaggaggag   7020
tgggttttcc agtcacacct caggtacctt taagaccaat gacttacaag gcagctgtag   7080
atcttagcca ctttttaaaa gaaaagaggg gactggaagg gctaattcac tcccaacgaa   7140
gacaagatat ccttgatctg tggatctacc acacacaagg ctacttccct gattagcaga   7200
actacacacc agggccaggg gtcagatatc cactgacctt tggatggtgc tacaagctag   7260
taccagttga gccagataag gtagaagagg ccaataaagg agaacaccag cttgttac   7320
accctgtgag cctgcatggg atggatgacc cggagagaga agtgttagag tggaggttg   7380
acagccgcct agcatttcat cacgtggccc gagagctgca tccggagtac ttcaagaact   7440
gctgatatcg agcttgctac aagggacttt ccgctgggga ctttccaggg aggcgtggcc   7500
```

```
tgggcgggac tggggagtgg cgagccctca gatcctgcat ataagcagct gcttttgcc   7560
tgtactgggt ctctctggtt agaccagatc tgagcctggg agctctctgg ctaactaggg   7620
aacccactgc ttaagcctca ataaagcttg ccttgagtgc ttcaagtagt gtgtgcccgt   7680
ctgttgtgtg actctggtaa ctagagatcc ctcagaccct tttagtcagt gtggaaaatc   7740
tctagcagta gtagttcatg tcatcttatt attcagtatt tataacttgc aaagaaatga   7800
atatcagaga gtgagaggcc ttgacattgc tagcgtttac cgtcgacctc tagctagagc   7860
ttggcgtaat catggtcata gctgtttcct gtgtgaaatt gttatccgct cacaattcca   7920
cacaacatac gagccggaag cataaagtgt aaagcctggg gtgcctaatg agtgagctaa   7980
ctcacattaa ttgcgttgcg ctcactgccc gctttccagt cgggaaacct gtcgtgccag   8040
ctgcattaat gaatcggcca acgcgcgggg agaggcggtt tgcgtattgg cgctcttcc   8100
gcttcctcgc tcactgactc gctgcgctcg tcgttcggc tgcggcgagc ggtatcagct   8160
cactcaaagg cggtaatacg ttatccaca gaatcagggg ataacgcagg aaagaacatg   8220
tgagcaaaag gccagcaaaa ggccaggaac cgtaaaaagg ccgcgttgct ggcgtttttc   8280
cataggctcc gcccccctga cgagcatcac aaaaatcgac gctcaagtca gaggtggcga   8340
aacccgacag gactataaag ataccaggcg tttccccctg gaagctccct cgtgcgctct   8400
cctgttccga ccctgccgct taccggatac ctgtccgcct ttctcccttc gggaagcgtg   8460
gcgctttctc atagctcacg ctgtaggtat ctcagttcgg tgtaggtcgt tcgctccaag   8520
ctgggctgtg tgcacgaacc cccgttcag cccgaccgct gcgccttatc cggtaactat   8580
cgtcttgagt ccaacccggt aagacacgac ttatcgccac tggcagcagc cactggtaac   8640
aggattagca gagcgaggta tgtaggcggt gctacagagt tcttgaagtg gtggcctaac   8700
tacggctaca ctagaagaac agtatttggt atctgcgctc tgctgaagcc agttaccttc   8760
ggaaaaagag ttggtagctc ttgatccggc aaacaaacca ccgctggtag cggtggtttt   8820
tttgtttgca agcagcagat tacgcgcaga aaaaaggat ctcaagaaga tcctttgatc   8880
ttttctacgg ggtctgacgc tcagtggaac gaaaactcac gttaagggat tttggtcatg   8940
agattatcaa aaaggatctt cacctagatc cttttaaatt aaaaatgaag ttttaaatca   9000
atctaaagta tatatgagta aacttggtct gacagttacc aatgcttaat cagtgaggca   9060
cctatctcag cgatctgtct atttcgttca tccatagttg cctgactccc cgtcgtgtag   9120
ataactacga tacgggaggg cttaccatct ggccccagtg ctgcaatgat accgcgagac   9180
ccacgctcac cggctccaga tttatcagca ataaccagc cagccggaag ggccgagcgc   9240
agaagtggtc ctgcaacttt atccgcctcc atccagtcta ttaattgttg ccgggaagct   9300
agagtaagta gttcgccagt taatagtttg cgcaacgttg ttgccattgc tacaggcatc   9360
gtggtgtcac gctcgtcgtt tggtatggct tcattcagct ccggttccca acgatcaagg   9420
cgagttacat gatcccccat gttgtgcaaa aaagcggtta gctccttcgg tcctccgatc   9480
gttgtcagaa gtaagttggc cgcagtgtta tcactcatgg ttatggcagc actgcataat   9540
tctcttactg tcatgccatc cgtaagatgc ttttctgtga ctggtgagta ctcaaccaag   9600
tcattctgag aatagtgtat gcggcgaccg agttgctctt gcccggcgtc aatacgggat   9660
aataccgcgc cacatagcag aactttaaaa gtgctcatca ttggaaaacg ttcttcgggg   9720
cgaaaactct caaggatctt accgctgttg agatccagtt cgatgtaacc cactcgtgca   9780
cccaactgat cttcagcatc ttttactttc accagcgttt ctgggtgagc aaaaacagga   9840
aggcaaaatg ccgcaaaaaa gggaataagg gcgacacgga aatgttgaat actcatactc   9900
ttcctttttc aatattattg aagcatttat cagggttatt gtctcatgag cggatacata   9960
tttgaatgta tttagaaaaa taacaaata ggggttccgc gcacatttcc ccgaaaagtg  10020
ccacctgacg tcgacggatc gggagatcaa cttgtttatt gcagcttata atggttacaa  10080
ataaagcaat agcatcacaa atttcacaaa taaagcattt ttttcactgc attctagttg  10140
tggtttgtcc aaactcatca atgtatctta tcatgtctgg atcaactgga taactcaagc  10200
taaccaaaat catcccaaac ttcccacccc atacccctatt accactgcca attacctgtg  10260
gtttcattta ctctaaaacct gtgattcctc tgaattattt tcattttaaa gaaattgtat  10320
ttgttaaata tgtactacaa acttagtagt                                    10350
```

| | | |
|---|---|---|
| SEQ ID NO: 78 | moltype = DNA  length = 9636 | |
| FEATURE | Location/Qualifiers | |
| misc_feature | 1..9636 | |
| | note = Synthetic | |
| misc_feature | 1..635 | |
| | note = LTR | |
| misc_feature | 636..653 | |
| | note = PBS | |
| misc_feature | 685..822 | |
| | note = Packaging§ignal | |
| misc_feature | 1303..1536 | |
| | note = RRE | |
| misc_feature | 2028..2151 | |
| | note = cPPT | |
| misc_feature | 2185..2668 | |
| | note = hSynapsin promoter | |
| misc_feature | 2681..3919 | |
| | note = CoHu hTau-412(1N4R) 3MUT | |
| misc_feature | 3926..3957 | |
| | note = MCS | |
| misc_feature | 3958..4556 | |
| | note = IRES | |
| misc_feature | 4557..5591 | |
| | note = HygR | |
| misc_feature | 5605..6196 | |
| | note = WPRE | |
| misc_feature | 6399..7035 | |
| | note = LTR | |
| misc_feature | 7504..8177 | |
| | note = pUCorigin | |

```
misc_feature        8322..9318
                    note = AmpR
source              1..9636
                    mol_type = other DNA
                    organism = synthetic construct
SEQUENCE: 78
tggaagggct aattcactcc caagaagac aagatatcct tgatctgtgg atctaccaca   60
cacaaggcta cttccctgat tagcagaact acacaccagg gccaggggtc agatatccac  120
tgaccttgg atggtgctac aagctagtac cagttgagcc agataaggta gaagaggcca  180
ataaaggaga gaacaccagc ttgttacacc ctgtgagcct gcatgggatg gatgacccgg  240
agagagaagt gttagagtgg aggtttgaca gccgcctagc atttcatcac gtgggcccga  300
agctgcatcc ggagtacttc aagaactgct gatatcgagc ttgctacaag gactttccg   360
ctggggactt tccagggagg cgtggcctgg gcgggactgg ggagtggcga gccctcagat  420
cctgcatata agcagctgct ttttgcctgt actgggtctc tctggttaga ccagatctga  480
gcctgggagc tctctggcta actagggaac ccactgctta agcctcaata aagcttgcct  540
tgagtgcttc aagtagtgtg tgcccgtctg ttgtgtgact ctggtaacta gagatccctc  600
agaccctttt agtcagtgtg gaaaatctct agcagtggcg cccgaacagg gacttgaaag  660
cgaaagggaa accagaggag ctctctcgac gcaggactcg cttgctgaa gcgcgcacgg   720
caagaggcga gggcggcga ctggtgagta cgccaaaaat tttgactagc ggaggctaga   780
aggagagaga tgggtgcgag agcgtcagta ttaagcgggg gagaattaga tcgcgatggg  840
aaaaaattcg gttaaggcca ggggaaaga aaaaatataa attaaaacat atagtatggg   900
caagcaggga gctagaacga ttcgcagtta atcctggcct gttagaaaca tcagaaggct  960
gtagacaaat actgggacag ctacaaccat cccttcagac aggatcagaa gaacttagat 1020
cattatataa tacagtagca accctctatt gtgtgcatca aggatagag ataaaagaca  1080
ccaaggaagc tttagacaag atagaggaag agcaaaacaa aagtaagacc accgcacagc 1140
aagcggccgg ccgctgatct tcagacctgg aggaggagat atgagggaca attggagaag 1200
tgaattatat aaatataaag tagtaaaaat tgaaccatta ggagtagcac ccaccaaggc 1260
aaagagaaga gtggtgcaga gagaaaaag agcagtggga ataggagctt tgttccttgg 1320
gttcttggga gcagcaggaa gcactatggg cgcagcgtca atgacgctga cggtacaggc 1380
cagacaatta ttgtctggta tagtgcagca gcagaacaat ttgctgaggg ctattgaggc 1440
gcaacagcat ctgttgcaac tcacagtctg gggcatcaag cagctccagg caagaatcct 1500
ggctgtggaa agatacctaa aggatcaaca gctcctgggg atttggggtt gctctggaaa 1560
actcatttgc accactgctg tgccttggaa tgctagttgg agtaataaat ctctggaaca 1620
gatttggaat cacacgacct ggatggagtg ggacagagaa attaacaatt acacaagctt 1680
aatacactcc ttaattgaag aatcgcaaaa ccagcaagaa aagaatgaac aagaattatt 1740
ggaattagat aaatgggcaa gtttgtggaa ttggtttaac ataacaaatt ggctgtggta 1800
tataaaatta ttcataatga tagtaggagg cttggtaggt ttaagaatag tttttgctgt 1860
actttctata gtgaatagag ttaggcaggg atattcacca ttatcgtttc agacccacct 1920
cccaaccccg aggggacccg acaggcccga aggaatagaa gaagaaggtg gagagagaga 1980
cagagacaga tccattcgat tagtgaacgg atctcgacgg tatcgccttt aaaagaaaag 2040
ggggggattgg ggggtacagt gcaggggaaa gaatagtaga cataatagca acagacatac 2100
aaactaaaga attacaaaaa caattacaa aaattcaaaa ttttcgggtt tattacaggg 2160
acagcagaga tccagtttat cgatctgcag aagtgggctt 2220
taggaccagg atgaggcggg gtggggggtgc ctacctgacg accgaccccg acccactgga 2280
caagcaccca accccattc cccaaattgc gcatccccta tcagagaggg ggaggggaaa 2340
caggatgcgc cgaggcgcgt gcgcactgcc agcttcagca ccgcggacag tgccttcgcc 2400
cccgcctggc ggcgcgcgcc accgccgcct cagcactgaa ggcgcgctga cgtcactcgc 2460
cggtcccccg caaactcccc ttcccggcca ccttggtcgc gtccgcgccg ccgccggccc 2520
agccggaccg caccacgcga ggcgcggagat aggggggcac gggcgcgacc atctgcgctg 2580
cggcgccggc gactcagcgc tgcctcagtc tgcggtgggc agcggaggag tcgtgtcgtg 2640
cctgacgcg cagggatcta tttccggtga attcgccacc atggcagagc cccggcaggc 2700
gttcgaggtt atggaggatc acgccggac ctatgggattg ggcgatagga agatcaggc 2760
cgggtatact atgcatcagg accaggaagg cgacacggac gctggtctca aggaaagccc 2820
acttcagacg ccgacagagg acgggtctga ggaactgggg agtgaaactt ctgacgctaa 2880
gtctacgcct atgtcgcgagg cggaggaggc aggaatagga gacacaccat cacttgaaga 2940
cgaggcagca ggacacgtaa cccaagcgag aatggtttct aagtccaaag atggaaccgg 3000
atccgatgac aaaaaggcca agggagcaga tggcaaaaca aaaataacga caccgagggg 3060
tgcggctccc cccggtcaaa agggacaggc aaatgccacg cgcatccctg ctaaaacacc 3120
cccggcgccg aaaaccccc cttcatccgg agagccaccc aagtctggtg ataagagcgg 3180
gtatagttcc cccggtagtc cggggactcc aggatcacgc agcagaacgc catccctgcc 3240
aacccccaccc actagagagc ccaaaaggt cgcagtcgtt cgcactccgc caaaagccc  3300
ttcctcagcg aaaagccgcc tgcagacggc acctgtcccc atgcctgacc ttaaaaatgt 3360
taaaagcaaa atcggtagta ccgaaaatct caagcatcag ccaggagggg gaaggttca  3420
gatcatcaat aagaagctgg acctgtctaa cgtgcagagc aagtgtggaa gcaaagataa 3480
cataaagcac gttttggggg gcggaagcgt acagattgtg tataagccgg tggacctctc 3540
aaaagtaaca ttcaagtgtg ggagtctggg caacatccat cacaaacccg ggcggtca   3600
ggtagaggtg aaaagcgaaa agctcgattt taaggatagg gtacagagta aaattgggtc 3660
tctggacaac ataacacacg taccaggcgg aggcaataaa aagatagaaa cgcataaact 3720
cacgttccga gagaacgcta aagcaaaagac tgaccacggg gctgagattg tatacaagag 3780
tccggtcgtc tctggggaca cttccccccg cacactttct aacgttagtt ccactgtag  3840
tattgacatg tcgacagcc ctcaacttgc cactttggca gacgaggtca gtgctagtct 3900
tgcaaagcag ggcttgtgaa attcgctcga gactagttct agagcggccg cggatccgc  3960
ccctctcct cccccccccc taacgttact ggccgaagcc gcttggaata aggccggtgt 4020
gcgttttgtct atatgttatt ttccaccata ttgccgtctt ttggcaatgt gaggggccc  4080
aaacctggcc ctgtcttctt gacgagcatt cctaggggtc tttccctct cgccaaagga 4140
atgcaaggtc tgttgaatgt cgtgaaggaa gcagttcctc tggaagcttc ttgaagacaa 4200
acaacgtctg tagcgaccct ttgcaggcag cggaacccc cacctggcga caggtgcctc 4260
tgcggccaaa agcacgtgt ataagataca cctgcaaagg cggcacaacc ccagtgccac 4320
gttgtgagtt ggatagttgt ggaaagagtc aatggctct cctcaagcgt attcaacaag 4380
```

```
gggctgaagg atgcccagaa ggtaccccat tgtatgggat ctgatctggg gcctcggtgc  4440
acatgcttta catgtgttta gtcgaggtta aaaaaacgtc taggcccccc gaaccacggg  4500
gacgtggttt tcctttgaaa aacacgatga taagcttgcc acaacccgta ccaaagatgg  4560
atagatccgg aaagcctgaa ctcaccgcga cgtctgtcga gaagtttctg atcgaaaagt  4620
tcgacagcgt ctccgacctg atgcagctct cggagggcga agaatctcgt gctttcagct  4680
tcgatgtagg agggcgtgga tatgtcctgc gggtaaatag ctgcgccgat ggttctaca  4740
aagatcgtta tgtttatcgg cactttgcat cggccgcgct cccgattccg gaagtgcttg  4800
acattgggga attcagcgag agcctgacct attgcatctc ccgccgtgca cagggtgtca  4860
cgttgcaaga cctgcctgaa accgaactgc ccgctgttct gcagccggtc gcggaggcca  4920
tggatgcgat cgctgcggcc gatcttagcc agacgagcgg gttcggccca ttcggaccgc  4980
aaggaatcgg tcaatacact acatggcgtg atttcatatg cgcgattgct gatccccatg  5040
tgtatcactg gcaaactgtg atggacgaca ccgtcagtgc gtccgtcgcg caggctctcg  5100
atgagctgat gctttgggcc gaggactgcc ccgaagtccg gcacctcctg cacgcggatt  5160
tcggctccaa caatgtcctg acggacaatg gccgcataac agcggtcatt gactggagcg  5220
aggcgatgtt cggggattcc caatacgagg tcgccaacat cttcttctgg aggccgtggt  5280
tggcttgtat ggagcagcag acgcgctact tcgagcggag gcatccggag cttgcaggat  5340
cgccgcggct ccgggcgtat atgctccgca ttggtcttga ccaactctat cagagcttgg  5400
ttgacggcaa tttcgatgat gcagcttggg cgcagggtcg atgcgacgca atcgtccgat  5460
ccggagccgg gactgtcggg cgtacacaaa tcgcccgcag aagcgcggcc gtctggaccg  5520
atggctgtgt agaagtactc gccgatagtg gaaaccgacg cccagcact cgtccgaggg  5580
caaaggaata gacgcgtctg aacaatcaa cctctggatt acaaaatttg tgaaagattg  5640
actggtattc ttaactatgt tgctcctttt acgctatgtg gatacgctgc tttaatgcct  5700
ttgtatcatg ctattgcttc ccgtatggct ttcatttct cctccttgta taaatcctga  5760
ttgctgtctc tttatgagga gttgtggccc gttgtcaggc aacgtggcgt ggtgtgcact  5820
gtgtttgctg acgcaacccc cactggttgg ggcattgcca ccacctgtca gctccttcc  5880
gggactttcg ctttcccct ccctattgcc acggcgaac tcatcgccgc ctgccttgcc  5940
cgctgctgga caggggctcg gctgttggc actgacaatt ccgtggtgtt gtcggggaag  6000
ctgacgtcct ttccatggct gctcgcctgt gttgccacct ggattctgcg cgggacgtcc  6060
ttctgctacg tcccttcggc cctcaatcca gcggaccttc cttcccgcgg cctgctgccg  6120
gctctgcggc ctcttccgcg tcttcgcctt cgccctcaga cgagtcggat ctccctttgg  6180
gccgcctccc cgcctggaat taattctgca gtcgagacct agaaaaacat ggagcaatca  6240
caagtagcaa tacagcagct accaatgctg attgtgcctg gctagaagca caagaggagg  6300
aggaggtggg ttttccagtc acacctcagg tacctttaag accaatgact acaaggcag  6360
ctgtagatct tagccacttt ttaaaagaaa agagggggat tggaagggct aattcactcc  6420
aacgaagaca agatatcctt gatctgtgga tctaccacac acaaggctac ttccctgatt  6480
agcagaacta cacaccaggg ccaggggtca gatatccact gacctttgga tggtgctaca  6540
agctagtacc agttgagcca gataaggtag aagaggccaa taaaggagag aacaccagct  6600
tgttacaccc tgtgagcctg catgggatgg atgacccgga gagagaagtg ttagagtgga  6660
ggtttgacag ccgcctagca tttcatcacg tggcccgaga gctgcatccg gagtacttca  6720
agaactgctg atatcgagct tgctacaagg gactttccgc tggggacttt ccagggaggc  6780
gtggcctggg cgggactggg gagtggcgag ccctcagatc ctgcatataa gcagctgctt  6840
tttgcctgta ctgggtctct ctggttagac cagatctgag cctgggagct ctctggctaa  6900
ctagggaacc cactgcttaa gcctcaataa agcttgcctt gagtgcttca agtagtgtgt  6960
gcccgtctgt tgtgtgactc tggtaactag agatccctca gacccttta gtcagtgtgg  7020
aaaatctcta gcagtagtag ttcatgtcat cttattattc agtatttata acttgcaaag  7080
aaatgaatat cagagagtga gaggccttga cattgctagc gtttaccgtc gacctctagc  7140
tagagcttgg cgtaatcatg gtcatagctg ttcctgtgt gaaattgtta tccgctcaca  7200
attccacaca acatacgagc cggaagcata aagtgtaaag cctggggtgc ctaatgagtg  7260
agctaactca cattaattgc gttgcgctca ctgcccgctt tccagtcggg aaacctgtcg  7320
tgccagctgc attaatgaat cggccaacgc gcggggagag gcggtttgcg tattgggcgc  7380
tcttccgctt cctcgctcac tgactcgctg cgctcggtcg ttcggctgcg gcgagcggta  7440
tcagctcact caaaggcggt aatacggtta tccacagaat caggggataa cgcaggaaag  7500
aacatgtgag caaaaggcca gcaaaaggcc aggaaccgta aaaaggccgc gttgctggcg  7560
tttttccata ggctccgccc ccctgacgag catcacaaaa atcgacgctc aagtcagagg  7620
tggcgaaacc cgacaggact ataaagatac caggcgtttc ccctgaag ctccctcgtg  7680
cgctctcctg ttccgaccct gccgcttacc ggatacctgt ccgcctttct cccttcggga  7740
agcgtggcgc tttctcatag ctcacgctgt aggtatctca gttcggtgta ggtcgttcgc  7800
tccaagctgg gctgtgtgca cgaaccccc gttcagcccg accgctgcgc cttatccggt  7860
aactatcgtc ttgagtccaa cccggtaaga cacgacttat cgccactggc agcagccact  7920
ggtaacagga ttagcagagc gaggtatgta ggcggtgcta cagagttctt gaagtggtga  7980
cctaactacg gctacactag aagaacagta tttggtatct gcgctctgct gaagccagtt  8040
accttcggaa aaagagttgg tagctcttga tccggcaaac aaaccaccgc tggtagcggt  8100
ggtttttttg tttgcaagca gcagattacg cgcagaaaaa aaggatctca agaagatcct  8160
ttgatctttt ctacggggtc tgacgctcag tggaacgaaa actcacgtta agggattttg  8220
gtcatgagat tatcaaaaag gatcttcacc tagatccttt taaattaaaa atgaagtttt  8280
aaatcaatct aaagtatata tgagtaaact tggtctgaca gttaccaatg cttaatcagt  8340
gaggcaccta tctcagcgat ctgtctattt cgttcatcca tagttgcctg actccccgtc  8400
gtgtagataa ctacgatacg ggagggctta ccatctggcc ccagtgctgc aatgataccg  8460
cgagacccac gctcaccggc tccagattta tcagcaataa accagccagc cggaagggcc  8520
gagcgcagaa gtggtcctgc aactttatcc gcctccatcc agtctattaa ttgttgccgg  8580
gaagctagag taagtagttc gccagttaat agtttgcgca acgttgttgc cattgctaca  8640
ggcatcgtgg tgtcacgctc gtcgtttggt atggcttcat tcagctccgg ttcccaacga  8700
tcaaggcgag ttacatgatc ccccatgttg tgcaaaaaag cggttagctc cttcggtcct  8760
ccgatcgttg tcagaagtaa gttggccgca gtgttatcac tcatggttat ggcagcactg  8820
cataattctc ttactgtcat gccatccgta agatgctttt ctgtgactgg tgagtactca  8880
accaagtcat tctgagaata gtgtatgcgg cgaccgagtt gctcttgccc ggcgtcaata  8940
cgggataata ccgcgccaca tagcagaact ttaaaagtgc tcatcattgg aaaacgttct  9000
tcggggcgaa aactctcaag gatcttaccg ctgttgagat ccagttcgat gtaacccact  9060
cgtgcaccca actgatcttc agcatctttt actttcacca gcgtttctgg gtgagcaaaa  9120
```

-continued

```
acaggaaggc aaaatgccgc aaaaagggga ataagggcga cacggaaatg ttgaatactc   9180
atactcttcc tttttcaata ttattgaagc atttatcagg gttattgtct catgagcgga   9240
tacatatttg aatgtattta gaaaaataaa caaataggg ttccgcgcac atttccccga    9300
aaagtgccac ctgacgtcga cggatcggga gatcaacttg tttattgcag cttataatgg   9360
ttacaaataa agcaatagca tcacaaattt cacaaataaa gcattttttt cactgcattc   9420
tagttgtggt ttgtccaaac tcatcaatgt atcttatcat gtctggatca actggataac   9480
tcaagctaac caaaatcatc ccaaacttcc cacccatac cctattacca ctgccaatta    9540
cctgtggttt catttactct aaacctgtga ttcctctgaa ttattttcat tttaaagaaa   9600
ttgtatttgt taaatatgta ctacaaactt agtagt                              9636
```

```
SEQ ID NO: 79            moltype = DNA  length = 10350
FEATURE                  Location/Qualifiers
misc_feature             1..10350
                         note = Synthetic
misc_feature             1..635
                         note = LTR
misc_feature             636..653
                         note = PBS
misc_feature             685..822
                         note = Packaging§signal
misc_feature             1303..1536
                         note = RRE
misc_feature             2028..2151
                         note = cPPT
misc_feature             2185..2668
                         note = hSynapsin promoter
misc_feature             2681..3916
                         note = CoHu hTau-412(1N4R) 3MUT
misc_feature             3917..4630
                         note = eGFP
misc_feature             4640..4671
                         note = MCS
misc_feature             4672..5270
                         note = IRES
misc_feature             5271..6305
                         note = HygR
misc_feature             6319..6910
                         note = WPRE
misc_feature             7113..7749
                         note = LTR
misc_feature             8218..8891
                         note = pUCørigin
misc_feature             9036..10032
                         note = AmpR
source                   1..10350
                         mol_type = other DNA
                         organism = synthetic construct
SEQUENCE: 79
tggaagggct aattcactcc caaagaagac aagatatcct tgatctgtgg atctaccaca     60
cacaaggcta cttccctgat tagcagaact acacaccagg gccaggggtc agatatccac    120
tgacctttgg atggtgctac aagctagtac cagttgagcc agataaggta gaagaggcca    180
ataaaggaga gaacaccagc ttgttacacc ctgtgagcct gcatgggatg gatgacccgg    240
agagagaagt gttagagtgg aggtttgaca gccgcctagc atttcatcac gtgggcccga    300
agctgcatcc ggagtacttc aagaactgct gatatcgagc ttgctacaag gactttccg     360
ctgggacttt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta gcctcaata aagcttgcct     540
tgagtgcttc aagtagtgtg tgcccgtctg ttgtgtgact ctggtaacta gagatccctc    600
agacccttt agtcagtgtg gaaaatctct agcagtggcg cccgaacagg gacttgaaag     660
cgaaagggaa accagaggag ctctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcagta ttaagcgggg gagaattaga tcgcgatggg    840
aaaaaattcg gttaaggcca gggggaaaga aaaaatataa attaaaacat atagtatggg    900
caagcagggga gctagaacga ttcgcagtta atcctggcct gttagaaaca tcagaaggct    960
gtagacaaat actgggacag ctacaaccat cccttcagac aggatcagaa gaacttagat   1020
cattatataa tacagtagca accctctatt gtgtgcatca aggatagag ataaaagaca    1080
ccaaggaagc tttagacaag atagaggaag agcaaaacaa agtaagacc accgcacagc    1140
aagcggccgg ccgctgatct tcagacctgg aggaggagat atgagggaca attggagaag   1200
tgaattatat aaatataaag tagtaaaaat tgaaccactag gagtagcac ccaccaaggc    1260
aaagagaaga gtggtgcaga gagaaaaaag agcagtggga ataggagctt tgttccttgg   1320
gttcttggga gcagcaggaa gcactatggg cgcagcgtca atgacgctga cggtacaggc   1380
cagacaatta ttgtctggta tagtgcagca gcagaacaat ttgctgaggg ctattgaggc    1440
gcaacagcat ctgttgcaac tcacagtctg gggcatcaag cagctccagg caagaatcct    1500
ggctgtggaa agatacctaa aggatcaaca gctcctgggg atttggggt gctctggaaa    1560
actcatttgc accactgctg tgccttggaa tgctagttgg agtaataaat ctctggaaca   1620
gatttggaat cacacgacct ggatggagtg ggacagagaa attaacaatt acacaagctt   1680
aatacactcc ttaattgaag aatcgcaaaa ccagcaagaa aagaatgaac aagaattatt   1740
ggaattagat aaatgggcaa gtttgtgaa ttggtttaac ataacaaatt ggctgtggta    1800
tataaaatta ttcataatga tagtaggagg cttggtaggt ttaagaatag ttttgctgt    1860
```

```
actttctata gtgaatagag ttaggcaggg atattcacca ttatcgtttc agacccacct   1920
cccaaccccg aggggacccg acaggcccga aggaatagaa gaagaaggtg gagagagaga   1980
cagagacaga tccattcgat tagtgaacgg atctcgacgg tatcgccttt aaaagaaaag   2040
gggggattgg ggggtacagt gcaggggaaa gaatagtaga cataatagca acagacatac   2100
aaactaaaga attacaaaaa caaattacaa aaattcaaaa ttttcgggtt tattacaggg   2160
acagcagaga tccagtttat cgatctgcag agggccctgc gtatgagtgc aagtgggttt   2220
taggaccagg atgaggcggg gtgggggtgc ctacctgacg accgaccccg acccactgga   2280
caagcaccca accccattc cccaaattgc gcatcccta tcagagaggg ggaggggaaa    2340
caggatgcgg cgaggcgcgt gcgcactgcc agcttcagca ccgcgacag tgccttcgcg    2400
cccgcctggc ggcgcgcgcc accgccgcct cagcactgaa ggcgcgctga cgtcactcgc   2460
cggtcccccg caaactcccc ttcccggcca ccttggtcgc gtccgcgccg ccgccggccc   2520
agccggaccg caccacgcga ggcgcgagat agggggcac gggcgcgacc atctgcgctg    2580
cggcgccggc gactcagcgc tgcctcagtc tgcggtgggc agcggaggag tcgtgtcgtg   2640
cctgagagcg cagggatcta tttccggtga attcgccacc atggcagagc cccggcagga   2700
gttcgaggtt atggaggatc acgccggac ctatggattg ggcgatagga aagatcaggg    2760
cgggtatact atgcatcagg accaggaagg cgacacggac gctggtctca aggaaagccc   2820
acttcagacg ccgacagagg acgggtctga ggaacctggg agtgaaactt ctgacgctaa   2880
gtctacgcct actgcggagg gcgaggaggc aggaatagga gacacaccat cacttgaaga   2940
cgaggcagca ggacacgtaa cccaagcgag aatggtttct aagtccaaag atggaaccgg   3000
atccgatgac aaaaaggcca agggagcaga tggcaaaaca aaaataacga caccgagggg   3060
tgcggctccc cccggtcaaa agggacaggc aaatgccacg cgcatccctg ctaaaacacc   3120
cccggccgcg aaaccccccc cttcatccgg agagccaccc aagtctggtg atagaagcgg   3180
gtatagttcc cccggtagtc cggggactcc aggatcacgc agcagaacgc catccctgcc   3240
aaccccaccc actagagagc ccaaaaaggt cgcagtcgtt cgcactccgc caaaaagccc   3300
ttcctcagcg aaaagccgcc tgcagacggc acctgtcccc atgcctgacc ttaaaaatgt   3360
taaaagcaaa atcggtagta ccgaaaatct caagcatcag ccagaggggg ggaaggttca   3420
gatcatcaat aagaagctgg acctgtctaa cgtgcagagc aagtgtggaa gcaaagataa   3480
cataaagcac gttttgggggg gcggaagcgt acagattgtg tataagccgg tggacctctc   3540
aaaagtaaca ttcaagtgtg ggagtctggg caacatccat cacaaacccg ggggcggtca   3600
ggtagaggtg aaaagcgaaa agctcgattt taaggatagg gtacagagta aaattgggtc   3660
tctggacaac ataacacacg taccaggcgg aggcaataag aagatagaaa cgcataaact   3720
cacgttccga gagaacgcta aagcaaagac tgaccacggg gctgagattg tatacaagag   3780
tccggtcgtc tctggggaca cttcccccg acacctttct aacgttagtt ccactggtag    3840
tattgacatg gtcgacagcc ctcaacttgc cactttggca gacgaggtca gtgctagtct   3900
tgcaaagcag ggcttggtga gcaagggcga ggagctgttc accgggggtgg tgcccatcct   3960
ggtcgagctg gacggcgacg taaacggcca caagttcagc gtgtccggcg agggcgaggg   4020
cgatgccacc tacggcaagc tgaccctgaa gttcatctgc accaccggca agctgcccgt   4080
gccctggccc accctcgtga ccaccctgac ctacggcgtg cagtgcttca gccgctaccc   4140
cgaccacatg aagcagcacg acttcttcaa gtccgccatg cccgaaggct acgtccagga   4200
gcgcaccatc ttcttcaagg acgacggcaa ctacaagacc cgcgccgagg tgaagttcga   4260
gggcgacacc ctggtgaacc gcatcgagct gaagggcatc gacttcaagg aggacggcaa   4320
catcctgggg cacaagctgg agtacaacta caacagccac aacgtctata tcatggccga   4380
caagcagaag aacggcatca aggtgaactt caagatccgc cacaacatcg aggacggcag   4440
cgtgcagctc gccgaccact accagcagaa caccccatc ggcgacgcc ccgtgctgct    4500
gcccgacaac cactacctga gcacccagtc cgccctgagc aaagacccca acgagaagcg   4560
cgatcacatg gtcctgctgg agttcgtgac cgccgccggg atcactctcg gcatggacga   4620
gctgtacaag tgaaattcgc tcgagactag ttctagagcg gccgccctct cccctccccc   4680
cccctaacgt tactggccga agccgcttgg aataaggccg gtgtgcgttt gtctatatgt   4740
tattttccac catattgccg tcttttggca atgtgagggc ccggaaacct ggccctgtct   4800
tcttgacgag cattcctagg gtctttccc ctctcgccaa aggaatgcaa ggtcgttga    4860
atgtcgtgaa ggaagcagtt cctctggaag cttcttgaag acaaacagga tctgtagcga   4920
cccttttgcag gcagcggaac cccccacctg cgacaggtg cctctgcggc              4980
caaaagccac gtgtataaga tacacctgca aaggcggcac aaccccagtg ccacgttgtg   5040
agttggatag ttgtggaaag agtcaaatgg ctctcctcaa gcgtattcaa caaggggctg   5100
aaggatgccc agaaggtacc ccattgtatg ggatctgatc tggggcctcg gtgcacatgc   5160
tttacatgtg tttagtcgag gttaaaaaaa cgtctaggcc ccccgaacca cgggggacgtg   5220
gttttccttt gaaaaacacg atgataagct tgccacaacc cgtaccaaag atggatagat   5280
ccggaaagcc tgaactcacc gcgacgtctg tcgagaagtt tctgatcgaa aagttcgaca   5340
gcgtctccga cctgatgcag ctctcggagg gcgaagaatc tcgtgctttc agcttcgatg   5400
taggagggcg tggatatgtc ctgcgggtaa atagctgcgc cgatggtttc tacaaagatc   5460
gttatgttta tcggcacttt gcatcggccg cgctcccgat tccggaagtg cttgacattg   5520
gggaattcag cgagagcctg acctattgca tctcccgccg tgcacagggt gtcacgttgc   5580
aagacctgcc tgaaaccgaa ctgccgctgt tctgcagcc ggtcgcggag gccatggatg    5640
cgatcgctgc ggccgatctt agccagacga gcgggttcgc ccattcgga ccgcaagga    5700
tcggtcaata cactacatgg cgtgatttca tatgcgcgat tgctgatccc catgtgtatc   5760
actggcaaac tgtgatggac gacaccgtca gtgcgtccgt cgcgcaggct ctcgatgagc   5820
tgatgctttg gccgaggac tgccccgaag tccggcacct cgtgcacgcg gatttcggct    5880
ccaacaatgt cctgacggac aatggccgca taacagcggt cattgactgg agcgaggcga   5940
tgttcgggga ttcccaatac gaggtcgcca acatcttctt ctggaggccg tggttgttca   6000
gtatggagca gcagacgcgc tacttcgagc ggaggcatcc ggagcttgca ggatcgccgc   6060
ggctccgggc gtatatgctc cgcattggtc ttgaccaact ctatcagagc ttggttgacg   6120
gcaatttcga tgatgcagct tgggcgcagg tcgatgcga cgcaatcgtc cgatccggag    6180
ccgggactgt cgggcgtaca caaatcgccc gcagaagcgc ggccgtctgg accgatggct   6240
gtgtagaagt actcgccgat agtggaaacc gacgccgtcg cactgtcgcg cggcaaagg    6300
aatagacgcg tctggaacaa tcaacctctg gattacaaaa tttgtgaaag attgactggt   6360
attcttaact atgttgctcc ttttacgcta tgtggatacg ctgctttaat gcctttgtat   6420
catgctattg cttcccgtat ggctttcatt ttctcctcct tgtataaatc ctggttgctg   6480
tctctttatg aggagttgtg gcccgttgtc aggcaacgtg gcgtggtgtg cactgtgttt   6540
gctgacgcaa ccccactggt tggggcatt gccaccacct gtcagctcct ttccgggact   6600
```

```
ttcgctttcc ccctcccta t tgccacggcg gaactcatcg ccgcctgcct tgcccgctgc  6660
tggacagggg ctcggctgtt gggcactgac aattccgtgg tgttgtcggg gaagctgacg  6720
tcctttccat ggctgctcgc ctgtgttgcc acctggattc tgcgcgggac gtccttctgc  6780
tacgtccctt cggccctcaa tccagcggac cttccttccc gcggcctgct gccggctctg  6840
cggcctcttc cgcgtcttcg ccttcgccct cagacgagtc ggatctccct ttgggccgcc  6900
tccccgcctg gaattaattc tgcagtcgag acctagaaaa acatggagca atcacaagta  6960
gcaatacagc agctaccaat gctgattgtg cctggctaga agcacaagag gaggaggagg  7020
tgggttttcc agtcacacct caggtacctt taagaccaat gacttacaag gcagctgtag  7080
atcttagcca cttttttaaaa gaaaagaggg gactggaagg gctaattcac tcccaacgaa  7140
gacaagatat ccttgatctg tggatctacc acacacaagg ctacttccct gattagcaga  7200
actcacacacc agggccaggg gtcagatatc cactgacctt tggatggtgc tacaagctag  7260
taccagttga gccagataag gtagaagagg ccaataaagg agagaacacc agcttgttac  7320
accctgtgag cctgcatggg atggatgacc cggagagaga agtgttagag tggaggtttg  7380
acagccgcct agcatttcat cacgtggccc gagagctgca tccggagtac ttcaagaact  7440
gctgatatcg agcttgctac aagggacttt ccgctgggga ctttccaggg aggcgtggcc  7500
tgggcgggac tggggagtgg cgagccctca gatcctgcat ataagcagct gcttttttgcc  7560
tgtactgggt ctctctggtt agaccagatc tgagcctggg agctctctgg ctaactaggg  7620
aacccactgc ttaagcctca ataaagcttg ccttgagtgc ttcaagtagt gtgtgcccgt  7680
ctgttgtgtg actctggtaa ctagagatcc ctcagaccct tttagtcagt gtggaaaatc  7740
tctagcagta gtagttcatg tcatcttatt attcagtatt tataacttgc aaagaaatga  7800
atatcagaga gtgagaggcc ttgacattgc tagcgtttac cgtcgacctc tagctagagc  7860
tggcgtaat catggtcata gctgtttcct gtgtgaaatt gttatccgct cacaattcca  7920
cacaacatac gagccggaag cataaagtgt aaagcctggg gtgcctaatg agtgagctaa  7980
ctcacattaa ttgcgttgcg ctcactgccc gctttccagt cgggaaacct gtcgtgccag  8040
ctgcattaat gaatcggcca acgcgcgggg agaggcggtt tgcgtattgg gcgctcttcc  8100
gcttcctcgc tcactgactc gctgcgctcg gtcgttcggc tgcggcgagc ggtatcagct  8160
cactcaaagg cggtaatacg gttatccaca gaatcagggg ataacgcagg aaagaacatg  8220
tgagcaaaag gccagcaaaa ggccaggaac cgtaaaaagg ccgcgttgct ggcgtttttc  8280
cataggctcc gccccctga cgagcatcac aaaaatcgac gctcaagtca gaggtggcga  8340
aacccgacag gactataaag ataccaggcg tttccccctg gaagctccct cgtgcgctct  8400
cctgttccga ccctgccgct taccggatac ctgtccgcct ttctcccttc gggaagcgtg  8460
gcgctttctc atagctcacg ctgtaggtat ctcagttcgg tgtaggtcgt tcgctccaag  8520
ctgggctgtg tgcacgaacc ccccgttcag cccgaccgct gcgccttatc cggtaactat  8580
cgtcttgagt ccaacccggt aagacacgac ttatcgccac tggcagcagc cactggtaac  8640
aggattagca gagcgaggta tgtaggcggt gctacagagt tcttgaagtg gtggcctaac  8700
tacggctaca ctagaagaac agtatttggt atctgcgctc tgctgaagcc agttaccttc  8760
ggaaaaagag ttggtagctc ttgatccggc aaacaaacca ccgctggtag cggtggtttt  8820
tttgtttgca agcagcagat tacgcgcaga aaaaaaggat ctcaagaaga tcctttgatc  8880
ttttctacgg ggtctgacgc tcagtggaac gaaaactcac gttaagggat tttggtcatg  8940
agattatcaa aaaggatctt cacctagatc cttttaaatt aaaaatgaag ttttaaatca  9000
atctaaagta tatatgagta aacttggtct gacagttacc aatgcttaat cagtgaggca  9060
cctatctcag cgatctgtct atttcgttca tccatagttg cctgactccc cgtcgtgtag  9120
ataactacga tacgggaggg cttaccatct ggccccagtg ctgcaatgat accgcgagac  9180
ccacgctcac cggctccaga tttatcagca ataaaccagc cagccggaag ggccgagcgc  9240
agaagtggtc ctgcaacttt atccgcctcc atccagtcta ttaattgttg ccgggaagct  9300
agagtaagta gttcgccagt taatagtttg cgcaacgttg ttgccattgc tacaggcatc  9360
gtggtgtcac gctcgtcgtt tggtatggct tcattcagct ccggttccca acgatcaagg  9420
cgagttacat gatcccccat gttgtgcaaa aaagcggtta gctccttcgg tcctccgatc  9480
gttgtcagaa gtaagttggc cgcagtgtta tcactcatgg ttatggcagc actgcataat  9540
tctcttactg tcatgccatc cgtaagatgc ttttctgtga ctggtgagta ctcaaccaag  9600
tcattctgag aatagtgtat gcggcgaccg agttgctctt gcccggcgtc aatacggata  9660
ataccgcgc cacatagcag aactttaaaa gtgctcatca ttggaaaacg ttcttcgggg  9720
cgaaaactct caaggatctt accgctgttg agatccagtt cgatgtaacc cactcgtgca  9780
cccaactgat cttcagcatc ttttactttc accagcgttt ctgggtgagc aaaaacagga  9840
aggcaaaatg ccgcaaaaaa gggaataagg gcgacacgga aatgttgaat actcatactc  9900
ttcctttttc aatattattg aagcatttat cagggttatt gtctcatgag cggatacata  9960
tttgaatgta tttagaaaaa taaacaaata ggggttccgc gcacatttcc ccgaaaagtg 10020
ccacctgacg tcgacggatc gggagatcaa cttgtttatt gcagcttata atggttacaa 10080
ataaagcaat agcatcacaa atttcacaaa taaagcattt ttttcactgc attctagttg 10140
tggtttgtcc aaactcatca atgtatctta tcatgtctgg atcaactgga taactcaagc 10200
taaccaaaat catcccaaac ttcccacccc atacccctatt accactgcca attacctgtg 10260
gtttcattta ctctaaacct gtgattcctc tgaattattt tcattttaaa gaaattgtat 10320
ttgttaaata tgtactacaa acttagtagt                                  10350

SEQ ID NO: 80          moltype = DNA   length = 10350
FEATURE                Location/Qualifiers
misc_feature           1..10350
                       note = Synthetic
misc_feature           1..635
                       note = LTR
misc_feature           636..653
                       note = PBS
misc_feature           685..822
                       note = Packaging§ignal
misc_feature           1303..1536
                       note = RRE
misc_feature           2028..2151
                       note = cPPT
misc_feature           2185..2668
```

|               | note = hSynapsin promoter |
| misc_feature  | 2681..3397 |
|               | note = eGFP |
| misc_feature  | 3398..4633 |
|               | note = CoHu hTau-412 (1N R4) 3MUT |
| misc_feature  | 4640..4671 |
|               | note = MCS |
| misc_feature  | 4672..5270 |
|               | note = IRES |
| misc_feature  | 5271..6305 |
|               | note = HygR |
| misc_feature  | 6319..6910 |
|               | note = WPRE |
| misc_feature  | 7113..7749 |
|               | note = LTR |
| misc_feature  | 8218..8891 |
|               | note = pUCorigin |
| misc_feature  | 9036..10032 |
|               | note = AmpR |
| source        | 1..10350 |
|               | mol_type = other DNA |
|               | organism = synthetic construct |

SEQUENCE: 80

```
tggaagggct aattcactcc caaagaagac aagatatcct tgatctgtgg atctaccaca    60
cacaaggcta cttccctgat tagcagaact acacaccagg gccaggggtc agatatccac   120
tgacctttgg atggtgctac aagctagtac cagttgagcc agataaggta gaagaggcca   180
ataaaggaga gaacaccagc ttgttacacc ctgtgagcct gcatgggatg gatgacccgg   240
agagagaagt gttagagtgg aggtttgaca gccgcctagc atttcatcac gtggcccgag   300
agctgcatcc ggagtacttc aagaactgct gatatcgagc ttgctacaag gactttccg   360
ctggggactt tccaggggag cgtggcctgg gcgggactgg ggagtggcga gccctcagat   420
cctgcatata agcagctgct ttttgcctgt actgggtctc tctggttaga ccagatctga   480
gcctgggagc tctctggcta actagggaac ccactgctta agcctcaata agcttgcct   540
tgagtgcttc aagtagtgtg tgcccgtctg ttgtgtgact ctggtaacta gagatccctc   600
agacccttt agtcagtgtg gaaaatctct agcagtggcg cccgaacagg gacttgaaag   660
cgaaagggaa accagaggag ctctctcgac gcaggactcg gcttgctgaa gcgcgcacgg   720
caagaggcga ggggcggcga ctggtgagta cgccaaaaat tttgactagc ggaggctaga   780
aggagagaga tgggtgcgag agcgtcagta ttaagcgggg gagaattaga tcgcgatggg   840
aaaaaattcg gttaaggcca gggggaaaga aaaatataa attaaaacat atagtatggg   900
caagcaggga gctagaacga ttcgcagtta atcctggcc gttagaaaca tcagaaggct   960
gtagacaaat actgggacag ctacaaccat cccttcagac aggatcagaa gaacttagat  1020
cattatataa tacagtagca accctctatt gtgtgcatca aaggatagag ataaaagaca  1080
ccaaggaagc tttagacaag atagaggaag agcaaaacaa aagtaagacc accgcacagc  1140
aagcggccgg ccgctgatct tcagacctgg aggaggagat atgagggaca attggagaag  1200
tgaattatat aaatataaag tagtaaaaat tgaaccatta ggagtagcac ccaccaaggc  1260
aaagagaaga gtggtgcaga gagaaaaaag agcagtggga ataggagctt tgttccttgg  1320
gttcttggga gcagcaggaa gcactatggg cgcagcgtca atgacgctga cggtacaggc  1380
cagacaatta ttgtctggta tagtgcagca gcagaacaat ttgctgaggg ctattgaggc  1440
gcaacagcat ctgttgcaac tcacagtctg gggcatcaag cagctccagg caagaatcct  1500
ggctgtggaa agatacctaa aggatcaaca gctcctgggg atttggggtt gctctggaaa  1560
actcatttgc accactgctg tgccttggaa tgctagttgg agtaataaat ctctggaaca  1620
gatttggaat cacacgacct ggatggagtg ggacagagaa attaacaatt acacaagctt  1680
aatacactcc ttaattgaag aatcgcaaaa ccagcaagaa aagaatgaac aagaattatt  1740
ggaattagat aaatgggcaa gtttgtgaa ttggtttaac ataacaaatt ggctgtggta  1800
tataaaatta ttcataatga tagtaggagg cttggtaggt ttaagaatag ttttgctgt  1860
actttctata gtgaatagag ttaggcaggg atattcacca ttatcgtttc agacccacct  1920
cccaaccccg aggggacccg acaggcccga aggaataaga gaagaaggtg gagagagaga  1980
cagagacaga tccattcgat tagtgaacgg atctcgacgg tatcgccttt aaaagaaaag  2040
gggggattgg ggggtacagt gcaggggaaa gaatagtaga cataatagca acagacatac  2100
aaactaaaga attacaaaaa caaattacaa aaattcaaaa ttttcgggtt tattacaggg  2160
acagcagaga tccagtttat cgatctgcag agggccctgc gtatgagtgc aagtgggttt  2220
taggaccagg atgaggcggg gtgggggtgc ctacctgacg accgaccccg acccactgga  2280
caagcaccca accccattc cccaaattgc gcatcccta tcagagaggg ggagggggaa   2340
caggatgcgc cgaggcgcgt gcgcactgcc agcttcagca ccgcgacag tgccttcgcc   2400
cccgcctggc ggcgcgcgcc accgccgcct cagcactgga ggcgctga cgtcactcgc    2460
cggtccccg caaactcccc ttcccggcca ccttggtcgc gtccgcgccg ccgccggccc   2520
agccggaccg caccacgcga ggcgcagat aggggggcac gggcgcgacc atctgcgctg  2580
cggcgccggc gactcagcgc tgcctcagtc tgcggtgggc agcggaggag tcgtgtcgtg  2640
cctgagagcg cagggatcta tttccggtga attcgccacc atggtgagca agggcgagga  2700
gctgttcacc ggggtggtgc ccatcctggt cgagctggac ggcgacgtaa acggccacaa  2760
gttcagcgtg tccggcgagg gcgagggcga tgccacctac ggcaagctga ccctgaagtt  2820
catctgcacc accggcaagc tgcccgtgcc ctggcccacc ctcgtgacca cctgacccta  2880
cggcgtgcag tgcttcagcc gctaccccga ccacatgaag cagcacgact tcttcaagtc  2940
cgccatgccc gaaggctacg tccaggagcg caccatcttc ttcaaggacg acggcaacta  3000
caagacccgc gccgaggtga agttcgaggg cgacaccctg gtgaaccgca tcgagctgaa  3060
gggcatcgac ttcaaggagg acggcaacat cctggggcac aagctggagt acaactacaa  3120
cagccacaac gtctatatca tggccgacaa gcagaagaac ggcatcaagg tgaacttcaa  3180
gatccgccac aacatcgagg acggcagcgt gcagctcgcc gaccactacc agcagaacac  3240
ccccatcggc gacggccccg tgctgctgcc cgacaaccac tacctgagca cccagtccgc  3300
cctgagcaaa gaccccaacg agaagcgcga tcacatggtc ctgctggagt tcgtgaccgc  3360
```

```
cgccgggatc actctcggca tggacgagct gtacaaggca gagccccggc aggagttcga   3420
ggttatggag gatcacgccg ggacctatgg attgggcgat aggaaagatc agggcgggta   3480
tactatgcat caggaccagg aaggcgacac ggacgctggt ctcaaggaaa gcccacttca   3540
gacgccgaca gaggacgggt ctgaggaacc tgggagtgaa acttctgacg ctaagtctac   3600
gcctactgcg gaggcggagg aggcaggaat aggagacaca ccatcacttg aagacgaggc   3660
agcaggacac gtaacccaag cgagaatggt ttctaagtcc aaagatggaa ccggatccga   3720
tgacaaaaag gccaagggag cagatggcaa aacaaaaata acgacaccga ggggtgcggc   3780
tcccccggt caaagggac aggcaaatgc cacgcgcatc cctgctaaaa caccccggc     3840
gccgaaaacc ccccttcat ccggaaggcc acccaagtc ggtgatagaa gcgggtatag    3900
ttccccggt agtccgggga ctccaggatc acgcagcaga acgccatccc tgccaaccccc  3960
acccactaga gagcccaaaa aggtcgcagt cgttcgcact ccgccaaaaa gcccttcctc   4020
agcgaaaagc cgcctgcaga cggcacctgt ccccatgcct gacctaaaaa atgttaaaag   4080
caaaatcggt agtaccgaaa atctcaagca tcagccagga gggggaagg ttcagatcat    4140
caataagaag ctggacctgt ctaacgtgca gagcaagtgt ggagcaaag ataacataaa    4200
gcacgttttg gggggcggaa gcgtacagat tgtgtataag ccggtggacc tctcaaaagt   4260
aacattcaag tgtgggagtc tggcaacat ccatcacaaa cccggggggcg tcaggtaga    4320
ggtgaaaagc gaaaagctcg atttaagga taggtacag agtaaaattg ggtctctgga    4380
caacataaca cacgtaccag gcggaggcaa taagaagata gaaacgcata aactcacgtt   4440
ccgagagaac gctaaagcaa agactgacca cggggctgag attgtataca agagtccggt   4500
cgtctctggg gacacttccc cccgacacct ttctaacgtt agttccactg gtagtattga   4560
catggtcgac agccctcaac ttgccacttt ggcagacgag gtcagtgcta gtcttgcaaa   4620
gcagggcttg tgaaattcgc tcgagactag ttctagacga gccgcggatc ccgccccctct  4680
cctccccccc ccctaacgt tactggccga agccgcttgg aataaggccg gtgtgcgttt    4740
gtctatatgt tatttccac catattgccg tcttttggca atgtgagggc ccggaaacct    4800
ggccctgtct tcttgacgag cattcctagg gtcttccc ctctcgccaa aggaatgcaa     4860
ggtctgttga atgtcgtgaa ggaagcagtt cctctgaag cttcttgaag acaaacaacg    4920
tctgtagcga cccctttgcag gcagcggaac cccccacctg gcgacaggtg cctctgcggc   4980
caaaagccac gtgtataaga tacacctgca aaggcggcac aaccccagtg ccacgttgtg   5040
agttggatag ttgtggaaag agtcaaatgg ctctcctcaa gcgtattcaa caaggggctg   5100
aaggatgccc agaaggtacc ccattgtatg ggatctgatc tggggcctcg gtgcacatgc   5160
tttacatgtg tttagtcgag gttaaaaaaa cgtctaggcc ccccgaacca cggggacgtg   5220
gttttccttt gaaaaacacg atgataagct tgccacaacc cgtaccaaag atggatagat    5280
ccggaaagcc tgaactcacc gcgacgtctg tcgagaagtt tctgatcgaa aagttcgaca   5340
gcgtctccga cctgatgcag ctctcggagg gcgaagaatc tcgtgctttc agcttcgatg   5400
taggagggcg tggatatgtc ctgcgggtaa atagctgcgc cgatggtttc tacaaagatc   5460
gttatgttta tcggcacttt gcatcggccg cgctcccgat tccggaagtg cttgacattg    5520
gggaattcag cgagagcctg acctattgca tctcccgccg tgcacagggt gtcacgttgc    5580
aagacctgcc tgaaaccgaa ctgcccgctg ttctgcagcc ggtcgcggag gccatggatg    5640
cgatcctgcc ggccgatctt agccagacga gcgggttcgg cccattcgga ccgcaaggaa    5700
tcggtcaata cactacatgg cgtgatttca tatgcgcgat tgctgatccc catgtgtatc    5760
actggcaaac tgtgatggac gacaccgtca gtgcgtccgt cgcgcaggct ctcgatgagc    5820
tgatgctttg ggccgaggac tgccccgaag tccggcacct cgtgcacgcg gatttcggct    5880
ccaacaatgt cctgacggac aatggccgca taacagcggt cattgactgg agcgaggcga    5940
tgttcggga ttcccaatac gaggtcgcca acatcttctt ctggaggccg tggttggctt      6000
gtatggagca gcagacgcgc tacttcgagc ggaggcatcc ggagcttgca ggatcgccgc    6060
ggctccggc gtatatgctc cgcattggtc ttgaccaact ctatcagagc ttggttgacg    6120
gcaatttcga tgatgcagct tgggcgcagg gtcgatgcga cgcaatcgtc cgatccggag    6180
ccgggactgt cgggcgtaca caaatcgccc gcagaagcgc ggccgtctgg accgatggct    6240
gtgtagaagt actcgccgat agtggaaacc gacgccccag cactcgtccg agggcaaagg    6300
aatagacgcg tctggaacaa tcaacctctg gattacaaaa tttgtgaaag attgactggt    6360
attcttaact atgttgctcc ttttacgcta tgtggatacg ctgctttaat gcctttgtat   6420
catgctattg cttcccgtat ggctttcatt ttctcctcct tgtataaatc ctggttgctg    6480
tctctttatg aggagttgtg gcccgttgtc aggcaacgtg gcgtggtgtg cactgtgttt   6540
gctgacgcaa ccccccactgg ttggggcatt gccaccacct gtcagctcct ttccgggact    6600
ttcgctttcc cctccctat tgccacggcg gaactcatcg ccgcctgcct tgcccgctgc    6660
tggacagggg ctcggctgtt gggcactgac aattccgtgg tgttgtcggg gaagctgacg    6720
tcctttccat ggctgctcgc ctgtgttgcc acctggattc tgcgcgggac gtccttctgc    6780
tacgtcccct cggccctcaa tccagcggac cttccttccc gcggcctgct gccggctctg    6840
cggcctcttc cgcgtcttcg ccttcgccct cagacgagtc ggatctccct ttgggccgcc    6900
tccccgcctg gaattaattc tgcagtcgag acctagaaaa acatgagga atcacaagta    6960
gcaatacagc agctaccaat gctgattgtg cctggctaga agcacaagag gaggaggagg   7020
tgggttttcc agtcacacct caggtacctt aagaccaat gacttacaag gcagctgtag    7080
atcttagcca ctttttaaaa gaaaagaggg gactggaagg gctaattcac tcccaacgaa    7140
gacaagatat ccttgatctg tggatctacc acacacagga ctactcccct gattagcaga    7200
actacacacc agggccaggg gtcagatatc cactgacctt tggatggtgc tacaagctag    7260
taccagttga gccagataag gtagaagagg ccaataaagg agagaacacc agcttgttac    7320
accctgtgag cctgcatggg atggatgacc cggagagaga agtgttagag tggaggtttg    7380
acagccgcct agcatttcat cacgtggccc gagagctgca tccggagtac ttcaagaact    7440
gctgatatcg agcttgctac aagggacttt ccgctgggga ctttccaggg aggcgtggcc    7500
tgggcgggac tggggagtgg cgagccctca gatcctgcat ataagcagct gcttttttgcc    7560
tgtactgggt ctctctggtt agaccagatc tgagcctggg agctctctgg ctaactaggg    7620
aacccactgc ttaagcctca ataaagcttg ccttgagtgc ttcaagtagt gtgtgcccgt    7680
ctgttgtgtg actctggtaa ctagagatcc ctcagaccct tttagtcagt gtggaaaatc    7740
tctagcagta gtagttcatg tcatcttatt attcagtatt ataacttgca aagaaatga     7800
atatcagaga gtgagaggcc ttgacattgc tagcgtttac cgtcgacctc tagctagagc    7860
ttggcgtaat catggtcata gctgtttcct gtgtgaaatt gttatccgct cacaattcca    7920
cacaacatac gagccggaag cataaagtgt aaagcctggg gtgcctaatg agtgagctaa    7980
ctcacattaa ttgcgttgcg ctcactgccc gctttccagt cggaaacct gtcgtgccag     8040
ctgcattaat gaatcggcca acgcgcgggg agaggcggtt tgcgtattgg gcgctcttcc    8100
```

```
gcttcctcgc tcactgactc gctgcgctcg gtcgttcggc tgcggcgagc ggtatcagct   8160
cactcaaagg cggtaatacg gttatccaca gaatcagggg ataacgcagg aaagaacatg   8220
tgagcaaaag gccagcaaaa ggccaggaac cgtaaaaagg ccgcgttgct ggcgtttttc   8280
cataggctcc gcccccctga cgagcatcac aaaaatcgac gctcaagtca gaggtggcga   8340
aacccgacag gactataaag ataccaggcg tttccccctg gaagctccct cgtgcgctct   8400
cctgttccga ccctgccgct taccggatac ctgtccgcct ttctcccttc gggaagcgtg   8460
gcgctttctc atagctcacg ctgtaggtat ctcagttcgg tgtaggtcgt tcgctccaag   8520
ctgggctgtg tgcacgaacc ccccgttcag cccgaccgct gcgccttatc cggtaactat   8580
cgtcttgagt ccaacccggt aagacacgac ttatcgccac tggcagcagc cactggtaac   8640
aggattagca gagcgaggta tgtaggcggt gctacagagt tcttgaagtg gtggcctaac   8700
tacggctaca ctagaagaac agtatttggt atctgcgctc tgctgaagcc agttaccttc   8760
ggaaaaagag ttggtagctc ttgatccggc aaacaaacca ccgctggtag cggtggtttt   8820
tttgtttgca agcagcagat tacgcgcaga aaaaaaggat ctcaagaaga tcctttgatc   8880
ttttctacgg ggtctgacgc tcagtggaac gaaaactcac gttaagggat tttggtcatg   8940
agattatcaa aaaggatctt cacctagatc cttttaaatt aaaaatgaag ttttaaatca   9000
atctaaagta tatatgagta aacttggtct gacagttacc aatgcttaat cagtgaggca   9060
cctatctcag cgatctgtct atttcgttca tccatagttg cctgactccc cgtcgtgtag   9120
ataactacga tacgggaggg cttaccatct ggccccagtg ctgcaatgat accgcgagac   9180
ccacgctcac cggctccaga tttatcagca ataaaccagc cagccggaag ggccgagcgc   9240
agaagtggtc ctgcaacttt atccgcctcc atccagtcta ttaattgttg ccgggaagct   9300
agagtaagta gttcgccagt taatagtttg cgcaacgttg ttgccattgc tacaggcatc   9360
gtggtgtcac gctcgtcgtt tggtatggct tcattcgcct ccggttccca acgatcaagg   9420
cgagttacat gatcccccat gttgtgcaaa aaagcggtta gctccttcgg tcctccgatc   9480
gttgtcagaa gtaagttggc cgcagtgtta tcactcatgg ttatggcagc actgcataat   9540
tctcttactg tcatgccatc cgtaagatgc ttttctgtga ctggtgagta ctcaaccaag   9600
tcattctgag aatagtgtat gcggcgaccg agttgctctt gcccggcgtc aatacgggat   9660
aataccgcgc cacatagcag aactttaaaa gtgctcatca ttggaaaacg ttcttcgggg   9720
cgaaaactct caaggatctt accgctgttg agatccagtt cgatgtaacc cactcgtgca   9780
cccaactgat cttcagcatc ttttactttc accagcgttt ctgggtgagc aaaaacagga   9840
aggcaaaatg ccgcaaaaaa gggaataagg gcgacacgga aatgttgaat actcatactc   9900
ttcctttttc aatattattg aagcatttat cagggttatt gtctcatgag cggatacata   9960
tttgaatgta tttagaaaaa taaacaaata ggggttccgc gcacatttcc ccgaaaagtg  10020
ccacctgacg tcgacggatc gggagatcaa cttgtttatt gcagcttata atggttacaa  10080
ataaagcaat agcatcacaa atttcacaaa taaagcattt tttcactgca ttctagttg   10140
tggtttgtcc aaactcatca atgtatctta tcatgtctgg atcaactgga taactcaagc  10200
taaccaaaat catcccaaac ttcccacccc atcccctatt accactgcca attacctgtg  10260
gtttcattta ctctaaacct gtgattcctc tgaattattt tcattttaaa gaaattgtat  10320
ttgttaaata tgtactacaa acttagtagt                                   10350
```

SEQ ID NO: 81          moltype = DNA   length = 1236
FEATURE                Location/Qualifiers
misc_feature           1..1236
                       note = Synthetic
source                 1..1236
                       mol_type = other DNA
                       organism = synthetic construct
SEQUENCE: 81
```
gctgagcccc gacaggagtt cgaggtaatg gaggatcacg cagggacgta tggtctggga     60
gacaggaagg atcaaggcgg ctatacgatg caccaggatc aggagggcga taccgatgcg    120
ggcctcaaag agtccccgct tcaaacacca actgaggatg ggagtgagga gccaggaagt    180
gagacaagcg acgcgaaatc aacccctact gccgaagcgg aggaggccgg gatcggagat    240
acaccatctc tcgaagacga agctgctggc cacgtgacgc aagcacgaat ggtgtccaaa    300
agcaaagacg gtacaggttc tgacgacaaa aaggcgaagg gggcagatgg gaaaactaaa    360
atcgccacgc cccggggtgc ggcgccgcct gggcagaaag gcaagcaaa tgcgacgcga    420
atacctgcca agacgcctcc ggctcctaag acccaccat catctggtga accgcctaaa    480
agcggggatc gaagcggtta ttcatcaccg ggtagtccgg gtacgccagg ctctaggagc    540
agaactcctt cactgcccac gcccccacg cgcgaaccta agaaagtggc agtggtgcga    600
acaccccaa aaagccctc aagtgcaaa tcacggctcc agactgcacc cgtaccgatg       660
cccgatctca aaaacgtgaa atctaagata ggtagtacag agaatctgaa gcatcaaccg    720
ggaggtggaa aggtcagat tatcaataag aaacttgacc tgagtaacgt tcaatccaag    780
tgtggatcaa aagataatat caagcacgtc cctggaggcg gttcagtgca gatcgtttac    840
aaacctgttg atcttagcaa ggtgacttcc aagtgcgggt ctctgggcaa cattcatcac    900
aaacctggtg gagggcaagt tgaggtcaaa agcgaaaagc tcgacttcaa agatcgagtt    960
cagagcaaga taggcagcct tgataatatt ccccatgtcc ccggcggagg gaacaagaag   1020
attgagactc ataagttgac gttcagaaa aatgctaaag cgaaaacgga tcatggcgca   1080
gaaatagttt ataaatctcc tgtggtcagt ggtgacactt cacccaggca cctctcaaac   1140
gtgtcatcaa cgggctcaat cgacatggtg gattctcccc aactcgcaac acttgctgat   1200
gaggtaagtg ccagcctcgc aaagcaagga ctctaa                              1236
```

SEQ ID NO: 82          moltype = AA   length = 411
FEATURE                Location/Qualifiers
REGION                 1..411
                       note = Synthetic
source                 1..411
                       mol_type = protein
                       organism = synthetic construct
SEQUENCE: 82
```
AEPRQEFEVM EDHAGTYGLG DRKDQGGYTM HQDQEGDTDA GLKESPLQTP TEDGSEEPGS     60
ETSDAKSTPT AEAEEAGIGD TPSLEDEAAG HVTQARMVSK SKDGTGSDDK KAKGADGKTK    120
```

```
IATPRGAAPP GQKGQANATR IPAKTPPAPK TPPSSGEPPK SGDRSGYSSP GSPGTPGSRS   180
RTPSLPTPPT REPKKVAVVR TPPKSPSSAK SRLQTAPVPM PDLKNVKSKI GSTENLKHQP   240
GGGKVQIINK KLDLSNVQSK CGSKDNIKHV PGGGSVQIVY KPVDLSKVTS KCGSLGNIHH   300
KPGGGQVEVK SEKLDFKDRV QSKIGSLDNI THVPGGGNKK IETHKLTFRE NAKAKTDHGA   360
EIVYKSPVVS GDTSPRHLSN VSSTGSIDMV DSPQLATLAD EVSASLAKQG L            411

SEQ ID NO: 83             moltype = DNA  length = 1236
FEATURE                   Location/Qualifiers
misc_feature              1..1236
                          note = Synthetic
source                    1..1236
                          mol_type = other DNA
                          organism = synthetic construct
SEQUENCE: 83
gcagagcccc ggcaggagtt cgaggttatg gaggatcacg ccgggaccta tggattgggc    60
gataggaaag atcagggcgg gtatactatg catcaggacc aggaaggcga cacggacgct   120
ggtctcaagg aaagcccact tcagacgccg acagaggacg ggtctgagga acctgggagt   180
gaaacttctg acgctaagtc tacgcctact gcggaggcgg aggaggcagg aataggagac   240
acaccatcac ttgaagacga ggcagcagga cacgtaaccc aagcgagaat ggtttctaag   300
tccaaagatg gaaccggatc cgatgacaaa aaggccaagg gagcagatgg caaaacaaaa   360
ataacgacac cgagggtgc ggctccccc ggtcaaaagg gacaggcaaa tgccacgcgc    420
atccctgcta aaacacccc ggcgccgaaa accccccctt catccggaga gccacccaag   480
tctggtgata agcgggta tagttccccc ggtagtccgg ggactccagg atcacgcagc    540
agaacgccat ccctgccaac cccacccact agagagccca aaaaggtcgc agtcgttcgc   600
actccgccaa aagcccttc ctcagcgaaa agccgcctgc agacggcacc tgtccccatg    660
cctgaccta aaaatgttaa aagcaaaatc ggtagtacca aaaatctcaa gcatcagcca   720
ggagggggga aggttcagat catcaataag aagctggacc tgtctaacgt gcagagcaag   780
tgtgaagca agataacat aaagcacgtt tggggggcg gaagcgtaca gattgtgtat    840
aagccggtgg acctctcaaa agtaacattc aagtgtggga gtctgggcaa catccatcac   900
aaacccgggg gcggtcaggt agaggtgaaa agcgaaaagc tcgatttaa ggatagggta    960
cagagtaaaa ttgggtctct ggacaacata acacacgtac caggcggagg caataagaag   1020
atagaaacgc ataaactcac gttccgagag aacgctaaag caaagactga ccacggggct   1080
gagattgtat acaagagtcc ggtcgtctct ggggacactt ccccccgaca cctttctaac   1140
gttagttcca ctggtagtat tgacatggtc gacagccctc aacttgccac tttggcagac   1200
gaggtcagtg ctagtcttgc aaagcagggc ttgtga                              1236

SEQ ID NO: 84             moltype = AA  length = 411
FEATURE                   Location/Qualifiers
REGION                    1..411
                          note = Synthetic
source                    1..411
                          mol_type = protein
                          organism = synthetic construct
SEQUENCE: 84
AEPRQEFEVM EDHAGTYGLG DRKDQGGYTM HQDQEGDTDA GLKESPLQTP TEDGSEEPGS    60
ETSDAKSTPT AEAEEAGIGD TPSLEDEAAG HVTQARMVSK SKDGTGSDDK KAKGADGKTK   120
ITTPRGAAPP GQKGQANATR IPAKTPPAPK TPPSSGEPPK SGDRSGYSSP GSPGTPGSRS   180
RTPSLPTPPT REPKKVAVVR TPPKSPSSAK SRLQTAPVPM PDLKNVKSKI GSTENLKHQP   240
GGGKVQIINK KLDLSNVQSK CGSKDNIKHV LGGGSVQIVY KPVDLSKVTF KCGSLGNIHH   300
KPGGGQVEVK SEKLDFKDRV QSKIGSLDNI THVPGGGNKK IETHKLTFRE NAKAKTDHGA   360
EIVYKSPVVS GDTSPRHLSN VSSTGSIDMV DSPQLATLAD EVSASLAKQG L            411

SEQ ID NO: 85             moltype = DNA  length = 14873
FEATURE                   Location/Qualifiers
misc_feature              1..14873
                          note = Synthetic
misc_feature              217..397
                          note = LTR
misc_feature              444..569
                          note = HIV-1 Psi
misc_feature              1062..1295
                          note = RRE
misc_feature              1822..1939
                          note = cPPT/CTS
misc_feature              4120..4195
                          note = gRNA Scaffold
misc_feature              4487..4496
                          note = Kozak
misc_feature              4493..8596
                          note = Cas9 CDS
misc_feature              8597..8644
                          note = NLS
misc_feature              8645..8668
                          note = FLAG
misc_feature              8678..8734
                          note = P2A
misc_feature              8735..9331
                          note = PuroR
misc_feature              9347..9935
```

| | | |
|---|---|---|
| | note = WPRE | |
| misc_feature | 9818..9829 | |
| | note = Factor Xa site | |
| misc_feature | 10007..10240 | |
| | note = LTR | |
| misc_feature | 10542..10970 | |
| | note = F1 ori | |
| misc_feature | 11164..11299 | |
| | note = SV40 ori | |
| misc_feature | 11427..11801 | |
| | note = BleoR | |
| misc_feature | 12125..12141 | |
| | note = Lac operator | |
| misc_feature | 12194..12215 | |
| | note = CAP binding site | |
| misc_feature | 12503..13091 | |
| | note = Ori | |
| misc_feature | 13262..14122 | |
| | note = AmpR | |
| source | 1..14873 | |
| | mol_type = other DNA | |
| | organism = synthetic construct | |

SEQUENCE: 85

```
tgatgcggtt ttggcagtac atcaatgggc gtggatagcg gtttgactca cggggatttc   60
caagtctcca ccccattgac gtcaatggga gtttgttttg gcaccaaaat caacgggact  120
ttccaaaatg tcgtaacaac tccgccccat tgacgcaaat gggcggtagg cgtgtacggt  180
gggaggtcta tataagcagc gcgttttgcc tgtactgggt ctctctggtt agaccagatc  240
tgagcctggg agctctctgg ctaactaggg aacccactgc ttaagcctca ataaagcttg  300
ccttgagtgc ttcaagtagt gtgtgcccgt ctgttgtgtg actctggtaa ctagagatcc  360
ctcagaccct tttagtcagt gtggaaaatc tctagcagtg gcgcccgaac agggacttga  420
aagcgaaagg gaaaccagag gagctctctc gacgcaggac tcggcttgct gaagcgcgca  480
cggcaagagg cgaggggcgg cgactggtga gtacgccaaa aattttgact agcggaggct  540
agaaggagag agatgggtgc gagagcgtca gtattaagcg gggagaatt agatcgcgat  600
gggaaaaaat tcggttaagg ccagggggaa agaaaaaata taaattaaaa catatagtat  660
gggcaagcag ggagctagaa cgattcgcag ttaatcctgg cctgttagaa acatcagaag  720
gctgtagaca aatactggga cagctacaac catcccttca gacaggatca gaagaactta  780
gatcattata taatacagta gcaaccctct attgtgtgca tcaaaggata gagataaaag  840
acaccaagga agctttagac aagatagagg aagagcaaaa caaagtaag accaccgcac  900
agcaagcggc cgctgatctt cagacctgga gaggagata tgagggacaa ttggagaagt  960
gaattatata aatataaagt agtaaaaatt gaaccattag gagtagcacc caccaagcga 1020
aagagaagtg tggtgcagag agaaaaaaga gcagtgggaa taggagcttt gttccttggg 1080
ttcttgggag cagcaggaag cactatgggc gcagcgtcaa tgacgctgac ggtacaggcc 1140
agacaattat tgtctggtat agtgcagcag cagaacaatt tgctgagggc tattgaggcg 1200
caacagcatc tgttgcaact cacagtctgg ggcatcaagc agctccaggc aagaatcctg 1260
gctgtggaaa gatacctaaa ggatcaacag ctcctgggga tttggggttg ctctggaaaa 1320
ctcatttgca ccactgctgt gccttggaat gctagttgga gtaataaaatc tctgaacag 1380
atttggaatc acacgacctg gatggagtgg gacagagaaa ttaacaatta cacaagctta 1440
atacactcct taattgaaga atcgcaaaac cagcaagaaa agaatgaaca agaattattg 1500
gaattagata aatgggcaag tttgtggaat tggtttaaca taacaaattg gctgtggtat 1560
ataaaattat tcataatgat agtaggaggc ttggtaggtt taagaatagt ttttgctgta 1620
ctttctatag tgaatagagt taggcaggga tattccacct tatcgtttca gacccacctc 1680
ccaaccccga ggggacccga caggcccgaa ggaatagaag aagaaggtgg agagagagac 1740
agagacagat ccattcgatt agtgaacgga tcggcactgc gtgcgccaat tctgcagaca 1800
aatggcagta ttcatccaca attttaaaag aaaaggggggg attgggggt acagtgcagg 1860
ggaaagaata gtagacataa tagcaacaga catacaaact aaagaattac aaaaacaaat 1920
tacaaaaatt caaaattttc gggtttatta cagggacagc agagatccag tttggttaat 1980
taaggtaccg agggcctatt tcccatgatt ccttcatatt tgcatatacg atacaaggct 2040
gttagagaga taattagaat taatttgact gtaaacacaa agatattagt acaaaatacg 2100
tgacgtagaa agtaataatt tcttgggtag tttgcagttt taaaattagt tttaaaatg 2160
gactatcata tgcttaccgt aacttgaaag tatttcgatt tcttggcttt atatatcttg 2220
tggaaaggac gaaacaccgg agacggttgt aaatgagcac acaaaataca catgctaaaa 2280
tattatattc tatgaccttt ataaaatcaa ccaaatctt cttttaata actttagtat 2340
caataattag aattttatg ttccttttg caaactttta ataaaatga gcaaaataaa 2400
aaaacgctag ttttagtaac tcgcgttgtt ttcttcacct ttaataatag ctactccaca 2460
acttgttcct aagcggtcag ctcctgcttc aatcattttt tgagcatctt caaatgttct 2520
aactccacca gctgctttaa ctaaagcatt gtctttaaca actgacttca ttagtttaac 2580
atcttcaaat gttgcacctg attttgaaaa tcctgttgat gttttaacaa attctaatcc 2640
agcttcaaca gctatttcac aagctttcat gatttcttct tttgttaata aacaattttc 2700
cataatacat ttaacaacat gtgatccagc tgcttttttt acagctttca tgtcttctaa 2760
aactaattca taattttgt cttttaatgc accaatattt aataccatat caatttctgt 2820
tgcaccatct ttaattgctt cagaaacttc gaatgctttt gtagctgttg tgcatgcacc 2880
tagaggaaaa cctacaacat tgttattcc tacatttgtg ccttttaata attctttaca 2940
atagcttgtt caatatgaat taacacaaac tgttgcaaaa tcaaattcaa ttgcttcatc 3000
acataattgt ttaatttcag ctttcgtagc atctgttttt aataatgtgt gatctatata 3060
tttgtttagt tcattttttt ctcctatata ttcattttta attttaattc tttaataatt 3120
tcgtctactt taactttagc gttttgaaca gattcaccaa cacctataaa ataaattttt 3180
agtttaggtt cagttccact tgggcgaaca gcaaatcatg acttatcttc taaataaaat 3240
tttagtaagt cttgtcctgg catattatac attccatcga tgtagtcttc aacattaaca 3300
actttaagtc cagcaatttg agttaagggt gttgctctca atgatttcat taatggttca 3360
```

```
attttaatt tcttttcttc tggtttaaaa ttcaagttta aagtgaaagt gtaatatgca 3420
cccatttctt taaataaatc ttctaaatag tctactaatg ttttattttg ttttttataa 3480
aatcaagcag cctctgctat taatatagaa gcttgtattc catctttatc tctagctgag 3540
tcatcaatta catatccata actttcttca taagcaaaaa caaaatttaa tccgttatct 3600
tcttctttag caatttctct acccattcat ttaaatccag ttaaagtttt tacaatatta 3660
actccatatt tttcatgagc gattctatca cccaaatcac ttgttacaaa acttgaatat 3720
agagccggat tttttggaat gctatttaag cgttttagat ttgataattt tcaatcaatt 3780
aaaattggtc ctgtttgatt tccatctaat cttacaaaat gaccatcatg ttttattgcc 3840
attccaaatc tgtcagcatc tgggtcattc ataataataa tatctgcatc atgtttaata 3900
ccatattcaa gcggtatttt tcatgcagga tcaaattctg gatttggatt tacaacatt 3960
ttaaatgttt catcttcaaa tgcatgctct tcaacctcaa taacgttata tcctgattca 4020
cgtaatattt ttgggtaaa tttagttcct gttccattaa ctgcgctaaa aataattttt 4080
aaatctttt tagcttcttg ctctttttg tacgtctctg ttttagagct agaaatagca 4140
agttaaaata aggctagtcc gttatcaact tgaaaaagtg gcaccgagtc ggtgcttttt 4200
tgaattcgct agctaggtct tgaaaggagt gggaattggc tccggtgccc gtcagtgggc 4260
agagcgcaca tcgcccacag tccccgagaa gttgggggga gggtcggca attgatccgg 4320
tgcctagaga aggtggcgcg gggtaaactg gaaagtgat gtcgtgtact ggctccgcct 4380
ttttcccgag ggtggggag aaccgtatat aagtgcagta gtccgcgtga acgttctttt 4440
tcgcaacggg tttgccgcca gaacacagga ccgttctag agcgctgcca ccatggacaa 4500
gaagtacagc atcggcctgg acatcggcac caactctgtg ggctgggccg tgatcaccga 4560
cgagtacaag gtgccagca agaaattcaa ggtgctgggc aacaccgacc ggcacagcat 4620
caagaacac ctgatcggag ccctgctgtt cgacagcggc gaaacagccg aggccacccg 4680
gctgaagaga accgccagaa gaagatacac cagacggaag aaccggatct gctatctgca 4740
agagatcttc agcaacgaga tggccaaggt ggacgacagc ttcttccaca gactggaaga 4800
gtccttcctg gtggaagagg ataagaagca cgagcggcac cccatcttcg gcaacatcgt 4860
ggacgaggtg gcctaccacg agaagtaccc caccatctac caccctgaaga agaaactgtt 4920
ggacagcacc gacaaggccg acctgcggct gatctatctg gccctggccc acatgatcaa 4980
gttccggggc cacttcctga tcgagggcga cctgaacccc gacaacagcg acgtggacaa 5040
gctgttcatc cagctggtgc agacctacaa ccagctgttc gaggaaaacc ccatcaacgc 5100
cagcggcgtg gacgccaagg ccatcctgtc tgccagactg agcaagagca gacggctgga 5160
aaatctgatc gcccagctgc ccggcgagaa gaagaatggc ctgttcggaa acctgattgc 5220
cctgagcctg ggcctgaccc ccaacttcaa gagcaacttc gacctggccg aggatgccaa 5280
actgcagctg agcaaggaca cctacgacga cgacctggac aacctgctgg cccagatcgg 5340
cgaccagtac gccgacctgt ttctggccgc caagaacctg tccgacgcca tcctgctgag 5400
cgacatcctg agagtgaaca ccgagatcac caaggccccc ctgagcgcct ctatgatcaa 5460
gagatacgac gagcaccacc aggacctgac cctgctgaaa gctctcgtgc ggcagcagct 5520
gcctgagaag tacaaagaga ttttcttcga ccagagcaag aacggctacg ccggctacat 5580
tgacggcgga gccagccagg aagagttcta caagttcatc aagcccatcc tggaaaagat 5640
ggacggcacc gaggaactgc tcgtgaagct gaacagagag gacctgctgc ggaagcagcg 5700
gaccttcgac aacggcagca tccccacca gatccacctg ggagagctgc acgccattct 5760
gcggcggcag gaagattttt acccattcct gaaggacaac cgggaaaaga tcgagaagat 5820
cctgaccttc cgcatcccct actacgtggg ccctctggcc aggggaaaaca gcagattcgc 5880
ctggatgacc agaaagagcg aggaaaccat caccccccg aacttcgagg aagtggtgga 5940
caagggcgct tccgcccaga gcttcatcga gcggatgacc aacttcgata gaacctgcc 6000
caacgagaag gtgctgccca gcacagcct gctgtacgag tacttcaccg tgtataacga 6060
gctgaccaaa gtgaaatacg tgaccgaggg aatgagaaag cccgccttcc tgagcggcga 6120
gcagaaaaag gccatcgtgg acctgctgtt caagaccaac cggaaagtga ccgtgaagca 6180
gctgaaagag gactacttca gaaaaatcga gtgcttcgac tccgtggaaa tctccggcgt 6240
ggaagatcgg ttcaacgcct ccctgggcac ataccacgat ctgctgaaaa ttatcaagga 6300
caaggacttc ctggacaatg aggaaaacga ggacattctg gaagatatcg tgctgaccct 6360
gacactgttt gaggacagag agatgatcga ggaacgctga aaaacctatg cccacctgtt 6420
cgacgacaaa gtgatgaagc agctgaagcg gcggagatac accggctggg gcaggctgag 6480
ccggaagctg atcaacggca tccgggacaa gcagtccggc aagacaatcc tggatttcct 6540
gaagtccgac ggcttcgcca acagaaactt catgcagctg atccacgacg acagcctgac 6600
ctttaaagag gacatccaga agcccaggt gtccggcagc ggcgatagcc tgcacgagca 6660
cattgccaat ctggccggca gccccgccat taagaaggc atcctgcaga cagtgaaggt 6720
ggtgacagag ctcgtgaaag tgatgggccg gcacaagccc gagaacatcg tgatcgaaat 6780
ggccagagag aaccagacca cccagaaggg acagaagaac agccgcgaga gaatgaagcg 6840
gatcgagag ggcataaaag agtcgggcag ccagatcctg aaagaacacc ccgtgggaaa 6900
caccccagctg cagaacgaga agctgtacct gtactacctg cagaatgggc gggatatgta 6960
cgtggaccag gaactggaca tcaaccggct gtccgactac gatgtggacc atatcgtgcc 7020
tcagagcttt ctgaaggacg actccatcga caacaaggtg ctgaccagaa gcgacaagaa 7080
ccggggcaag agcgacaacg tgcctccga agaggtcgtg aagaagatga gaactactg 7140
gcggcagctg ctgaacgcca gctgattac ccagaagaag ttcgacaatc tgaccaaggc 7200
cgagagaggc ggcctgagcg aactggataa ggccggcttc atcaagagac agctggtgga 7260
aacccggcag atcacaaagc acgtggcaca gatcctggac tccgatgac acactaagta 7320
cgacgagaat gacaagctga tccgggaagt gaaagtgatc accctgaagt ccaagctggt 7380
gtccgatttc cggaaggatt tccagtttta caaagtgcgc gagatcaaca actaccacca 7440
cgcccacgac gcctacctga acgccgtcgt gggaaccgcc ctgatcaaaa agtaccctaa 7500
gctggaaagc gagttcgtgt acggcgacta caaggtgtac gacgtgcgga gatgatcgc 7560
caagagcgag caggaaatcg gcaaggctac cgccaagtac ttcttctaca gcaacatcat 7620
gaactttttc aagaccgaga ttaccctggc caacggcgag atccgaagc ggctctgat 7680
cgagacaaac ggcgaaaccg gggagatcgt gtgggataag gccgggat ttgccaccgt 7740
gcggaaagtg ctgagcatgc cccaagtgaa tatcgtgaaa aagaccgagg tgcagacagg 7800
cggcttcagc aaaagagtcta tcctgcccaa gaggaacagc gataagctga tcgccagaaa 7860
gaaggactgg gaccctaaga agtacggcgg cttcgacagc cccaccgtgg cctattctgt 7920
gctggtggtg gccaaagtgg aaaagggcaa gtccaagaaa ctgaagagtg tgaaagagct 7980
gctggggatc accatcatgg aaaagaagcag cttcgagaag aatcccatcg actttctgga 8040
agccaagggc tacaaagaag tgaaaaagga cctgatcatc aagctgccta agtactccct 8100
```

-continued

```
gttcgagctg gaaaacggcc ggaagagaat gctggcctct gccggcgaac tgcagaaggg   8160
aaacgaactg gccctgccct ccaaatatgt gaacttcctg tacctggcca gccactatga   8220
gaagctgaag ggctcccccg aggataatga gcagaaacag ctgtttgtgg aacagcacaa   8280
gcactacctg gacgagatca tcgagcagat cagcgagttc tccaagagag tgatcctggc   8340
cgacgctaat ctggacaaag tgctgtccgc ctacaacgag caccgggata agcccatcag   8400
agagcaggcc gagaatatca tccacctgtt taccctgacc aatctgggag ccctgccgc    8460
cttcaagtac tttgacacca ccatcgaccg gaagaggtac accagcacca agaggtgct    8520
ggacgccacc ctgatccacc agagcatcac cggcctgtac gagacacgga tcgacctgtc   8580
tcagctggga ggcgacaagc gacctgccgc cacaaagaag gctggacagg ctaagaagaa   8640
gaaagattac aaagacgatg acgataaggg atccggcgca acaaacttct ctctgctgaa   8700
acaagccgga gatgtcgaag agaatcctgg accgaccgag tacaagccca cggtgcgcct   8760
cgccacccgc gacgacgtcc cagggccgt acgcaccctc gccgccgcgt cgccgacta    8820
ccccgccacg cgccacaccg tcgatccgga ccgccacatc gagcgggtca ccgagctgca   8880
agaactcttc ctcacgcgcg tcgggctcga catcggcaag gtgtgggtcg cggacgacgg   8940
cgccgcggtg gcggtctgga ccacgccgga gagcgtcgaa gcgggggcgg tgttcgccga   9000
gatcggcccg cgcatggccg agttgagcgg ttccggcctg gccgcgcagc aacagatgga   9060
aggcctcctg gcgccgcacc ggcccaagga gcccgcgtgg ttcctggcca ccgtcggagt   9120
ctcgcccgac caccagggca agggtctggg cagcgccgtc gtgctccccg gagtggaggc   9180
ggccgagcgc gccggggtgc ccgccttcct ggagacctcc gcgccccgca acctcccctt   9240
ctacgagcgg ctcggcttca ccgtcaccgc cgacgtcgag gtgcccgaag accgcgcac    9300
ctggtgcatg acccgcaagc ccggtgcctg aacgcgttaa gtcgacaatc aacctctgga   9360
ttacaaaatt tgtgaaagat tgactggtat tcttaactat gttgctcctt ttacgctatg   9420
tggatacgct gctttaatgc ctttgtatca tgctattgct tcccgtatgg ctttcatttt   9480
ctcctccttg tataaatcct ggttgctgtc tctttatgag gagttgtggc ccgttgtcag   9540
gcaacgtggc gtggtgtgca ctgtgtttgc tgacgcaacc cccactggtt ggggcattgc   9600
caccacctgt cagctccttt ccgggactt cgctttcccc ctccctattg ccacgcgga    9660
actcatcgcc gcctgccttg cccgctgctg gacaggggcc cggtcgttgg gcactgacaa   9720
ttccgtggtg ttgtcgggga atcatcgtc ctttccttgg ctgctcgcct gtgttgccac    9780
ctggattctg cgcgggacgt ccttctgcta cgtcccttcg gccctcaatc cagcggacct   9840
tccttcccgc ggcctgctgc cggctctgcg gcctcttccg cgtcttcgcc ttcgccctca   9900
gacgagtcgg atctcccttt gggccgcctc cccgcgtcga ctttaagacc aatgacttac   9960
aaggcagctg tagatcttag ccactttta aaagaaaagg ggggactgga agggctaatt   10020
cactcccaac gaagacaaga tctgcttttt gcttgtactg ggtctctctg gttagaccag   10080
atctgagcgt gggagctctc tggctaacta gggaacccac tgcttaagcc tcaataaagc   10140
ttgccttgag tgcttcaagt agtgtgtgcc cgtctgttgt gtgactctgg taactagaga   10200
tccctcagac cctttagtc agtgtggaaa atctctagca gggcccgttt aaacccgctg    10260
atcagcctcg actgtgcctt ctagttgcca gccatctgtt gtttgcccct ccccgtgcc    10320
ttccttgacc ctggaaggtg ccactcccac tgtcctttcc taataaaatg aggaaattgc   10380
atcgcattgt ctgagtaggt gtcattctat tctggggggt ggggtgggc aggacagcaa    10440
gggggaggat tgggaagaca atagcaggca tgctggggat gcggtgggct ctatggcttc   10500
tgaggcggaa agaaccagct ggggctcag ggggtatccc cacgcgccct gtagcggcgc    10560
attaagcgcg gcgggtgtgg tggttacgcg cagcgtgacc gctacacttg ccagcgccct   10620
agcgcccgct cctttcgctt tcttcccttc ctttctcgcc acgttcgccg gctttccccg   10680
tcaagctcta aatcggggc tccctttagg gttccgattt agtgctttac ggcacctcga   10740
ccccaaaaaa cttgattagg gtgatggttc acgtagtttg ggccatcgccct gatagacggt    10800
ttttcgccct ttgacgttgg agtccacgtt ctttaatagt ggactcttgt tccaaactgg   10860
aacaactc aaccctatct cggtctatc ttttgattta tagggattt tgccgatttc        10920
ggcctattgg ttaaaaatg agctgattta acaaaaattt aacgcgaatt aattctgtgg   10980
aatgtgtgtc agttagggtg tggaaagtcc ccaggctccc cagcaggcag aagtatgcaa   11040
agcatgcatc tcaattagtc agcaaccagg tgtgaaagt ccccaggctc cccagcaggc     11100
agaagtatgc aaagcatgca tctcaattag tcagcaacca tagtcccgcc cctaactccg   11160
cccatcccgc ccctaactcc gcccagttcc gcccattctc cgccccatgg ctgactaatt   11220
tttttatt atgcagaggc cgaggccgcc tctgcctctg agctattcca gaagtagtga      11280
ggaggctttt ttggaggcct aggcttttgc aaaaagctcc cgggagcttg tatatccatt   11340
ttcggatctg atcagcacgt gttgacaatt aatcatcggc atagtatatc ggcatagtat   11400
aatacgacaa ggtgaggaac taaaccatgg ccaagttgac cagtgccgtt ccggtgctca   11460
ccgcgcgcga cgtcgccgga gcggtcgagt tctggaccga ccgctcgggg ttctcccggg   11520
acttcgtgga ggacgacttc gccggtgtgg tccgggacga cgtgaccctg ttcatcagcg   11580
cggtccagga caaggtggtg ccggacaaca ccctggcctg ggtgtgggtg cgcggcctgg   11640
acgagctgta cgccgagtgg tcggaggtcg tgtccacgag cttccgggag gcctccgggc   11700
cggccatgac cgagatcggc gagcagccgt ggggcgggga gttcgccctg cgcgacccgg   11760
ccggcaactg cgtgcacttc gtggccgagg agcaggactg cacgtgcta cgagatttcg     11820
attccaccgc cgccttctat gaaaggttgg gcttcggaat cgttttccgg gacgccggct   11880
ggatgatcct ccagcgcggg gatctcatgc tggagttcgc ccacccc aacttgttta      11940
ttgcagctta taatggttac aaataaagca atagcatcac aaatttcaca aataaagcat   12000
tttttcact gcattctagt tgtggtttgt ccaaactcat caatgtatct tatcatgtct   12060
gtataccgtc gacctctagc tagagcttgg cgtaatcatg gtcatagctg tttcctgtgt   12120
gaaattgtta tccgctcaca attccacaca acatacgagc cggaagcata aagtgtaaag   12180
cctggggtgc ctaatgagtg agctaactca cattaattgc gttgcgctca ctgcccgctt   12240
tccagtcggg aaacctgtcg tgccagctgc attaatgaat cggccaacgc gcggggagag   12300
gcggtttgcg tattgggcgc tcttccgctt cctcgctcac tgactcgctg cgctcggtcg   12360
ttcggctgcg gcgagcggta tcagctcact caaaggcgg aatacggtta ccacagaat     12420
cagggaataa cgcaggaaag aacatgtgag caaaaggcca gcaaaggcc aggaaccgta    12480
aaaaggccgc gttgctggcg ttttccata ggctccgccc cctgacgag catcacaaa      12540
atcgacgctc aagtcagagg tggcgaaacc cgacaggact ataaagatac caggcgtttc   12600
ccctgaaag ctccctcgtg cgctctcctg ttccgaccct gccgcttacc ggatacctgt     12660
ccgcctttct cccttcggga agcgtggcgc tttctcatag ctcacgctgt aggtatctca   12720
gttcggtgta ggtcgttcgc tccaagctgg gctgtgtgca cgaacccccc gttcagcccg   12780
accgctgcgc cttatccggt aactatcgtc ttgagtccaa cccggtaaga cacgacttat   12840
```

-continued

```
cgccactggc agcagccact ggtaacagga ttagcagagc gaggtatgta ggcggtgcta   12900
cagagttctt gaagtggtgg cctaactacg gctacactag aagaacagta tttggtatct   12960
gcgctctgct gaagccagtt accttcggaa aaagagttgg tagctcttga tccggcaaac   13020
aaaccaccgc tggtagcggt ggttttttg tttgcaagca gcagattacg cgcagaaaaa    13080
aaggatctca agaagatcct ttgatctttt ctacggggtc tgacgctcag tggaacgaaa   13140
actcacgtta agggattttg gtcatgagat tatcaaaaag gatcttcacc tagatccttt   13200
taaattaaaa atgaagtttt aaatcaatct aaagtatata tgagtaaact tggtctgaca   13260
gttaccaatg cttaatcagt gaggcaccta tctcagcgat ctgtctattt cgttcatcca   13320
tagttgcctg actcccgtc gtgtagataa ctacgatacg ggagggctta ccatctggcc    13380
ccagtgctgc aatgataccg cgagacccac gctcaccggc tccagattta tcagcaataa   13440
accagccagc cggaagggcc gagcgcagaa gtggtcctgc aactttatcc gcctccatcc   13500
agtctattaa ttgttgccgg gaagctagag taagtagttc gccagttaat agtttgcgca   13560
acgttgttgc cattgctaca ggcatcgtgg tgtcacgctc gtcgtttggt atggcttcat   13620
tcagctccgg ttcccaacga tcaaggcgag ttacatgatc cccatgttg tgcaaaaaag   13680
cggttagctc cttcggtcct ccgatcgttg tcagaagtaa gttggccgca gtgttatcac   13740
tcatggttat ggcagcactg cataattctc ttactgtcat gccatccgta agatgctttt   13800
ctgtgactgg tgagtactca accaagtcat tctgagaata gtgtatgcgg cgaccgagtt   13860
gctcttgccc ggcgtcaata cgggataata ccgcgccaca tagcagaact ttaaaagtgc   13920
tcatcattgg aaaacgttct cggggcgaaa actctcaag gatcttaccg ctgttgagat    13980
ccagttcgat gtaacccact cgtgcaccca actgatcttc agcatctttt actttcacca   14040
gcgtttctgg gtgagcaaaa acaggaaggc aaaatgccgc aaaaaaggga ataagggcga   14100
cacggaaatg ttgaatactc atactcttcc tttttcaata ttattgaagc atttatcagg   14160
gttattgtct catgagcgga tacatatttg aatgtattta gaaaaataaa caaataggg    14220
ttccgcgcac atttccccga aaagtgccac ctgacgtcga cggatcggga gatctcccga   14280
tcccctatgg tgcactctca gtacaatctg ctctgatgcc gcatagttaa gccagtatct   14340
gctccctgct tgtgtgttgg aggtcgctga gtagtgcgcg agcaaaattt aagctacaac   14400
aaggcaaggc ttgaccgaca attgcatgaa gaatctgctt agggttagc gttttgcgct    14460
gcttcgcgat gtacgggcca gatatacgcg ttgacattga ttattgacta gttattaata   14520
gtaatcaatt acgggtcat tagttcatag cccatatatg gagttccgcg ttacataact    14580
tacggtaaat ggcccgcctg gctgaccgcc caacgacccc cgcccattga cgtcaataat   14640
gacgtatgtt cccatagtaa cgccaatagg gactttccat tgacgtcaat gggtggagta   14700
tttacggtaa actgcccact tggcagtaca tcaagtgtat catatgccaa gtacgccccc   14760
tattgacgtc aatgacggta aatggcccgc ctggcattat gcccagtaca tgaccttatg   14820
ggactttcct acttggcagt acatctacgt attagtcatc gctattacca tgg          14873

SEQ ID NO: 86           moltype = DNA   length = 4104
FEATURE                 Location/Qualifiers
misc_feature            1..4104
                        note = Synthetic
source                  1..4104
                        mol_type = other DNA
                        organism = synthetic construct
SEQUENCE: 86
atggacaaga agtacagcat cggcctggac atcggcacca actctgtggg ctgggccgtg    60
atcaccgacg agtacaaggt gcccagcaag aaattcaagg tgctgggcaa caccgaccgg   120
cacagcatca agaagaacct gatcggagcc ctgctgttcg acagcggcga aacagccgag   180
gccacccggc tgaagagaac cgccagaaga agatacacca gacgaagaa ccggatctgc    240
tatctgcaag agatcttcag caacgagatg gccaaggtgg acgacagctt cttccacaga   300
ctggaagagt ccttcctggt ggaagaggat aagaagcacg agcggcaccc catcttcggc   360
aacatcgtgg acgaggtggc ctaccacgag aagtacccca ccatctacca cctgagaaag   420
aaactggtgg acagcaccga caaggccgac ctgcggctga tctatctggc cctggcccac   480
atgatcaagt tccggggcca cttcctgatc gagggcgacc tgaaccccga caacagcgac   540
gtggacaagc tgttcatcca gctggtgcag acctacaacc agctgttcga ggaaaacccc   600
atcaacgcca gcggcgtgga cgccaaggcc atcctgtctg ccagactgag caagagcaga   660
cggctggaaa atctgatcgc ccagctgccc ggcgagaaga agaatggcct gttcggaaac   720
ctgattgccc tgagcctggg cctgaccccc aacttcaaga gcaacttcga cctggccgag   780
gatgccaaac tgcagctgag caaggacacc tacgacgacg acctggacaa cctgctggcc   840
cagatcggcg accagtacgc cgacctgttt ctggccgcca gaaccctgtc cgacgccatc   900
ctgctgagcg acatcctgag agtgaacacc gagatcacca aggcccccct gagcgcctct   960
atgatcaaga gatacgacga gcaccaccag gacctgaccc tgctgaaagc tctcgtgcgg   1020
cagcagctgc ctgagaagta caaagagatt ttcttcgacc agagcaagaa cggctacgcc   1080
ggctacattg acggcggagc cagccaggaa gagttctaca agttcatcaa gcccatcctg   1140
gaaaagatgg acggcaccga ggaactgctc gtgaagctga acagagagga cctgctgcgg   1200
aagcagcgga ccttcgacaa cggcagcatc ccccaccagg tccacctggg agagctgcac   1260
gccattctgc ggcggcagga agattttac ccattcctga aggacaaccg ggaaaagatc    1320
gagaagatcc tgaccttccg catccctac tacgtgggcc ctctggccag gggaaacagc    1380
agattcgcct ggatgaccag aaagagcgag gaaaccatca cccctggaa cttcgaggaa    1440
gtggtggaca agggcgcttc cgcccagagc ttcatcgagc ggatgaccaa cttcgataag   1500
aacctgccca acgagaaggt gctgcccaag cacagcctgc tgtacgagta cttcaccgtg   1560
tataacgagc tgaccaaagt gaaatacgtg accgagggaa tgagaaagcc cgccttcctg   1620
agcggcgagc agaaaaaggc catcgtggac ctgctgttca gaccaaccg gaaagtgacc    1680
gtgaagcagc tgaaagagga ctacttcaag aaaatcgagt gcttcgactc cgtggaaatc   1740
tccggcgtgg aagatcggtt caacgcctcc ctgggcacat accacgatct gctgaaaatt   1800
atcaaggaca aggacttcct ggacaatgag gaaaacgagg acattctgga agatatcgtg   1860
ctgaccctga cactgtttga ggacagagag atgatcgagg aacggctgaa aacctatgcc   1920
cacctgttcg acgacaaagt gatgaagcag ctgaagcgga ggagatacac cggctggggc   1980
aggctgagcc ggaagctgat caacggcatc cgggacaagc agtccggcaa gacaatcctg   2040
gatttcctga agtccgacgg cttcgccaac agaaacttca tgcagctgat ccacgacgac   2100
agcctgacct ttaaagagga catccagaaa gcccaggtgt ccggccaggg cgatagcctg   2160
```

```
cacgagcaca ttgccaatct ggccggcagc cccgccatta agaagggcat cctgcagaca  2220
gtgaaggtgg tggacgagct cgtgaaagtg atgggccggc acaagcccga gaacatcgtg  2280
atcgaaatgg ccagagagaa ccagaccacc cagaagggac agaagaacag ccgcgagaga  2340
atgaagcgga tcgaagaggg catcaaagag ctggcagcc agatcctgaa agaacacccc  2400
gtggaaaaca cccagctgca gaacgagaag ctgtacctgt actacctgca gaatgggcgg  2460
gatatgtacg tggaccagga actggacatc aaccggctgt ccgactacga tgtggaccat  2520
atcgtgcctc agagctttct gaaggacgac tccatcgaca caaaggtgct gaccagaagc  2580
gacaagaacc ggggcaagag cgacaacgtg ccctccgaag aggtcgtgaa gaagatgaag  2640
aactactggc ggcagctgct gaacgccaag ctgattaccc agagaaagtt cgacaatctg  2700
accaaggccg agagaggcgg cctgagcgaa ctggataagg ccggcttcat caagagacag  2760
ctggtggaaa cccggcagat cacaaagcac gtgcacagat cctggactcc cggatgaac  2820
actaagtacg acgagaatga caagctgatc cgggaagtga agtgatcac cctgaagtcc  2880
aagctggtgt ccgatttccg gaaggatttc cagtttaca aagtgcgcga gatcaacaac  2940
taccaccacg cccacgacgc ctacctgaac gccgtcgtgg gaaccgccct gatcaaaaag  3000
taccctaagc tggaaagcga gttcgtgtac ggcgactaca aggtgtacga cgtgcggaag  3060
atgatcgcca gagcgagca ggaaatcggc aaggctaccg ccaagtactt cttctacagc  3120
aacatcatga acttttcaa gaccgagatt accctggcca acggcgagat ccggaagcgg  3180
cctctgatcg agacaaacgg cgaaaccggg gatgtcgtgt gggataaggg ccggattc  3240
gccaccgtgc ggaaagtgct gagcatgccc caagtgaata tcgtgaaaaa gaccgaggtg  3300
cagacaggcg gcttcagcaa agagtctatc ctgcccaaga ggaacagcga taagctgatc  3360
gccagaaaga aggactggga ccctaagaag tacgcggct cgacagccc caccgtggcc  3420
tattctgtgc tggtggtggc caaagtgaaa aggggaaaagt ccaagagtgtg  3480
aaagagctgc tggggatcac catcatgaa agaagcagct cgagaagaa tcccatcgac  3540
tttctggaag ccaagggcta caaagaagtg aaaaaggacc tgatcatcaa gctgcctaag  3600
tactccctgt tcgagctgga aaacggccgg aagaatgc tggcctctgc cggcgaactg  3660
cagaagggaa acgaactggc cctgccctcc aaatatgtga acttcctgta cctggccagc  3720
cactatgaga agctgaaggg ctccccccgag gataatgagc agaaacagct gttgtggaa  3780
cagcacaagc actacctgga cgagatcatc gagcagatca gcgagttctc caagagagtg  3840
atcctggccg acgctaatct ggacaaagtg ctgtccgcct acaacaagca ccgggataag  3900
cccatcagag agcaggccga aatatcatc cacctgttta ccctgaccaa tctgggagcc  3960
cctgccgcct tcaagtactt tgacaccacc atcgaccgga agaggtacac cagcaccaaa  4020
gaggtgctgg acgccaccct gatccaccag agcatcaccg gcctgtacga gacacggatc  4080
gacctgtctc agctggggagg cgac                                         4104
```

```
SEQ ID NO: 87          moltype = AA   length = 1368
FEATURE                Location/Qualifiers
REGION                 1..1368
                       note = Synthetic
source                 1..1368
                       mol_type = protein
                       organism = synthetic construct
SEQUENCE: 87
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 88          moltype = AA   length = 31
FEATURE                Location/Qualifiers
source                 1..31
                       mol_type = protein
                       organism = Homo sapiens
SEQUENCE: 88
QTAPVPMPDL KNVKSKIGST ENLKHQPGGG K                                    31

SEQ ID NO: 89          moltype = AA   length = 31
FEATURE                Location/Qualifiers
source                 1..31
                       mol_type = protein
                       organism = Homo sapiens
```

-continued

```
SEQUENCE: 89
VQIINKKLDL SNVQSKCGSK DNIKHVPGGG S                                  31

SEQ ID NO: 90           moltype = AA  length = 31
FEATURE                 Location/Qualifiers
source                  1..31
                        mol_type = protein
                        organism = Homo sapiens
SEQUENCE: 90
VQIVYKPVDL SKVTSKCGSL GNIHHKPGGG Q                                  31

SEQ ID NO: 91           moltype = AA  length = 32
FEATURE                 Location/Qualifiers
source                  1..32
                        mol_type = protein
                        organism = Homo sapiens
SEQUENCE: 91
VEVKSEKLDF KDRVQSKIGS LDNITHVPGG GN                                 32

SEQ ID NO: 92           moltype = DNA  length = 93
FEATURE                 Location/Qualifiers
source                  1..93
                        mol_type = other DNA
                        organism = Homo sapiens
SEQUENCE: 92
cagacagccc ccgtgccat gccagacctg aagaatgtca agtccaagat cggctccact    60
gagaacctga agcaccagcc gggaggcggg aag                                93

SEQ ID NO: 93           moltype = DNA  length = 93
FEATURE                 Location/Qualifiers
source                  1..93
                        mol_type = other DNA
                        organism = Homo sapiens
SEQUENCE: 93
gtgcagataa ttaataagaa gctggatctt agcaacgtcc agtccaagtg tggctcaaag   60
gataatatca aacacgtccc gggaggcggc agt                                93

SEQ ID NO: 94           moltype = DNA  length = 93
FEATURE                 Location/Qualifiers
source                  1..93
                        mol_type = other DNA
                        organism = Homo sapiens
SEQUENCE: 94
gtgcaaatag tctacaaacc agttgacctg agcaaggtga cctccaagtg tggctcatta   60
ggcaacatcc atcataaacc aggaggtggc cag                                93

SEQ ID NO: 95           moltype = DNA  length = 96
FEATURE                 Location/Qualifiers
source                  1..96
                        mol_type = other DNA
                        organism = Homo sapiens
SEQUENCE: 95
gtggaagtaa aatctgagaa gcttgacttc aaggacagag tccagtcgaa gattgggtcc   60
ctggacaata tcacccacgt ccctggcgga ggaaat                             96

SEQ ID NO: 96           moltype = AA  length = 133
FEATURE                 Location/Qualifiers
source                  1..133
                        mol_type = protein
                        organism = Homo sapiens
SEQUENCE: 96
LQTAPVPMPD LKNVKSKIGS TENLKHQPGG KVQIINKKL DLSNVQSKCG SKDNIKHVPG   60
GGSVQIVYKP VDLSKVTSKC GSLGNIHHKP GGGQVEVKSE KLDFKDRVQS KIGSLDNITH  120
VPGGGNKKIE THK                                                     133

SEQ ID NO: 97           moltype = DNA  length = 399
FEATURE                 Location/Qualifiers
source                  1..399
                        mol_type = other DNA
                        organism = Homo sapiens
SEQUENCE: 97
ctgcagacag ccccgtgcc catgccagac ctgaagaatg tcaagtccaa gatcggctcc    60
actgagaacc tgaagcacca gccgggaggc gggaaggtgc agataattaa taagaagctg  120
gatcttagca acgtccagtc caagtgtggc tcaaaggata atatcaaaca cgtcccggga  180
ggcggcagtg tgcaaatagt ctacaaacca gttgacctga gcaaggtgac ctccaagtgt  240
ggctcattag gcaacatcca tcataaacca ggaggtggcc aggtgaaagt aaaatctgag  300
aagcttgact tcaaggacag agtccagtcg aagattgggt ccctggacaa tatcacccac  360
gtccctggcg aggaaataa aaagattgaa acccacaag                          399
```

```
SEQ ID NO: 98              moltype = AA  length = 133
FEATURE                    Location/Qualifiers
source                     1..133
                           mol_type = protein
                           organism = Homo sapiens
SEQUENCE: 98
LQTAPVPMPD LKNVKSKIGS TENLKHQPGG GKVQIINKKL DLSNVQSKCG SKDNIKHVSG      60
GGSVQIVYKP VDLSKVTSKC GSLGNIHHKP GGGQVEVKSE KLDFKDRVQS KIGSLDNITH     120
VPGGGNKKIE THK                                                        133

SEQ ID NO: 99              moltype = DNA  length = 399
FEATURE                    Location/Qualifiers
source                     1..399
                           mol_type = other DNA
                           organism = Homo sapiens
SEQUENCE: 99
ctgcagacag cccccgtgcc catgccagac ctgaagaatg tcaagtccaa gatcggctcc      60
actgagaacc tgaagcacca gccgggaggc gggaaggtgc agataattaa taagaagctg     120
gatcttagca acgtccagtc caagtgtggg tcaaaggata atatcaaaca cgtctcggga     180
ggcggcagtg tgcaaatagt ctacaaacca gttgacctga gcaaggtgac ctccaagtgt     240
ggctcattag gcaacatcca tcataaacca ggaggtggcc aggtggaagt aaaatctgag     300
aagcttgact tcaaggacag agtccagtcg aagattgggt ccctggacaa tatcacccac     360
gtccctggcg gaggaaataa aaagattgaa acccacaag                            399

SEQ ID NO: 100             moltype = RNA  length = 72
FEATURE                    Location/Qualifiers
misc_feature               1..72
                           note = Synthetic
source                     1..72
                           mol_type = other RNA
                           organism = synthetic construct
SEQUENCE: 100
aaacagcata gcaagttaaa ataaggctag tccgttatca acttgaaaaa gtggcaccga      60
gtcggtgctt tt                                                          72

SEQ ID NO: 101             moltype = RNA  length = 82
FEATURE                    Location/Qualifiers
misc_feature               1..82
                           note = Synthetic
source                     1..82
                           mol_type = other RNA
                           organism = synthetic construct
SEQUENCE: 101
gttggaacca ttcaaaacag catagcaagt taaaataagg ctagtccgtt atcaacttga      60
aaaagtggca ccgagtcggt gc                                               82

SEQ ID NO: 102             moltype = RNA  length = 83
FEATURE                    Location/Qualifiers
misc_feature               1..83
                           note = Synthetic
source                     1..83
                           mol_type = other RNA
                           organism = synthetic construct
SEQUENCE: 102
gttttagagc tagaaatagc aagttaaaat aaggctagtc cgttatcaac ttgaaaaagt      60
ggcaccgagt cggtgctttt ttt                                              83

SEQ ID NO: 103             moltype = RNA  length = 80
FEATURE                    Location/Qualifiers
misc_feature               1..80
                           note = Synthetic
source                     1..80
                           mol_type = other RNA
                           organism = synthetic construct
SEQUENCE: 103
gttttagagc tagaaatagc aagttaaaat aaggctagtc cgttatcaac ttgaaaaagt      60
ggcaccgagt cggtgctttt                                                  80

SEQ ID NO: 104             moltype = RNA  length = 92
FEATURE                    Location/Qualifiers
misc_feature               1..92
                           note = Synthetic
source                     1..92
                           mol_type = other RNA
                           organism = synthetic construct
SEQUENCE: 104
gtttaagagc tatgctggaa acagcatagc aagtttaaat aaggctagtc cgttatcaac      60
ttgaaaaagt ggcaccgagt cggtgctttt tt                                    92
```

```
SEQ ID NO: 105           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 105
tgggaggttg tcatcgtgat                                                       20

SEQ ID NO: 106           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 106
cagcctcttg ctcaggacgt                                                       20

SEQ ID NO: 107           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 107
cataagcctt gtcaaagccc                                                       20

SEQ ID NO: 108           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 108
ggaccacata agccttgtca                                                       20

SEQ ID NO: 109           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 109
catctttctt tagcaccaga                                                       20

SEQ ID NO: 110           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 110
ggtcttcatc tttctttagc                                                       20

SEQ ID NO: 111           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 111
ccattctcgg aagaggtctt                                                       20

SEQ ID NO: 112           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 112
tcagccattc tcggaagagg                                                       20
```

```
SEQ ID NO: 113          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 113
catgtatcct tcagccattc                                                   20

SEQ ID NO: 114          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 114
tgcttggcat tggcaccaca                                                   20

SEQ ID NO: 115          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 115
ggactgcttg gcattggcac                                                   20

SEQ ID NO: 116          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 116
gaaggcaccc aaagcagtcc                                                   20

SEQ ID NO: 117          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 117
tcgaaggcac ccaaagcagt                                                   20

SEQ ID NO: 118          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 118
tctcgaaggc acccaaagca                                                   20

SEQ ID NO: 119          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 119
attctcgaag gcacccaaag                                                   20

SEQ ID NO: 120          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 120
```

```
caccattctc gaaggcaccc                                              20

SEQ ID NO: 121           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 121
cacaccattc tcgaaggcac                                              20

SEQ ID NO: 122           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 122
atcacaccat tctcgaaggc                                              20

SEQ ID NO: 123           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 123
agagaacact acaagaaggc                                              20

SEQ ID NO: 124           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 124
tgcagactct ggaaactgtg                                              20

SEQ ID NO: 125           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 125
ccatagaccc tggagtacat                                              20

SEQ ID NO: 126           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 126
gaaacgatcc cagaaagatt                                              20

SEQ ID NO: 127           moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 127
gggactcggc tttctgtaat                                              20

SEQ ID NO: 128           moltype = DNA   length = 20
FEATURE                  Location/Qualifiers
misc_feature             1..20
                         note = Synthetic
source                   1..20
                         mol_type = other DNA
                         organism = synthetic construct
```

```
SEQUENCE: 128
caacttctcg tccatgatgc                                                    20

SEQ ID NO: 129          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 129
tgctcgatcc actggtccag                                                    20

SEQ ID NO: 130          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 130
ctcggagagc tgcttgcact                                                    20

SEQ ID NO: 131          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 131
cttgacctgg gactcggaga                                                    20

SEQ ID NO: 132          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 132
ccttctcgca gaggctcttg                                                    20

SEQ ID NO: 133          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 133
gtcaggattt ctttagcctt                                                    20

SEQ ID NO: 134          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 134
gacatcgaac ctcttgaacg                                                    20

SEQ ID NO: 135          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 135
agtgactgga catcgaacct                                                    20

SEQ ID NO: 136          moltype = DNA   length = 20
FEATURE                 Location/Qualifiers
misc_feature            1..20
                        note = Synthetic
source                  1..20
                        mol_type = other DNA
```

```
                        organism = synthetic construct
SEQUENCE: 136
gtacatctcc acacacagtg                                                  20

SEQ ID NO: 137          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 137
caggtaattt gtatctggtg                                                  20

SEQ ID NO: 138          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 138
gtctcccata aacaggtaat                                                  20

SEQ ID NO: 139          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 139
ctctcggtaa cgaaccttaa                                                  20

SEQ ID NO: 140          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 140
gtgatgcgct ctcggtaacg                                                  20

SEQ ID NO: 141          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 141
attccctcgg agtatggtga                                                  20

SEQ ID NO: 142          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 142
ctctcgtgat tccctcggag                                                  20

SEQ ID NO: 143          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 143
gaacccataa acctgtgtga                                                  20

SEQ ID NO: 144          moltype = DNA   length = 20
FEATURE                 Location/Qualifiers
misc_feature            1..20
                        note = Synthetic
source                  1..20
```

```
                          mol_type = other DNA
                          organism = synthetic construct
SEQUENCE: 144
tcgtcgtaga acccataaac                                                      20

SEQ ID NO: 145            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 145
aaggtctgtg aagtatttcc                                                      20

SEQ ID NO: 146            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 146
gtgagaggaa gatagtcaaa                                                      20

SEQ ID NO: 147            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 147
ccaaggcagt gagaggaaga                                                      20

SEQ ID NO: 148            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 148
accaccgtgt agacagaaga                                                      20

SEQ ID NO: 149            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 149
cagtgtgtct atggatggtg                                                      20

SEQ ID NO: 150            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 150
tcgagtgctc ggatgtgatc                                                      20

SEQ ID NO: 151            moltype = DNA   length = 20
FEATURE                   Location/Qualifiers
misc_feature              1..20
                          note = Synthetic
source                    1..20
                          mol_type = other DNA
                          organism = synthetic construct
SEQUENCE: 151
gtcacacatt ggaccctcat                                                      20

SEQ ID NO: 152            moltype = DNA   length = 20
FEATURE                   Location/Qualifiers
misc_feature              1..20
                          note = Synthetic
```

| | | |
|---|---|---|
| source | 1..20<br>mol_type = other DNA<br>organism = synthetic construct | |
| SEQUENCE: 152<br>ccaccacggt catctggatc | | 20 |
| SEQ ID NO: 153<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 153<br>gccaaaggta taaccagctc | | 20 |
| SEQ ID NO: 154<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 154<br>tgaggccatt ggcatgatta | | 20 |
| SEQ ID NO: 155<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 155<br>tggacaccaa cgtgaggcca | | 20 |
| SEQ ID NO: 156<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 156<br>gttatatccc tccatcacca | | 20 |
| SEQ ID NO: 157<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 157<br>tggcaccagt tatatccctc | | 20 |
| SEQ ID NO: 158<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 158<br>acgttccggt catggcacca | | 20 |
| SEQ ID NO: 159<br>FEATURE<br>misc_feature<br>source | moltype = DNA   length = 20<br>Location/Qualifiers<br>1..20<br>note = Synthetic<br>1..20<br>mol_type = other DNA<br>organism = synthetic construct | |
| SEQUENCE: 159<br>ttgttactac gttccggtca | | 20 |
| SEQ ID NO: 160<br>FEATURE<br>misc_feature | moltype = DNA   length = 20<br>Location/Qualifiers<br>1..20 | |

```
                        note = Synthetic
source                  1..20
                        mol_type = other DNA
                        organism = synthetic construct
SEQUENCE: 160
agcaatagtt tggagcactg                                              20

SEQ ID NO: 161          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 161
taccacaacg atagcaatag                                              20

SEQ ID NO: 162          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 162
agcttggtta ccacaacgat                                              20

SEQ ID NO: 163          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 163
agtgtcgtca agttccatga                                              20

SEQ ID NO: 164          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 164
gctgggtcaa actgcaagaa                                              20

SEQ ID NO: 165          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 165
acggttcatg gcaatactgt                                              20

SEQ ID NO: 166          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 166
gtcaatatac ggttcatggc                                              20

SEQ ID NO: 167          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 167
tgttgctctt cccatttcca                                              20

SEQ ID NO: 168          moltype = DNA  length = 20
FEATURE                 Location/Qualifiers
```

```
misc_feature            1..20
                        note = Synthetic
source                  1..20
                        mol_type = other DNA
                        organism = synthetic construct
SEQUENCE: 168
tttggtccgt gtgaaaacaa                                               20

SEQ ID NO: 169          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 169
caagagtttc agtcgagcca                                               20

SEQ ID NO: 170          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 170
gtcatctgga ttcaagagtt                                               20

SEQ ID NO: 171          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 171
agtccttgag gtgccctgga                                               20

SEQ ID NO: 172          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 172
ggcctgctga gtttgtttcc                                               20

SEQ ID NO: 173          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 173
agggttcaag cccacactgt                                               20

SEQ ID NO: 174          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 174
tgggtggaca ctggatgcta                                               20

SEQ ID NO: 175          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 175
gtggttgtca ttcctggtag                                               20

SEQ ID NO: 176          moltype = DNA  length = 20
```

```
                               -continued

FEATURE                 Location/Qualifiers
misc_feature            1..20
                        note = Synthetic
source                  1..20
                        mol_type = other DNA
                        organism = synthetic construct
SEQUENCE: 176
agggccatcc tcatatactg                                                   20

SEQ ID NO: 177          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 177
ctcatgtctc acagggccat                                                   20

SEQ ID NO: 178          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 178
taagggcgta gttttgttgg                                                   20

SEQ ID NO: 179          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 179
ttcagccagg cacaagccat                                                   20

SEQ ID NO: 180          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 180
gtaactgttt gctcgttctt                                                   20

SEQ ID NO: 181          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 181
ggaagcctgg ttctctttgg                                                   20

SEQ ID NO: 182          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 182
acgcataaac tcagggttct                                                   20

SEQ ID NO: 183          moltype = DNA  length = 20
FEATURE                 Location/Qualifiers
misc_feature            1..20
                        note = Synthetic
source                  1..20
                        mol_type = other DNA
                        organism = synthetic construct
SEQUENCE: 183
catgttgtca tctgggtaca                                                   20
```

```
SEQ ID NO: 184        moltype = DNA   length = 20
FEATURE               Location/Qualifiers
misc_feature          1..20
                      note = Synthetic
source                1..20
                      mol_type = other DNA
                      organism = synthetic construct
SEQUENCE: 184
gtcaacaacg tagaggatgc                                                  20

SEQ ID NO: 185        moltype = DNA   length = 20
FEATURE               Location/Qualifiers
misc_feature          1..20
                      note = Synthetic
source                1..20
                      mol_type = other DNA
                      organism = synthetic construct
SEQUENCE: 185
caggagtggc acatagtagt                                                  20

SEQ ID NO: 186        moltype = DNA   length = 20
FEATURE               Location/Qualifiers
misc_feature          1..20
                      note = Synthetic
source                1..20
                      mol_type = other DNA
                      organism = synthetic construct
SEQUENCE: 186
agtatttgag gcttcagctt                                                  20

SEQ ID NO: 187        moltype = DNA   length = 20
FEATURE               Location/Qualifiers
misc_feature          1..20
                      note = Synthetic
source                1..20
                      mol_type = other DNA
                      organism = synthetic construct
SEQUENCE: 187
aggtcccacg aaagctctca                                                  20

SEQ ID NO: 188        moltype = DNA   length = 20
FEATURE               Location/Qualifiers
misc_feature          1..20
                      note = Synthetic
source                1..20
                      mol_type = other DNA
                      organism = synthetic construct
SEQUENCE: 188
atcttctgct ttggatggac                                                  20

SEQ ID NO: 189        moltype = DNA   length = 20
FEATURE               Location/Qualifiers
misc_feature          1..20
                      note = Synthetic
source                1..20
                      mol_type = other DNA
                      organism = synthetic construct
SEQUENCE: 189
tttctttcga ggtggagttt                                                  20

SEQ ID NO: 190        moltype = DNA   length = 20
FEATURE               Location/Qualifiers
misc_feature          1..20
                      note = Synthetic
source                1..20
                      mol_type = other DNA
                      organism = synthetic construct
SEQUENCE: 190
aatgcctcgt tctgggtcag                                                  20

SEQ ID NO: 191        moltype = DNA   length = 20
FEATURE               Location/Qualifiers
misc_feature          1..20
                      note = Synthetic
source                1..20
                      mol_type = other DNA
                      organism = synthetic construct
SEQUENCE: 191
tccaactctc tcaatgcctc                                                  20
```

```
SEQ ID NO: 192              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 192
ttcccagtat tcaacccagg                                                    20

SEQ ID NO: 193              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 193
acatcccaga aattcccagt                                                    20

SEQ ID NO: 194              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 194
gcagccttca ttttctcgta                                                    20

SEQ ID NO: 195              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 195
ctttccactg ccaaaatctg                                                    20

SEQ ID NO: 196              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 196
cacggagatg gagttgctgt                                                    20

SEQ ID NO: 197              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 197
gggctgactc tgacttggaa                                                    20

SEQ ID NO: 198              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 198
agaggtttgg aacttatcag                                                    20

SEQ ID NO: 199              moltype = DNA   length = 20
FEATURE                     Location/Qualifiers
misc_feature                1..20
                            note = Synthetic
source                      1..20
                            mol_type = other DNA
                            organism = synthetic construct
SEQUENCE: 199
```

```
agttccaact gaggtttctc                                                    20

SEQ ID NO: 200          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 200
gtcactgtct gctgcaccct                                                    20

SEQ ID NO: 201          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 201
agatgccagc aagtcactgt                                                    20

SEQ ID NO: 202          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 202
agtgttggtc ctgacttgct                                                    20

SEQ ID NO: 203          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 203
gagtataggt tccagaccag                                                    20

SEQ ID NO: 204          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 204
ggtggaatct accgtggcag                                                    20

SEQ ID NO: 205          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 205
ttttgatggt tcctctccag                                                    20

SEQ ID NO: 206          moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 206
cgcacactca agagctgcta                                                    20

SEQ ID NO: 207          moltype = DNA   length = 20
FEATURE                 Location/Qualifiers
misc_feature            1..20
                        note = Synthetic
source                  1..20
                        mol_type = other DNA
                        organism = synthetic construct
```

```
SEQUENCE: 207
tgggtacaga ccagggtcaa                                                   20

SEQ ID NO: 208           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 208
gtctgagggc gagtagcaca                                                   20

SEQ ID NO: 209           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 209
cttcctttg agtgcaggac                                                    20

SEQ ID NO: 210           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 210
atgagagcaa tcgagatcca                                                   20

SEQ ID NO: 211           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 211
gccagaagag gaggaggtgt                                                   20

SEQ ID NO: 212           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 212
cccatgtgct ggactgtagc                                                   20

SEQ ID NO: 213           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 213
atgaatccca ggagtaagct                                                   20

SEQ ID NO: 214           moltype = DNA  length = 20
FEATURE                  Location/Qualifiers
misc_feature             1..20
                         note = Synthetic
source                   1..20
                         mol_type = other DNA
                         organism = synthetic construct
SEQUENCE: 214
ctcacttgtc tatgcctttg                                                   20

SEQ ID NO: 215           moltype = RNA  length = 20
FEATURE                  Location/Qualifiers
misc_feature             1..20
                         note = Synthetic
source                   1..20
                         mol_type = other RNA
```

```
                          organism = synthetic construct
SEQUENCE: 215
tgggaggttg tcatcgtgat                                                    20

SEQ ID NO: 216            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 216
cagcctcttg ctcaggacgt                                                    20

SEQ ID NO: 217            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 217
cataagcctt gtcaaagccc                                                    20

SEQ ID NO: 218            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 218
ggaccacata agccttgtca                                                    20

SEQ ID NO: 219            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 219
catctttctt tagcaccaga                                                    20

SEQ ID NO: 220            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 220
ggtcttcatc tttctttagc                                                    20

SEQ ID NO: 221            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 221
ccattctcgg aagaggtctt                                                    20

SEQ ID NO: 222            moltype = RNA   length = 20
FEATURE                   Location/Qualifiers
misc_feature              1..20
                          note = Synthetic
source                    1..20
                          mol_type = other RNA
                          organism = synthetic construct
SEQUENCE: 222
tcagccattc tcggaagagg                                                    20

SEQ ID NO: 223            moltype = RNA   length = 20
FEATURE                   Location/Qualifiers
misc_feature              1..20
                          note = Synthetic
source                    1..20
```

```
                            mol_type = other RNA
                            organism = synthetic construct
SEQUENCE: 223
catgtatcct tcagccattc                                                   20

SEQ ID NO: 224              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 224
tgcttggcat tggcaccaca                                                   20

SEQ ID NO: 225              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 225
ggactgcttg gcattggcac                                                   20

SEQ ID NO: 226              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 226
gaaggcaccc aaagcagtcc                                                   20

SEQ ID NO: 227              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 227
tcgaaggcac ccaaagcagt                                                   20

SEQ ID NO: 228              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 228
tctcgaaggc acccaaagca                                                   20

SEQ ID NO: 229              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 229
attctcgaag gcacccaaag                                                   20

SEQ ID NO: 230              moltype = RNA   length = 20
FEATURE                     Location/Qualifiers
misc_feature                1..20
                            note = Synthetic
source                      1..20
                            mol_type = other RNA
                            organism = synthetic construct
SEQUENCE: 230
caccattctc gaaggcaccc                                                   20

SEQ ID NO: 231              moltype = RNA   length = 20
FEATURE                     Location/Qualifiers
misc_feature                1..20
                            note = Synthetic
```

```
source                  1..20
                        mol_type = other RNA
                        organism = synthetic construct
SEQUENCE: 231
cacaccattc tcgaaggcac                                             20

SEQ ID NO: 232          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 232
atcacaccat tctcgaaggc                                             20

SEQ ID NO: 233          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 233
agagaacact acaagaaggc                                             20

SEQ ID NO: 234          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 234
tgcagactct ggaaactgtg                                             20

SEQ ID NO: 235          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 235
ccatagaccc tggagtacat                                             20

SEQ ID NO: 236          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 236
gaaacgatcc cagaaagatt                                             20

SEQ ID NO: 237          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 237
gggactcggc tttctgtaat                                             20

SEQ ID NO: 238          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 238
caacttctcg tccatgatgc                                             20

SEQ ID NO: 239          moltype = RNA   length = 20
FEATURE                 Location/Qualifiers
misc_feature            1..20
```

```
                    note = Synthetic
source              1..20
                    mol_type = other RNA
                    organism = synthetic construct
SEQUENCE: 239
tgctcgatcc actggtccag                                                    20

SEQ ID NO: 240      moltype = RNA  length = 20
FEATURE             Location/Qualifiers
misc_feature        1..20
                    note = Synthetic
source              1..20
                    mol_type = other RNA
                    organism = synthetic construct
SEQUENCE: 240
ctcggagagc tgcttgcact                                                    20

SEQ ID NO: 241      moltype = RNA  length = 20
FEATURE             Location/Qualifiers
misc_feature        1..20
                    note = Synthetic
source              1..20
                    mol_type = other RNA
                    organism = synthetic construct
SEQUENCE: 241
cttgacctgg gactcggaga                                                    20

SEQ ID NO: 242      moltype = RNA  length = 20
FEATURE             Location/Qualifiers
misc_feature        1..20
                    note = Synthetic
source              1..20
                    mol_type = other RNA
                    organism = synthetic construct
SEQUENCE: 242
ccttctcgca gaggctcttg                                                    20

SEQ ID NO: 243      moltype = RNA  length = 20
FEATURE             Location/Qualifiers
misc_feature        1..20
                    note = Synthetic
source              1..20
                    mol_type = other RNA
                    organism = synthetic construct
SEQUENCE: 243
gtcaggattt ctttagcctt                                                    20

SEQ ID NO: 244      moltype = RNA  length = 20
FEATURE             Location/Qualifiers
misc_feature        1..20
                    note = Synthetic
source              1..20
                    mol_type = other RNA
                    organism = synthetic construct
SEQUENCE: 244
gacatcgaac ctcttgaacg                                                    20

SEQ ID NO: 245      moltype = RNA  length = 20
FEATURE             Location/Qualifiers
misc_feature        1..20
                    note = Synthetic
source              1..20
                    mol_type = other RNA
                    organism = synthetic construct
SEQUENCE: 245
agtgactgga catcgaacct                                                    20

SEQ ID NO: 246      moltype = RNA  length = 20
FEATURE             Location/Qualifiers
misc_feature        1..20
                    note = Synthetic
source              1..20
                    mol_type = other RNA
                    organism = synthetic construct
SEQUENCE: 246
gtacatctcc acacacagtg                                                    20

SEQ ID NO: 247      moltype = RNA  length = 20
FEATURE             Location/Qualifiers
```

```
                        1..20
                        note = Synthetic
source                  1..20
                        mol_type = other RNA
                        organism = synthetic construct
SEQUENCE: 247
caggtaattt gtatctggtg                                                  20

SEQ ID NO: 248          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 248
gtctcccata aacaggtaat                                                  20

SEQ ID NO: 249          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 249
ctctcggtaa cgaaccttaa                                                  20

SEQ ID NO: 250          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 250
gtgatgcgct ctcggtaacg                                                  20

SEQ ID NO: 251          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 251
attccctcgg agtatggtga                                                  20

SEQ ID NO: 252          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 252
ctctcgtgat tccctcggag                                                  20

SEQ ID NO: 253          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 253
gaacccataa acctgtgtga                                                  20

SEQ ID NO: 254          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 254
tcgtcgtaga acccataaac                                                  20

SEQ ID NO: 255          moltype = RNA   length = 20
```

```
FEATURE                 Location/Qualifiers
misc_feature            1..20
                        note = Synthetic
source                  1..20
                        mol_type = other RNA
                        organism = synthetic construct
SEQUENCE: 255
aaggtctgtg aagtatttcc                                                   20

SEQ ID NO: 256          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 256
gtgagaggaa gatagtcaaa                                                   20

SEQ ID NO: 257          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 257
ccaaggcagt gagaggaaga                                                   20

SEQ ID NO: 258          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 258
accaccgtgt agacagaaga                                                   20

SEQ ID NO: 259          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 259
cagtgtgtct atggatggtg                                                   20

SEQ ID NO: 260          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 260
tcgagtgctc ggatgtgatc                                                   20

SEQ ID NO: 261          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 261
gtcacacatt ggaccctcat                                                   20

SEQ ID NO: 262          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 262
ccaccacggt catctggatc                                                   20
```

| | | |
|---|---|---|
| SEQ ID NO: 263<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 263<br>gccaaaggta taaccagctc | | 20 |
| SEQ ID NO: 264<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 264<br>tgaggccatt ggcatgatta | | 20 |
| SEQ ID NO: 265<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 265<br>tggacaccaa cgtgaggcca | | 20 |
| SEQ ID NO: 266<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 266<br>gttatatccc tccatcacca | | 20 |
| SEQ ID NO: 267<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 267<br>tggcaccagt tatatccctc | | 20 |
| SEQ ID NO: 268<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 268<br>acgttccggt catggcacca | | 20 |
| SEQ ID NO: 269<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 269<br>ttgttactac gttccggtca | | 20 |
| SEQ ID NO: 270<br>FEATURE<br>misc_feature<br>source | moltype = RNA   length = 20<br>Location/Qualifiers<br>1..20<br>note = Synthetic<br>1..20<br>mol_type = other RNA<br>organism = synthetic construct | |
| SEQUENCE: 270<br>agcaatagtt tggagcactg | | 20 |

```
SEQ ID NO: 271           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 271
taccacaacg atagcaatag                                                     20

SEQ ID NO: 272           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 272
agcttggtta ccacaacgat                                                     20

SEQ ID NO: 273           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 273
agtgtcgtca agttccatga                                                     20

SEQ ID NO: 274           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 274
gctgggtcaa actgcaagaa                                                     20

SEQ ID NO: 275           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 275
acggttcatg gcaatactgt                                                     20

SEQ ID NO: 276           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 276
gtcaatatac ggttcatggc                                                     20

SEQ ID NO: 277           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 277
tgttgctctt cccatttcca                                                     20

SEQ ID NO: 278           moltype = RNA  length = 20
FEATURE                  Location/Qualifiers
misc_feature             1..20
                         note = Synthetic
source                   1..20
                         mol_type = other RNA
                         organism = synthetic construct
SEQUENCE: 278
```

```
tttggtccgt gtgaaaacaa                                                     20

SEQ ID NO: 279          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 279
caagagtttc agtcgagcca                                                     20

SEQ ID NO: 280          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 280
gtcatctgga ttcaagagtt                                                     20

SEQ ID NO: 281          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 281
agtccttgag gtgccctgga                                                     20

SEQ ID NO: 282          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 282
ggcctgctga gtttgtttcc                                                     20

SEQ ID NO: 283          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 283
agggttcaag cccacactgt                                                     20

SEQ ID NO: 284          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 284
tgggtggaca ctggatgcta                                                     20

SEQ ID NO: 285          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 285
gtggttgtca ttcctggtag                                                     20

SEQ ID NO: 286          moltype = RNA   length = 20
FEATURE                 Location/Qualifiers
misc_feature            1..20
                        note = Synthetic
source                  1..20
                        mol_type = other RNA
                        organism = synthetic construct
```

```
SEQUENCE: 286
agggccatcc tcatatactg                                                  20

SEQ ID NO: 287          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 287
ctcatgtctc acagggccat                                                  20

SEQ ID NO: 288          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 288
taagggcgta gttttgttgg                                                  20

SEQ ID NO: 289          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 289
ttcagccagg cacaagccat                                                  20

SEQ ID NO: 290          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 290
gtaactgttt gctcgttctt                                                  20

SEQ ID NO: 291          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 291
ggaagcctgg ttctctttgg                                                  20

SEQ ID NO: 292          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 292
acgcataaac tcagggttct                                                  20

SEQ ID NO: 293          moltype = RNA  length = 20
FEATURE                 Location/Qualifiers
misc_feature            1..20
                        note = Synthetic
source                  1..20
                        mol_type = other RNA
                        organism = synthetic construct
SEQUENCE: 293
catgttgtca tctgggtaca                                                  20

SEQ ID NO: 294          moltype = RNA  length = 20
FEATURE                 Location/Qualifiers
misc_feature            1..20
                        note = Synthetic
source                  1..20
                        mol_type = other RNA
```

```
                              organism = synthetic construct
SEQUENCE: 294
gtcaacaacg tagaggatgc                                                    20

SEQ ID NO: 295             moltype = RNA  length = 20
FEATURE                    Location/Qualifiers
misc_feature               1..20
                           note = Synthetic
source                     1..20
                           mol_type = other RNA
                           organism = synthetic construct
SEQUENCE: 295
caggagtggc acatagtagt                                                    20

SEQ ID NO: 296             moltype = RNA  length = 20
FEATURE                    Location/Qualifiers
misc_feature               1..20
                           note = Synthetic
source                     1..20
                           mol_type = other RNA
                           organism = synthetic construct
SEQUENCE: 296
agtatttgag gcttcagctt                                                    20

SEQ ID NO: 297             moltype = RNA  length = 20
FEATURE                    Location/Qualifiers
misc_feature               1..20
                           note = Synthetic
source                     1..20
                           mol_type = other RNA
                           organism = synthetic construct
SEQUENCE: 297
aggtcccacg aaagctctca                                                    20

SEQ ID NO: 298             moltype = RNA  length = 20
FEATURE                    Location/Qualifiers
misc_feature               1..20
                           note = Synthetic
source                     1..20
                           mol_type = other RNA
                           organism = synthetic construct
SEQUENCE: 298
atcttctgct ttggatggac                                                    20

SEQ ID NO: 299             moltype = RNA  length = 20
FEATURE                    Location/Qualifiers
misc_feature               1..20
                           note = Synthetic
source                     1..20
                           mol_type = other RNA
                           organism = synthetic construct
SEQUENCE: 299
tttctttcga ggtggagttt                                                    20

SEQ ID NO: 300             moltype = RNA  length = 20
FEATURE                    Location/Qualifiers
misc_feature               1..20
                           note = Synthetic
source                     1..20
                           mol_type = other RNA
                           organism = synthetic construct
SEQUENCE: 300
aatgcctcgt tctgggtcag                                                    20

SEQ ID NO: 301             moltype = RNA  length = 20
FEATURE                    Location/Qualifiers
misc_feature               1..20
                           note = Synthetic
source                     1..20
                           mol_type = other RNA
                           organism = synthetic construct
SEQUENCE: 301
tccaactctc tcaatgcctc                                                    20

SEQ ID NO: 302             moltype = RNA  length = 20
FEATURE                    Location/Qualifiers
misc_feature               1..20
                           note = Synthetic
source                     1..20
```

```
                        mol_type = other RNA
                        organism = synthetic construct
SEQUENCE: 302
ttcccagtat tcaacccagg                                                   20

SEQ ID NO: 303          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 303
acatcccaga aattcccagt                                                   20

SEQ ID NO: 304          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 304
gcagccttca ttttctcgta                                                   20

SEQ ID NO: 305          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 305
ctttccactg ccaaaatctg                                                   20

SEQ ID NO: 306          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 306
cacggagatg gagttgctgt                                                   20

SEQ ID NO: 307          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 307
gggctgactc tgacttggaa                                                   20

SEQ ID NO: 308          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 308
agaggtttgg aacttatcag                                                   20

SEQ ID NO: 309          moltype = RNA   length = 20
FEATURE                 Location/Qualifiers
misc_feature            1..20
                        note = Synthetic
source                  1..20
                        mol_type = other RNA
                        organism = synthetic construct
SEQUENCE: 309
agttccaact gaggtttctc                                                   20

SEQ ID NO: 310          moltype = RNA   length = 20
FEATURE                 Location/Qualifiers
misc_feature            1..20
                        note = Synthetic
```

```
source                     1..20
                           mol_type = other RNA
                           organism = synthetic construct
SEQUENCE: 310
gtcactgtct gctgcaccct                                              20

SEQ ID NO: 311             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 311
agatgccagc aagtcactgt                                              20

SEQ ID NO: 312             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 312
agtgttggtc ctgacttgct                                              20

SEQ ID NO: 313             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 313
gagtataggt tccagaccag                                              20

SEQ ID NO: 314             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 314
ggtggaatct accgtggcag                                              20

SEQ ID NO: 315             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 315
ttttgatggt tcctctccag                                              20

SEQ ID NO: 316             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 316
cgcacactca agagctgcta                                              20

SEQ ID NO: 317             moltype = RNA   length = 20
FEATURE                    Location/Qualifiers
misc_feature               1..20
                           note = Synthetic
source                     1..20
                           mol_type = other RNA
                           organism = synthetic construct
SEQUENCE: 317
tgggtacaga ccagggtcaa                                              20

SEQ ID NO: 318             moltype = RNA   length = 20
FEATURE                    Location/Qualifiers
misc_feature               1..20
```

```
                          note = Synthetic
source                    1..20
                          mol_type = other RNA
                          organism = synthetic construct
SEQUENCE: 318
gtctgagggc gagtagcaca                                          20

SEQ ID NO: 319            moltype = RNA  length = 20
FEATURE                   Location/Qualifiers
misc_feature              1..20
                          note = Synthetic
source                    1..20
                          mol_type = other RNA
                          organism = synthetic construct
SEQUENCE: 319
cttccctttg agtgcaggac                                          20

SEQ ID NO: 320            moltype = RNA  length = 20
FEATURE                   Location/Qualifiers
misc_feature              1..20
                          note = Synthetic
source                    1..20
                          mol_type = other RNA
                          organism = synthetic construct
SEQUENCE: 320
atgagagcaa tcgagatcca                                          20

SEQ ID NO: 321            moltype = RNA  length = 20
FEATURE                   Location/Qualifiers
misc_feature              1..20
                          note = Synthetic
source                    1..20
                          mol_type = other RNA
                          organism = synthetic construct
SEQUENCE: 321
gccagaagag gaggaggtgt                                          20

SEQ ID NO: 322            moltype = RNA  length = 20
FEATURE                   Location/Qualifiers
misc_feature              1..20
                          note = Synthetic
source                    1..20
                          mol_type = other RNA
                          organism = synthetic construct
SEQUENCE: 322
cccatgtgct ggactgtagc                                          20

SEQ ID NO: 323            moltype = RNA  length = 20
FEATURE                   Location/Qualifiers
misc_feature              1..20
                          note = Synthetic
source                    1..20
                          mol_type = other RNA
                          organism = synthetic construct
SEQUENCE: 323
atgaatccca ggagtaagct                                          20

SEQ ID NO: 324            moltype = RNA  length = 20
FEATURE                   Location/Qualifiers
misc_feature              1..20
                          note = Synthetic
source                    1..20
                          mol_type = other RNA
                          organism = synthetic construct
SEQUENCE: 324
ctcacttgtc tatgcctttg                                          20
```